US006455672B1

(12) United States Patent
Benfey et al.

(10) Patent No.: US 6,455,672 B1
(45) Date of Patent: *Sep. 24, 2002

(54) SCARECROW GENE, PROMOTER AND USES THEREOF

(75) Inventors: Philip N. Benfey; Laura Di Laurenzio; Joanna Wysocka-Diller; Jocelyn E. Malamy; Leonard Pysh; Yrjo Helariutta, all of New York, NY (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/186,188

(22) Filed: Nov. 5, 1998

Related U.S. Application Data

(60) Division of application No. 08/842,445, filed on Apr. 24, 1997, which is a continuation-in-part of application No. 08/638,617, filed on Apr. 26, 1996, now abandoned.

(51) Int. Cl.[7] .................. C07K 14/475; C07K 14/00
(52) U.S. Cl. .................. 530/350; 530/300; 435/69.1; 435/69.7
(58) Field of Search ............... 530/350, 300; 435/69.1, 69.7

(56) References Cited

PUBLICATIONS

Callard et al. The Cytokine FactsBook, Academic Press, London, p. 31, 1994.*
Bowie et al. Science 247:1306–1310, 1990.*
Ngo et al. The Protein Folding Problem and Tertiary Structure Prediction, Merz et al., eds., Birkhauser, Boston, pp. 492–495, 1994.*
Wells. Biochemistry 29:8509–8517, 1990.*
Schulz et al. Principles of Protein Structure, Springer–Verlag, New York, pp. 14–16, 1979.*
Wolffe. BioEssays 16:245–251, 1994.*
Bork et al., 2000, Genome Research 10:398–400.*
Skolnick et al., 2000, Trends in Biotech. 18:34–39.*
Doerks et al., 1998, Trends in Genetics 14:248–250.*
Smith et al., 1997, Nature Biotechnology 15:1222–1223.*
Brenner, 1999, Trends in Genetics 15:132–133.
Bork et al., 1996, Trends in Genetics 12:425–427.
Aeschbacher et al., 1995, *Genes & Development* 9:330–340.
Benfey et al., 1990, *EMBO J.* 9:1677–1684.
Benfey et al., 1993, *Development* 119:57–70.
Di Laurenzio et al., 1996, *Cell* 86:423–433.
K.A. Feldmann, 1991, *Plant J.* 1:71–82.
Fukaki et al., 1996, *Plant Physiol.* 110:933–943.
Fukaki et al., 1996, *Plant Physiol.* 110:945–955.
Fukaki et al., 1996, *J. Plant Res.* 109:129–137.
H.C. Hurst, 1994, *Protein Profile* 1:123–168.
Jarvis et al., 1994, *Plant Mol. Biol.* 24:685–687.
Johnson et al., 1993, *J. Nutr. Biochem.* 4:386–398.
Koncz et al., 1994, *Plant Mol. Biol. Mannual*, Gelvin & Schilperoort, ed; Kluover Academic Press, Dordrecht, The Netherlands B2:1–2.
Laskowski et al., 1995, *Development* 121:3303–3310.
Lukowitz et al., 1996, *Cell* 84:61–71.
Malamy & Benfey, 1997, *Development* 124:33–44.
Scheres et al., 1995, *Development* 121:53–62.
Torres–Ruiz & Jurgens, 1994, *Development* 120:2967–2978.
van den Berg et al., 1995, *Nature* 378:62–65.
Varagona et al., 1992, *Plant Cell* 4:1213–1227.

* cited by examiner

*Primary Examiner*—Elizabeth Kemmerer
(74) *Attorney, Agent, or Firm*—Nixon Peabody LLP

(57) ABSTRACT

The structure and function of a regulatory gene, SCARECROW (SCR), is described. The SCR gene is expressed specifically in root progenitor tissues of embryos, and in roots and stems of seedlings and plants. SCR expression controls cell division of certain cell types in roots and affects the organization of root and stem tissues, and affects gravitropism of aerial structures. The invention relates to the SCARECROW (SCR) gene, SCR gene products, (including but not limited to transcriptional products such as mRNAs, antisense, and ribozyme molecules, and translational products such the SCR protein, polypeptides, peptides and fusion proteins related thereto), antibodies to SCR gene products, SCR promoters and regulatory regions and the use of the foregoing to improve agronomically valuable plants.

6 Claims, 74 Drawing Sheets

Figure 1A:
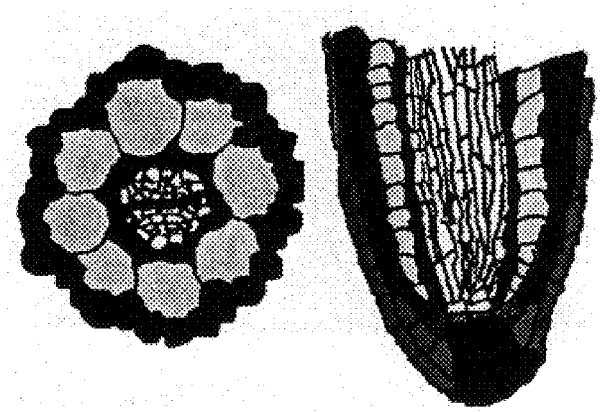

EPIDERMIS
CORTEX
ENDODERMIS
PERICYCLE
ROOT CAP

VASCULAR TISSUE
CORTEX/ENDODERMAL INITIAL
EPIDERMAL/ROOT CAP INITIAL
QUIESCENT CENTER

FIG.5A-1

```
TCGTGTCTCGGAATTTACGGGCTTTGCCCTTCACGGTGGAATGCCTCAAACGCTCAAAGGCATAGCTTGAAATGGTCTCTGCGTTTCAGGTCTTTAATGGGATAAGCCCTTAGTGAAATTCTCACAC    384
 S  C  L  G  I  Y  A  A  L  P  S  R  W  M  P  Q  T  H  S  L  K  M  V  S  A  F  Q  V  F  N  G  I  S  P  L  V  K  F  S  H

TTTACAGGCAATCAGGCGATTCAAGAAGCATTTGAGAAAGAAGACACAGTGTACACATCATTGACTGGACACTTCAATGCCTGGTTTATTCCACATTCTGCTTCTAGA    424
 F  T  N  Q  A  I  Q  E  A  F  E  K  E  D  S  V  H  I  I  D  L  D  I  M  Q  G  L  Q  W  P  G  L  F  H  I  L  A  S  R

CCTGGAGACCTCCACACGTGCGACTCACGGGACTTGTACTTCCATGGAAGCTCTTCAGGCTACACGGAAGCTCTTCGGATTCACAGATAAGCTTCCCCTGCCTTTGAGTTCTGC    464
 P  G  G  P  P  H  V  R  L  T  G  L  G  T  S  M  E  A  L  Q  A  T  G  K  R  L  S  D  F  T  D  K  L  G  L  P  F  E  F  C

CCCTTTAGCTGAGAAAGTTGGAAACTGGACACTGAGAGACTCAATGTGAGGAAAAGGGAAGCTGTGGCTGTCACTGGCTTCAACATTCTCTTTATGATGTCACTGCCTCTGATGCACAC    504
 P  L  A  E  K  V  G  N  L  D  T  E  R  L  N  V  R  K  R  E  A  V  A  V  H  W  L  Q  H  S  L  Y  D  V  T  G  S  D  A  M

ACTCTCTGGTTACTCCAAAGTAAAATAAACATTACCTTTAATCACTCTTTATCTATAAATTATTTTAAGATTATATAGGAAAGATATGTCTAAAAGCTGGCTTTTTCGTAATGA    511
 T  L  W  L  L  Q  R

TTCGGGAATGAACACAGATTAGCTCCTAAAGTGTCGACAGTAGTGGTTGTAGAGGCAATACATTACTCTGCACTCTTTGA    546
             L  A  P  K  V  V  T  V  V  E  Q  D  L  S  H  A  G  S  F  L  G  R  F  V  E  A  I  H  Y  Y  S  A  L  F  D

CTCACTGGGAGCAAGCTACGGCGCGAAGAGTGAAGAGACATGTCGTCGAACAGCAGCTATATCGGAACTTAGCCGTTGCAGCACCATCGAGAAGCCGTCAAGT    586
 S  L  G  A  S  Y  G  E  E  S  E  E  E  R  H  V  V  E  Q  Q  L  L  S  K  E  I  R  N  V  L  A  V  G  G  P  S  R  S  G  E  V

GAAGTTTGAGAGCTGCAGGGAGGAGAAAATGCAACAATGTGGGTTTAAACGTATATCTTTAGCTGGAAATGCAGCTACACAAGGACTCTACTGTGGAATGTTTCCTTCGGATGGTTACAC    626
 K  F  E  S  W  R  E  K  M  Q  Q  C  G  F  K  G  I  S  L  A  G  N  A  A  T  Q  A  T  L  L  G  H  F  P  S  D  G  Y  T

TTTGGTTGATGATAATGGTACACTTAAGCTTGGATGGAAAGATCTTTCGTTACTCACTGCTTCAGCTGCACGCCTCGTTCTTAGTTTCTCTCCTTTTCACAAACAATGTGCCCATA    653
 L  V  D  D  N  G  T  L  K  L  G  W  K  D  L  S  L  L  T  A  S  A  W  T  P  R  S  STOP

2163
AAT
```

FIG.5A-2

| | | | 1 |
|---|---|---|---|
| SCR bZIP-like domain | | PAVQTNTAEALRERKEEIKRQKQ | D |
| | | ‖ ‖‖‖  : ‖‖ | |
| GCN4 | (yeast) | LKRARNTEAARRSRARKLQRMKQ | L |
| TGA1 | (Arabidopsis) | RRLAQNREAARKSRLRKKAYVQQ | L |
| C-Fos | (mouse) | IRRERNKMAAAKCRNRRRELTDT | L |
| c-JUN | (human) | RKRMRNRIAASKCRKRKLERIAR | L |
| CREB | (human) | VRLMKNREAARECRRKKKEYVKC | L |
| Opaque-2 | (maize) | KRKESNRESARRSRYRKAAHLKE | L |
| OBF2 | (maize) | MRQIRNRDSAMKSRERKKSYIKD | L |
| RAF-1 | (rice) | RRMVSNRESARRSRKKKQAHLAD | L |

FIG.5C

```
SCR VHIID domain                                              1
SCR         AFEKEDSVHIIDLDIMQGLQWPGLFHILASRPGGPPHVRLTGL
F13896      AVKNESFVHIIDFQISQGGQWVSLIRALGARPGGPPNVRITGI
Z37192      AMEGEKMVHVIDLDASEPAQWLALLQAFNSRPEGPPHLRITGV
Z25645      AIKGEEEVHIIDFDINQGNQYMTLIRSIA
D41474              IHVIDFXLGVGGQWASFLQELAHRRG
T18310      VHIIXFXLMQGLQWPALMDVFSARKGGPPKLRITGI
```

FIG. 5D

FIG. 5E-1

MetAlaGluSerGlyAspPheAsnGlyGlyGlnProProHisSerProLeuArgThr
ThrSerSerGlySerSerSerSerAsnArgGlyProProProProProProProPro
LeuValMetValArgLysArgLeuAlaSerGluMetSerSerAsnProAspTyrAsnAsn
SerSerArgProArgArgValSerHisLeuLeuAspSerAsnTyrAsnThrValThr
ProGlnProProSerLeuThrAlaAlaAlaThrValSerSerGlnProAsnProPro
LeuSerValCysGlyPheSerGlyLeuProValPheProSerAspArgGlyGlyArgAsn
ValMetMetSerValGlnProMetAspSerSerSerSerSerAlaSerProThr
ValTrpValAspAlaIleIleArgAspLeuIleHisSerSerThrSerValSerIlePro
GlnLeuIleGlnAsnValArgAspIleIlePheProCysAsnProAsnLeuGlyAlaLeu
LeuGluTyrArgLeuArgSerLeuMetLeuAspProSerSerSerSerAspProSer
ProGlnThrPheGluProLeuTyrGlnIleSerAsnProSerProProGlnGln
GlnGlnHisGlnGlnGlnGlnHisLysProProProProProIleGlnGlnGln
GluArgGluAsnSerSerThrAspAlaProProGlnProGluThrValThrAlaThrVal
ProAlaValGlnThrAlaAsnThrAlaGluAlaLeuArgLysGluLeuIleLysArg
GlnLysGlnAspGluGluGlyLeuHisLeuLeuThrLeuLeuLeuGlnCysAlaGluAla
ValSerAlaAspAsnLeuGluAlaAsnLysLeuLeuLeuGluIleSerGlnLeuSer
ThrProTyrGlyThrSerAlaGlnArgValAlaAlaTyrPheSerGluAlaMetSerAla

FIG. 5E-2

ArgLeuAsnSerCysLeuGlyIleTyrAlaAlaLeuProSerArgTrpMetProGln
ThrHisSerLeuLysMetValSerAlaPheGlnValPheAsnGlyIleSerProLeuVal
LysPheSerHisPheThrAlaAsnGlnAlaIleGlnAlaPheGluLysGluAspSer
ValHisIleIleAspLeuAspIleMetGlnGlyLeuGlnTrpProGlyLeuPheHisIle
LeuAlaSerArgProGlyProProHisValArgLeuThrGlyLeuGlyThrSerMet
GluAlaLeuGlnAlaThrGlyLysArgLeuSerAspPheThrAspLysLeuGlyLeuPro
PheGluPheCysProLeuAlaGluLysValGlyAsnLeuAspThrGluArgLeuAsnVal
ArgLysArgGluAlaValAlaAlaValHisTrpLeuGlnHisSerLeuTyrAspValThrGly
SerAspAlaHisThrLeuTrpLeuLeuGlnArgLeuAlaProLysValValThrValVal
GluGlnAspLeuSerHisAlaGlySerPheLeuGlyArgPheValGluAlaIleHisTyr
TyrSerAlaLeuPheAspSerLeuGlyAlaSerTyrGlyGluSerGluArgHis
ValValGlnLeuLeuSerLysGluIleArgAsnValLeuAlaValGlyGlyPro
SerArgSerGlyGluValLysPheGluSerTrpArgGluLysMetGlnCysGlyPhe
LysGlyIleSerLeuAlaGlyAsnAlaAlaThrGlnAlaThrLeuLeuGlyMetPhe
ProSerAspGlyTyrThrLeuValAspAspAsnGlyThrLeuLysLeuGlyTrpLysAsp
LeuSerLeuLeuThrAlaSerAlaTrpThrProArgSerSTOP

```
             10         20         30         40         50
     1234567890 1234567890 1234567890 1234567890 1234567890
     GGCACGAGCC CAACGGGTCC TGAGCTTCTT ACTTATATGC ATATCTTGTA    50
      G  T  S  P   T  G  P   E  L  L   T  Y  M  H   I  L  Y

TGAAGCCTGC CCTTATTTCA AATTCGGTTA TGAATCTGCT AATGGAGCTA   100
      E  A  C   P  Y  F  K   F  G  Y   E  S  A   N  G  A  I

TAGCTGAAGC TGTGAAGAAC GAAAGTTTTG TGCACATTAT CGATTTCCAG   150
       A  E  A   V  K  N   E  S  F  V   H  I  I   D  F  Q

ATTTCTCAAG GTGGTCAATG GGTGAGTTTG ATCCGTGCTC TTGGTGCTAG   200
      I  S  Q  G   G  Q  W   V  S  L   I  R  A  L   G  A  R

ACCTGGTGGA CCTCCGAACG TTAGGATAAC GGGAATTGAT GATCCGAGAT   250
       P  G  G   P  P  N  V   R  I  T   G  I  D   D  P  R  S

CATCGTTTGC TCGTCAAGGA GGACTTGAGT TAGTTGGACA AAGACTTGGG   300
       S  F  A   R  Q  G   G  L  E  L   V  G  Q   R  L  G

AAGCTAGCTG AAATGTGCGG TGTTCCGTTT GAGTTCCATG GAGCTGCTTT   350
       K  L  A  E   M  C  G   V  P  F   E  F  H  G   A  A  L

ATGCTGCACG GAAGTCGAAA TCGAGAAGCT AGGAGTTAGA AATGGAGAAG   400
       C  C  T   E  V  E  I   E  K  L   G  V  R   N  G  E  A

CGCTCGCGGT TAACTTCCCG CTTGTTCTTC ACCACATGCC TGATGAGAGT   450
        L  A  V   N  F  P   L  V  L  H   H  M  P   D  E  S

GTAACTGTGG AGAATCACAG AGATAGATTG TTGAGATTGG TCAAACACTT   500
       V  T  V  E   N  H  R   D  R  L   L  R  L  V   K  H  L

GTCACCAAAC GTTGTGACTC TGGTTGAGCA AGAAGCGAAT ACAAACACTG   550
       S  P  N   V  V  T  L   V  E  Q   E  A  N   T  N  T  A

CGCCGTTTCT TCCCCGGTTT GTCGAGACAA TGAACCATTA CTTGGCAGTT   600
       P  F  L   P  R  F   V  E  T  M   N  H  Y   L  A  V
```

FIG.8A

```
          10         20         30         40         50
 1234567890 1234567890 1234567890 1234567890 1234567890
 TTCGAATCAA TAGATGTGAA ACTCGCTAGA GATCACAAGG AAAGGATCAA   650
  F E S I    D V K     L A R      D H K E    R I N

TGTTGAGCAG CATTGTTTGG CTAGAGAGGT TGTGAATCTT ATAGCTTGTG   700
  V E Q     H C L      R E V      V N L      I A C E

AAGGTGTTGA AAGAGAAGAG AGGCACGAGC CACTAGGGAA ATGGAGGTCT   750
  G V E     R E E      R H E P    L G K      W R S

CGGTTTCACA TGGCGGGATT TAAACCGTAT CCTTTGAGCT CGTATGTGAA   800
  R F H M   A G F      K P Y      P L S S    Y V N

CGCAACAATC AAAGGATTGC TTGAGAGTTA TTCAGAGAAG TATACACTTG   850
  A T I     K G L L    E S Y      S E K      Y T L E

AAGAAAGAGA TGGAGCATTG TATTTAGGAT GGAAGAATCA ACCTCTTATC   900
  E R D     G A L      Y L G      W K N Q    P L I

ACTTCTTGTG CTTGGAGGTA ACTAATAAAA ACCTTGTTCG GTTTCAGAAG   950
  T S C A   W R X

AGATTAGAAA CTTCTTTTAA AGTTTGCAGA ATCTGTTTGT AAAAGTAAAA  1000

CTCATGCATG ATCCGNAGGA ACAAGTTGTC AAATGTTGTA GTAGTAAGTG  1050

ATATGTTGAT GACCCAAAAA AAAAAAAAAA AAAAA                 1085
```

FIG. 8B

```
           10         20         30         40         50
   1234567890 1234567890 1234567890 1234567890 1234567890
   GCTATGGAAG GAGAGAAGAT GGTTCATGTG ATTGATCTCG ATGCTTCTGA    50
    A M E G    E K M      V H V     I D L D    A S E

GCCAGCTCAA TGGCTTGCTT TGCTTCAAGC TTTTAACTCT AGGCCTGAAG   100
    P A Q     W L A L     L Q A     F N S      R P E G

GTCCACCTCA TTTGAGAATC ACTGGTGTTC ATCACCAGAA GGAAGTGCTT   150
    P P H     L R I      T G V H    H Q K      E V L

GAACAAATGG CTCATAGACT CATTGAGGAA GCAGAGAAAC TCGATATCCC   200
    E Q M A    H R L     I E E      A E K L    D I P

GTTTCAGTTT AATCCCGTTG TGAGTAGGTT AGACTGTTTA AATGTAGAAC   250
    F Q F     N P V V    S R L      D C L      N V E Q

AGTTGCGGGT TAAAACAGGA GAGGCCTTAG CCGTTAGCTC GGTTCTTCAA   300
    L R V     K T G      E A L A    V S S      V L Q

TTGCATACCT TCTTGGCCTC TGATGATGAT CTCATGAGAA AGAACTGCGC   350
    L H T F    L A S     D D D      L M R      K N C A

TTTACGGTTT CAGAACAACC CTAGTGGAGT TGACTTGCAG AGAGTTCTAA   400
    L R F     Q N N P    S G V      D L Q      R V L M

TGATGAGCCA TGGCTCTGCA GCTGAGGCAC GTGAGAATGA TATGAGTAAC   450
    M S H     G S A      A E A R    E N D      M S N

AACAATGGGT ATAGCCCTAG CGGTGAGTCG GCCTCATCTT TGCCTTTACC   500
    N N G Y    S P S     G D S      A S S L    P L P

AAGTTCAGGA AGGACTGATA GCTTCCTCAA TGCTATTTGG GGTTTGTCTC   550
    S S G     R T D S    F L N      A I W      G L S P

CAAAGGTCAT GGTGGTCACT GAGCAAGACT CAGACCACAA CGGCTCCACA   600
    K V M     V V T      E Q D S    D H N      G S T
```

FIG.9A

```
              10         20         30         40         50
         1234567890 1234567890 1234567890 1234567890 1234567890
         CTAATGGAGA GGCTATTAGA ATCACTTTAC ACCTACGCAG CATTGTTTGA   650
          L  M  E   R  L  L   E  S  L  Y  T  Y  A  A  L  F  D

TTGCTTGGAA ACAAAAGTTC CAAGAACGTC TCAAGATAGG ATCAAAGTGG   700
          C  L  E   T  K  V  P  R  T  S   Q  D  R   I  K  V  E

AGAAGATGCT CTTCGGGGAG GAGATCAAGA ACATCATATC CTGCGAGGGA   750
          K  M  L   F  G  E   E  I  K  N  I  I  S   C  E  G

TTTGAGAGAA GAGAAAGACA CGAGAAGCTT GAGAAATGGA GCCAGAGGAT   800
          F  E  R  R   E  R  H  E  K  L   E  K  W  S  Q  R  I

DGATTTGGCT GGTTTTGGGA ATGTTCCTCT TAGCTATTAT GCGATGTTGC   850
          D  L  A   G  F  G  N  V  P  L   S  Y  Y   A  M  L  Q

AGGCTAGGAG ATTGCTTCAA GGGTGCGGTT TTGATGGGTA TAGAATCAAG   900
          A  R  R   L  L  Q   G  C  G  F  D  G  Y   R  I  K

GAAGAGAGCG GGTGCGCAGT AATTTGCTGG CAAGATCGAC CTCTATACTC   950
          E  E  S  G   C  A  V  I  C  W   Q  D  R   P  L  Y  S

GGTATCAGCT TGGAGATGCA GGAAGTGAAT GATATATTAC AGTTTGTCTT   1000
          V  S  A  W   R  C  R  K  X

CTATTTTGGT TATGAGCAGA GTCCCTTTCT TTTTTGTATA CATGGGGACA   1050

CAATCTTAGT TGTTTTGTGA TGGTGACTTT CTGTCTCTTT ATGCTATTTT   1100

GGCTTAAATG CTTCTACTGC CTCTGCATGT AAAGCCTTTG TGTGTTGGTT   1150

CAATTTGGTC TGGTGTGGGT GTAATACCAA ACCAAATCCA ATTTGAGCTG   1200

AAGATAACTA ATTTGATGAT CGGCTCGTGC C                       1231
```

FIG.9B

FIG. 10

```
CTTGTCAAT GGTAAATGAG CTGAGGCAGA TAGTTTCTAT CCAAGGAGAC        50
CCTCTCAGA GAATCGCAGC TTACATGGTG GAAGGTCTAG CTGCAAGAAT       100
GGCCGCTTCA GGAAAATTCA TCTACAGAGC ATTGAAATGC AAAGAGCCTC      150
CTTCGGATGA GAGGCTTGCA GCTATGCAAG TCCTGTTTGA AGTCTGCCCT      200
TGTTTCAAGT TCGGGTTTTT AGCAGCTAAT GGTGCGATAC TTGAAGCAAT      250
CAAAGGTGAA GAAGAAGTTC ACATAATCGA TTTCGATATA AACCAAGGGA      300
ACCAATACAT GACACTGATA CGAAGCATTG CTGAGTTGCC TGGTAAACGA      350
CCTCGCCTGA GGTTAACAGG AATTGATGAC CCTGAAATCAG TCCAACGCTC     400
CATTGGAGGG CTAAGAATCA TCAATCTAAG ACTCGAGCAA CTCGCAGAGG      450
ATAATGGAGT ATCCTTCAAA TTCAAAGCAA TGCCCTTCAAA GACTTCGATT    500
GTCTCTCCAT CAACACTCGG TTGCAAACCA GGAGAAACCT TAATCAGTGA      550
ACTTTGCATT CCAACTTCAC CACATGCCCTG ACGAGAGTGT CACAACAGTA    600
AACCAGCGGG ACGAGCTACT TCACATGGTC AAAAGCTTAA ACCCGCTTGT     650
CACGGTCGTT GAACAAGACG TGAACACAAA CACTTCACCG TTCTTTCCCA     700
GATTCATAGA GGCTTACGAA TACTACTCAG CAGTTTTCGA GTCTCTAGAC     750
ATGACACTTC CAAGAGAAAG CCAAGAGAGG ATGAATGTAG AAAGACAGTG     800
TCTCGCTAGA GACATAGTCA ACATTGTTGC TTGCGAAGGA GAAGAACGGA     850
TAGAGAGATA CGAGGCTGCG GGAAAATGGA GAGCAAGGAT GATGATGGCT     900
GGATTCAATC CAAAACCAAT GAGTGCTAAA GTAACCAACA ATATACAAAA     950
CCTGATAAAG CAACAATATT GCAATAAGTA CAAGCTTAAA GAAGAAATGG    1000
GTGAGCTCCA TTTTTGCTGG GAGGAGAAAA GCTTAATCGT TGCTTCAGCT    1050
TGGAGGTAAG ATAAGTGACA AGAGCATATA GTCTTTATGT TTCATAAAAC    1100
ATAATTATGT TTTTACTGTA ATCTTGGGTT ATGTGTAAC TGGTTAAATC     1150
ATCTCCATGT ATTATTACCA GAGGTTAGGG GTGATCACAG GTACTAAAAG    1200
CTAATCTAAC ACTTATGGAA GAATTTTTCT TTCTTTTTT TCCCTATTAT     1250
ATAAAAATAA TTAGAGTTTT GGTTCTAAAC CTATTTGCTA AGTGTGAATG    1300
AGTCTTTACA TGTTCATATATT TCAGTTCAAA TGGTTAAATT TGTTAAGGTT  1350
CTCACTTAAA AAAAAA
```

Zm-scl1

```
           10          20         30         40         50
CCAGGAGGCGTTCGAGCGGGAGGAGCGTGTGCACATCATCGACCTCGACA
 Q  E  A  F  E  R  E  E  R  V  H  I  I  D  L  D  I 60          70         80         90         100
TCATGCAGGGGCTGCAGTGGCCGGGCCTCTTCCACATCCTTGCCTCCCGC
 M  Q  G  L  Q  W  P  G  L  F  H  I  L  A  S  R
```

FIG.11A

```
          10         20         30         40         50
     1234567890 1234567890 1234567890 1234567890 1234567890
     CACGCGTCCG TCAAAGGATA CAACCATGTA CACATAATTG ACTTTTCCCT   50
      H A S V   K G Y   N H V   H I I D   F S L

GATGCAAGGT CTCCAGTGGC CGGCACTCAT GGATGTCTTC TCCGCCCGTG  100
      M Q G   L Q W P   A L M   D V F   S A R E

AGGGTGGGCC ACCAAAGCTC CGAATCACAG GCATTGGCCC GAACCCAATA  150
      G G P   P K L   R I T G   I G P   N P I

GGTGGCCGTG ACGAGCTCCA TGAAGTGGGA ATTCGCCTCG CCAAGTATGC  200
      G G R D   E L H   E V G   I R L A   K Y A

ACACTCGGTG GGTATCGACT TCACTTTCCA GGGAGTCTGT GTCGATCAAC  250
      H S V   G I D F   T F Q   G V C   V D Q L

TTGATAGGTT GTGCGACTGG ATGCTTCTCA AACCAATCAA AGGAGAGGCA  300
      D R L   C D W   M L L   K P I K   G E A

GTTGCCATAA ACTCCATCCT ACAACTCCAT CGCCTCCTCG TTGACCCAGA  350
      V A I N   S I L   Q L H   R L L V   D P D

TGCAAACCCA GTGGTGCCCG CACCAATAGA TATCCTCCTC AAATTGGTCA  400
      A N P   V V P A   P I D   I L L   K L V I

TCAAGATAAA CCCCATGATC TTCACGGTGG TTGAGCATGA GGCAGATCAC  450
      K I N   P M I   F T V V   E H E   A D H

AACAGACCAC CACTACTAGA GAGGTTCACT AATGCCCTCT TCCACTATGC  500
      N R P P   L L E   R F T   N A L F   H Y A

GACCATGTTT GACTCTTTGG AGGCCATGCA TCGTTGTACC AGTGGTAGAG  550
      T M F   D S L E   A M H   R C T   S G R D

ACATCACCGA CTCACTCACA GAGGTGTACC TTGAGGTGA GATTTTTGAC  600
      I T D   S L T   E V Y L   R G E   I F D
```

FIG.11B1

```
          10         20         30         40         50
 1234567890 1234567890 1234567890 1234567890 1234567890
ATTGTCTGCG GCGAGGGCAG TGCACGCACC GAACGTCATG AGTTGTTTGG   650
 I  V  C  G  E  G  S  A  R  T  E  R  H  E  L  F  G

TCACTGGAGG GAGAGGCTCA CCTATGCTGG GCTAACTCAA GTGTGGTTCG   700
 H  W  R  E  R  L  T  Y  A  G  L  T  Q  V  W  F  D

ACCCCGATGA GGTTGACACG CTAAAAGACC AGTTGATCCA TGTGACATCC   750
 P  D  E  V  D  T  L  K  D  Q  L  I  H  V  T  S

TTATCTGGCT CTGGGTTCAA CATCCTAGTG TGTGATGGCA GCCTTGCACT   800
 L  S  G  S  G  F  N  I  L  V  C  D  G  S  L  A  L

AGCGTGGCAT AATCGCCCGT TATATGTGGC AACAGCTTGG TGTGTGACAG   850
 A  W  H  N  R  P  L  Y  V  A  T  A  W  C  V  T  G

GAGGAAATGC TGCCAGTTCC ATGGTTGGCA ACATCTGTAA GGGTACAAAT   900
 G  N  A  A  S  S  M  V  G  N  I  C  K  G  T  N

GATAGTAGAA GAAAGGAAAA CCGTAATGGA CCCATGGAGT AGCAGGAAGA   950
 D  S  R  R  K  E  N  R  N  G  P  M  E  X

ATAACCATGT CATGAGCAAA TCGATCAAGT AATAAAATGC ACTGATGACA  1000

TGCATGGTGA TCTAAAGTTT TTTTGCGTGA ATGTGCAATG ACGAATTGTT  1050

CAATTTGAAT AACCTAATCA TGAGACTCAA AAAAAAAAAA AAA         1093
```

FIG. 11B2

| | | | | |
|---|---|---|---|---|
| CCCAACTTGG | GAAGCCCTTC | CTCCGCTCCG | CCTCCTACCT | CAAGGAGGCC | 50
| CTCCTCCTCG | CACTCGCCGA | CAGCCACCAT | GGCTCCTCCG | GGTCACCTC | 100
| GCCGCTCGAC | GTTGCCCTCA | AGCTTGCAGC | ATACAAGTCT | TTCTCTGACC | 150
| TGTCACCTGT | GCTCCAGTTC | ACTAACTTTA | CCGCAACAAG | GCGCTTCTTG | 200
| ATGAGATTGG | TGGCATGGCA | ACTTCCTGCA | TCCATGTCAT | TGACTTTGAT | 250
| CTCGGTGTTG | GTGGTCAGTG | GGCTTCCTTC | TTGCAGGAGC | TTGCCCACCG | 300
| CCGGGAGCT | GGAGGTATGG | CCTTGCCGTT | GTGAAGCTC | ACGGCTTTCA | 350
| TGTCGACTGC | TTCTCACCAT | CCACTGGAGC | TGCACCTTAC | CCAGGATAAC | 400
| CTCTCTCAGT | TTGCCGCAGA | GCTCAGAATT | CCTTTCGAAT | TCAATGCCGT | 450
| CAGTCTTGAT | GCATTCAATC | CTGCGGAAATC | TATTTCTTCC | TCTGGTGATG | 500
| AAGTGTGC | TGTTAGCCTC | CCTGTTGGCT | GCTCTGCTCG | TGCACCACCG | 550
| CTGCCAGCGA | TTCTTCGGTT | GGTGAAACAG | CTTTGTCCTA | AGTTGTGTGT | 600
| GGCTATTGAT | C | | | |

FIG. 12A

```
                                                              50
TTTTTTTTTT  TTTTTTTTTT  TTTTTTTTTT  TACAGAGCAA  CAGCAGTATA
                                                             100
ATATTAATTC  TGTACCACAC  AACCATTTGA  TAGGTTAAAT  TACCCTCTAG
                                                             150
TCTCTACTCA  TAAGCAGTGT  TTCCAATGAG  ATGATCATGG  CTAATTGAGC
                                                             200
AGAGCATGGC  AACAACCTAA  AGCAACATCA  TTAGCTATAG  AGACTGACAC
                                                             250
CAATATTCCT  AAATCCACTA  GGCTAGCTAA  TAAGCTGCAA  CGAAAAGCAA
                                                             300
TATGAAGAGT  TCAACAGCTC  AAGACAACAA  TTTCATTTGC  AACATTAAAT
                                                             350
TGCAAGAATA  AATGGACATT  ACTGGAGTGG  TCGATGCTTG  CAAACGGTGG
                                                             400
TGGAACCTTG  GTGGAGTGAA  GCTTATGGCT  GATCAGCACC  GCCAAGATGA
                                                             450
TATGGATACA  AGCTCCCCAC  GCTGCCAGTA  GAGCGTAAGA  GCAGCTCCGC
                                                             500
GTTTCTCCAC  ATGGAATCCT  CGGACCTGCA  CCCGCTTCAG  GAGGCAGTCT
GC
```

FIG. 12B

```
SCR   MAESGDFNGGQPPPHSPLRTTSSGSSSSSNNRGPPPPPPPLVMVRKR----LASEMSS
TF1   MKRD---HHQFQGRLSNHGTSSSSSSISKDK--MMVKKEEDGGGNMDDELLAV----
TF4   MKRDHHHHHQ------------------------DKKTMMM--NEEDDGNGM-DELLAV----
```

|-------------- MOTIF I --------------|

```
SCR   NPDYNNSSRPPRRVSHLLDSNYNTVTPQQPPSLTAAATVSSQPNPPLSVCGFSG
TF1   -LGYKVRSSEMAEVALKLEQLETMMSNAQEDGLSHLATDAAHYNPSELYS----
TF4   -LGYKVRSSEMADVAQKLEQLEVMMSNVQEDDLSQLATETVHYNPAELYT----

SCR   LPVFPSDRGGRNVMMSVQPMDQDSSSSSASPTVWVDAIIRDLIHS----STSVSIPQL
TF1   ------------------------------------WLDNMLSELNPPPLPASSNGLDPVL
TF4   ------------------------------------WLDSMLTDLNPP----SSN-AEYDL

SCR   IQNVRDIIFPCNPNLGALLEYRLRSLMLLDPSSSSDPSPQTFEPLYQISNNPSP
TF1   PSPEICGFPXSDYDLKVIPXNAIYQFPAIDSSSSSNN---Q-------------
TF4   ----KAI-P--------GDILNQF-AIDSASSSN---Q-------------
```

FIG. 13A

```
SCR         PQQQQHQQQQQHKPPPPPIQQQERENSSTDAPPQPETVTATVPAVQTNTAEA
TF1         ---------NKRLKSCSSPDSMVTSTSTGTQIGGVIGTTVTTTTTTTAAAES
TF4         ------------GGGGDTYTTNKRLKCSNGVVETTTATAES
```

-------- MOTIF II (DIMERIZATION?) ---------

```
SCR         LRERKEEIKRQKQDEEGLHLLTLLLQCAEAVSADNLEEANKLLLEISQLSTPYG
1110
TF1         ----TRSVILVDSQENGVRLVHALMACAEAIQQNNLTLAEALVKQIGCLAVSQA
TF4         ----TRHVVLVDSQENGVRLVHALLACAEAVQKENLTVAEALVKQIGFLAVSQI
3898                                                     QLGKPFL
```

```
SCR         TSAQRVAAYFSEAMSARLLNSCLGIYAALPSRWMPQTHSLKMVSAFQVFNGISP
4818                                                GTSPT-GPELLTYMHILYEACP
1110        DPSQRIAAYMVEGLAARMAASGKFIYRAL-KCKEPPS--DERLAAMQVLFEVCP
TF1         GAMRKVATYFAEALARR------IY-RL-SPPQNQIDHCLSDTLQMHFYETCP
TF4         GAMRQVATYFAEALARR------IY-RL-SPSQSPIDHSLSDTLQMHFYETCP
3989        ----RSASYLKEALLLALADSHHGSSGVT-SPLDVA----LKLAAYKSFSDLSP
```

FIG. 13B

```
-------------        MOTIF III    (VHIID)      -------------
SCR       LVRFSHFTANQAIQEAFEK--EDSVHIIDLDIMQGLQWPGLFHILASRPGGPP-----HVR
4818      YFKFGYESANGAIAEAVKN--ESFVHIIDFQISQGGQWVSLIRALGARPGGPP-----NVR
1110      CFKFGFLAANGAILEAIKG--EEEVHIIDFDINQGNQYMTLIRSIAELPGKRP-----RLR
3935                      AMEG--EKMVHVIDLDASEPAQWLALLQAFNSRPEGPP-----HLR
TF1       YLKFAHFTANQAILEAFEG--KKRVHVIDFSMNQGLQWPALMQALALREGGPP-----TFR
TF4       YLKFAHFTANQAILEAFQG--KKRVHVIDFSMSQGLQWPALMQALALRPGGPP-----VFR
3989      VLQFTNFTANKALLDEIGGMATSCIHVIDFNLGVGGQWASFLQELAHRRGAGGMALPLLK-KLR
18310                  HASVKG--YNHVHIIDFSLMQGLQWPALMDVFSAREGGPP-----KLR
Zm-Scl1                QEAFER--EERVHIIDLDIMQGLQWPGLFHILASR
Zm-Scl2                   FAG--CRRVHVVDFGIKQGMQWPALLXDLAL
Human     GRNGRTL--WLGEGHIDLWPLQGLLSQGLQRALCARPLGAP-----HVF-
```

FIG. 13C

```
                MOTIF                    MOTIF IV (DIMERIZATION)              MOTIF V
SCR     LTG     LGTSMEA         LQATGKR  LSDFTDK   LGLPFEFCPLAEKVGNDLTERLNV
4818    ITGIDDPRSSFARQGG        LELVGQR  LGKLAEM   CGVPFEFHGAALCCTEVEIEKLGV
1110    LTGIDDPESVQRSIGG        LRIINLR  LEQLAED   NGVSFKFKAMPSKTSIVSPSTLGC
3935    ITG     VHHQKEV         LEQMAHR  LIEEAEK   LDIPFQFNPVVSRLDCLNVEQLRV
TF1     LTGIGPPAPDNSDH          LHEVGCK  LAQLAEA   IHVEFEYRGF  VANSLAD  LDASMLELRP
TF4     LTGIGPPAPDNFDY          LHEVGCK  LAHLAEA   IHVEFEYRGF  VANTLAD  LDASMLELRP
3989    LTAFMSTASHHPLE          LHLTQDN  LSQFAAE   LRIPFEFNAVSLDAFNPAESISSSGDE
18310   ITGIGPNPIGGRDE          LHEVGIR  LAKYAHS   VGIDFTFQGVCVDQLDRLCDWMLLKPI
Human   LPGLHTLS...             LGLQXRH  LLVHMMA   LSYSYGRXP...

SCR     RKREAAVHWLQHSLYDVTGSDAHTLWLL---QRLAPK----------------------
4818    RNGEALAVNFPLVLHHMPDESVTVENHR---DRLLRL----------------------
1110    KPGETL  VNFAFQLHHMPDESVTTVNQR---DELLHM-------------
3935    KTGEALAVSSVLQLHTFLASDDDLMRKNC-ALRFQNNPSGVDLQRVLMMSHGS
TF1     SDTEAVAVNSVFELHKLLGRXGGIEKVLG-----------------
TF4     SEIESVAVNSVFELHKLLGRPGAIDKVLG-----------------
18310   K-GEAVAINSILQLHRLLVDPDANPVVPAPIDILLK---
3989    VVAVSLPVGCSARAPPLPAILRLVKQLCPKVVVAID
```

FIG. 13D

```
SCR     ------------------------------------------------           -------
4818    ------------------------------------------------           -VVTV--
1110    ------------------------------------------------           VKHLSPN--VVTL-
3935    ------------------------------------------------           VKSLNPK-LVTV-
TF1     AAEARENDMSNNNGYSPSGDSASSLPLPSSGRTDSFLNAIWGLSPKVMVT-
TF4     ------------------------------------------------           VVKQD*TGDFHXW
18310   ------------------------------------------------           VVNQIKPEIFTV-
                                                                   LVIKINPMIFTV-

-------- MOTIF VI --------
SCR     VEQDLSHAGS--FLG-RFVEAIHYYSALFDSLGASYGEESE----ERHVVEQQ
4818    VEQEANTNTAP-FLP-RFVETMNHYLAVFESIDVKLARDHK----ERINVEQH
1110    VEQDVNTNTSP-FFP-RFIEAYEYYSAVFESLDMTLPRESQ----ERMNVERQ
3935    -EQDSDHNGS--TLMERLLESLYTYAALFDCLETKVPRTSQ----DRIKVEKM
TF1     XRQEPNHNG-PGFLD-GXTESLHYYSTXFDSLEG----XPNSQ---DKLMSEXY
TF4     VEQESNHNS-PIFLD-RFTESLHYYSTLFDSLEG----VPSGQ---DKVMSEVY
18310   VEHEADHNR-PPLLE-RFTNALFHYATMFDSLEAMHTCTSGRDITDSLTEVY
```

FIG.13E

```
SCR     ----------------LLSKEIRNVLAVGGPSRSGEVKFE-SWREKMQQCGFKGIS-
4818    ----------------CLAREVVNLIACEGVEREERHEPLGKWRSRFHMAGFKPYP-
1110    ----------------CLARDIVNIVACEGERIERYEAAGKWRARMMAGFNPKP-
3935    ----------------LFGEEIKNIISCEGFERRERHEKLEKWSQRIDLAGFGNVP-
TF1     -----------------LGXQICNLVACEGPDRVERHETLSQWGNRFGSSGLAPAH-
TF4     -----------------LGKQICNVVACDGPDRVERHETLSQWRNRFGSAGFAAAH-
3989    -----------------LRGEIFDIVCGEGSARTERHELFGHWRERLTYAGLTQVWF
18310

SCR     LAGNAATQATLLLGMFPS-DGYTLVDDN-GTLKLGWKDLSLLTASAWTPRS*
4818    LSSYVNATIKGLLES-YS-EKYTL-EERDGALYLGWKNQPLITSCAWR*
1110    MSAKVTNNIQNLIKQQYC-NKYKLKEEM-GELHFCWEEKSLIVASAWR*
3935    LSYYAMLQARRLLQGCGF-DGYRIKEES-GCAVICWQDRPLYSVSAWRCRK*
TF1     LGSNAFKQASMLLSVFNSGQGYRV-EESNGCLMLGWHTRPLITTSAWKLSTAAH*
TF4     IGSNAFKQASMLLALFNGGEGYRV-EESDGCLMLGWHTRPLIATSAWKLSTN*
3989    ADCLL--KRVQVRGFHV-EKRGAALTLYWQRGELVSISSWRC*
18310   DPDEVDTLKDQLIHVTSLSGSGFNILVCDGSLALAWHNRPLYVATAWCVTGGNAA

18310   SSMVGNICKGTNDSRRKENRNGPME*
```

FIG. 13F

FIG. 15A

| Old Name | | | | | | New Name |
|---|---|---|---|---|---|---|
| | -150 | | | | -101 | |
| scr | .......... | .......... | .......... | .......... | .......... | SCR |
| 3989 | .......... | .......... | .......... | .......... | .......... | SRPo3 |
| 12398 | .......... | .......... | .......... | .......... | .......... | SRPa6 |
| 4871 | .......... | .......... | .......... | .......... | .......... | SRPa5 |
| 11846 | .......... | .......... | .......... | .......... | .......... | SRPo4 |
| 2504 | .......... | .......... | .......... | .......... | .......... | SRPo2 |
| 3935 | .......... | .......... | .......... | .......... | .......... | SRPa3 |
| 11261 | .......... | .......... | .......... | .......... | .......... | SRPa10 |
| 713 | .......... | .......... | .......... | .......... | .......... | SRPo1 |
| 10964 | .......... | .......... | .......... | .......... | .......... | SRPa9 |
| 23196 | ........LL | KVLLCHLVAE | STKRRIKIRP | LLDINDSGFL | GFWSWIHMGS | SRPa12 |
| Tf1 | .......... | .......... | .......... | .......... | .......... | SRPa8 |
| Tf4 | .......... | .......... | .......... | .......... | .......... | SRPa2 |
| 18310 | .......... | .......... | .......... | .......... | .......... | SRPm1 |
| 18652 | .......... | .......... | .......... | .......... | .......... | SRPa11 |
| 4818 | .......... | .......... | .......... | .......... | .......... | SRPa4 |
| 21729 | .......... | .......... | .......... | .......... | .......... | SRPa7 |
| 1110 | .......... | .......... | .......... | .......... | .......... | SRPa1 |
| 174 | .......... | .......... | .......... | .......... | .......... | SRPb1 |
| 33/08 | .......... | .......... | .......... | .......... | .......... | SRPa13 |

|       |        |        |        |        |        |
|-------|--------|--------|--------|--------|--------|
| Scr   | ...... | ...... | ...... | ...... | ...... |
| 3989  | ...... | ...... | ...... | ...... | ...... |
| 12398 | ...... | ...... | ...... | ...... | ...... |
| 4871  | ...... | ...... | ...... | ...... | ...... |
| 11846 | ...... | ...... | ...... | ...... | ...... |
| 2504  | ...... | ...... | ...... | ...... | ...... |
| 3935  | ...... | ...... | ...... | ...... | ...... |
| 11261 | ...... | ...... | ...... | ...... | ...... |
| 713   | ...... | ...... | ...... | ...... | ...... |
| 10964 | YPDGFPGSMD | ELDFNKDFDL | PPSSNQTLGL | ANGFYLDDLD | FSSLDPPEAY |
| 23196 | ...... | ...... | ...... | ...... | ...... |
| Tf1   | ...... | ...... | ...... | ...... | ...... |
| Tf4   | ...... | ...... | ...... | ...... | ...... |
| 18310 | ...... | ...... | ...... | ...... | ...... |
| 18652 | ...... | ...... | ...... | ...... | ...... |
| 4818  | ...... | ...... | ...... | ...... | ...... |
| 21729 | ...... | ...... | ...... | ...... | ...... |
| 1110  | ...... | ...... | ...... | ...... | ...... |
| 174   | ...... | ...... | ...... | ...... | ...... |
| 33/08 | ...... | ...... | ...... | ...... | ...... |
|       | -100   |        |        |        | -51    |

FIG.15B

```
Scr    ..........  ..........  ..........  ..........  ..........
3989   ..........  ..........  ..........  ..........  ..........
12398  ..........  ..........  ..........  ..........  ..........
4871   ..........  ..........  ..........  ..........  ..........
11846  ..........  ..........  ..........  ..........  ..........
2504   ..........  ..........  ..........  ..........  ..........
3935   ..........  ..........  ..........  ..........  ..........
11261  ..........  ..........  ..........  ..........  ..........
713    ..........  ..........  ..........  ..........  ..........
10964  ..........  ..........  ..........  ..........  ..........
23196  PSQNNNNNNI  NNKAVAGDLL  SSSSDDADFS  DSVLKYISQV  LMEEDMEEKP
Tf1    ..........  ..........  ..........  ..........  ..........
Tf4    ..........  ..........  ..........  ..........  ..........
18310  ..........  ..........  ..........  ..........  ..........
18652  ..........  ..........  ..........  ..........  ..........
4818   ..........  ..........  ..........  ..........  ..........
21729  ..........  ..........  ..........  ..........  ..........
1110   ..........  ..........  ..........  ..........  ..........
174    ..........  ..........  ..........  ..........  ..........
33/08  ..........  ..........  ..........  ..........  ..........
       -50                                                      -1
```

FIG. 15C

```
Scr    MAESGDFNGG QPPPHSPLRT TSSGSSSSNN RGPPPPPPP LVMVRKRLAS
3989   .......... .......... .......... .......... ..........
12398  .......... .......... .......... .......... ..........
4871   .......... .......... .......... .......... ..........
11846  .......... .......... .......... .......... ..........
2504   .......... .......... .......... .......... ..........
3935   .......... .......... .......... .......... ..........
11261  .......... .......... .......... .......... ..........
713    .......... .......... .......... .......... ..........
10964  .......... .......... .......... .......... ..........
23196  .CMFHDALALQ AAEKSLYEAL GEKDPSSSSA SSVDHPERLA SHSPDGSCSG
Tf1    .......... .......... .......... .......... ..........
Tf4    .......... .......... .......... .......... ..........
18310  .......... .......... .......... .......... ..........
18652  .......... .......... .......... .......... ..........
4818   .......... .......... .......... .......... ..........
21729  .......... .......... .......... .......... ..........
1110   .......... .......... .......... .......... ..........
174    .......... .......... .......... .......... ..........
33/08  .....TSDSA SSFNIPTSAQ NHYATGSFST
       1                                                   50
```

FIG. 15D

```
          |-----Motif I ------------------|
Scr    EMSSNPDYNN SSRPPRRVSH LLDSNYNTVT PQQPPSLTAA ATVSSQPNPP
3989   .......... .......... .......... .......... ..........
12398  .......... .......... .......... .......... ..........
4871   .......... .......... .......... .......... ..........
11846  .......... .......... .......... .......... ..........
2504   .......... .......... .......... .......... ..........
3935   .......... .......... .......... .......... ..........
11261  .......... .......... .......... .......... ..........
713    .......... .......... .......... .......... ..........
10964  .......... .......... .......... .......... ..........
23196  GAFSDYASTT TTTSSDSHWS VDGLENRPSW LHTPMPSNFV FQSTSRSNSV
Tf1    .......... .MKRDHHQFQ GRLSNHGTSS SSSSISKDKM MMVKKEEDGG
Tf4    .......... .MKRDHHHHH .......... ...QDKK TMMNEEDDG
18310  .......... .......... .......... .......... ..........
18652  .......... .......... .......... .......... ..........
4818   .......... .......... .......... .......... ..........
21729  .......... .......... .......... .......... ..........
1110   .......... .......... .......... .......... ..........
174    .......... .......... .......... .......... ..........
33/08  NSRTTNVATA TTNSATAHWV ATDAEHTDTI IAQP
       51                                              100
```

FIG. 15E

| Scr | LSVCGFSGLP | VFPSDRGGRN | VMMSVQPMDQ | DSSSSSASPT | VWVDAIIRDL |
|---|---|---|---|---|---|
| 3989 | .......... | .......... | .......... | .......... | .......... |
| 12398 | .......... | .......... | .......... | .......... | .......... |
| 4871 | .......... | .......... | .......... | .......... | .......... |
| 11846 | .......... | .......... | .......... | .......... | .......... |
| 2504 | .......... | .......... | .......... | .......... | .......... |
| 3935 | .......... | .......... | .......... | .......... | .......... |
| 11261 | .......... | .......... | .......... | .......... | .......... |
| 713 | .......... | .......... | .......... | .......... | .......... |
| 10964 | .......... | .......... | .......... | .......... | .......... |
| 23196 | TGGGGGGNSA | VYGSGFGDDL | VSNMFKDDEL | AMQFKKGVEE | ASKFLPKSSQ |
| Tf1 | GNMDDELLAV | LGYKVRSSEM | AEVALKLEQL | ETMMSNAQED | GLSHLATDAA |
| Tf4 | NGM.DELLAV | LGYKVRSSEM | ADVAQKLEQL | EVMMSNVQED | DLSQLATETV |
| 18310 | .......... | .......... | .......... | .......... | .......... |
| 18652 | .......... | .......... | .......... | .......... | .......... |
| 4818 | .......... | .......... | .......... | .......... | .......... |
| 21729 | .......... | .......... | .......... | .......... | ........D |
| 1110 | .......... | .......... | .......... | .......... | .......... |
| 174 | 101 | | | | 150 |

FIG. 15F

```
Scr     IHSSTSVSIP QLIQNVRDII FPCNPNLGAL LEYRLRSLML LDPSSSSDPS
3989    .......... .......... .......... .......... ..........
12398   .......... .......... .......... .......... ..........
4871    .......... .......... .......... .......... ..........
11846   .......... .......... .......... .......... ..........
2504    .......... .......... .......... .......... ..........
3935    .......... .......... .......... .......... ..........
11261   .......... .......... .......... .......... ..........
713     .......... .......... .......... .......... ..........
10964   LFIDVDSYIP MNSGSKENGS EVFVKTEKKD ETEHHHHSY  APPPNRLTGK
23196   HYNPSELYSW LDNMLSELNP PPLPASSNGL DPVLPSPEIC GFPXSDYDLK
Tf1     HYNPAELYTW LDSMLTDLNP P...SSNA.. .......... .EYDLK
Tf4     .......... .......... .......... .......... ..........
18310   .......... .......... .......... .......... ..........
18652   .......... .......... .......... .......... ..........
4818    LTSVNDMSLF GGSGSSQRYG LPVPRSQTQQ QQSDYGLFGG IRMGIGSGIN
21729   .......... .......... .......... .......... ..........
1110    .......... .......... .......... .......... ..........
174     .......... .......... .......... .......... ..........
        151                                                 200
```

FIG. 15G

```
Scr    PQTFEPLYQI SNNPSPPQQQ QQHQQQQQQH KPPPPPIQQQ ERENSSTDAP
3989   .......... .......... .......... .......... ..........
12398  .......... .......... .......... .......... ..........
4871   .......... .......... .......... .......... ..........
11846  .......... .......... .......... .......... ..........
2504   .......... .......... .......... .......... ..........
3935   .......... .......... .......... .......... ..........
11261  .......... .......... .......... .......... ..........
713    .......... .......... .......... .......... ..........
10964  .......... .......... .......... .......... ..........
23196  KSHWRDEDED VEERSNKQSA VYVEESELSE MFDNMFLCGP GKPVCILNQN
Tf1    VIPXNAIYQF PAIDSSSSSN NQ........ NKRLKSCSSP DSMVTSTSTG
Tf4    AIPGDAILNQ FAIDSASSSN QGGGGDTYTT NKRLKCS... ..........
18310  .......... .......... .......... .......... ..........
18652  .......... .......... .......... .......... ..........
4818   .......... .......... .......... .......... ..........
21729  NYPTLTGVPC IEPVQNRVHE SENMLNSLRE LEKQLLDDDD ESGGDDDVSV
1110   .......... .......... .......... .......... ..........
174    .......... .......... .......... .......... ..........
       201                                                250
```

FIG. 15H

```
            |--- bZIP like domain --->|
              |--- Motif II (dimerization) --->|
Scr    PQPETVTATV PAVQTNTAEA LRERKEEIKR QKQDEEGLHL LTLLLQCAEA
3989   .......... .......... .......... .......... ..........
12398  .......... .......... .......... .......... ..........
4871   .......... .......... ....AAIFYG HHHHTPPPAK RLNPGPVGIT
11846  .......... .......... .......... .......... ..........
2504   .......... .......... .......... .......... ..........
3935   .......... .......... .......... .......... ..........
11261  .......... .......... .......... .......... ..........
713    .......... .......... .......... .......... ..........
10964  .......... .......... .......... .......... ..........
23196  ..NFPTESAKVV TAQSNGAKIR GKKSTSTSHS NDSKKETADL RTLLVLCAQA
Tf1    TQIGGVIGTT VTTTTTTTA AAESTRSVIL VDSQENGVRL VHALMACAEA
Tf4    ..NGVVE.. ....TTTA TAESTRHVVL VDSQENGVRL VHALLACAEA
18310  .......... .......... .......... .......... ..........
18652  .......... .......... .......... .......... ..........
4818   .......... .......... .......... .......... ..........
21729  ..ITNSNSDWIQ NLVTPNPNPN PVLSFSPSSS SSSSSPSTAS TTTSVCSRQT
1110   .......... .......... .......... .......... ..........
174    .......... .......... .......... .......... ..........
       251                                                 300
```

FIG. 15I

```
              |------ Motif II (dimerization) ------->|
Scr     VSADNLEEAN KLLEISQLS TPYGTSAQRV AAYFSEAMSA RLLNSCLGIY
3989    .......... .......... .......... .......... ..........
12398   .......... .......... .......... .......... ..........
4871    EQLVKAAEVI ESDTCLAQGIL ARLNQQLSS PVGKPLERAA FYFKEALNNL
11846   .......... .......... .......... .......... ..........
2504    .......... .......... .......... .......... ..........
3935    .......... .......... .......... .......... ..........
11261   .......... .......... .......... .......... ..........
713     .......... .......... .......... .......... ..........
10964   .......... .......... .......... .......... ..........
23196   VSVDDRRTAN EMLRQIREHS SPLGNGSERL AHYFANSLEA RLAGTGTQIY
Tf1     IQQNNLTLAE ALVKQIGCLA VSQAGAMRKV ATYFAEALAR RIYRLSPPQN
Tf4     VQKENLTVAE ALVKQIGFLA VSQIGAMRQV ATYFAEALAR RIYRLSPSQS
18310   .......... .......... .......... .......... ..........
18652   .......... .......... .......... .......... ..........
4818    .......... .......... .......... .......... .......GT
21729   VMEIATAIAE GKTEIATEIL ARVSQTPNLE RNSEEKLVDF MVAALRSRIA
1110    ..LSMVNEL RQIVSIQGDP SQRIAAYMVE GLAARMAASG KFIYRALKCK
174     .......... .......... .......... .......... ..........
        301                                                 350
```

FIG. 15J

```
                                  |←— Motif III (SCR VHIID) ——|
Scr    AALPSRWMPQ THSLKMVSAF QVFNGISPLV KFSHFTANQA IQEAFEKEDS
3989   .......... .......... .......... ..LYRNKALL DEIGGMATSC
12398  .......... .......... .......... .......... ..........
4871   LHNVSQTLSA CSLIFKVAAY KSFSEISPVL QFANFTSNQA LLESFHGFHR
11846  .......... .......... .......... .......... ..........
2504   .......... .......... .......... .......... ..........
3935   .......... .......... .......... .......... ...AMEGEKM
11261  .......... .......... .......... .......... ..........
713    .......... .......... .......... .......... ..........
10964  .......... .......... .......... .......... ..........
23196  TALS...SKK TSAADMLKAY QTYMSVCPFK KAAIIFANHS MMRFTANANT
Tf1    QIDHCLSDT. ........LQ MHFYETCPYL KFAHFTANQA ILEAFEGKKR
Tf4    PIDHSLSDT. ........LQ MHFYETCPYL KFAHFTANQA ILEAFQGKKR
18310  .......... .......... .......... .......HA SVKGYN...H
18652  .......... .......YM HILYEACPYF .....ANVE ILEAIAGETR
4818   SPTGPELLT. .......... .......... KFGYESANGA IAEAVKNESF
21729  SPVTELYGKE HLISTQL... ..LYELSPCF KLGFEAANLA ILDAADNNDGGMMI
1110   EPPSDERLA. .......AM QVLFEVCPCF KFGFLAANGA ILEAIKGEEE
174    .......... .......... .......... .......... ..........
       351                                                400
```

FIG. 15K

```
       -- Motif III (VHIID)  ------------------>|<-- Motif IV ---|
  Scr  VHIIDLDIMQ GLQWPGLFHI LASRPGGPPH VRLTGLGTSM EA.....LQ
 3989  IHVIDFDLGV GGQWASFLQE LAHRRGAGGM ALPLLKLTAF MSTASHHPLE LH
12398  .......... .......... .......... .......... ..........
 4871  LHIIDFDIGY GGQWASLMQE LVLRDNAAPL SLKITVFASPA NHVQLELG..
11846  .......... .......... .......... .......... ..........
 2504  .......... .......... .......... .......... ..........
 3935  VHVIDLDASE PAQWLALLQA FNSRPEGPPH LRITGVHHQK EVLE......
11261  .......... .......... .......... .......... ..........
10964  .......... .......... .......... .......... ..........
23196  IHIIDFGISY GFQWPALIHRL SLSRPGGSPK LRITGIELPQ RGFRPAE...
  Tf1  VHVIDFSMNQ GLQWPALMQA LALREGGPPT FRLTGIGPPA PDNSDHLH..
  Tf4  VHVIDFSMSQ GLQWPALMQA LALRPGGPPV FRLTGIGPPA PDNFDYLH..
18310  VHIIDFSLMQ GLQWPALMDV FSAREGGPPK LRITGIGPNP IGGRDELH..
18652  VHIIDFQIAQ GSQYMFLIQE LAKRPGG... ...PPLLRVT GVDDSQSTYARGGGLS
 4818  VHIIDFQISQ GGQWVSLIRA LGARPGG... ...PPNVRIT GIDDPRSSFARQGGLE
 1110  VHIIDFDINQ GNQYMTLIRS IAELPGK... ...RPRLRLT GIDDPESVQRSIGGLR
21729  PHVIDFDIGE GGQYVNLLRT LSTRRNGKSQ SQNSPVVKIT AVANNVYGDCLVDDGGEERLK
  174  .......... .......... .......... .......... ..........
       401                                                  450
```

FIG. 15L

|       | ← Motif IV ——————→ | | | ← Motif V ——————→ | |
|---|---|---|---|---|---|
| Scr | ATGKRLSDFT | DKLGLPFEFC | PLAEKVGNDL | TERLNVRKRE | AVAVHWL.... |
| 3989 | LHLTQDNLSQ | FAAELRIPFE | FNAVSLDAFN | PAESISSSGD | EVVAVSL.... |
| 12398 | .......... | .......... | .......... | .......... | .......... |
| 4871 | FTQDNLKHFA | SEINISLDIQ | VL..SLDLLG | SISWPNSS.. | EKEAVAVNIS |
| 11846 | .......... | .......... | .......... | .......... | .......... |
| 2504 | .......... | .......... | .......... | .....NGGAF | APSTWTA... |
| 3935 | QMAHRLIEEA | EKLDIPFQFN | PVVSRLDCLN | VE..QLRVK | TGEALAVSSV |
| 11261 | .......... | .......... | .......K | KWETITLDEL | MINPGETTVV |
| 713 | .......... | .......... | .......... | .......... | .......... |
| 10964 | .......... | .......... | .......... | .......... | .......... |
| 23196 | EFRRQVIAWL | DTVSDTMFRL | STTQLLRNGE | TIQVEDLKLR | QGEYVVVNSL |
| Tf1 | EVGCKLAQLA | EAIHVEFEYR | GFVANSLADL | DASMELRPS | DTEAVAVNSV |
| Tf4 | EVGCKLAHLA | EAIHVEFEYR | GFVANTLADL | DASMELRPS | EIESVAVNSV |
| 18310 | EVGIRLAKYA | HSVGIDFTFQ | GVCVDQLDRL | CDWML.LKPI | KGEAVAINSI |
| 18652 | LVGERLATLA | QSCGVPFEFH | D...AIMSGC | KVQREHLGLE | PGFAVVVNFP |
| 4818 | LVGQRLGKLA | EMCGVPFEFH | G....AALFCT | EVEIEKLGVR | NGEALAVNFP |
| 21729 | AVGDLLSQLG | DHSISVSFNV | V...TSLRLG | DLNRESLGCD | PDETLAVNLA |
| 1110 | IIGLRLEQLA | EDNGVSFKFK | A...MPSKTS | IVSPSTLGCK | PGETLIVNFA |
| 174 | .......... | | | | |
| | 451 | | | | 500 |

FIG.15M

```
      ----- Motif V -----
Scr    ...QHS...........................................................
3989   ............P VG..................................................
12398  .........AA.......................................................
4871   ..................................................................
11846  ..........R SL....................................................
2504   ..................................................................
3935   LQLHTFLASD DDLMRKNCAL RFHNNPSGVD LQRVLMMSHG SAAEEARENDM ............
11261  NCIHRLQYTP DE.......................................................
713    ..................................................................
10964  ..................................................................
23196  FRFRNLL... DE.......................................................
Tf1    FELHKLLGRX GG.......................................................
Tf4    FELHKLLGRP GA.......................................................
18310  LQLHRLLVDP DA.......................................................
18652  YVLHHM...P DE.......................................................
4818   LVLHHM...P DE.......................................................
21729  FKLYRV...P DE.......................................................
1110   FQLHHM...P DE.......................................................
174    ..................................................................
       501                                                            550
```

FIG. 15N

```
        Motif V ---------|                               |-- Motif VI ---|
Scr                 ...LYDVTGSD  AHTLWLLQRL  APKVVTVVEQ  DLSHAGS.FL
3989                ...CSARAPPL  PAILRLVKQL  CPKVVVAIDH  GGDRADLPFS
12398               ...SFSHLPLV  LRFVKHLSPT  IIVCSDRGCE  RTDLPFSQQL
4871                .........   DSF.......  .........Q  EADHNKTGFL
11846    .NGGAFAPST WTARSLPVPSSPST
2504     SNNNGYSPSG DSASSLPLPSSGRT DSFLNAIWGL  SPKVMVVTEQ  DSDHNGSTLM
3935                ...TVSLDSPR  DTVLKLFRDI  NPDLFVFAEI  NGMYNSPFFM
11261               .........   .........  .........  NGSYNAPFFV
713                 .........   .........  .........  ..AYNAPFFV
10964               ...TVLVNSPR  DAVLKLIRKI  NPNVFIPAIL  SGNYNAPFFV
23196               .........I  EKVLGVVKQD  TGDFHXWXRQ  EPNHNGPGFL
Tf1                 .........I  DKVLGVVNQI  KPEIFTVVEQ  ESNHNSPIFL
Tf4                 ...NPVVPAPI DILLKLVIKI  NPMIFTVVEH  EADHNRPPLL
18310               ...SVSVEKYR DRLLHLIKSL  SPNLVTLVEQ  EDNTNTSPLV
18652               ...SVTVENHR DRLLRLVKHL  SPNVVTLVEQ  EANTNTAPFL
4818                ...SVCTENPR DELLRRVKGL  KPRVVTLVEQ  EMNSNTAPFL
21729               ...SVTTVNQR DELLHMVKSL  NPKLVTVVEQ  DVNTNTSPFF
1110                .........   .........  .........  .........
174
         551                                                      600

FIG. 150
```

```
       ------ Motif VI ------
Scr    GRFVEAIHYY SALFDSLGAS Y..GEESEER HVVEQQLLSK EIRNVLAVGG
3989   QHFLNCFQSC VFLDSLDAAG I..DADSA..                RVEDAVIG..
12398  ..........  .....SLEPN L..DRDSKER LRVERVLFGR RIMDLVRSDD
4871   AHSLHSHTAL FESLDAVNAN L..DAM.....  QKIERFLIQP EIEKLVLD..
11846  DRFTEALFYY SAVFDSLDAA N..NNNNNNN QRMEAEYLQR EICDIVCGEG
2504   ..........  .......... ..........  ..........
3935   ERLLESLYTY AALFDCLETK V..PRTSQDR IKVEKMLFGE EIKNIISCEG
11261  TRFREALFHY SSLFDMFDTT IHAEDEYKNR SLLERELLVR DAMRVISCEG
713    TRFREALFHY SAIFDMLETN I..PKDNEQR LLIESALFSR E.XNVISCEG
10964  TRFREALFHF SSIFDMLETI V..PREDEER MFLEMEVFGR EALNVIACEG
23196  TRFREALFHY SAVFDMCDSK L..AREDEMR LMYVFEFYGR EIVNVVASEG
Tf1    DGXTESLHYY STXFDSLEGX ...PNSQD..  KLMSEXYLGX QICNLVACEG
Tf4    DRFTESLHYY STLFDSLEGV ...PSGQD..  KVMSEVYLGK QICNVVACDG
18310  ERFTNALFHY ATMFDSLEAM HRCTSGRDIT DSLTEVYLRG EIFDIVCGEG
18652  SRFVETLDYY TAMFESIDAA R..PRDDKQR ISAEQHCVAR DIVNMIACEE
4818   PRFVETMNHY LAVFESIDVK L..ARDHKER INVEQHCLAR EVENLIACEG
21729  GRVSESCACY GALLESVEST V..PSTNSDR AKVE.EGIGR KLVNAVACEG
1110   PRFIEAYEYY SAVFESLDMT L..PRESQER MNVERQCLAR DIVNIVACEG
174    ..........  .RXFDSLEHD A..SKGEPRE DERGRXCLAR NIVNIVXCKX
       601                                                 650
```

FIG.15P

```
Scr     PSRSGEVKF.     ......ESWRE  KMQQCGFKGI  SLAG..NAAT  QATLLGMFP
3989    .RHKA..Q..     ...KAIAWRS   VFAATGFKPV  QLSN..LAEA  QADCLLKRVQ
12398   DNNKPGTRFG     LMEEKEQWRV   LMEKAGFEPV  KPSN..YAVS  QAKLLWNYN
4871    .RSRPIER..     ...PMMTWQA   MFLQMGFSPV  THSN..FTES  QAECLVQRTP
11846   AARXERHE..     ...PLSRWRD   RLTRAGLSAV  PLG...SNA   .........
2504    ..........     ..........   ..........  ..........  .........
3935    FERRERHE..     ...KLEKWSQ   RIDLAGFGNV  PLSY..YAML  QARRLLQGCG
11261   AERFARPE..     ...TYKQWRV   RILRAGFKPA  TIS....KQI  MKEAKEIVRK
713     LERMERPE..     ...TYKQWQV   RNQRVGFKQL  PLN....QDM  MKRARXEGQV
10964   WERVERPE..     ...TYKQWHV   RAMRSGLVQV  PFD....PSI  MKTSLHKVHT
23196   TERVESRE..     ...TYKQWQA   RLIRAGFRQL  PLE....KEL  MQNLKLKIEN
Tf1     PDRVERHE..     ...TLSQWGN   RFGSSGLAPA  HLGS...NAF  KQASMLLSVF
Tf4     PDRVERHE..     ...TLSQWRN   RFGSAGFAAA  HIGS...NAF  KQASMLLALF
18310   SARTERHE..     ...LFGHWRE   RLTYAGLTQV  WFDPDEVDTL  KDQLIHVTSL
18652   SERVERHE..     ...VLGKWRV   RMMMAGFTGW  PVSTSAAFAA  SE.....MLK.
4818    VEREERHE..     ...PLGKWRS   RFHMAGFKPY  PLSSYVNATI  KG.....LLE.
21729   IDRIERCE..     ...VFGKWRM   RMSMAGFELM  PLSEKIAESM  KS.....RGNR
1110    EERIERYE..     ...AAGKWRA   RMMMAGFNPK  PMSAKVTNNI  QN.....LIKQ
174     EERIERYE..     ...VTGKWRA   RMMMAGFSPR  PMSGRVTSNI  ES.....LIKR
651                                                                 700
```

FIG.15Q

```
         |------- Motif VI -------→|
Scr      .SDGYTLVD. DNGTLKLGWK DLSLLTASAW TPRSX...........
3989     VRGFH..VEK RGAALTLYWQ RGELVSISSW RCX.............
12398    YSTLYSLVES EPGFISLAWN NVPLLTVSSW RX..............
4871     VRGFH..VEE KHNSLLLCWQ RTELVGVSAW RCRSSX..........
11846    .......... .......... .......... ................
2504     .......... .......... .......... ................
3935     FDGYR..IKE ESGCAVICWQ DRPLYSVSAW RCRKX...........
11261    RYHRDFVIDS DNNWMLQGWK GRVIYAFSCW KPAEKFTNNN LNIX.
713      LPTRTFIIDE DNRWLLQGWK GRILFALSTW KPDNRSSSX.......
10964    FYHKDFVIDQ DNRWLLQGWK GRTVMALSVW KPESX...........
23196    GYDKNFDVDQ NGNWLLQGWK GRIVYASSLW VPSSSX..........
Tf1      NSGQQGYRVEE SNGCLMLGWH TRPLITTSAW KLSTAAHX........
Tf4      NGGEGYRVEE SDGCLMLGWH TRPLIATSAW KLSTNX..........
18310    .SGSGFNILV CDGSLALAWH NRPLYVATAW CVTGGNAASS MVGNICKGTN
18652    AYDKNYKLGG HEGALYLFWK RRPMATCSVW KPNPNYIGX.......
4818     SYSEKYTLEE RDGALYLGWK NQPLITSCAW RX..............
21729    VHPG.FTVKE DNGGVCFGWM GRALTVASAW RX..............
1110     QYCNKYKLKE EMGELHFCWE EKSLIVASAW RX..............
174      DYCSKYKVKE EMGELHFSWE EKSLIVASAW SX..............
701                                                    750

FIG.15R
```

```
Scr      .    .    .    .    .    .    .    .    .    .    .    .    .    .    .    .
3989     .    .    .    .    .    .    .    .    .    .    .    .    .    .    .    .
12398    .    .    .    .    .    .    .    .    .    .    .    .    .    .    .    .
4871     .    .    .    .    .    .    .    .    .    .    .    .    .    .    .    .
11846    .    .    .    .    .    .    .    .    .    .    .    .    .    .    .    .
2504     .    .    .    .    .    .    .    .    .    .    .    .    .    .    .    .
3935     .    .    .    .    .    .    .    .    .    .    .    .    .    .    .    .
11261    .    .    .    .    .    .    .    .    .    .    .    .    .    .    .    .
713      .    .    .    .    .    .    .    .    .    .    .    .    .    .    .    .
10964    .    .    .    .    .    .    .    .    .    .    .    .    .    .    .    .
23196    .    .    .    .    .    .    .    .    .    .    .    .    .    .    .    .
Tf1      .    .    .    .    .    .    .    .    .    .    .    .    .    .    .    .
Tf4      DSRRKENRNG PMEX
18310    .    .    .    .    .    .    .    .    .    .    .    .    .    .    .    .
18652    .    .    .    .    .    .    .    .    .    .    .    .    .    .    .    .
4818     .    .    .    .    .    .    .    .    .    .    .    .    .    .    .    .
21729    .    .    .    .    .    .    .    .    .    .    .    .    .    .    .    .
1110     .    .    .    .    .    .    .    .    .    .    .    .    .    .    .    .
174      .    .    .    .    .    .    .    .    .    .    .    .    .    .    .    .
         751                   764
```

FIG. 15S

SRPa1 (1110)

CTTGTCAATGGTAAATGAGCTGAGGCAGATAGTTTCTATCCAAGGAGACCCTCTCAGA
GAATCGCAGCTTACATGGTGGAAGGTCTAGCTGCAAGAATGGCCGTTCAGGAAATTCA
TCTACAGAGCATTGAAATGCAAAGAGCCTCCTTCGGATGAGAGGCTTGCAGCTATGCAAG
TCCTGTTTGAAGTCTGCCCTGTTCAAGTTCGGGTTTTTAGCAGTAATGGTGCGATAC
TTGAAGCAATCAAAGGTGAAGAAGAAGTTCACATAATCGATTTCGATATAAACCAAGGGA
ACCAATACATGACACTGATGATGACCCTGAGTTGCCTGGTAAACGACCTCGCCTGA
GGTTAACAGGAATTGATGACCCTGAATCAGTCCAACGCTCCATTGGAGGGCTAAGAATCA
TCGGTCTAAGACTCGAGCAACTCGCAGAGGATAAATGGAGTATCCTTCAAATTCAAAGCAA
TGCCTTCAAAGACTTTCGATTGTCTCTCCATCAACACTCGGTTGCAAACCAGGAGAAACCT
TAATAGTGAACTTTGCATTCCAACTTCACCACATGCCTGACGAGAGTGTCACAACAGTAA
ACCAGCGGGACGAGCTACTTCACATGGTCAAAAGCTTAAACCAAAGCTTGTCACGGTCG
TTGAACAAGACGTGAACACAACACACTTCACCGTTCTCTTCCCAGATTCATAGAGGCTTACG
AATACTCAGCAGTTTTCGAGTCTCTAGACATGACACTTCCAAGAGAAAGCCAAGAGA
GGATGAATGTAGAAAGACAGTGTCTCGCTAGAGACATAGTCAACATTGTTGCTTGCGAAG
GAGAAGAACGGATAGAGAGATACGAGCCTGCGGGAAATGGAGAGCAAGGATGATGATGG
CTGGATTCAATCCAAAACCAATAAGTGCTAAAGTAACCAAACAAATAACAAAACCTGATAA
AGCAACAATATTGCAATAAGTACAAGCTTAAAGAAGAAATGGGGTGAGCTCCATTTTTGCT
GGGAGGAGAAAAGCTTAATCGTTGCTTCAGCTTGGAGGTAAGATAAGTGACAAGAGCATA
TAGTCTTTATGTTTCATAAAACATAAATTATGTTTTTACTGTAATCTTGGTTATTGTGTA
ACTGGTTAAATCATCTCCATGTATTATTACCAGAGGTTAGGGGTGATCACAGGTACTAAA
AGCTAATCTAACACTTATGGAAGAATTTTCTTCTTTTTTTCCCTATTATATAAAAAT
AATTAGAGTTTTGGTTCTAAACCTATTGCTAAGTGTAAGTGAATGAGTCTTTACATGTTCATA
TTTCAGTTCAAATGGTTAAATTTGTTAAGGTTCTCACTTAAAAAAAAA

FIG. 16A

SRPa3 (3935)

GCTATGGAAGGAGAAGATGGTTCATGTGATTGATCTCGATGCTTCTGAGCCAGCTCAA
TGGCTTGCTTTGCTTCAAGCTTTTAACTCTAGGCCTGAAGGTCCACCTCATTGAGAATC
ACTGGTGTTCATCACCAGAAGGAAGTGCTTGAACAAATGGCTCATAGACTCATTGAGGAA
GCAGAGAAACTCGATATCCCGTTTCAGTTTAATCCCGTTGTGAGTAGGTTAGACTGTTTA
AATGTAGAACAGTTGCGGGTTAAAACAGGAGAGGCCCTTAGCCGTTAGCTCGGTTCTTCAA
TTGCATACCTTCTTGGCCTCTGATGATCTCATGAGAAAGAACTGCGCTTTACGGTTT
CAGAACAACCCCTAGTGGAGTTGACTTGCAGAGAGTTCTAATGATGAGCCCTCTGCA
GCTGAGGCACGTGAGAATGATATGAGTAACAACAATGGTATAGCCCTAGCGGTGACTCG
GCCCTCATCTCTTTGCCTTTACCAAGTTCAGGAAGGACTCAGAGCTTCCTCAATGCTATTTGG
GGTTTGTCTCCAAAGTCATGGTGTCACTGAGCAAGACTCAGACCATTGTTGATTGCTTGGAA
CTAATGGAGAGGCTATTAGAGAATCACTTTACACCTACGCAGCATTGTTTGATTGCTTGGAA
ACAAAAGTTCCAAGAACGTCTCAAGATAGGATCAAAGTGGAGAAGATGCTCTTCGGGAG
GAGATCAAGAACAACATCATATCCTGCGAGGGATTTGAGAGAAGAAAGACACGAGAAGCTT
GAGAAATGGAGCCAGGATCGATTTGGCTGCGTTGGGAATGTTCCTCTAGCTATTAT
GCGATGTTGCAGGCTAGGAGGATTGCTTCAAGGGTGCGGTTTGATGGTGATAGAATCAAG
GAAGAGAGCGGGGTGCCGCAGTAATTGCTGCAAGATCGACCTCTATACTCGGTATCAGCT
TGGAGATGCAGGAAGTGAATGATATATTACAGTTTGTCTTCTATTTTGGTTATGAGCAGA
GTCCCTTCTTTTTTGTATACATGGGACACAATCTTAGTTGTTTGTGATGGTGACTTT
CTGTCTCTTATGCTATTTGGCTTAAATGCTTCTACTGCCTCTGCATGTAAAGCCTTTG
TGTGTTGGTTCAATTTGGTCTGGGTGTGGTTAATACCAAACCAAATCCAATTTGAGCTG
AAGATAACTAATTTGATGATCGGCTCCGTGCC

FIG. 16B

SRPa4 (4818)

GGCACGAGCCCAACGGGTCCTGAGCTTCTTACTTATATGCATATCTTGTATGAAGCCTGC
CCTTATTCAAATTCGGTTATGAATCTGCTAAGGAGCTATAGCTGAAGCTGTGAAGAAC
GAAGTTTTGTGCACATTATCGATTTCCAGATTCTCAAGGTGGTCAATGGGTGAGTTTG
ATCCGTGCTCTCTTGGTGCTAGACCTGGTCAAGGAGGACTTGAGTAGTTGGACAAAGACTTGGG
GATCCGAGATCATCGTTTGCTCGTCAAGGAGGACTTGAGTTCCATGGAGCTGCTTTATGCTCACG
AAGCTAGTCGAAATGTGCGGTTTCCGTGTTCCGTGTTAGAAATGTAGAGAGCGCTAACTTCCCG
GAAGTCGAAATCGAGAAGCTAGAGTTAGAGAGTGTAACTGTGGAGAATCACAGATAGATTG
CTTGTTCTTCACCACATGCCTGATGAGAGTTGTGACTCTCGTTGAGCAAGAAGCGAAT
TTGAGATTGGTCAAACACTGTCAACACTTGTCACCAAACGTTGTGACTCTCGTTGAGCAAGAAGCCGAAT
ACAAACACTGCGCCGTTCTTCCCCGGTTGTGAAACTCGCTAGAGATCAAGGAAAGGATCAATGTTGAGCAG
TTCGAATCAATAGAGTGAAACTCGCTAGAGATCTTATAGCTTGTGAAGGTGTTGAAAGAGAAGAG
CATTGTTGGCTAGAGAGGTTGTGAATGGAGGTCTCGGTTTGCACATGCGGGATTTAACCGTAT
AGGCACGAGCCACTAGGGACTATGTGAACGCAACAATCAAAGATTGCTTGAGAGTTATTCAGAGAAG
CCTTTGAGCTCGTATGTGAACGCAACAATCAAAGATTGCTTGAGAGTTATTCAGAGAAG
TATACACTTGAAGAAAGAGATGTATTAGGATGGAGAATCAACCTCTTATC
ACTTCTTGTCTTGGAGGTAACTAATAAAAAATCTGTTTGTAAAGTAAACTCATGCATTAGAAA
CTTCTTTTAAAGTTTGCAGAATCTGTTTCGGTTCGGTTTCAAGAGATAGATTAGAAA
ACAAGTTGTCAAATGTTGTAGTAGTGATATGTTGATGACCCAAAAAAAAAAAAAA
AAAAA

FIG. 16C

SRPa5 (4871)

```
GCGGCTATCTTCTACGGCCACCACCATACACCTCCGCCGGCAAAGCGGCTCAACCCT
GGTCCCGTGGGGATAACAGAGCAGCTGGTTAAGGCAGCAGAGGTCATAGAGAGGACACG
TGTCTAGCTCAGGGGATATTGGCGCGGCTCAATCAACAGCTCTCTTCTCCCGTCGGAAG
CCATTAGAAAGAGCAGCTTTTACTTCAAAGAAGCTCTCAATAATCTCCTTCACAACGTC
TCCCAAACCCTAAACCCTTATTCCCTCATCTTCAAGATCGCTGCTTACAAATCCTTCTCA
GAGATCTCTCCCGTTCTTCAGTTCGCCAACTTACCTCCAACCAAGCCCTCTTAGAGTCC
TTCCATGGCTTCCACCGTCTCCACATCATCGACTTCGATATCGGCTACGGTGGCCAATGG
GCTTCCCTCATGCAAGAGCTTGTTCTCCGGCAACCAGACCTCGAACTTGGCTTCACTCAAG
ACCGTTTCGCTTCTCCGGCGAACCAGACCAGCTCGAACATCTCCCCTTGACATCAAGTTTT
CTCAAGCACACTTCGCCCTCGTGGCCTCATCTCGTGGCCTAACTCGTCGGCCGTTAACATC
CTCCTCGGCTCCATCTCGCTGCCCACCTCCGGAGAAGAAGCTTCGTGAAGCATCTATCTCCG
ACGATCATCGTCTGCTCCGACAGAGATGCGAGAGGACGATCTGCCCTTCTCTCAACAG
CTGCCCACTCGCTGCTGCACTCACACAAGATCGAGAGGTTTCTTATACAGCCGGAGATAGAGAAGCTG
AACCTCGACGCAATGCCAGCCGTAGCGTCCGATAGAAAGGCCGACAGTAACTTCACGAAGCCGATGTTCTA
GTGTTGGATCGTAGCCGTTCTCACCGGTGACGAGAGGCTTCACGTCGGAGTTTCACGGAGTCCTTCCTTA
CAGATGGGGTTTCTCACCGGTGACGAGAGGCTTCACGTCGGAGTTTCACGGAGTCCTTCCTTA
GTCCAACGGACGCCAGTGACGAGAACTCGTCGGAGTTTCAGCAGTCGTCGCTCTCCTGATTT
TGTTGGCAAAGGACGTTTCAATTATTAAAAAAAATATTTCCTTAATTCAATTATCTTAAATGACA
CCACCGGAGTTTCAATTATTAAAAAAAATATTTCCTTAATTCAATTATCTTAAATGACA
AATTTTAGTTTCTGATTTTATTTGCTCAGTGCGATGGATTTTAATTTAAGTTTCAC
ACAAATATATAAATTTTTG
```

FIG. 16D

SRPa6 (12398)

AATCGCTTGAACCGAATTTGGATCGAGATTCGAAAGAAAGGCTGAGAGTGGAGAGAGTGC
TGTTCGGTAGGAGGATTATGGATTGGTCCGATCAGATGATGATAATAAACCGGGAA
CCCGGTTTGGGTTAAATGGAGAGAAGAACAATGGAGAGTGTTGATGGAAAGCTGGAT
TTGAGCCGGTTAAACCGAGTAATTACGCGGTTAGCCAAGCGCTACTATGGAACT
ACAATTATAGTACATTGTATTCACTTGTTGAATCGGAGCCAGGTTTCATCTCCTTGGCTT
GGAACAATGCCCTCCTCCACCGTTCCCTCCTTGGCGTTGACTACTTGGTCCGATAAGTT
AATCTAGTATTTTGAGTTAGCTTTTAGAATTGAATTGTTTGGGTTAGATTTGGATGTTT
AATTAGTCTCTAGCCCTATTCTTTACTCTTTTTTGTCTAGTGCTTGGAGTGATGATGGTT
TGTCGTTTATGTTCATTTGTAATGTATGTAACATTTGACTAAAAAAAAAA
AAAAAAA

FIG. 16E

FIG. 16F-1

SRPa7 (21729/3635/17410)

AAAGACTTAGCAGATTTCAAGCGGGCTCAGAACATCAACAACAACAACAACCG
TTTATAGTCAAGCAGCTCTCAACGCTTTCTTCAAGGTCTGTGAAGCCTCGAAATTAT
CAGAATTTCAATCTCCGTCGGCCGATGATTCACGTCGGTGAATGATATGAGTTT
GTTGGTGGTTCTGTTCATCTCAGCGTTACGGTTACCGGTTCCCAGGTCTCAGACGCA
ACAGCAACAATCGGATTACGGTTTATTTGGTGGGATCCGAATGGAATCGGGTCGGTAT
TAATAATTATCCAACATTAACCGGCGTTCCGTGTATTGAACCGGTTCAAAACCGGTTCA
TGAATCGGAGAACATGTTGAATAGTTAAGAGCTTGAGAAACAGCTTTTAGATGATGA
CGATGAGAGTGGTGGTGATGATGACGTGTCAGTTATAACAAATTCAAATTCCGATTGGAT
TCAAAATCTCGTGCTCTCTTGCCTTCTACAGCTTCGACGACACATCGGTATGTTCTAGGCA
TTCTTCTTCGTGTTTCTCAAACGCCTAATCTTGAGAGGAATTCAGAGGAGAAGCTTGTGA
AACGGTTATGGAAATCGCGACGGCGATCGCGAAAACAGAGATAGCGACGAGAT
TTTGGCGCGTGTTCTCAAACGCCTAATCTTGAGAGGAATTCAGAGGAGAAGCTTGTGA
TTCATGGTGGCTGCGCTTCGATCGAGATAGCTTCTCCAGTGACGAATTGTATGGGAA
GGAGCATTAATCTCGACTCAATTGCTCTACGAGCTCTCTCCTTGTTTCAAACTCGGTTT
CGAGCCGCCGAATCTCGCCATTCTGACGCCGCGATAACAACGACGGTGAATGATGAT
ACCGGCACGTTATCGATTCGATATCGGAGAGAAGGTGGACAATACGTTAACCTTCTCCGTAC
ATTATCCACGCGCCGGAATGGTAAAAGTTCAGAGTCAGAATTCTCCGGTTAAGATCAC
CGCCGTGGCGAACAACGTTACGGATGTTAGTCGGTGACGGTGGAAGAGAGGTTAAA
AGCCGTCGAGAGATTTGTTGAGCCAACTCGGTGATCGACTCGGTATCTCCGTAAGTTTCAA
CGTGGTGACGAGTTTACGACTCGGTGATCTGAATCGTGAATCTGTGATCCCGA
CGAGACTTGCGCTGTGAACTTGACGAACTTCTCGTGAAGCTTATCGTGTTCCCGACGAAAGCGTATG
CACGGAGAATCCAAGAGACGAACTTCTCCGTGAAGGGACTTAAACCGCGCGTGGT
TACTCTAGTGGAGCAAGAGTTGCCGAAGTCGAATAACGGCCGCTCGAGTCTACGGTTCCTAGTGA
GTCATGCGCGTGTTACGGTTGCTTGAGTCGGTTCGAGTCTTCCCGAGTCCTAGTGA
TTCCGACCGTGCCAAGTCGTATAGAGCGTTCGGGAAATGGCCGGTGGCGTG
CGAAGGAATCGATCGTATAGAGCGTTCGGGAAATGGCGGATGCGGATGAG
CATGGCTGGGTTTGAGTTAATGCCATTGAGTGAGTGAGATAGCGGAGTCGAAGAGTCG

TGGAAACCGAGTCCACCCGGGCTTTACCGTTAAAGAAGATAACGGAGGTGTGTGCTTTGG
TTGGATGGGACGGGCACTCACTGTCGCATCCGCTTGGCGTTAACTTCACACACTCTTTTT
TTTCTTCTTATTATTACCATATTATTATTAATTTCGAGATTATTCTGATATTATTATCA
TTGTGATTTTCCGTTTCGAAAAGTGTAGGAATCTTATGTAACAAAGAAAAAAAGACT
TTTATGTTTTTCTAATAAATAAAAGAAAGAGTGATTGGGTTCAAAAAAAAAAAAAAAAA
AAAAAAA

FIG.16F-2

SRPa8 (10964)

TGCATACAACGCACCGTTTTCGTAACACGGTTTCGCGAAGCTCTATTTCATTTCTCCTC
GATTTTGACATGCTTGAGACAATTGTGCCACGAGAAGAAGAAGAGGATGTTCCTTGA
GATGGAGGTCTTTGGGAGAGAGAGGCACTGAATGTGCTTGCGAAGGTTGGGAAAGAGT
GGAGAGGCCCTGAGACATACAAGCAGTGGCACGTACGGGCTATGAGGTCAGGGTTGGTGCA
GGTTCCATTGACCCAAGCATTATGAAGACATCGCTGCATAAGGTCCACACATTCTACCA
CAAGGATTTTGTGATCGATCAAGATAACCGGTGGCTCTTGCAAGGCTGGAAGGGAAGAAC
TGTCATGGCTCTCTTTCTGTTTGGAAACCAGAGTCCAAGGCTTGACCGAGAAATCCTCGTTG
GCATATGAGAGAGACCATCTCTTGATTTTCTCCTGTAATTCCCAGAGACAGAATTACAG
ATGTAAGAAGAGAATGCTGCACAAAGAACTTGTTGTTTCTCAGCTAGATTCCTAACGGTAAGTCCTG
TTTTATAACTTTCTAGCTGTGTTTTTGTTTGTATATTGTTGTATATTGTTTGTCTAGATTG
TTGTAGCTAGGGTGATCAGATTGTTTGTATATTGTTCTATGGTTTAAAGAGAAGTTTTTCCTTCTC
TAACACATATAAGAGAAGCTTAGAGTTTCTATGGTTTAAAGAGAAGTTTTTCCTTCTC
CAATGTAAAAAAAAAAAAAAAA

FIG. 16G

SRPa10 (11261)

AAAAAATGGGAAACCATCACTCTTGATGAACTTATGATCAATCCAGGAGAGACAACGGTC
GTCAACTGCATTCATCGGTTACAATACACTCCTGATGAAACTGTGTCATTAGACTCTCCA
AGAGACACGGTTCTGAAGCTATTCAGAGATATCAATCCTGACCTCTTTGTGTTTGCAGAG
ATTAACGGAATGTACAACTCTCCTTTCTCATGCGAGGTTCCGAGAAGCGCTTTTTCAT
TACTCTTCACTCTGTTTGACATGTTTGACACCACAATACACGCAGAGGATGAGTACAAAAAC
AGGTCACTGTTGGAGAGAGAGTTACTTGTGAGACGCCTGATGAGCCGTGAGTTCCTGCGAG
GGTGCAGAGCGGGTTTGCGAGGCCTGAAACCTACAAGCAATGGCGAGTTAGGATTTGAGA
GCCGGGTTTAAGCCAGCAACTATTAGCAAACAGATCATGAAGGAGGCTAAGGAAATGTG
AGGAAACGTTACCATAGAGATTTGTGATCGATACTATAGCGATAACAATTGGATGCTTCAAGGA
TGGAAAGGAAGAGTCATCATCTGAAAAATGTTACTTCTCAATTACATCATTTGTTCACAAAC
AATAATTTAAACATCTGAAAAATGTTTGATCCCGTGAGTGGATGCAACTCTTTTTTCCAATGG
TTTGTAGAATATGTTTGATCCCGTGAGTGGATGCAACTCTTTTTTCCTGCAAGTACATA
TTGTATTCAAATCCTTGTGGGAAATGATAAATTGTTAATCAAAAAAAAAAAAAAAA

FIG.16H

SRPa11 (18652)

GCGAATGTTGAGATCTTGGAAGCAATAGCTGGGGAAACCAGAGTCCACATTATCGATTTT
CAGATTGCACAGGGATCACAATACATGTTTTTGATTCAGGAGCTTGCGAAACGCCCTGGT
GGGCCGCGCCGTTGCTGCGTGTGACGGGTGTGGATGATTCACAGTCCACCTATGCTCGTGGG
GGAGGACTCAGTTGGTAGGTGAGAGGCTTGCAACTTTGGCGCAGTCATGTGGTGTCCCG
TTTGAGTTTCACGATGCCATCATGTCTGGGTGCAAGGTGCAGCGGGAACATCTCGGGTTG
GAACCTGGCTTTGCTTGTTGTGAACTTCCCATATGTATTACACCACATGCCAGACGAG
AGCGTAAGTGTTGAAAATACAGAGACAGGCTGCATCTGATCGAAGAGCCCTCTCCCCA
AAACTGGTTACTCTAGTAGACAGAATCCAACACACCTCGCCATTGGTCTGTCACGG
TTTGTGGAAACACTGGATTACTACACAGCAGTGTTTGAGTCGATAGATGCAGCACGGCCA
CGGGATGATAAGCAGAGAATCAGCAGGCAGAGAGTAGCAAGGTACTGGGGAAATGGAGG
ATGATAGCATGTGAGGAGTCAGAGAGACACGAGGTCAGCAGCATCTGCAGCGTTTGCA
GTCAGAATGATGATGGGCTGGGTTCACGGGTTCACAAACTACAAACTGGGAGGCCATGAAGGAGCG
GCGAGTGAGATGCTGAAAGCTTATGAGAGACGACCCATGGCTACATGTTCCGTGAAGCCAAACCA
CTCTACCTCTTCTGGAAGTTGGTAAGTTATAGTGGTACTTGAGTGGATAAAGAAGAGCACAAC
AACTATATTGGGTAAGTCGCTGTAAATTTTACAAACCAAACCTGGTTGTTTCTCTGTAAATTG
AAAAACACATCTGTCCTGTAAATTGTATACAAACCAAACCTGGTTGTTTTCTCTGTAAATTG
CAACCTAAGTTATATATGTAATGTAAGCTAGTAATAACAAAACATTGATTAGGTCAA
TCATGTGGTTGTGGGTTGGGAAGCTAGTAATAACATTGAAATATAACCAAAACATTGATTAGGTCAA
AAAAAAAAAA

FIG. 16I

SRPa12 (23196)*

```
TCTTACTCAAGGTTCTTCTTTGTCATCTTGTGTGCCGAATCCCACAAAGAGGAGAATAAAGA
TTCGACCTTTATTAGATATTAACGACTCTGGATTTTTGGGTTTTTGGAGTTGGATCCACA
TGGGTTCTTATCCGATGGATTCCCCTGGATCCCATGGACGAGTTGGATTTCAATAAGGACT
TTGATTGCCTCCCTCCTCAAACCTAGGTTTAGCTAATGGGTTCTATTTAGATG
ACTTAGATTTCTCATCCTTGGATCCTCCAGAGGAGATCGTTATCATCTTCATCTGATGACGCTG
ACAACATCAACAACAAAGCTGTAGCAGGACATCGTTATCATCTTCATCTGATGACGCTG
ATTTCTCTGATTCTGTTTTGAAGTATATAAGCCAAGTTCTTATGAAGAGGATATGGAAG
AGAAGCCTTGTATGTTTCATGATGCTTTGGCTCTTCAAGCTGCTGAGAAATCTCTATG
AGGCTCTTGGTGAGAAAGACCCCTCTGCTTCTTCGTCTTCTGTGCTTTGATCATCCTGAGA
GATTGGCTAGTCATAGCCCCTGACGGTTCTTGTTGTTCAGGTGAGTGTTTAGTGATTACGCTA
GCACCACTACCATACACCTACTTCCTCTGATTCTCACTGGAGTGTTGATGGTTTGGAATAGAC
CTTCTTGGTTACATACACCTATGCCCGAGTAATTTGTTTTCCAGTCTTCTACTTCTAGTCCA
ACAGTGTCACCGGTGGGTGGTGGTGTAATAGTGCGGTTTACGGTTCAGTTTTGGCG
ATGATTTGGTTTCGAATATGTTTAAAGATGAATTGGCTATGCCAGTCAAGAAAGGGG
TTGAGGAAGCTAGTAAGTTCCTTCCTCCAAGTCTTCTCCAGCTCTTTATTGATGTGGATAGTT
ACATCCCTATGAATTCTGGTTCAGAGACGATCAGAGCATCATAGCTATGCAAGATTTGTTAAGACGAGA
AGAAAGATGAGAGACAGAGCATCATCATCATCAGCTATGCAAGATTTCGTTGAAGAAGTAACA
CTGGTAAGAAAGCCATTGGCGCGACAGAGAAAGCGAGCTTTCTGAAATGTTGATAACATGTTCC
TATGTGGCCCTGGGAAACCTGTATGCATTCTTAACCAGAACTTCCTACAGAATCAACTTCTACTA
AGTGCTGACCGCACAGTCAGTTCTAAGAAGATTCGTGGGAAGAAATCAACTTCTACTA
GTCATAGTAACGATTCTAAGAAGAAACTGCTGATTGAGGACTCTTTTGGTGTTATGTG
CACAAGCTGTATCAGTGGATGATCGTAGAACCGCCAACGTTTAGCTAAGGCAGATACGAG
AGCATTCTTCGCCTCAGCGTTGGGACCGGTTGGCTCATTATTTGCAAATAGTC
TTGAAGCACGCTTAGCTGGGACCGGTACACAGATCTACACCGCTTTATCTTCGAAGAAAA
CGTCTGCAGCAGACATGTTGAAGGCTTACCAGTACCAGATCATGTCGGTCGTCTGCCCTTTCAAGA
AAGCTGCTATCATATTTGCTAACCACAGCATGATGCGTTTCACTGCGTTTCAGTGGCCTGCAAACGCCAACACGA
TCCACATAATAGATTTCGGAATATCTTACGGTTTCAGTGGCCTGCTCTGATTCATCGCC
TCTCGCTCAGCAGACCTGGTTCGCCCTAAGCTTCGAATTACCGGTNNNNNNNN
```

FIG. 16J-1

```
NNNNNNNNNNNNNNNNNGAGTTCAGGAGACAGGTCATCGCTTGGCTCGATACT
GTCAGCGACACAATGTTCCGTTTGAGTAGTACAACGCAATTGCTCAGAAATGGGAAACGATC
CAAGTCGAAGACTTAAGCTTCGACAAGGAGAGTAGTGGTTGTGAACTCTTGTTCCGT
TTCAGGAACCTTCTAGATGAGACCGTTCTGGTAAACAGCCCGAGAGATGCAGTTTGAAG
CTGATAAGAAAAATAAACCCGAATGTCTTCATTCCAGCGTTGTTCTTAAGCGGGAATTACAAC
GCGCCATTCTCTTTGTCGAGGTTCAGAGAAGCGTTGTTTCATTACTCGGCTGTGTTTGAT
ATGTGTGACTCGAAGCTAGCTAGGGAAGACGAGATGAGGCTGATGTGTGTTTGAGTTT
TATGGGAGAGATTGTGAATGTGTGGCTGAAGAACAGAGAGAGTGGAGAGCCCGA
GAGACATATAAGCAGTGCAGGCGAGACTGATCCGAGCCGATTTAGACAGCTTCCGCTT
GAGAAGGAACTGATGCAGAATCTGAAGTTACTTGAAAACGGGTACGAGAATCGTATGCT
GATGTTGATCAAAACTGGTTCCTTCGTCTTCATAGATGTTGTTCTTACGTTCTAAGCGACTGGG
TCATCTCTATGGGTTCCTTCGTCTTCGTTGATAGTCTCTCCGCCAACACGAGTGGATTAAGTTCAGAG
ATTTATGTAGGGCTTTTCTGTTGATAGTGTTGTTATATTATGCTTGTGACATAGCGTGTGTAAGA
TTAGGGTTCTTGAACACTAGAATGTTCATTGCATCTTTTGCTATATGTTNCATGT
GTGTAGCCCTAAGAGAGATATAGTACTCATTGCATGATCTTTTGCTATATGTTNCATGT
```

FIG.16J-2

SRPd1

TCTGCAGACAATTTTNAGGAGGCCAATACCATGCTATTGGAAATTTCAGAACTG
TCCACACCTNNNNNNNNNNNNNNNNNNNNNNNNGTACTTCTCAGAGGN
AATGTCGGNNAGATTAGTTAGCTCCTGCTTAGGAATCTATGCTTCTTCCNGC
AACAGTGGTGCCCTCCTCATGGTCAGAAAGTGGCCCTCA

FIG. 16K

SRPq1

TCAACTGAGAATCTAGAAGATGCCAACAAGATGCTTCTGGAGATTTCTCAGTTA
TCAACACCGTTCNNCACTTCAGCACAGCGTGTGGCAGCATATTCTCAGAAGCC
ATATCAGCAGCAAGGTTGGTGAGTTCATGTCTAGGATATACGCAACTTTGCCACAC
ACACCAAGCACCAAGGCCACAGGCTTCAGCTTTCAAGTGTTCAATGGTATTAGT
CCTTTAGTGGAGTTCTCACACTTCACAGCAAACCAAGCAATTCAAGAAGCCTTC
GAAAGAGAGAGAGAGGGTGCACATCATAGAGATCTTGATATAATGCAAGGGTTG

FIG. 16L

SRPp1

TCTGCAGACAACTTTGAAGAAGCCAATACAATACTGCCTCAGATCACAGAACTC
TCCACCCCTATNGCAACTCGGTGCAACGAGTGCTGCCTATNNNNNNNNNN
NNNNNNNNNNNNNNNNNNNNNNTGCATAGGAATGTATTCTCCTCTCCCTCCT
ATTCACATGTCCCCAGAGCCCAGAGCCCAGAAAATTGTGAAT

FIG. 16M

FIG. 17A-1

Partial DNA sequence of ZCARECROW gene

```
GATATCAGCATCATCAATTTAAATGTAAGTTGGCAAAAGATCATGAGGGTTCTCATAGT
AATTTGGCCACAAGGTATGACACTGTCTCAATTGAGCAATCTAGTAGAGAAACTGATCCA
TCATATATTGCTCATATTGAAAGTGAAAAGATAATGCTCAAGAACCTAGTAGAAGCTA
AAAATTGAAAAAATCTAGCTCTACTAGAGAAAAAAATATGATAGGTTGCCTGTTTCTCATGAAAA
TTTATTAGATAATCATATCATGGCTAGATGTCGCTCATGAGGTTGTTCTTGCTAGTTTAG
ATTCCGTGGGCATTCATCTCTTTTAGATGCACTAACATGATAGGAAGTTTCTAATCTGG
TGCTTCACAATTCTGTGTATTCATGCTTCCTTCATTGCAATTGATATATTGATGCTTGATTC
ATGCTTCAGTCACTTGTGCGTTAACTATTGGTATTGTATCACTAGATTGTAGGTGT
CTGCAACTAGTGTTTTCACCATGTGGTTTTTTAGTATCATTCGTATTAGTTTCTAACTTTC
TATTGATATATTAAAGTGATAACTAGTTTTAGAAAATATTTCCTTATTGTGCCATTAATGCTAC
AACTTGTTTTTAGCGTGTACGTTAGCATTATAATATATTCCTTATTGAAAGCGGAAGAG
AAACGCCCAACCAGAGCATCCACGTCGTTGTCTCCACGTCCTCATCGTTGGATCATGA
TGAGCGGTCCACGGTGAACTCACGATGTGCCTTGCCCGTCCCGCCGCCGGATCCGGC
TAGCTTCTAGAAACATCACGATGTCCCGACCGCCCAGGTCCCCCAAGGTCGCCCAAGTC
GCCGCAGTGCGCGGGAAGCAGCGCGGAGGCGGTGAACGCGACAACCTCGACGCGCACCAGACGC
GGAGGTGCAGCGCGGGAAGCAGCGCGGAGGCCGTGAACGCGACAACCTCGAGTGCTGACGC
TGCTGCTGCAGTGCCGCGGAGGCGGTGAACGCGACAACCTCGAGTGCTGACGC
TGCTGGAGATCCGCGAGCTCGGCGCGCCGGCGCGCCAGCCGTCGACCCCCAGCCGCCCT
ACTTCGCGGAGGCCATGTCGGCCCCGGGCCCCGGGCCTCCAGGCCTGCTACGCGCCGC
TGCCGCCGGGCCTCCCCCGGGAGGAGCTCTCCACGGCCGCGCCCGGGCCGTTCCAGG
TGTTCAACGGCCATCAGCCCCTCGTCAAGTTCTCGCACTTCGCCACCGCCAACCAGGCCATCC
AGGAGGCGTTCGAGCGGGACCTCGAGAGCGGTGTGCACATCATCGACACCTCGACATCGCAGGGC
TGCAGTGCCCGGCCCTCTTCCACATCCTTGTCTCCCGCGCTCGAGCGCGACGGGAAGCGCCTCTCCG
GGCTCACCGGCCTGGGGCCGTCATGGGCGTCGAGTTCTCGCGGGCGTCCGAGAAGGCCGGCA
ACTTCGCCGACACGCGCAGAAGCTCGGACGTCATCGGCTCCGACTCCAACACGCTCGGCTCATCCAAAGT
ACCACTCGCTTTACGACGTCATCGGCTCCGACTCCAAACACGCTCGGCTCATCATGACCACTT
CCTCCATTTCCTTCTCTGCCTTTCTTCCATGTCAAATCTGATGCAATCATGACCACTT
TTCAGCTGCTGACATTGGATAATGTGAGCTTTACGGCAAGCATCAAGTCGTGTAGTACA
```

```
TCCATTACAGCTATTTCTAAAATATTCTTCGGAGGTTTCCTGCTCATAGTAAAAAAAT
CGCGTTTGAAGCTCAAAAGGCGATTCTTCCGAGGTTGCTGTGTTGAGCGCTATTTGGA
AACCCCATTTCTCAATTGATTTTTATTTTTAAAGAAAAATTAGTTCATTTTCTCTTG
TGAAATGGAGTCCCAAACTAACCTAATATTAAAAAAACGCGCTTTGGAGCTCAAAACG
CTCGTTGTTATGACCAACCAGCTTTATAGGTTTAAAAGGTTGAATCTTGACAATGCTTT
TGAAAAGGTTGAATCTTGACAATGCTTTGAGATGATACTGTAGTGTAGTCTGTAGTGGA
GCATCCTCCATGGTCTTTGGTGATCGAGAATTCCTGCAGCCCGGGGATCC
```

FIG. 17A-2

Partial amino acid sequence of ZCARECROW protein

```
YQHHQFXMXVGKRSXGFSXXFGHKVXHCLNXAIXXRNXSIIYCSYXKXKRYAQEPSREAK
NXKIXLYXKNMIGCLFLMKIYXIIISWLDVAHEVVLASLDSCGHSSLLDALTXXEVSNLV
LHNSGDSCFLHCNYXCLIHASVTLCVXLVLYVSLDCRVSATSVSPCGFLVSFVLVSNFL
LIYXSDNXFXKYSLVPLMLQLVFSVYVSIIIFPYYESGRETRPTRASTSSHFTFIVGSXM
SGPRXTPFACKTTSSTRCXVASRNITMCPVHSFRRSRIRRRSRPPRSRPPPPPRSGR
RCSGGSSATRRASTCXVLTLLQCAEAVNADNLDDAHQTLLEAELATPFGTSTQRVAAY
FAEAMSARVVSSCLGLYAPLPPGSPAAARLHGRVAAFQVFNGISPFVKFSHFTANQAIQ
EAFEREERVHIIDLDIMQGLQWPGLFHILVSRPGGPPRVRLTGLGASMDALEATGKRLSD
FADTLGLPFEFCAVAEKAGNVDPQKLGVTRREAVAVHWPHHSLYDVIGSDNTLWLIQRS
SIFLLCLSSMSNLDAIMTTFQLLTLDNVSFTASIKSWXYIHYSYFXNILRRFPAHSKKKS
RFEAQKAISSEVCCXALFWKPHFLNXFLFFKEKLVHFSLVKWSPKLTLILKKTRFGAQNA
RCYDQPALXVXKGXILTMLLKRILNLDNAFEMILXCSLXWSILHGLWXSRIPAARGI
```

FIG. 17B

```
         302                                             349
SCR      SADNLEEANKLLLEISQLSTPYGTSAQRVAAYFSEAMSARLLNSCLGI
SRPd1    SADNFxEANTMLLEISELSTPxxxxxxxxxxYFSxxMSxRLVSSxLxI
SRPg1    STENLEDANKMLLEISQLSTGxxxxxxxxxxxxxxxxxxxxxxSCLGI
SRPp1    SADNFEEANTILPQITELSTPYxNSVGRVAAYxxxxxxxxxxxxCIGM 350                                            396
SCR      YAALPSRWMPQTH-SLKMVSAFQVFNGISPLVKFSHFTANQAIQEAFE
SRPd1    YASLPATVVP--PHGQKVAS
SRPg1    YATLP-----HTHQSHKVASAFQVFNGISPLVEFSHFTANQAIQEAFE
SRPp1    YSPLPPIxMSQ---SQKIVN 397            412
SCR      KEDSVHIIDLDIMQGL
SRPg1    REERVHIIDLDIMQGL
```

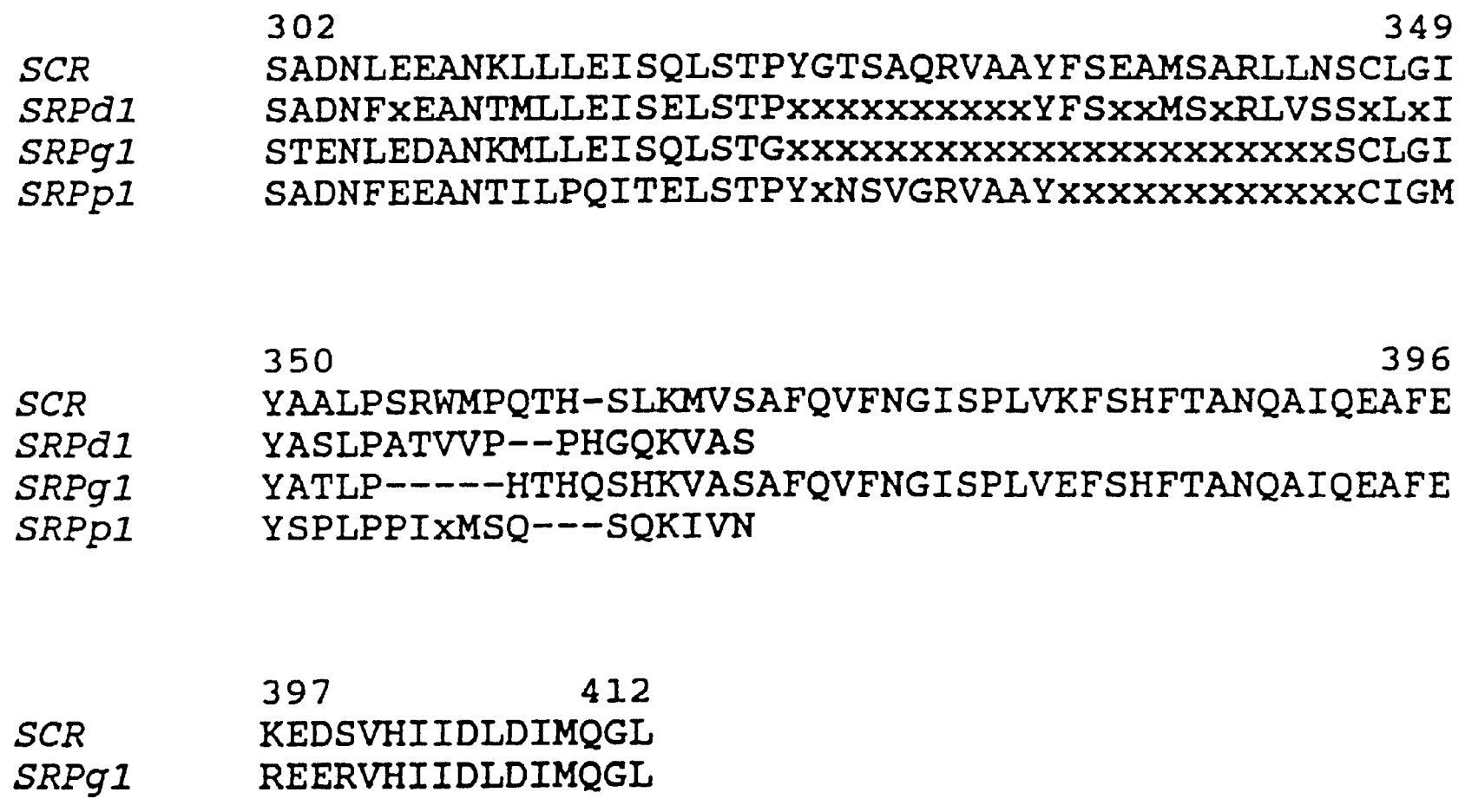

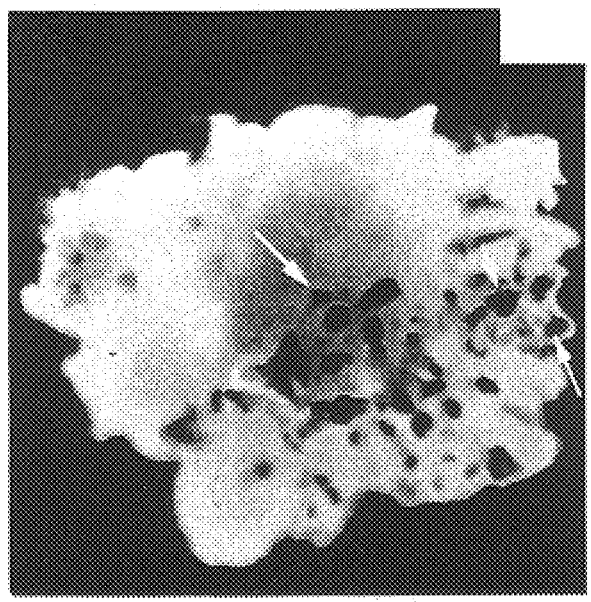
FIG.20A
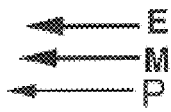
FIG.20B

SCR Promoter::GUS

SCR Promoter::SCR

SEQUENCE LISTING

<160> NUMBER OF SEQ ID NOS: 79

<210> SEQ ID NO 1
<211> LENGTH: 2163
<212> TYPE: DNA
<213> ORGANISM: Plant

<400> SEQUENCE: 1

```
ccttatttat aaccatgcaa tctcacgacc aacaacccct caatctccat ggcggaatcc      60
ggcgatttca acggtggtca acctcctcct catagtcctc tgagaacaac ttcttccggt     120
agtagcagca gcaacaaccg tggtcctcct cctcctcctc ctcctccttt agtgatggtg     180
agaaaaagat tagcttccga gatgtcttct aaccctgact acaacaactc ctctcgtcct     240
cctcgccgtg tctctcacct tcttgactcc aactacaata ctgtcacacc acaacaacca     300
ccgtctctta cggcggcggc tactgtatct tctcaaccaa acccaccact ctctgtttgt     360
ggcttctctg gtcttcccgt ttttccttca gaccgtggtg gtcggaatgt tatgatgtcc     420
gtacaaccaa tggatcaaga ctcttcatct tcttctgctt cacctactgt atgggttgac     480
gccattatca gagaccttat ccattcctca acttcagtct ctattcctca acttatccaa     540
aacgttagag acattatctt cccttgtaac ccaaatctcg gtgctcttct tgaatacagg     600
ctccgatctc tcatgctcct tgatccttcc tcttcctctg acccttctcc tcaaactttc     660
gaacctctct atcagatctc caacaatcct tctcctccac aacagcaaca gcagcaccaa     720
caacaacaac aacagcataa gcctcctcct cctccgattc agcagcaaga aagagaaaat     780
tcttctaccg atgcaccacc gcaaccagag acagtgacgg ccactgttcc cgccgtccaa     840
acaaatacgg cggaggcttt aagagagagg aaggaagaga ttaagaggca gaagcaagac     900
gaagaaggat tacaccttct cacattgctg ctacagtgtg ctgaagctgt ctctgctgat     960
aatctcgaag aagcaaacaa gcttcttctt gagatctctc agttatcaac tccttacggg    1020
acctcagcgc agagagtagc tgcttacttc tcggaagcta tgtcagcgag attactcaac    1080
tcgtgtctcg gaatttacgc ggctttgcct tcacggtgga tgcctcaaac gcatagcttg    1140
aaaatggtct ctgcgtttca ggtctttaat gggataagcc ctttagtgaa attctcacac    1200
tttacagcga atcaggcgat tcaagaagca tttgagaaag aagacagtgt acacatcatt    1260
gacttggaca tcatgcaggg acttcaatgg cctggtttat ccacattcct tgcttctaga    1320
cctggaggac ctccacacgt gcgactcacg ggacttggta cttccatgga agctcttcag    1380
gctacaggga aacgtctttc ggatttcaca gataagcttg gcctgccttt tgagttctgc    1440
cctttagctg agaaagttgg aaacttggac actgagagac tcaatgtgag gaaaagggaa    1500
gctgtggctg ttcactggct tcaacattct ctttatgatg tcactggctc tgatgcacac    1560
actctctggt tactccaaag gtaaaataaa cattacctt taatcactct ttatctataa    1620
attatttaa gattatatag gaaagatatg ttctaaaaag ctggctttt tggttaatga    1680
ttggggaatg aacagattag ctcctaaagt tgtgacagta gtggagcaag atttgagcca    1740
cgctggttct ttcttaggaa gatttgtaga ggcaatacat tactactctg cactctttga    1800
ctcactggga gcaagctacg gcgaagagag tgaagagaga catgtcgtgg aacagcagct    1860
attatcgaaa gagatacgga atgtattagc ggttggagga ccatcgagaa gcggtgaagt    1920
gaagtttgag agctggaggg agaaaatgca acaatgtggg tttaaaggta tatctttagc    1980
tggaaatgca gctacacaag cgactctact gttgggaatg tttccttcgg atggttacac    2040
tttggttgat gataatggta cacttaagct tggatggaaa gatctttcgt tactcactgc    2100
ttcagcttgg acgcctcgtt cttagttttc ttctcctttt tcacaaacaa tgtgcccata    2160
aat                                                                  2163
```

<210> SEQ ID NO 2

-continued

```
<211> LENGTH: 653
<212> TYPE: PRT
<213> ORGANISM: Plant

<400> SEQUENCE: 2
```

| | | | | | | | | | | | | | | | |
|---|---|---|---|---|---|---|---|---|---|---|---|---|---|---|---|
| Met | Ala | Glu | Ser | Gly | Asp | Phe | Asn | Gly | Gly | Gln | Pro | Pro | His | Ser |
| 1 | | | | 5 | | | | | 10 | | | | | 15 |
| Pro | Leu | Arg | Thr | Thr | Ser | Ser | Gly | Ser | Ser | Ser | Asn | Asn | Arg | Gly |
| | | | 20 | | | | | 25 | | | | | 30 | |
| Pro | Pro | Pro | Pro | Pro | Pro | Pro | Leu | Val | Met | Val | Arg | Lys | Arg | Leu |
| | | 35 | | | | | 40 | | | | 45 | | | |
| Ala | Ser | Glu | Met | Ser | Ser | Asn | Pro | Asp | Tyr | Asn | Asn | Ser | Ser | Arg | Pro |
| | 50 | | | | | 55 | | | | | 60 | | | | |
| Pro | Arg | Arg | Val | Ser | His | Leu | Leu | Asp | Ser | Asn | Tyr | Asn | Thr | Val | Thr |
| 65 | | | | | 70 | | | | | 75 | | | | | 80 |
| Pro | Gln | Gln | Pro | Pro | Ser | Leu | Thr | Ala | Ala | Thr | Val | Ser | Ser | Gln |
| | | | | 85 | | | | | 90 | | | | | 95 |
| Pro | Asn | Pro | Pro | Leu | Ser | Val | Cys | Gly | Phe | Ser | Gly | Leu | Pro | Val | Phe |
| | | | 100 | | | | | 105 | | | | | 110 | | |
| Pro | Ser | Asp | Arg | Gly | Gly | Arg | Asn | Val | Met | Met | Ser | Val | Gln | Pro | Met |
| | | 115 | | | | | 120 | | | | | 125 | | | |
| Asp | Gln | Asp | Ser | Ser | Ser | Ser | Ala | Ser | Pro | Thr | Val | Trp | Val | Asp |
| | 130 | | | | | 135 | | | | | 140 | | | | |
| Ala | Ile | Ile | Arg | Asp | Leu | Ile | His | Ser | Ser | Thr | Ser | Val | Ser | Ile | Pro |
| 145 | | | | | 150 | | | | | 155 | | | | | 160 |
| Gln | Leu | Ile | Gln | Asn | Val | Arg | Asp | Ile | Ile | Phe | Pro | Cys | Asn | Pro | Asn |
| | | | | 165 | | | | | 170 | | | | | 175 | |
| Leu | Gly | Ala | Leu | Leu | Glu | Tyr | Arg | Leu | Arg | Ser | Leu | Met | Leu | Leu | Asp |
| | | | 180 | | | | | 185 | | | | | 190 | | |
| Pro | Ser | Ser | Ser | Ser | Asp | Pro | Ser | Pro | Gln | Thr | Phe | Glu | Pro | Leu | Tyr |
| | | 195 | | | | | 200 | | | | | 205 | | | |
| Gln | Ile | Ser | Asn | Asn | Pro | Ser | Pro | Gln | Gln | Gln | Gln | His | Gln |
| | 210 | | | | | 215 | | | | | 220 | | | |
| Gln | Gln | Gln | Gln | His | Lys | Pro | Pro | Pro | Pro | Ile | Gln | Gln |
| 225 | | | | | 230 | | | | | 235 | | | | 240 |
| Glu | Arg | Glu | Asn | Ser | Ser | Thr | Asp | Ala | Pro | Pro | Gln | Pro | Glu | Thr | Val |
| | | | | 245 | | | | | 250 | | | | | 255 | |
| Thr | Ala | Thr | Val | Pro | Ala | Val | Gln | Thr | Asn | Thr | Ala | Glu | Ala | Leu | Arg |
| | | | 260 | | | | | 265 | | | | | 270 | | |
| Glu | Arg | Lys | Glu | Glu | Ile | Lys | Arg | Gln | Lys | Gln | Asp | Glu | Glu | Gly | Leu |
| | | 275 | | | | | 280 | | | | | 285 | | | |
| His | Leu | Leu | Thr | Leu | Leu | Gln | Cys | Ala | Glu | Ala | Val | Ser | Ala | Asp |
| | 290 | | | | | 295 | | | | | 300 | | | | |
| Asn | Leu | Glu | Glu | Ala | Asn | Lys | Leu | Leu | Leu | Glu | Ile | Ser | Gln | Leu | Ser |
| 305 | | | | | 310 | | | | | 315 | | | | | 320 |
| Thr | Pro | Tyr | Gly | Thr | Ser | Ala | Gln | Arg | Val | Ala | Ala | Tyr | Phe | Ser | Glu |
| | | | | 325 | | | | | 330 | | | | | 335 | |
| Ala | Met | Ser | Ala | Arg | Leu | Leu | Asn | Ser | Cys | Leu | Gly | Ile | Tyr | Ala | Ala |
| | | | 340 | | | | | 345 | | | | | 350 | | |
| Leu | Pro | Ser | Arg | Trp | Met | Pro | Gln | Thr | His | Ser | Leu | Lys | Met | Val | Ser |
| | | 355 | | | | | 360 | | | | | 365 | | | |
| Ala | Phe | Gln | Val | Phe | Asn | Gly | Ile | Ser | Pro | Leu | Val | Lys | Phe | Ser | His |
| | 370 | | | | | 375 | | | | | 380 | | | | |
| Phe | Thr | Ala | Asn | Gln | Ala | Ile | Gln | Glu | Ala | Phe | Glu | Lys | Glu | Asp | Ser |

-continued

```
385                 390                 395                 400

Val His Ile Ile Asp Leu Asp Ile Met Gln Gly Leu Gln Trp Pro Gly
                405                 410                 415

Leu Phe His Ile Leu Ala Ser Arg Pro Gly Pro Pro His Val Arg
                420                 425                 430

Leu Thr Gly Leu Gly Thr Ser Met Glu Ala Leu Gln Ala Thr Gly Lys
                435                 440                 445

Arg Leu Ser Asp Phe Thr Asp Lys Leu Gly Leu Pro Phe Glu Phe Cys
            450                 455                 460

Pro Leu Ala Glu Lys Val Gly Asn Leu Asp Thr Glu Arg Leu Asn Val
465                 470                 475                 480

Arg Lys Arg Glu Ala Val Ala Val His Trp Leu Gln His Ser Leu Tyr
                485                 490                 495

Asp Val Thr Gly Ser Asp Ala His Thr Leu Trp Leu Leu Gln Arg Leu
                500                 505                 510

Ala Pro Lys Val Val Thr Val Val Glu Gln Asp Leu Ser His Ala Gly
                515                 520                 525

Ser Phe Leu Gly Arg Phe Val Glu Ala Ile His Tyr Tyr Ser Ala Leu
                530                 535                 540

Phe Asp Ser Leu Gly Ala Ser Tyr Gly Glu Glu Ser Glu Arg His
545                 550                 555                 560

Val Val Glu Gln Gln Leu Leu Ser Lys Glu Ile Arg Asn Val Leu Ala
                565                 570                 575

Val Gly Gly Pro Ser Arg Ser Gly Glu Val Lys Phe Glu Ser Trp Arg
                580                 585                 590

Glu Lys Met Gln Gln Cys Gly Phe Lys Gly Ile Ser Leu Ala Gly Asn
                595                 600                 605

Ala Ala Thr Gln Ala Thr Leu Leu Gly Met Phe Pro Ser Asp Gly
                610                 615                 620

Tyr Thr Leu Val Asp Asp Asn Gly Thr Leu Lys Leu Gly Trp Lys Asp
625                 630                 635                 640

Leu Ser Leu Leu Thr Ala Ser Ala Trp Thr Pro Arg Ser
                645                 650

<210> SEQ ID NO 3
<211> LENGTH: 23
<212> TYPE: PRT
<213> ORGANISM: Plant

<400> SEQUENCE: 3

Pro Ala Val Gln Thr Asn Thr Ala Glu Ala Leu Arg Glu Arg Lys Glu
1               5                   10                  15

Glu Ile Lys Arg Gln Lys Gln
            20

<210> SEQ ID NO 4
<211> LENGTH: 23
<212> TYPE: PRT
<213> ORGANISM: Plant

<400> SEQUENCE: 4

Leu Lys Arg Ala Arg Asn Thr Glu Ala Ala Arg Arg Ser Arg Ala Arg
1               5                   10                  15

Lys Leu Gln Arg Met Lys Gln
            20
```

-continued

```
<210> SEQ ID NO 5
<211> LENGTH: 23
<212> TYPE: PRT
<213> ORGANISM: Plant

<400> SEQUENCE: 5

Arg Arg Leu Ala Gln Asn Arg Glu Ala Ala Arg Lys Ser Arg Leu Arg
 1               5                  10                  15

Lys Lys Ala Tyr Val Gln Gln
            20

<210> SEQ ID NO 6
<211> LENGTH: 23
<212> TYPE: PRT
<213> ORGANISM: Plant

<400> SEQUENCE: 6

Ile Arg Arg Glu Arg Asn Lys Met Ala Ala Lys Cys Arg Asn Arg
 1               5                  10                  15

Arg Arg Glu Leu Thr Asp Thr
            20

<210> SEQ ID NO 7
<211> LENGTH: 23
<212> TYPE: PRT
<213> ORGANISM: Plant

<400> SEQUENCE: 7

Arg Lys Arg Met Arg Asn Arg Ile Ala Ala Ser Lys Cys Arg Lys Arg
 1               5                  10                  15

Lys Leu Glu Arg Ile Ala Arg
            20

<210> SEQ ID NO 8
<211> LENGTH: 23
<212> TYPE: PRT
<213> ORGANISM: Plant

<400> SEQUENCE: 8

Val Arg Leu Met Lys Asn Arg Glu Ala Ala Arg Glu Cys Arg Arg Lys
 1               5                  10                  15

Lys Lys Glu Tyr Val Lys Cys
            20

<210> SEQ ID NO 9
<211> LENGTH: 23
<212> TYPE: PRT
<213> ORGANISM: Plant

<400> SEQUENCE: 9

Lys Arg Lys Glu Ser Asn Arg Glu Ser Ala Arg Arg Ser Arg Tyr Arg
 1               5                  10                  15

Lys Ala Ala His Leu Lys Glu
            20

<210> SEQ ID NO 10
<211> LENGTH: 23
<212> TYPE: PRT
<213> ORGANISM: Plant

<400> SEQUENCE: 10

Met Arg Gln Ile Arg Asn Arg Asp Ser Ala Met Lys Ser Arg Glu Arg
 1               5                  10                  15
```

```
Lys Lys Ser Tyr Ile Lys Asp
            20

<210> SEQ ID NO 11
<211> LENGTH: 23
<212> TYPE: PRT
<213> ORGANISM: Plant

<400> SEQUENCE: 11

Arg Arg Met Val Ser Asn Arg Glu Ser Ala Arg Arg Ser Arg Lys Lys
1               5                   10                  15

Lys Gln Ala His Leu Ala Asp
            20

<210> SEQ ID NO 12
<211> LENGTH: 43
<212> TYPE: PRT
<213> ORGANISM: Plant

<400> SEQUENCE: 12

Ala Phe Glu Lys Glu Asp Ser Val His Ile Ile Asp Leu Asp Ile Met
1               5                   10                  15

Gln Gly Leu Gln Trp Pro Gly Leu Phe His Ile Leu Ala Ser Arg Pro
            20                  25                  30

Gly Gly Pro Pro His Val Arg Leu Thr Gly Leu
        35                  40

<210> SEQ ID NO 13
<211> LENGTH: 43
<212> TYPE: PRT
<213> ORGANISM: Plant

<400> SEQUENCE: 13

Ala Val Lys Asn Glu Ser Phe Val His Ile Ile Asp Phe Gln Ile Ser
1               5                   10                  15

Gln Gly Gly Gln Trp Val Ser Leu Ile Arg Ala Leu Gly Ala Arg Pro
            20                  25                  30

Gly Gly Pro Pro Asn Val Arg Ile Thr Gly Ile
        35                  40

<210> SEQ ID NO 14
<211> LENGTH: 43
<212> TYPE: PRT
<213> ORGANISM: Plant

<400> SEQUENCE: 14

Ala Met Glu Gly Glu Lys Met Val His Val Ile Asp Leu Asp Ala Ser
1               5                   10                  15

Glu Pro Ala Gln Trp Leu Ala Leu Leu Gln Ala Phe Asn Ser Arg Pro
            20                  25                  30

Glu Gly Pro Pro His Leu Arg Ile Thr Gly Val
        35                  40

<210> SEQ ID NO 15
<211> LENGTH: 29
<212> TYPE: PRT
<213> ORGANISM: Plant

<400> SEQUENCE: 15

Ala Ile Lys Gly Glu Glu Glu Val His Ile Ile Asp Phe Asp Ile Asn
1               5                   10                  15
```

-continued

Gln Gly Asn Gln Tyr Met Thr Leu Ile Arg Ser Ile Ala
            20                  25

<210> SEQ ID NO 16
<211> LENGTH: 26
<212> TYPE: PRT
<213> ORGANISM: Plant
<220> FEATURE:
<221> NAME/KEY: VARIANT
<222> LOCATION: (1)...(26)
<223> OTHER INFORMATION: Xaa = Any Amino Acid

<400> SEQUENCE: 16

Ile His Val Ile Asp Phe Xaa Leu Gly Val Gly Gly Gln Trp Ala Ser
1               5                   10                  15

Phe Leu Gln Glu Leu Ala His Arg Arg Gly
            20                  25

<210> SEQ ID NO 17
<211> LENGTH: 36
<212> TYPE: PRT
<213> ORGANISM: Plant
<220> FEATURE:
<221> NAME/KEY: VARIANT
<222> LOCATION: (1)...(36)
<223> OTHER INFORMATION: Xaa = Any Amino Acid

<400> SEQUENCE: 17

Val His Ile Ile Xaa Phe Xaa Leu Met Gln Gly Leu Gln Trp Pro Ala
1               5                   10                  15

Leu Met Asp Val Phe Ser Ala Arg Lys Gly Gly Pro Pro Lys Leu Arg
            20                  25                  30

Ile Thr Gly Ile
        35

<210> SEQ ID NO 18
<211> LENGTH: 1085
<212> TYPE: DNA
<213> ORGANISM: Plant
<220> FEATURE:
<221> NAME/KEY: misc_feature
<222> LOCATION: (1)...(1085)
<223> OTHER INFORMATION: n = A,T,C or G

<400> SEQUENCE: 18
ggcacgagcc caacgggtcc tgagcttctt acttatatgc atatcttgta tgaagcctgc      60
ccttatttca aattcggtta tgaatctgct aatggagcta tagctgaagc tgtgaagaac     120
gaaagttttg tgcacattat cgatttccag atttctcaag gtggtcaatg ggtgagtttg     180
atccgtgctc ttggtgctag acctggtgga cctccgaacg ttaggataac gggaattgat     240
gatccgagat catcgtttgc tcgtcaagga ggacttgagt tagttggaca aagacttggg     300
aagctagctg aaatgtgcgg tgttccgttt gagttccatg gagctgcttt atgctgcacg     360
gaagtcgaaa tcgagaagct aggagttaga atggagaag cgctcgcggt taacttcccg     420
cttgttcttc accacatgcc tgatgagagt gtaactgtgg agaatcacag agatagattg     480
ttgagattgg tcaaacactt gtcaccaaac gttgtgactc tggttgagca agaagcgaat     540
acaaacactg cgccgtttct tccccggttt gtcgagacaa tgaaccatta cttggcagtt     600
ttcgaatcaa tagatgtgaa actcgctaga gatcacaagg aaaggatcaa tgttgagcag     660
cattgtttgg ctagagaggt tgtgaatctt atagcttgtg aaggtgttga agagaagag     720

-continued

```
aggcacgagc cactagggaa atggaggtct cggtttcaca tggcgggatt taaaccgtat    780
cctttgagct cgtatgtgaa cgcaacaatc aaaggattgc ttgagagtta ttcagagaag    840
tatacacttg aagaaagaga tggagcattg tatttaggat ggaagaatca acctcttatc    900
acttcttgtg cttggaggta actaataaaa accttgttcg gtttcagaag agattagaaa    960 cttctttaa agtttgcaga atctgtttgt aaaagtaaaa ctcatgcatg atccgnagga   1020
acaagttgtc aaatgttgta gtagtaagtg atatgttgat gacccaaaaa aaaaaaaaaa   1080
aaaaa                                                              1085
```

<210> SEQ ID NO 19
<211> LENGTH: 306
<212> TYPE: PRT
<213> ORGANISM: Plant

<400> SEQUENCE: 19

```
Gly Thr Ser Pro Thr Gly Pro Glu Leu Leu Thr Tyr Met His Ile Leu
 1               5                  10                  15

Tyr Glu Ala Cys Pro Tyr Phe Lys Phe Gly Tyr Glu Ser Ala Asn Gly
             20                  25                  30

Ala Ile Ala Glu Ala Val Lys Asn Glu Ser Phe Val His Ile Ile Asp
         35                  40                  45

Phe Gln Ile Ser Gln Gly Gly Gln Trp Val Ser Leu Ile Arg Ala Leu
     50                  55                  60

Gly Ala Arg Pro Gly Gly Pro Pro Asn Val Arg Ile Thr Gly Ile Asp
 65                  70                  75                  80

Asp Pro Arg Ser Ser Phe Ala Arg Gln Gly Gly Leu Glu Leu Val Gly
                 85                  90                  95

Gln Arg Leu Gly Lys Leu Ala Glu Met Cys Gly Val Pro Phe Glu Phe
            100                 105                 110

His Gly Ala Ala Leu Phe Cys Thr Glu Val Glu Ile Glu Lys Leu Gly
        115                 120                 125

Val Arg Asn Gly Glu Ala Leu Ala Val Asn Phe Pro Leu Val Leu His
    130                 135                 140

His Met Pro Asp Glu Ser Val Thr Val Glu Asn His Arg Asp Arg Leu
145                 150                 155                 160

Leu Arg Leu Val Lys His Leu Ser Pro Asn Val Val Thr Leu Val Glu
                165                 170                 175

Gln Glu Ala Asn Thr Asn Thr Ala Pro Phe Leu Pro Arg Phe Val Glu
            180                 185                 190

Thr Met Asn His Tyr Leu Ala Val Phe Glu Ser Ile Asp Val Lys Leu
        195                 200                 205

Ala Arg Asp His Lys Glu Arg Ile Asn Val Glu Gln His Cys Leu Ala
    210                 215                 220

Arg Glu Val Glu Asn Leu Ile Ala Cys Glu Gly Val Glu Arg Glu Glu
225                 230                 235                 240

Arg His Glu Pro Leu Gly Lys Trp Arg Ser Arg Phe His Met Ala Gly
                245                 250                 255

Phe Lys Pro Tyr Pro Leu Ser Ser Tyr Val Asn Ala Thr Ile Lys Gly
            260                 265                 270

Leu Leu Glu Ser Tyr Ser Glu Lys Tyr Thr Leu Glu Glu Arg Asp Gly
        275                 280                 285

Ala Leu Tyr Leu Gly Trp Lys Asn Gln Pro Leu Ile Thr Ser Cys Ala
    290                 295                 300
```

Trp Arg
305

<210> SEQ ID NO 20
<211> LENGTH: 1231
<212> TYPE: DNA
<213> ORGANISM: Plant

<400> SEQUENCE: 20

| | | |
|---|---|---|
| gctatggaag gagagaagat ggttcatgtg attgatctcg atgcttctga gccagctcaa | 60 |
| tggcttgctt tgcttcaagc ttttaactct aggcctgaag gtccacctca tttgagaatc | 120 |
| actggtgttc atcaccagaa ggaagtgctt gaacaaatgg ctcatagact cattgaggaa | 180 |
| gcagagaaac tcgatatccc gtttcagttt aatcccgttg tgagtaggtt agactgttta | 240 |
| aatgtagaac agttgcgggt taaaacagga gaggccttag ccgttagctc ggttcttcaa | 300 |
| ttgcataccl tcttggcctc tgatgatgat ctcatgagaa agaactgcgc tttacggttt | 360 |
| cagaacaacc ctagtggagt tgacttgcag agagttctaa tgatgagcca tggctctgca | 420 |
| gctgaggcac gtgagaatga tatgagtaac aacaatgggt atagccctag cggtgactcg | 480 |
| gcctcatctt tgcctttacc aagttcagga aggactgata gcttcctcaa tgctatttgg | 540 |
| ggtttgtctc caaaggtcat ggtggtcact gagcaagact cagaccacaa cggctccaca | 600 |
| ctaatggaga ggctattaga atcactttac acctacgcag cattgtttga ttgcttggaa | 660 |
| acaaaagttc caagaacgtc tcaagatagg atcaaagtgg agaagatgct cttcggggag | 720 |
| gagatcaaga acatcatatc ctgcgaggga tttgagagaa gagaaagaca cgagaagctt | 780 |
| gagaaatgga gccagaggat cgatttggct ggttttggga atgttcctct tagctattat | 840 |
| gcgatgttgc aggctaggag attgcttcaa gggtgcggtt ttgatgggta tagaatcaag | 900 |
| gaagagagcg ggtgcgcagt aatttgctgg caagatcgac ctctatactc ggtatcagct | 960 |
| tggagatgca ggaagtgaat gatatattac agtttgtctt ctattttggt tatgagcaga | 1020 |
| gtcccttlct tttttgtata catggggaca caatcttagt tgttttgtga tggtgacttt | 1080 |
| ctgtctcttt atgctatttt ggcttaaatg cttctactgc ctctgcatgt aaagcctttg | 1140 |
| tgtgttggtt caatttggtc tggtgtgggt gtaataccaa accaaatcca atttgagctg | 1200 |
| aagataacta atttgatgat cggctcgtgc c | 1231 |

<210> SEQ ID NO 21
<211> LENGTH: 325
<212> TYPE: PRT
<213> ORGANISM: Plant

<400> SEQUENCE: 21

Ala Met Glu Gly Glu Lys Met Val His Val Ile Asp Leu Asp Ala Ser
1               5                   10                  15

Glu Pro Ala Gln Trp Leu Ala Leu Leu Gln Ala Phe Asn Ser Arg Pro
                20                  25                  30

Glu Gly Pro Pro His Leu Arg Ile Thr Gly Val His His Gln Lys Glu
            35                  40                  45

Val Leu Glu Gln Met Ala His Arg Leu Ile Glu Glu Ala Glu Lys Leu
        50                  55                  60

Asp Ile Pro Phe Gln Phe Asn Pro Val Val Ser Arg Leu Asp Cys Leu
65                  70                  75                  80

Asn Val Glu Gln Leu Arg Val Lys Thr Gly Glu Ala Leu Ala Val Ser
                85                  90                  95

-continued

```
Ser Val Leu Gln Leu His Thr Phe Leu Ala Ser Asp Asp Leu Met
            100                 105                 110

Arg Lys Asn Cys Ala Leu Arg Phe His Asn Asn Pro Ser Gly Val Asp
        115                 120                 125

Leu Gln Arg Val Leu Met Met Ser His Gly Ser Ala Ala Glu Ala Arg
    130                 135                 140

Glu Asn Asp Met Ser Asn Asn Gly Tyr Ser Pro Ser Gly Asp Ser
145                 150                 155                 160

Ala Ser Ser Leu Pro Leu Pro Ser Ser Gly Arg Thr Asp Ser Phe Leu
                165                 170                 175

Asn Ala Ile Trp Gly Leu Ser Pro Lys Val Met Val Thr Glu Gln
            180                 185                 190

Asp Ser Asp His Asn Gly Ser Thr Leu Met Glu Arg Leu Leu Glu Ser
        195                 200                 205

Leu Tyr Thr Tyr Ala Ala Leu Phe Asp Cys Leu Glu Thr Lys Val Pro
    210                 215                 220

Arg Thr Ser Gln Asp Arg Ile Lys Val Glu Lys Met Leu Phe Gly Glu
225                 230                 235                 240

Glu Ile Lys Asn Ile Ile Ser Cys Glu Gly Phe Glu Arg Arg Glu Arg
                245                 250                 255

His Glu Lys Leu Glu Lys Trp Ser Gln Arg Ile Asp Leu Ala Gly Phe
            260                 265                 270

Gly Asn Val Pro Leu Ser Tyr Tyr Ala Met Leu Gln Ala Arg Arg Leu
        275                 280                 285

Leu Gln Gly Cys Gly Phe Asp Gly Tyr Arg Ile Lys Glu Glu Ser Gly
    290                 295                 300

Cys Ala Val Ile Cys Trp Gln Asp Arg Pro Leu Tyr Ser Val Ser Ala
305                 310                 315                 320

Trp Arg Cys Arg Lys
                325

<210> SEQ ID NO 22
<211> LENGTH: 1368
<212> TYPE: DNA
<213> ORGANISM: Plant

<400> SEQUENCE: 22
ctttgtcaat ggtaaatgag ctgaggcaga tagtttctat ccaaggagac ccttctcaga      60
gaatcgcagc ttacatggtg gaaggtctag ctgcaagaat ggccgcttca ggaaaattca    120
tctacagagc attgaaatgc aaagagcctc cttcggatga gaggcttgca gctatgcaag    180
tcctgtttga agtctgccct tgtttcaagt tcgggttttt agcagctaat ggtgcgatac    240
ttgaagcaat caaaggtgaa gaagaagttc acataatcga tttcgatata aaccaaggga    300
accaatacat gacactgata cgaagcattg ctgagttgcc tggtaaacga cctcgcctga    360
ggttaacagg aattgatgac cctgaatcag tccaacgctc cattggaggg ctaagaatca    420
tcggtctaag actcgagcaa ctcgcagagg ataatggagt atccttcaaa ttcaaagcaa    480
tgccttcaaa gacttcgatt gtctctccat caacactcgg ttgcaaacca ggagaaacct    540
taatagtgaa ctttgcattc caacttcacc acatgcctga cgagagtgtc acaacagtaa    600
accagcggga cgagctactt cacatggtca aaagcttaaa cccaaagctt gtcacggtcg    660
ttgaacaaga cgtgaacaca aacacttcac cgttctttcc cagattcata gaggcttacg    720
aatactactc agcagttttc gagtctctag acatgacact tccaagagaa agccaagaga    780
```

-continued

```
ggatgaatgt agaaagacag tgtctcgcta gagacatagt caacattgtt gcttgcgaag      840
gagaagaacg gatagagaga tacgaggctg cgggaaaatg gagagcaagg atgatgatgg      900
ctggattcaa tccaaaacca atgagtgcta agtaaccaa caatatacaa aacctgataa       960
agcaacaata ttgcaataag tacaagctta agaagaaat gggtgagctc cattttgct      1020 gggaggagaa aagcttaatc gttgcttcag cttggaggta agataagtga caagagcata    1080
tagtctttat gtttcataaa acataattat gtttttactg taatcttggg ttattgtgta    1140
actggttaaa tcatctccat gtattattac cagaggttag gggtgatcac aggtactaaa    1200
agctaatcta acacttatgg aagaattttt ctttcttttt tttccctatt atataaaaat    1260
aattagagtt ttggttctaa acctatttgc taagtgtgaa tgagtcttta catgttcata    1320
tttcagttca aatggttaaa tttgttaagg ttctcactta aaaaaaaa                 1368
```

<210> SEQ ID NO 23
<211> LENGTH: 351
<212> TYPE: PRT
<213> ORGANISM: Plant

<400> SEQUENCE: 23

```
Leu Ser Met Val Asn Glu Leu Arg Gln Ile Val Ser Ile Gln Gly Asp
 1               5                  10                  15

Pro Ser Gln Arg Ile Ala Ala Tyr Met Val Glu Gly Leu Ala Ala Arg
                20                  25                  30

Met Ala Ala Ser Gly Lys Phe Ile Tyr Arg Ala Leu Lys Cys Lys Glu
            35                  40                  45

Pro Pro Ser Asp Glu Arg Leu Ala Ala Met Gln Val Leu Phe Glu Val
        50                  55                  60

Cys Pro Cys Phe Lys Phe Gly Phe Leu Ala Ala Asn Gly Ala Ile Leu
65                  70                  75                  80

Glu Ala Ile Lys Gly Glu Glu Val His Ile Ile Asp Phe Asp Ile
                85                  90                  95

Asn Gln Gly Asn Gln Tyr Met Thr Leu Ile Arg Ser Ile Ala Glu Leu
            100                 105                 110

Pro Gly Lys Arg Pro Arg Leu Arg Leu Thr Gly Ile Asp Asp Pro Glu
        115                 120                 125

Ser Val Gln Arg Ser Ile Gly Gly Leu Arg Ile Ile Asn Leu Arg Leu
130                 135                 140

Glu Gln Leu Ala Glu Asp Asn Gly Val Ser Phe Lys Phe Lys Ala Met
145                 150                 155                 160

Pro Ser Lys Thr Ser Ile Val Ser Pro Ser Thr Leu Gly Cys Lys Pro
                165                 170                 175

Gly Glu Thr Leu Ile Val Asn Phe Ala Phe Gln Leu His His Met Pro
            180                 185                 190

Asp Glu Ser Val Thr Thr Val Asn Gln Arg Asp Glu Leu Leu Met
        195                 200                 205

Val Lys Ser Leu Asn Pro Leu Val Thr Val Glu Gln Asp Val Asn
    210                 215                 220

Thr Asn Thr Ser Pro Phe Phe Pro Arg Phe Ile Glu Ala Tyr Glu Tyr
225                 230                 235                 240

Tyr Ser Ala Val Phe Glu Ser Leu Asp Met Thr Leu Pro Arg Glu Ser
                245                 250                 255

Gln Glu Arg Met Asn Val Glu Arg Gln Cys Leu Ala Arg Asp Ile Val
            260                 265                 270
```

```
Asn Ile Val Ala Cys Glu Gly Glu Arg Ile Glu Arg Tyr Glu Ala
            275                 280                 285

Ala Gly Lys Trp Arg Ala Arg Met Met Met Ala Gly Phe Asn Pro Lys
        290                 295                 300

Pro Met Ser Ala Lys Val Thr Asn Asn Ile Gln Asn Leu Ile Lys Gln
305                 310                 315                 320

Gln Tyr Cys Asn Lys Tyr Lys Leu Lys Glu Met Gly Glu Leu His
                325                 330                 335

Phe Cys Trp Glu Glu Lys Ser Leu Ile Val Ala Ser Ala Trp Arg
            340                 345                 350
```

<210> SEQ ID NO 24
<211> LENGTH: 100
<212> TYPE: DNA
<213> ORGANISM: Plant

<400> SEQUENCE: 24

```
ccaggaggcg ttcgagcggg aggagcgtgt gcacatcatc gacctcgaca tcatgcaggg    60
gctgcagtgg ccgggcctcc tccacatcct gcctcccgc                          100
```

<210> SEQ ID NO 25
<211> LENGTH: 33
<212> TYPE: PRT
<213> ORGANISM: Plant

<400> SEQUENCE: 25

```
Gln Glu Ala Phe Glu Arg Glu Arg Val His Ile Ile Asp Leu Asp
  1               5                  10                  15

Ile Met Gln Gly Leu Gln Trp Pro Gly Leu Phe His Ile Leu Ala Ser
                20                  25                  30

Arg
```

<210> SEQ ID NO 26
<211> LENGTH: 1094
<212> TYPE: DNA
<213> ORGANISM: Plant

<400> SEQUENCE: 26

```
ccacgcgtcc gtcaaaggat acaaccatgt acacataatt gacttttccc tgatgcaagg    60
tctccagtgg ccggcactca tggatgtctt ctccgcccgt gagggtgggc accaaaagct   120
ccgaatcaca ggcattggcc cgaacccaat aggtggccgt gacgagctcc atgaagtggg   180
aattcgcctc gccaagtatg cacactcggt gggtatcgac ttcactttcc agggagtctg   240
tgtcgatcaa cttgataggt tgtgcgactg gatgcttctc aaaccaatca aggagaggc    300
agttgccata aactccatcc tacaactcca tcgcctcctc gttgacccag atgcaaaccc   360
agtggtgccc gcaccaatag atatcctcct caaattggtc atcaagataa accccatgat   420
cttcacggtg gttgagcatg aggcagatca acagaccca ccactactag agaggttcac    480
taatgccctc ttccactatg cgaccatgtt tgactctttg gaggccatgc atcgttgtac   540
cagtggtaga gacatcaccg actcactcac agaggtgtac cttcgaggtg agattttga    600
cattgtctgc ggcgagggca gtgcacgcac cgaacgtcat gagttgtttg gtcactggag   660
ggagaggctc acctatgctg gctaactca gtgtggttc gaccccgatg aggttgacac    720
gctaaaagac cagttgatcc atgtgacatc cttatctggc tctgggttca acatcctagt   780
gtgtgatggc agccttgcac tagcgtggca taatcgcccg ttatatgtgg caacagcttg   840
```

-continued

```
gtgtgtgaca ggaggaaatg ctgccagttc catggttggc aacatctgta agggtacaaa    900
tgatagtaga agaaaggaaa accgtaatgg acccatggag tagcaggaag aataaccatg    960
tcatgagcaa atcgatcaag taataaaatg cactgatgac atgcatggtg atctaaagtt   1020
tttttgcgtg aatgtgcaat gacgaattgt tcaatttgaa taacctaatc atgagactca   1080
aaaaaaaaaa aaaa                                                     1094
```

<210> SEQ ID NO 27
<211> LENGTH: 313
<212> TYPE: PRT
<213> ORGANISM: Plant

<400> SEQUENCE: 27

```
His Ala Ser Val Lys Gly Tyr Asn His Val His Ile Ile Asp Phe Ser
 1               5                  10                  15

Leu Met Gln Gly Leu Gln Trp Pro Ala Leu Met Asp Val Phe Ser Ala
                20                  25                  30

Arg Glu Gly Gly Pro Pro Lys Leu Arg Ile Thr Gly Ile Gly Pro Asn
            35                  40                  45

Pro Ile Gly Gly Arg Asp Glu Leu His Glu Val Gly Ile Arg Leu Ala
        50                  55                  60

Lys Tyr Ala His Ser Val Gly Ile Asp Phe Thr Phe Gln Gly Val Cys
 65                  70                  75                  80

Val Asp Gln Leu Asp Arg Leu Cys Asp Trp Met Leu Leu Lys Pro Ile
                85                  90                  95

Lys Gly Glu Ala Val Ala Ile Asn Ser Ile Leu Gln Leu His Arg Leu
            100                 105                 110

Leu Val Asp Pro Asp Ala Asn Pro Val Val Pro Ala Pro Ile Asp Ile
        115                 120                 125

Leu Leu Lys Leu Val Ile Lys Ile Asn Pro Met Ile Phe Thr Val Val
    130                 135                 140

Glu His Glu Ala Asp His Asn Arg Pro Pro Leu Leu Glu Arg Phe Thr
145                 150                 155                 160

Asn Ala Leu Phe His Tyr Ala Thr Met Phe Asp Ser Leu Glu Ala Met
                165                 170                 175

His Arg Cys Thr Ser Gly Arg Asp Ile Thr Asp Ser Leu Thr Glu Val
            180                 185                 190

Tyr Leu Arg Gly Glu Ile Phe Asp Ile Val Cys Gly Glu Gly Ser Ala
        195                 200                 205

Arg Thr Glu Arg His Glu Leu Phe Gly His Trp Arg Glu Arg Leu Thr
    210                 215                 220

Tyr Ala Gly Leu Thr Gln Val Trp Phe Asp Pro Asp Glu Val Asp Thr
225                 230                 235                 240

Leu Lys Asp Gln Leu Ile His Val Thr Ser Leu Ser Gly Ser Gly Phe
                245                 250                 255

Asn Ile Leu Val Cys Asp Gly Ser Leu Ala Leu Ala Trp His Asn Arg
            260                 265                 270

Pro Leu Tyr Val Ala Thr Ala Trp Cys Val Thr Gly Gly Asn Ala Ala
        275                 280                 285

Ser Ser Met Val Gly Asn Ile Cys Lys Gly Thr Asn Asp Ser Arg Arg
    290                 295                 300

Lys Glu Asn Arg Asn Gly Pro Met Glu
305                 310
```

-continued

```
<210> SEQ ID NO 28
<211> LENGTH: 611
<212> TYPE: DNA
<213> ORGANISM: Plant

<400> SEQUENCE: 28
cccaacttgg gaagcccttc ctccgctccg cctcctacct caaggaggcc ctcctcctcg     60
cactcgccga cagccaccat ggctcctccg cgtcacctc gccgctcgac gttgccctca    120
agcttgcagc atacaagtct ttctctgacc tgtcacctgt gctccagttc actaacttta    180
ccgcaacaag gcgcttcttg atgagattgg tggcatggca acttcctgca tccatgtcat    240
tgactttgat ctcggtgttg gtggtcagtg ggcttccttc ttgcaggagc ttgcccaccg    300
ccggggagct ggaggtatgg ccttgccgtt gttgaagctc acggctttca gtcgactgc    360 ttctcaccat ccactggagc tgcaccttac ccaggataac ctctctcagt ttgccgcaga    420
gctcagaatt cctttcgaat tcaatgccgt cagtcttgat gcattcaatc ctgcggaatc    480
tatttcttcc tctggtgatg aagttgttgc tgttagcctc cctgttggct gctctgctcg    540
tgcaccaccg ctgccagcga ttcttcggtt ggtgaaacag ctttgtccta aggttgtcgt    600
ggctattgat c                                                        611

<210> SEQ ID NO 29
<211> LENGTH: 502
<212> TYPE: DNA
<213> ORGANISM: Plant

<400> SEQUENCE: 29
tttttttttt tttttttttt tttttttttt tacagagcaa cagcagtata atattaattc     60
tgtaccacac aaccatttga taggttaaat taccctctag tctctactca taagcagtgt    120
ttccaatgag atgatcatgg ctaattgagc agagcatggc aacaacctaa agcaacatca    180
ttagctatag agactgacac caatattcct aaatccacta ggctagctaa taagctgcaa    240
cgaaaagcaa tatgaagagt tcaacagctc aagacaacaa tttcatttgc aacatttaat    300
tgcaagaata aatggacatt actggagtgg tcgatgcttg caaacggtgg tggaaccttg    360
gtggagtgaa gcttatggct gatcagcacc gccaagatga tatggataca agctccccac    420
gctgccagta gagcgtaaga gcagctccgc gtttctccac atggaatcct cggacctgca    480
cccgcttcag gaggcagtct gc                                            502

<210> SEQ ID NO 30
<211> LENGTH: 298
<212> TYPE: PRT
<213> ORGANISM: Plant

<400> SEQUENCE: 30

Pro Gln Gln Gln Gln His Gln Gln Gln Gln Gln His Lys Pro
 1               5                  10                  15

Pro Pro Pro Ile Gln Gln Gln Glu Arg Glu Asn Ser Ser Thr Asp
            20                  25                  30

Ala Pro Pro Gln Pro Glu Thr Val Thr Ala Thr Val Pro Ala Val Gln
        35                  40                  45

Thr Asn Thr Ala Glu Ala Leu Arg Glu Arg Lys Glu Glu Ile Lys Arg
    50                  55                  60

Gln Lys Gln Asp Glu Glu Gly Leu His Leu Leu Thr Leu Leu Leu Gln
65                  70                  75                  80

Cys Ala Glu Ala Val Ser Ala Asp Asn Leu Glu Glu Ala Asn Lys Leu
```

```
                    85                  90                  95
Leu Leu Glu Ile Ser Gln Leu Ser Thr Pro Tyr Gly Thr Ser Ala Gln
                100                 105                 110
Arg Val Ala Ala Tyr Phe Ser Glu Ala Met Ser Ala Arg Leu Leu Asn
            115                 120                 125
Ser Cys Leu Gly Ile Tyr Ala Ala Leu Pro Ser Arg Trp Met Pro Gln
        130                 135                 140
Thr His Ser Leu Lys Met Val Ser Ala Phe Gln Val Phe Asn Gly Ile
145                 150                 155                 160
Ser Pro Leu Val Lys Phe Ser His Phe Thr Ala Asn Gln Ala Ile Gln
                165                 170                 175
Glu Ala Phe Glu Lys Glu Asp Ser Val His Ile Ile Asp Leu Asp Ile
            180                 185                 190
Met Gln Gly Leu Gln Trp Pro Gly Leu Phe His Ile Leu Ala Ser Arg
        195                 200                 205
Pro Gly Gly Pro Pro His Val Arg Leu Thr Gly Leu Gly Thr Ser Met
    210                 215                 220
Glu Ala Leu Gln Ala Thr Gly Lys Arg Leu Ser Asp Phe Thr Asp Lys
225                 230                 235                 240
Leu Gly Leu Pro Phe Glu Phe Cys Pro Leu Ala Glu Lys Val Gly Asn
                245                 250                 255
Asp Leu Thr Glu Arg Leu Asn Val Arg Lys Arg Glu Ala Ala Val His
            260                 265                 270
Trp Leu Gln His Ser Leu Tyr Asp Val Thr Gly Ser Asp Ala His Thr
        275                 280                 285
Leu Trp Leu Leu Gln Arg Leu Ala Pro Lys
    290                 295

<210> SEQ ID NO 31
<211> LENGTH: 307
<212> TYPE: PRT
<213> ORGANISM: Plant
<220> FEATURE:
<221> NAME/KEY: VARIANT
<222> LOCATION: (1)...(307)
<223> OTHER INFORMATION: Xaa = Any Amino Acid

<400> SEQUENCE: 31

Gly Thr Ser Pro Thr Gly Pro Glu Leu Leu Thr Tyr Met His Ile Leu
1               5                   10                  15
Tyr Glu Ala Cys Pro Tyr Phe Lys Phe Gly Tyr Glu Ser Ala Asn Gly
                20                  25                  30
Ala Ile Ala Glu Ala Val Lys Asn Glu Ser Phe Val His Ile Ile Asp
            35                  40                  45
Phe Gln Ile Ser Gln Gly Gly Gln Trp Val Ser Leu Ile Arg Ala Leu
        50                  55                  60
Gly Ala Arg Pro Gly Gly Pro Pro Asn Val Arg Ile Thr Gly Ile Asp
65                  70                  75                  80
Asp Pro Arg Ser Ser Phe Ala Arg Gln Gly Gly Leu Glu Leu Val Gly
                85                  90                  95
Gln Arg Leu Gly Lys Leu Ala Glu Met Cys Gly Val Pro Phe Glu Phe
            100                 105                 110
His Gly Ala Ala Leu Cys Cys Thr Glu Val Glu Ile Glu Lys Leu Gly
        115                 120                 125
Val Arg Asn Gly Glu Ala Leu Ala Val Asn Phe Pro Leu Val Leu His
    130                 135                 140
```

```
His Met Pro Asp Glu Ser Val Thr Val Glu Asn His Arg Asp Arg Leu
145                 150                 155                 160

Leu Arg Leu Val Lys His Leu Ser Pro Asn Val Val Thr Leu Val Glu
                165                 170                 175

Gln Glu Ala Asn Thr Asn Thr Ala Pro Phe Leu Pro Arg Phe Val Glu
            180                 185                 190

Thr Met Asn His Tyr Leu Ala Val Phe Glu Ser Ile Asp Val Lys Leu
        195                 200                 205

Ala Arg Asp His Lys Glu Arg Ile Asn Val Gln His Cys Leu Ala
210                 215                 220

Arg Glu Val Val Asn Leu Ile Ala Cys Glu Gly Val Glu Arg Glu Glu
225                 230                 235                 240

Arg His Glu Pro Leu Gly Lys Trp Arg Ser Arg Phe His Met Ala Gly
                245                 250                 255

Phe Lys Pro Tyr Pro Leu Ser Ser Tyr Val Asn Ala Thr Ile Lys Gly
            260                 265                 270

Leu Leu Glu Ser Tyr Ser Glu Lys Tyr Thr Leu Glu Glu Arg Asp Gly
        275                 280                 285

Ala Leu Tyr Leu Gly Trp Lys Asn Gln Pro Leu Ile Thr Ser Cys Ala
    290                 295                 300

Trp Arg Xaa
305

<210> SEQ ID NO 32
<211> LENGTH: 353
<212> TYPE: PRT
<213> ORGANISM: Plant
<220> FEATURE:
<221> NAME/KEY: VARIANT
<222> LOCATION: (1)...(353)
<223> OTHER INFORMATION: Xaa = Any Amino Acid

<400> SEQUENCE: 32

Leu Ser Met Val Asn Glu Leu Arg Gln Ile Val Ser Ile Gln Gly Asp
1               5                   10                  15

Pro Ser Gln Arg Ile Ala Ala Tyr Met Val Glu Gly Leu Ala Ala Arg
                20                  25                  30

Met Ala Ala Ser Gly Lys Phe Ile Tyr Arg Ala Leu Lys Cys Lys Glu
            35                  40                  45

Pro Pro Ser Asp Glu Arg Leu Ala Ala Met Gln Val Leu Phe Glu Val
        50                  55                  60

Cys Pro Cys Phe Lys Phe Gly Phe Leu Ala Ala Asn Gly Ala Ile Leu
65                  70                  75                  80

Glu Ala Ile Lys Gly Glu Glu Val His Ile Ile Asp Phe Asp Ile
                85                  90                  95

Asn Gln Gly Asn Gln Tyr Met Thr Leu Ile Arg Ser Ile Ala Glu Leu
            100                 105                 110

Pro Gly Lys Arg Pro Arg Leu Arg Leu Thr Gly Ile Asp Asp Pro Glu
        115                 120                 125

Ser Val Gln Arg Ser Ile Gly Gly Leu Arg Ile Ile Gly Leu Arg Leu
    130                 135                 140

Glu Gln Leu Ala Glu Asp Asn Gly Val Ser Phe Lys Phe Lys Ala Met
145                 150                 155                 160

Pro Ser Lys Thr Ser Ile Val Ser Pro Ser Thr Leu Gly Cys Lys Pro
                165                 170                 175
```

```
Gly Glu Thr Leu Ile Val Asn Phe Ala Phe Gln Leu His His Met Pro
            180                 185                 190

Asp Glu Ser Val Thr Thr Val Asn Gln Arg Asp Glu Leu Leu His Met
            195                 200                 205

Val Lys Ser Leu Asn Pro Lys Leu Val Thr Val Glu Gln Asp Val
210                 215                 220

Asn Thr Asn Thr Ser Pro Phe Pro Arg Phe Ile Glu Ala Tyr Glu
225                 230                 235                 240

Tyr Tyr Ser Ala Val Phe Glu Ser Leu Asp Met Thr Leu Pro Arg Glu
            245                 250                 255

Ser Gln Glu Arg Met Asn Val Glu Arg Gln Cys Leu Ala Arg Asp Ile
            260                 265                 270

Val Asn Ile Val Ala Cys Glu Gly Glu Arg Ile Glu Arg Tyr Glu
            275                 280                 285

Ala Ala Gly Lys Trp Arg Ala Arg Met Met Met Ala Gly Phe Asn Pro
            290                 295                 300

Lys Pro Met Ser Ala Lys Val Thr Asn Asn Ile Gln Asn Leu Ile Lys
305                 310                 315                 320

Gln Gln Tyr Cys Asn Lys Tyr Lys Leu Lys Glu Glu Met Gly Glu Leu
            325                 330                 335

His Phe Cys Trp Glu Glu Lys Ser Leu Ile Val Ala Ser Ala Trp Arg
            340                 345                 350

Xaa

<210> SEQ ID NO 33
<211> LENGTH: 326
<212> TYPE: PRT
<213> ORGANISM: Plant
<220> FEATURE:
<221> NAME/KEY: VARIANT
<222> LOCATION: (1)...(326)
<223> OTHER INFORMATION: Xaa = Any Amino Acid

<400> SEQUENCE: 33

Ala Met Glu Gly Glu Lys Met Val His Val Ile Asp Leu Asp Ala Ser
 1               5                  10                  15

Glu Pro Ala Gln Trp Leu Ala Leu Leu Gln Ala Phe Asn Ser Arg Pro
            20                  25                  30

Glu Gly Pro Pro His Leu Arg Ile Thr Gly Val His His Gln Lys Glu
            35                  40                  45

Val Leu Glu Gln Met Ala His Arg Leu Ile Glu Glu Ala Glu Lys Leu
50                  55                  60

Asp Ile Pro Phe Gln Phe Asn Pro Val Val Ser Arg Leu Asp Cys Leu
65                  70                  75                  80

Asn Val Glu Gln Leu Arg Val Lys Thr Gly Glu Ala Leu Ala Val Ser
            85                  90                  95

Ser Val Leu Gln Leu His Thr Phe Leu Ala Ser Asp Asp Leu Met
            100                 105                 110

Arg Lys Asn Cys Ala Leu Arg Phe Gln Asn Asn Pro Ser Gly Val Asp
            115                 120                 125

Leu Gln Arg Val Leu Met Met Ser His Gly Ser Ala Ala Glu Ala Arg
            130                 135                 140

Glu Asn Asp Met Ser Asn Asn Gly Tyr Ser Pro Ser Gly Asp Ser
145                 150                 155                 160

Ala Ser Ser Leu Pro Leu Pro Ser Ser Gly Arg Thr Asp Ser Phe Leu
            165                 170                 175
```

```
Asn Ala Ile Trp Gly Leu Ser Pro Lys Val Met Val Thr Glu Gln
                180                 185                 190

Asp Ser Asp His Asn Gly Ser Thr Leu Met Glu Arg Leu Leu Glu Ser
            195                 200                 205

Leu Tyr Thr Tyr Ala Ala Leu Phe Asp Cys Leu Glu Thr Lys Val Pro
        210                 215                 220

Arg Thr Ser Gln Asp Arg Ile Lys Val Glu Lys Met Leu Phe Gly Glu
225                 230                 235                 240

Glu Ile Lys Asn Ile Ile Ser Cys Glu Gly Phe Glu Arg Arg Glu Arg
                245                 250                 255

His Glu Lys Leu Glu Lys Trp Ser Gln Arg Ile Asp Leu Ala Gly Phe
            260                 265                 270

Gly Asn Val Pro Leu Ser Tyr Tyr Ala Met Leu Gln Ala Arg Arg Leu
        275                 280                 285

Leu Gln Gly Cys Gly Phe Asp Gly Tyr Arg Ile Lys Glu Glu Ser Gly
        290                 295                 300

Cys Ala Val Ile Cys Trp Gln Asp Arg Pro Leu Tyr Ser Val Ser Ala
305                 310                 315                 320

Trp Arg Cys Arg Lys Xaa
                325

<210> SEQ ID NO 34
<211> LENGTH: 277
<212> TYPE: PRT
<213> ORGANISM: Plant
<220> FEATURE:
<221> NAME/KEY: VARIANT
<222> LOCATION: (1)...(277)
<223> OTHER INFORMATION: Xaa = Any Amino Acid

<400> SEQUENCE: 34

Asn Lys Arg Leu Lys Ser Cys Ser Ser Pro Asp Ser Met Val Thr Ser
1               5                   10                  15

Thr Ser Thr Gly Thr Gln Ile Gly Gly Val Ile Gly Thr Thr Val Thr
            20                  25                  30

Thr Thr Thr Thr Thr Thr Thr Ala Ala Ala Glu Ser Thr Arg Ser Val
        35                  40                  45

Ile Leu Val Asp Ser Gln Glu Asn Gly Val Arg Leu Val His Ala Leu
    50                  55                  60

Met Ala Cys Ala Glu Ala Ile Gln Gln Asn Asn Leu Thr Leu Ala Glu
65                  70                  75                  80

Ala Leu Val Lys Gln Ile Gly Cys Leu Ala Val Ser Gln Ala Gly Ala
                85                  90                  95

Met Arg Lys Val Ala Thr Tyr Phe Ala Glu Ala Leu Ala Arg Arg Ile
            100                 105                 110

Tyr Arg Leu Ser Pro Pro Gln Asn Gln Ile Asp His Cys Leu Ser Asp
        115                 120                 125

Thr Leu Gln Met His Phe Tyr Glu Thr Cys Pro Tyr Leu Lys Phe Ala
    130                 135                 140

His Phe Thr Ala Asn Gln Ala Ile Leu Glu Ala Phe Glu Gly Lys Lys
145                 150                 155                 160

Arg Val His Val Ile Asp Phe Ser Met Asn Gln Gly Leu Gln Trp Pro
                165                 170                 175

Ala Leu Met Gln Ala Leu Ala Leu Arg Glu Gly Gly Pro Pro Thr Phe
            180                 185                 190
```

-continued

Arg Leu Thr Gly Ile Gly Pro Pro Ala Pro Asp Asn Ser Asp His Leu
            195                 200                 205
His Glu Val Gly Cys Lys Leu Ala Gln Leu Ala Glu Ala Ile His Val
        210                 215                 220
Glu Phe Glu Tyr Arg Gly Phe Val Ala Asn Ser Leu Ala Asp Leu Asp
225                 230                 235                 240
Ala Ser Met Leu Glu Leu Arg Pro Ser Asp Thr Glu Ala Val Ala Val
                245                 250                 255
Asn Ser Val Phe Glu Leu His Lys Leu Leu Gly Arg Xaa Gly Gly Ile
            260                 265                 270
Glu Lys Val Leu Gly
        275

<210> SEQ ID NO 35
<211> LENGTH: 262
<212> TYPE: PRT
<213> ORGANISM: Plant

<400> SEQUENCE: 35

Gly Gly Gly Gly Asp Thr Tyr Thr Thr Asn Lys Arg Leu Lys Cys Ser
1               5                   10                  15
Asn Gly Val Val Glu Thr Thr Thr Ala Thr Ala Glu Ser Thr Arg His
            20                  25                  30
Val Val Leu Val Asp Ser Gln Glu Asn Gly Val Arg Leu Val His Ala
        35                  40                  45
Leu Leu Ala Cys Ala Glu Ala Val Gln Lys Glu Asn Leu Thr Val Ala
    50                  55                  60
Glu Ala Leu Val Lys Gln Ile Gly Phe Leu Ala Val Ser Gln Ile Gly
65                  70                  75                  80
Ala Met Arg Gln Val Ala Thr Tyr Phe Ala Glu Ala Leu Ala Arg Arg
                85                  90                  95
Ile Tyr Arg Leu Ser Pro Ser Gln Ser Pro Ile Asp His Ser Leu Ser
            100                 105                 110
Asp Thr Leu Gln Met His Phe Tyr Glu Thr Cys Pro Tyr Leu Lys Phe
        115                 120                 125
Ala His Phe Thr Ala Asn Gln Ala Ile Leu Glu Ala Phe Gln Gly Lys
    130                 135                 140
Lys Arg Val His Val Ile Asp Phe Ser Met Ser Gln Gly Leu Gln Trp
145                 150                 155                 160
Pro Ala Leu Met Gln Ala Leu Ala Leu Arg Pro Gly Gly Pro Pro Val
                165                 170                 175
Phe Arg Leu Thr Gly Ile Gly Pro Pro Ala Pro Asp Asn Phe Asp Tyr
            180                 185                 190
Leu His Glu Val Gly Cys Lys Leu Ala His Leu Ala Glu Ala Ile His
        195                 200                 205
Val Glu Phe Glu Tyr Arg Gly Phe Val Ala Asn Thr Leu Ala Asp Leu
    210                 215                 220
Asp Ala Ser Met Leu Glu Leu Arg Pro Ser Glu Ile Glu Ser Val Ala
225                 230                 235                 240
Val Asn Ser Val Phe Glu Leu His Lys Leu Leu Gly Arg Pro Gly Ala
                245                 250                 255
Ile Asp Lys Val Leu Gly
            260

<210> SEQ ID NO 36

```
<211> LENGTH: 203
<212> TYPE: PRT
<213> ORGANISM: Plant

<400> SEQUENCE: 36

Gln Leu Gly Lys Pro Phe Leu Arg Ser Ala Ser Tyr Leu Lys Glu Ala
1               5                   10                  15

Leu Leu Leu Ala Leu Ala Asp Ser His His Gly Ser Ser Gly Val Thr
            20                  25                  30

Ser Pro Leu Asp Val Ala Leu Lys Leu Ala Ala Tyr Lys Ser Phe Ser
        35                  40                  45

Asp Leu Ser Pro Val Leu Gln Phe Thr Asn Phe Thr Ala Asn Lys Ala
    50                  55                  60

Leu Leu Asp Glu Ile Gly Gly Met Ala Thr Ser Cys Ile His Val Ile
65                  70                  75                  80

Asp Phe Asn Leu Gly Val Gly Gly Gln Trp Ala Ser Phe Leu Gln Glu
                85                  90                  95

Leu Ala His Arg Arg Gly Ala Gly Gly Met Ala Leu Pro Leu Leu Lys
            100                 105                 110

Leu Thr Ala Phe Met Ser Thr Ala Ser His His Pro Leu Glu Leu His
        115                 120                 125

Leu Thr Gln Asp Asn Leu Ser Gln Phe Ala Ala Glu Leu Arg Ile Pro
    130                 135                 140

Phe Glu Phe Asn Ala Val Ser Leu Asp Ala Phe Asn Pro Ala Glu Ser
145                 150                 155                 160

Ile Ser Ser Ser Gly Asp Glu Val Val Ala Val Ser Leu Pro Val Gly
                165                 170                 175

Cys Ser Ala Arg Ala Pro Pro Leu Pro Ala Ile Leu Arg Leu Val Lys
            180                 185                 190

Gln Leu Cys Pro Lys Val Val Val Ala Ile Asp
        195                 200

<210> SEQ ID NO 37
<211> LENGTH: 131
<212> TYPE: PRT
<213> ORGANISM: Plant

<400> SEQUENCE: 37

His Ala Ser Val Lys Gly Tyr Asn His Val His Ile Ile Asp Phe Ser
1               5                   10                  15

Leu Met Gln Gly Leu Gln Trp Pro Ala Leu Met Asp Val Phe Ser Ala
            20                  25                  30

Arg Glu Gly Gly Pro Pro Lys Leu Arg Ile Thr Gly Ile Gly Pro Asn
        35                  40                  45

Pro Ile Gly Gly Arg Asp Glu Leu His Glu Val Gly Ile Arg Leu Ala
    50                  55                  60

Lys Tyr Ala His Ser Val Gly Ile Asp Phe Thr Phe Gln Gly Val Cys
65                  70                  75                  80

Val Asp Gln Leu Asp Arg Leu Cys Asp Trp Met Leu Lys Pro Ile
                85                  90                  95

Lys Gly Glu Ala Val Ala Ile Asn Ser Ile Leu Gln Leu His Arg Leu
            100                 105                 110

Leu Val Asp Pro Asp Ala Asn Pro Val Val Pro Ala Pro Ile Asp Ile
        115                 120                 125

Leu Leu Lys
    130
```

<210> SEQ ID NO 38
<211> LENGTH: 33
<212> TYPE: PRT
<213> ORGANISM: Plant

<400> SEQUENCE: 38

Gln Glu Ala Phe Glu Arg Glu Arg Val His Ile Ile Asp Leu Asp
1               5                   10                  15

Ile Met Gln Gly Leu Gln Trp Pro Gly Leu Phe His Ile Leu Ala Ser
                20                  25                  30

Arg

<210> SEQ ID NO 39
<211> LENGTH: 29
<212> TYPE: PRT
<213> ORGANISM: Plant
<220> FEATURE:
<221> NAME/KEY: VARIANT
<222> LOCATION: (1)...(29)
<223> OTHER INFORMATION: Xaa = Any Amino Acid

<400> SEQUENCE: 39

Phe Ala Gly Cys Arg Arg Val His Val Val Asp Phe Gly Ile Lys Gln
1               5                   10                  15

Gly Met Gln Trp Pro Ala Leu Leu Xaa Asp Leu Ala Leu
                20                  25

<210> SEQ ID NO 40
<211> LENGTH: 73
<212> TYPE: PRT
<213> ORGANISM: Plant
<220> FEATURE:
<221> NAME/KEY: VARIANT
<222> LOCATION: (1)...(73)
<223> OTHER INFORMATION: Xaa = Any Amino Acid

<400> SEQUENCE: 40

Gly Arg Asn Gly Arg Thr Leu Trp Leu Gly Glu Gly His Ile Asp Leu
1               5                   10                  15

Trp Pro Leu Gln Gly Leu Leu Ser Gln Gly Leu Gln Arg Ala Leu Cys
                20                  25                  30

Ala Arg Pro Leu Gly Ala Pro His Val Phe Leu Pro Gly Leu His Thr
            35                  40                  45

Leu Ser Leu Gly Leu Gln Xaa Arg His Leu Leu Val His Met Met Ala
    50                  55                  60

Leu Ser Tyr Ser Tyr Gly Arg Xaa Pro
65                  70

<210> SEQ ID NO 41
<211> LENGTH: 59
<212> TYPE: PRT
<213> ORGANISM: Plant

<400> SEQUENCE: 41

Thr Ser Asp Ser Ala Ser Ser Phe Asn Ile Pro Thr Ser Ala Gln Asn
1               5                   10                  15

His Tyr Ala Thr Gly Ser Phe Ser Thr Asn Ser Arg Thr Thr Asn Val
                20                  25                  30

Ala Thr Ala Thr Thr Asn Ser Ala Thr Ala His Trp Val Ala Thr Asp
            35                  40                  45

```
Ala Glu His Thr Asp Thr Ile Ile Ala Gln Pro
    50                  55
```

<210> SEQ ID NO 42
<211> LENGTH: 110
<212> TYPE: PRT
<213> ORGANISM: Plant
<220> FEATURE:
<221> NAME/KEY: VARIANT
<222> LOCATION: (1)...(110)
<223> OTHER INFORMATION: Xaa = Any Amino Acid

<400> SEQUENCE: 42

```
Arg Xaa Phe Asp Ser Leu Glu His Asp Ala Ser Lys Gly Glu Pro Arg
 1               5                  10                  15

Glu Asp Glu Arg Gly Arg Xaa Cys Leu Ala Arg Asn Ile Val Asn Ile
            20                  25                  30

Val Xaa Cys Lys Xaa Glu Glu Arg Ile Glu Arg Tyr Glu Val Thr Gly
        35                  40                  45

Lys Trp Arg Ala Arg Met Met Met Ala Gly Phe Ser Pro Arg Pro Met
    50                  55                  60

Ser Gly Arg Val Thr Ser Asn Ile Glu Ser Leu Ile Lys Arg Asp Tyr
65                  70                  75                  80

Cys Ser Lys Tyr Lys Val Lys Glu Glu Met Gly Glu Leu His Phe Ser
                85                  90                  95

Trp Glu Glu Lys Ser Leu Ile Val Ala Ser Ala Trp Ser Xaa
            100                 105                 110
```

<210> SEQ ID NO 43
<211> LENGTH: 137
<212> TYPE: PRT
<213> ORGANISM: Plant
<220> FEATURE:
<221> NAME/KEY: VARIANT
<222> LOCATION: (1)...(137)
<223> OTHER INFORMATION: Xaa = Any Amino Acid

<400> SEQUENCE: 43

```
Asn Gly Ser Tyr Asn Ala Pro Phe Phe Val Thr Arg Phe Arg Glu Ala
 1               5                  10                  15

Leu Phe His Tyr Ser Ala Ile Phe Asp Met Leu Glu Thr Asn Ile Pro
            20                  25                  30

Lys Asp Asn Glu Gln Arg Leu Leu Ile Glu Ser Ala Leu Phe Ser Arg
        35                  40                  45

Glu Xaa Asn Val Ile Ser Cys Glu Gly Leu Glu Arg Met Glu Arg Pro
    50                  55                  60

Glu Thr Tyr Lys Gln Trp Gln Val Arg Asn Gln Arg Val Gly Phe Lys
65                  70                  75                  80

Gln Leu Pro Leu Asn Gln Asp Met Met Lys Arg Ala Arg Xaa Glu Gly
                85                  90                  95

Gln Val Leu Pro Thr Arg Thr Phe Ile Ile Asp Glu Asp Asn Arg Trp
            100                 105                 110

Leu Leu Gln Gly Trp Lys Gly Arg Ile Leu Phe Ala Leu Ser Thr Trp
        115                 120                 125

Lys Pro Asp Asn Arg Ser Ser Xaa
    130                 135
```

<210> SEQ ID NO 44
<211> LENGTH: 41
<212> TYPE: PRT

<213> ORGANISM: Plant

<400> SEQUENCE: 44

Asn Gly Gly Ala Phe Ala Pro Ser Thr Trp Thr Ala Arg Ser Leu Asn
 1               5                  10                  15

Gly Gly Ala Phe Ala Pro Ser Thr Trp Thr Ala Arg Ser Leu Pro Val
            20                  25                  30

Pro Ser Ser Pro Ser Thr Asp Ser Phe
        35                  40

<210> SEQ ID NO 45
<211> LENGTH: 1279
<212> TYPE: DNA
<213> ORGANISM: Plant

<400> SEQUENCE: 45

| | | |
|---|---|---|
| gcggctatct tctacggcca ccaccaccat acacctccgc cggcaaagcg gctcaaccct | 60 |
| ggtcccgtgg ggataacaga gcagctggtt aaggcagcag aggtcataga gagcgacacg | 120 |
| tgtctagctc agggatatt ggcgcggctc aatcaacagc tctcttctcc cgtcgggaag | 180 |
| ccattagaaa gagcagcttt ttacttcaaa gaagctctca ataatctcct tcacaacgtc | 240 |
| tcccaaaccc taaacccta ttccctcatc ttcaagatcg ctgcttacaa atccttctca | 300 |
| gagatctctc ccgttcttca gttcgccaac tttacctcca accaagccct cttagagtcc | 360 |
| ttccatggct tccaccgtct ccacatcatc gacttcgata tcggctacgg tggccaatgg | 420 |
| gcttccctca tgcaagagct tgttctccgc gacaacgccg ctcctctctc cctcaagatc | 480 |
| accgttttcg cttctccggc gaaccacgac cagctcgaac ttggcttcac tcaagacaac | 540 |
| ctcaagcact cgcctctga gatcaacatc tcccttgaca tccaagtttt gagcttagac | 600 |
| ctcctcggct ccatctcgtg gcctaactcg tcggagaaag aagctgtcgc cgttaacatc | 660 |
| tccgccgcgt ccttctcgca cctcccttg gtcctccgtt tcgtgaagca tctatctccg | 720 |
| acgatcatcg tctgctccga cagaggatgc gagaggacgg atctgccctt ctctcaacag | 780 |
| ctcgcccact cgctgcactc acacaccgct ctcttcgaat ccctcgacgc cgtcaacgcc | 840 |
| aacctcgacg caatgcagaa gatcgagagg tttcttatac agccggagat agagaagctg | 900 |
| gtgttggatc gtagccgtcc gatagaaagg ccgatgatga cgtggcaagc gatgtttcta | 960 |
| cagatgggtt tctcaccggt gacgcacagt aacttcacgg agtctcaagc cgagtgttta | 1020 |
| gtccaacgga cgccagtgag aggctttcac gtcgagaaga aacataactc acttctccta | 1080 |
| tgttggcaaa ggacagaact cgtcggagtt tcagcatgga gatgtcgctc ctcctgattt | 1140 |
| ccaccggagt ttcaattatt aaaaaaatat tttccttaat tcaatttatc ttaaatgaca | 1200 |
| aattttagt ttctgatttt attttgctca gtgcgatgga ttttaaatt taagtttcac | 1260 |
| acaaatatat aaattttg | 1279 |

<210> SEQ ID NO 46
<211> LENGTH: 379
<212> TYPE: PRT
<213> ORGANISM: Plant
<220> FEATURE:
<221> NAME/KEY: VARIANT
<222> LOCATION: (1)...(379)
<223> OTHER INFORMATION: Xaa = Any Amino Acid

<400> SEQUENCE: 46

Ala Ala Ile Phe Tyr Gly His His His Thr Pro Pro Pro Ala Lys
 1               5                  10                  15

-continued

```
Arg Leu Asn Pro Gly Pro Val Gly Ile Thr Glu Gln Leu Val Lys Ala
             20                  25                  30
Ala Glu Val Ile Glu Ser Asp Thr Cys Leu Ala Gln Gly Ile Leu Ala
         35                  40                  45
Arg Leu Asn Gln Gln Leu Ser Ser Pro Val Gly Lys Pro Leu Glu Arg
     50                  55                  60
Ala Ala Phe Tyr Phe Lys Glu Ala Leu Asn Asn Leu Leu His Asn Val
 65                  70                  75                  80
Ser Gln Thr Leu Asn Pro Tyr Ser Leu Ile Phe Lys Ile Ala Ala Tyr
                 85                  90                  95
Lys Ser Phe Ser Glu Ile Ser Pro Val Leu Gln Phe Ala Asn Phe Thr
            100                 105                 110
Ser Asn Gln Ala Leu Leu Glu Ser Phe His Gly Phe His Arg Leu His
        115                 120                 125
Ile Ile Asp Phe Asp Ile Gly Tyr Gly Gly Gln Trp Ala Ser Leu Met
    130                 135                 140
Gln Glu Leu Val Leu Arg Asp Asn Ala Ala Pro Leu Ser Leu Lys Ile
145                 150                 155                 160
Thr Val Phe Ala Ser Pro Ala Asn His Asp Gln Leu Glu Leu Gly Phe
                165                 170                 175
Thr Gln Asp Asn Leu Lys His Phe Ala Ser Glu Ile Asn Ile Ser Leu
            180                 185                 190
Asp Ile Gln Val Leu Ser Leu Asp Leu Leu Gly Ser Ile Ser Trp Pro
        195                 200                 205
Asn Ser Ser Glu Lys Glu Ala Val Ala Val Asn Ile Ser Ala Ala Ser
    210                 215                 220
Phe Ser His Leu Pro Leu Val Leu Arg Phe Val Lys His Leu Ser Pro
225                 230                 235                 240
Thr Ile Ile Val Cys Ser Asp Arg Gly Cys Glu Arg Thr Asp Leu Pro
                245                 250                 255
Phe Ser Gln Gln Leu Ala His Ser Leu His Ser His Thr Ala Leu Phe
            260                 265                 270
Glu Ser Leu Asp Ala Val Asn Ala Asn Leu Asp Ala Met Gln Lys Ile
        275                 280                 285
Glu Arg Phe Leu Ile Gln Pro Glu Ile Glu Lys Leu Val Leu Asp Arg
    290                 295                 300
Ser Arg Pro Ile Glu Arg Pro Met Met Thr Trp Gln Ala Met Phe Leu
305                 310                 315                 320
Gln Met Gly Phe Ser Pro Val Thr His Ser Asn Phe Thr Glu Ser Gln
                325                 330                 335
Ala Glu Cys Leu Val Gln Arg Thr Pro Val Arg Gly Phe His Val Glu
            340                 345                 350
Lys Lys His Asn Ser Leu Leu Leu Cys Trp Gln Arg Thr Glu Leu Val
        355                 360                 365
Gly Val Ser Ala Trp Arg Cys Arg Ser Ser Xaa
    370                 375
```

<210> SEQ ID NO 47
<211> LENGTH: 745
<212> TYPE: DNA
<213> ORGANISM: Plant

<400> SEQUENCE: 47
tgcatacaac gcaccgtttt tcgtaacacg gtttcgcgaa gctctatttc atttctcctc     60

```
gatttttgac atgcttgaga caattgtgcc acgagaagac gaagagagga tgttccttga    120
gatggaggtc tttgggagag aggcactgaa tgtgattgct tgcgaaggtt gggaaagagt    180
ggagaggcct gagacataca agcagtggca cgtacgggca atgaggtcag ggttggtgca    240
ggttccattt gacccaagca ttatgaagac atcgctgcat aaggtccaca cattctacca    300
caaggatttt gtgatcgatc aagataaccg gtggctcttg caaggctgga agggaagaac    360
tgtcatggct ctttctgttt ggaaaccaga gtccaaggct tgaccgagaa atcctcgttg    420
gcatatgaga gaccatctct tgattttctt cctgtgtaat tcccagagac agaattacag    480
atgtaagaag agaatgctgc acaaagaact tgttcaaaga taatattgat gtaagtcctg    540
ttttataact ttctagctgt gtttttgttg tttctcagct agattctcct aacggtattc    600
ttgtagctag ggtgatcaga ttgtttgtat attgctagca gagttagttt gtctagattg    660
taacacatat aagaggaagc ttagagtttc tatggtttaa agagaagttt tttccttctc    720
caatgtaaaa aaaaaaaaaa aaaaa                                          745

<210> SEQ ID NO 48
<211> LENGTH: 134
<212> TYPE: PRT
<213> ORGANISM: Plant
<220> FEATURE:
<221> NAME/KEY: VARIANT
<222> LOCATION: (1)...(134)
<223> OTHER INFORMATION: Xaa = Any Amino Acid

<400> SEQUENCE: 48

Ala Tyr Asn Ala Pro Phe Phe Val Thr Arg Phe Arg Glu Ala Leu Phe
  1               5                  10                  15

His Phe Ser Ser Ile Phe Asp Met Leu Glu Thr Ile Val Pro Arg Glu
                 20                  25                  30

Asp Glu Glu Arg Met Phe Leu Glu Met Glu Val Phe Gly Arg Glu Ala
             35                  40                  45

Leu Asn Val Ile Ala Cys Glu Gly Trp Glu Arg Val Glu Arg Pro Glu
         50                  55                  60

Thr Tyr Lys Gln Trp His Val Arg Ala Met Arg Ser Gly Leu Val Gln
 65                  70                  75                  80

Val Pro Phe Asp Pro Ser Ile Met Lys Thr Ser Leu His Lys Val His
                 85                  90                  95

Thr Phe Tyr His Lys Asp Phe Val Ile Asp Gln Asp Asn Arg Trp Leu
            100                 105                 110

Leu Gln Gly Trp Lys Gly Arg Thr Val Met Ala Leu Ser Val Trp Lys
        115                 120                 125

Pro Glu Ser Lys Ala Xaa
    130

<210> SEQ ID NO 49
<211> LENGTH: 775
<212> TYPE: DNA
<213> ORGANISM: Plant

<400> SEQUENCE: 49
aaaaaatggg aaaccatcac tcttgatgaa cttatgatca atccaggaga gacaacggtc     60
gtcaactgca ttcatcggtt acaatacact cctgatgaaa ctgtgtcatt agactctcca    120
agagacacgg ttctgaagct attcagagat atcaatcctg acctctttgt gtttgcagag    180
attaacggaa tgtacaactc tcctttcttc atgacgaggt tccgagaagc gcttttttcat    240
```

```
tactcttcac tctttgacat gtttgacacc acaatacacg cagaggatga gtacaaaaac      300
aggtcactgt tggagagaga gttacttgtg agagacgcga tgagcgtgat ttcctgcgag      360
ggtgcagagc ggtttgcgag gcctgaaacc tacaagcaat ggcgagttag gattttgaga      420
gccgggttta agccagcaac tattagcaaa cagatcatga aggaggctaa ggaaattgtg      480
aggaaacgtt accatagaga ttttgtgatc gatagcgata caattggat gcttcaagga       540 tggaaggaa gagtcatcta tgcttttct tgctggaaac ctgctgagaa gttcacaaac        600
aataatttaa acatctgaaa atgttactt ctcaattaca tcattttgt ttcccaatgg        660 ttttgtagaa tatgtttgat cccgtgagtg gatgcaactc ttttttcctg caagtacata     720
ttgtattcaa atccttgtgg aaatgataaa ttgtttaatc aaaaaaaaaa aaaaa           775
```

<210> SEQ ID NO 50
<211> LENGTH: 206
<212> TYPE: PRT
<213> ORGANISM: Plant
<220> FEATURE:
<221> NAME/KEY: VARIANT
<222> LOCATION: (1)...(206)
<223> OTHER INFORMATION: Xaa = Any Amino Acid

<400> SEQUENCE: 50

```
Lys Lys Trp Glu Thr Ile Thr Leu Asp Glu Leu Met Ile Asn Pro Gly
 1               5                  10                  15

Glu Thr Thr Val Val Asn Cys Ile His Arg Leu Gln Tyr Thr Pro Asp
             20                  25                  30

Glu Thr Val Ser Leu Asp Ser Pro Arg Asp Thr Val Leu Lys Leu Phe
         35                  40                  45

Arg Asp Ile Asn Pro Asp Leu Phe Val Phe Ala Glu Ile Asn Gly Met
     50                  55                  60

Tyr Asn Ser Pro Phe Phe Met Thr Arg Phe Arg Glu Ala Leu Phe His
 65                  70                  75                  80

Tyr Ser Ser Leu Phe Asp Met Phe Asp Thr Thr Ile His Ala Glu Asp
                 85                  90                  95

Glu Tyr Lys Asn Arg Ser Leu Leu Glu Arg Glu Leu Leu Val Arg Asp
            100                 105                 110

Ala Met Ser Val Ile Ser Cys Glu Gly Ala Glu Arg Phe Ala Arg Pro
        115                 120                 125

Glu Thr Tyr Lys Gln Trp Arg Val Arg Ile Leu Arg Ala Gly Phe Lys
    130                 135                 140

Pro Ala Thr Ile Ser Lys Gln Ile Met Lys Glu Ala Lys Glu Ile Val
145                 150                 155                 160

Arg Lys Arg Tyr His Arg Asp Phe Val Ile Asp Ser Asp Asn Asn Trp
                165                 170                 175

Met Leu Gln Gly Trp Lys Gly Arg Val Ile Tyr Ala Phe Ser Cys Trp
            180                 185                 190

Lys Pro Ala Glu Lys Phe Thr Asn Asn Asn Leu Asn Ile Xaa
        195                 200                 205
```

<210> SEQ ID NO 51
<211> LENGTH: 548
<212> TYPE: DNA
<213> ORGANISM: Plant

<400> SEQUENCE: 51

```
aatcgcttga accgaatttg gatcgagatt cgaaagaaag gctgagagtg gagagagtgc      60
```

-continued

```
tgttcggtag gaggattatg gatttggtcc gatcagatga tgataataat aaaccgggaa    120
cccggtttgg gttaatggag gagaaagaac aatggagagt gttgatggag aaagctggat    180
ttgagccggt taaaccgagt aattacgcgg ttagccaagc gaagctgcta ctatggaact    240
acaattatag tacattgtat tcacttgttg aatcggagcc aggtttcatc tccttggctt    300
ggaacaatgt gcctctcctc accgtttcct cttggcgttg actacttggt ccgataagtt    360
aatctagtat tttgagttag cttttagaat tgaattgttt ggggttagat ttggatgttt    420
aattagtctc tagcctattc tcttactctt ttttgtctag tgcttggagt gatgatggtt    480
tgtcgtttat gttcatttgt aatatatatt gtatgtaaca tttgactaaa aaaaaaaaa    540 aaaaaaaa                                                              548
```

<210> SEQ ID NO 52
<211> LENGTH: 113
<212> TYPE: PRT
<213> ORGANISM: Plant
<220> FEATURE:
<221> NAME/KEY: VARIANT
<222> LOCATION: (1)...(113)
<223> OTHER INFORMATION: Xaa = Any Amino Acid

<400> SEQUENCE: 52

```
Ser Leu Glu Pro Asn Leu Asp Arg Asp Ser Lys Glu Arg Leu Arg Val
 1               5                  10                  15

Glu Arg Val Leu Phe Gly Arg Arg Ile Met Asp Leu Val Arg Ser Asp
            20                  25                  30

Asp Asp Asn Asn Lys Pro Gly Thr Arg Phe Gly Leu Met Glu Glu Lys
        35                  40                  45

Glu Gln Trp Arg Val Leu Met Glu Lys Ala Gly Phe Glu Pro Val Lys
    50                  55                  60

Pro Ser Asn Tyr Ala Val Ser Gln Ala Lys Leu Leu Trp Asn Tyr
65                  70                  75                  80

Asn Tyr Ser Thr Leu Tyr Ser Leu Val Glu Ser Glu Pro Gly Phe Ile
                85                  90                  95

Ser Leu Ala Trp Asn Asn Val Pro Leu Leu Thr Val Ser Ser Trp Arg
            100                 105                 110

Xaa
```

<210> SEQ ID NO 53
<211> LENGTH: 1093
<212> TYPE: DNA
<213> ORGANISM: Plant

<400> SEQUENCE: 53

```
gcgaatgttg agatcttgga agcaatagct ggggaaacca gagtccacat tatcgatttt     60
cagattgcac aggatcaca atacatgttt ttgattcagg agcttgcgaa acgccctggt    120
gggccgccgt tgctgcgtgt gacgggtgtg atgattcac agtccaccta tgctcgtggg    180
ggaggactca gcttggtagg tgagaggctt gcaactttgg cgcagtcatg tggtgtcccg    240
tttgagtttc acgatgccat catgtctggg tgcaaggtgc agcgggaaca tctcgggttg    300
gaacctggct tgctgttgt tgtgaacttc ccatatgtat tacaccacat gccagacgag    360
agcgtaagtg ttgaaaaata cagagacagg ctgctgcatc tgatcaagag cctctcccca    420
aaactggtta ctctagtaga gcaagaatcc aacacaaaca cctcgccatt ggtgtcacgg    480
tttgtggaaa cactggatta ctacacagcg atgtttgagt cgatagatgc agcacggcca    540
```

-continued

```
cgggatgata agcagagaat cagcgcagaa caacactgtg tagcaagaga catagtgaac     600
atgatagcat gtgaggagtc agagagagta gagagacacg aggtactggg gaaatggagg     660
gtcagaatga tgatggctgg gttcacgggt tggccggtca gcacatctgc agcgtttgca     720
gcgagtgaga tgctgaaagc ttatgacaaa aactacaaac tgggaggcca tgaaggagcg     780
ctctacctct tctggaagag acgacccatg gctacatgtt ccgtgtggaa gccaaaccca     840
aactatattg ggtaagttat agtgatgatg gttacttgag tggataaaga agagcacaac     900
aaaaacacat ctgtcgctgt aaattttta ggatgtgcaa tgatgtttta agttgtaaca     960
caacctaagt tatatatgta tacaaaccaa acctggtggt tgttttctc ttgtaaattg    1020 tcatgtggtt gtgggtggga agctagtaat gaaatataac caaaacattg attaggtcaa    1080
aaaaaaaaaa aaa                                                      1093
```

<210> SEQ ID NO 54
<211> LENGTH: 285
<212> TYPE: PRT
<213> ORGANISM: Plant
<220> FEATURE:
<221> NAME/KEY: VARIANT
<222> LOCATION: (1)...(285)
<223> OTHER INFORMATION: Xaa = Any Amino Acid

<400> SEQUENCE: 54

```
Ala Asn Val Glu Ile Leu Glu Ala Ile Ala Gly Glu Thr Arg Val His
  1               5                  10                  15

Ile Ile Asp Phe Gln Ile Ala Gln Gly Ser Gln Tyr Met Phe Leu Ile
             20                  25                  30

Gln Glu Leu Ala Lys Arg Pro Gly Pro Pro Leu Leu Arg Val Thr
         35                  40                  45

Gly Val Asp Asp Ser Gln Ser Thr Tyr Ala Arg Gly Gly Leu Ser
     50                  55                  60

Leu Val Gly Glu Arg Leu Ala Thr Leu Ala Gln Ser Cys Gly Val Pro
 65                  70                  75                  80

Phe Glu Phe His Asp Ala Ile Met Ser Gly Cys Lys Val Gln Arg Glu
                 85                  90                  95

His Leu Gly Leu Glu Pro Gly Phe Ala Val Val Val Asn Phe Pro Tyr
            100                 105                 110

Val Leu His His Met Pro Asp Glu Ser Val Ser Val Glu Lys Tyr Arg
        115                 120                 125

Asp Arg Leu Leu His Leu Ile Lys Ser Leu Ser Pro Lys Leu Val Thr
    130                 135                 140

Leu Val Glu Gln Glu Ser Asn Thr Asn Thr Ser Pro Leu Val Ser Arg
145                 150                 155                 160

Phe Val Glu Thr Leu Asp Tyr Tyr Thr Ala Met Phe Glu Ser Ile Asp
                165                 170                 175

Ala Ala Arg Pro Arg Asp Asp Lys Gln Arg Ile Ser Ala Glu Gln His
            180                 185                 190

Cys Val Ala Arg Asp Ile Val Asn Met Ile Ala Cys Glu Glu Ser Glu
        195                 200                 205

Arg Val Glu Arg His Glu Val Leu Gly Lys Trp Arg Val Arg Met Met
    210                 215                 220

Met Ala Gly Phe Thr Gly Trp Pro Val Ser Thr Ser Ala Ala Phe Ala
225                 230                 235                 240

Ala Ser Glu Met Leu Lys Ala Tyr Asp Lys Asn Tyr Lys Leu Gly Gly
```

|   |   |   |   | 245 |   |   |   | 250 |   |   |   | 255 |
|---|---|---|---|-----|---|---|---|-----|---|---|---|-----|

His Glu Gly Ala Leu Tyr Leu Phe Trp Lys Arg Pro Met Ala Thr
            260                 265                 270

Cys Ser Val Trp Lys Pro Asn Pro Asn Tyr Ile Gly Xaa
            275                 280             285

<210> SEQ ID NO 55
<211> LENGTH: 1928
<212> TYPE: DNA
<213> ORGANISM: Plant

<400> SEQUENCE: 55

```
aaagacttta gcagattttc aagcggctca gaacatcaac aacaacaaca acaacaaccg    60
ttttatagtc aagcagctct caacgctttt ctttcaaggt ctgtgaagcc tcgaaattat   120
cagaattttc aatctccgtc ggccgatgat tgatctcacg tcggtgaatg atatgagttt   180
gtttggtggt tctggttcat ctcagcgtta cggtttaccg gttcccaggt ctcagacgca   240
acagcaacaa tcggattacg gtttatttgg tgggatccga atgggaatcg ggtcgggtat   300
taataattat ccaacattaa ccggcgttcc gtgtattgaa ccggttcaaa ccgggttca   360
tgaatcggag aacatgttga atagtttaag agagcttgag aaacagcttt tagatgatga   420
cgatgagagt ggtggtgatg atgacgtgtc agttataaca aattcaaatt ccgattggat   480
tcaaaatctc gtgactccga acccgaaccc gaacccggtt ttgtcttttt caccgagctc   540
ttcttcttcg tcttcttcgc cttctacagc ttcgacgacg catcggtat gttctaggca   600
aacggttatg gaaatcgcga cggcgatcgc ggaagggaaa acagagatag cgacggagat   660
tttggcgcgt gtttctcaaa cgcctaatct tgagaggaat tcagaggaga gcttgttga   720
tttcatggtg gctgcgcttc gatcgaggat agcttctcca gtgacggaat tgtatgggaa   780
ggagcattta atctcgactc aattgctcta cgagctctct ccttgtttca aactcggttt   840
cgaggccgcg aatctcgcca ttctcgacgc cgccgataac aacgacggtg aatgatgat   900
accgcacgtt atcgatttcg atatcggaga aggtggacaa tacgttaacc ttctccgtac   960
attatccacg cgccggaatg gtaaaagtca gagtcagaat tctccggtgg ttaagatcac  1020
cgccgtggcg aacaacgttt acggatgttt agtcgatgac ggtggagaag agaggttaaa  1080
agccgtcgga gatttgttga gccaactcgg tgatcgactc ggtatctccg taagtttcaa  1140
cgtggtgaca gtttacgac tcggtgatct gaatcgtgaa tctctcgggt gtgatcccga  1200
cgagactttg gctgtgaact tagcttcaa gctttatcgt gttcccgacg aaagcgtatg  1260
cacggagaat ccaagagacg aacttctccg gcgcgtgaag ggacttaaac cgcgcgtggt  1320
tactctagtg gagcaagaaa tgaattcgaa tacggcgccg ttttaggga gagtgagtga  1380
gtcatgcgcg tgttacggtg cgttgcttga gtcggtcgag tctacggttc ctagtacgaa  1440
ttccgaccgt gccaaagttg aggaaggaat tggccggaag ctagtaaacg cggtggcgtg  1500
cgaaggaatc gatcgtatag agcggtgcga ggtgttcggg aaatggcgaa tgcggatgag  1560
catggctggg tttgagttaa tgccattgag tgagaagata gcggagtcga tgaagagtcg  1620
tggaaaccga gtccacccgg gctttaccgt taaagaagat aacggaggtg tgtgctttgg  1680
ttggatggga cgggcactca ctgtcgcatc cgcttggcgt taacttcaca cactcttttt  1740
tttcttctta ttattaccat attattatta attttcgaga ttattctgat attattatca  1800
ttgtgatttt ccgtttcgaa aagtgtagga atcttatgta acaagaaaaa aaaaaagact  1860
tttatgtttt tctaataata aaagaaagag tgattgggtt caaaaaaaaa aaaaaaaaa   1920
``` aaaaaaaa                                                                                              1928

<210> SEQ ID NO 56
<211> LENGTH: 524
<212> TYPE: PRT
<213> ORGANISM: Plant
<220> FEATURE:
<221> NAME/KEY: VARIANT
<222> LOCATION: (1)...(524)
<223> OTHER INFORMATION: Xaa = Any Amino Acid

<400> SEQUENCE: 56

Asp Leu Thr Ser Val Asn Asp Met Ser Leu Phe Gly Gly Ser Gly Ser
 1               5                  10                  15

Ser Gln Arg Tyr Gly Leu Pro Val Pro Arg Ser Gln Thr Gln Gln Gln
            20                  25                  30

Gln Ser Asp Tyr Gly Leu Phe Gly Gly Ile Arg Met Gly Ile Gly Ser
        35                  40                  45

Gly Ile Asn Asn Tyr Pro Thr Leu Thr Gly Val Pro Cys Ile Glu Pro
    50                  55                  60

Val Gln Asn Arg Val His Glu Ser Glu Asn Met Leu Asn Ser Leu Arg
65                  70                  75                  80

Glu Leu Glu Lys Gln Leu Leu Asp Asp Asp Glu Ser Gly Gly Asp
                85                  90                  95

Asp Asp Val Ser Val Ile Thr Asn Ser Asn Ser Asp Trp Ile Gln Asn
            100                 105                 110

Leu Val Thr Pro Asn Pro Asn Pro Asn Pro Val Leu Ser Phe Ser Pro
        115                 120                 125

Ser Ser Ser Ser Ser Ser Ser Pro Ser Thr Ala Ser Thr Thr Thr
    130                 135                 140

Ser Val Cys Ser Arg Gln Thr Val Met Glu Ile Ala Thr Ala Ile Ala
145                 150                 155                 160

Glu Gly Lys Thr Glu Ile Ala Thr Glu Ile Leu Ala Arg Val Ser Gln
                165                 170                 175

Thr Pro Asn Leu Glu Arg Asn Ser Glu Glu Lys Leu Val Asp Phe Met
            180                 185                 190

Val Ala Ala Leu Arg Ser Arg Ile Ala Ser Pro Val Thr Glu Leu Tyr
        195                 200                 205

Gly Lys Glu His Leu Ile Ser Thr Gln Leu Leu Tyr Glu Leu Ser Pro
    210                 215                 220

Cys Phe Lys Leu Gly Phe Glu Ala Ala Asn Leu Ala Ile Leu Asp Ala
225                 230                 235                 240

Ala Asp Asn Asn Asp Gly Gly Met Met Ile Pro His Val Ile Asp Phe
                245                 250                 255

Asp Ile Gly Glu Gly Gly Gln Tyr Val Asn Leu Leu Arg Thr Leu Ser
            260                 265                 270

Thr Arg Arg Asn Gly Lys Ser Gln Ser Gln Asn Ser Pro Val Val Lys
        275                 280                 285

Ile Thr Ala Val Ala Asn Asn Val Tyr Gly Cys Leu Val Asp Asp Gly
    290                 295                 300

Gly Glu Glu Arg Leu Lys Ala Val Gly Asp Leu Leu Ser Gln Leu Gly
305                 310                 315                 320

Asp Arg Leu Gly Ile Ser Val Ser Phe Asn Val Val Thr Ser Leu Arg
                325                 330                 335

Leu Gly Asp Leu Asn Arg Glu Ser Leu Gly Cys Asp Pro Asp Glu Thr

```
                 340              345              350
Leu Ala Val Asn Leu Ala Phe Lys Leu Tyr Arg Val Pro Asp Glu Ser
            355              360              365

Val Cys Thr Glu Asn Pro Arg Asp Glu Leu Leu Arg Arg Val Lys Gly
    370              375              380

Leu Lys Pro Arg Val Val Thr Leu Val Glu Gln Glu Met Asn Ser Asn
385              390              395              400

Thr Ala Pro Phe Leu Gly Arg Val Ser Glu Ser Cys Ala Cys Tyr Gly
                405              410              415

Ala Leu Leu Glu Ser Val Glu Ser Thr Val Pro Ser Thr Asn Ser Asp
            420              425              430

Arg Ala Lys Val Glu Glu Gly Ile Gly Arg Lys Leu Val Asn Ala Val
        435              440              445

Ala Cys Glu Gly Ile Asp Arg Ile Glu Arg Cys Glu Val Phe Gly Lys
    450              455              460

Trp Arg Met Arg Met Ser Met Ala Gly Phe Glu Leu Met Pro Leu Ser
465              470              475              480

Glu Lys Ile Ala Glu Ser Met Lys Ser Arg Gly Asn Arg Val His Pro
                485              490              495

Gly Phe Thr Val Lys Glu Asp Asn Gly Gly Val Cys Phe Gly Trp Met
            500              505              510

Gly Arg Ala Leu Thr Val Ala Ser Ala Trp Arg Xaa
        515              520
```

<210> SEQ ID NO 57
<211> LENGTH: 2635
<212> TYPE: DNA
<213> ORGANISM: Plant
<220> FEATURE:
<221> NAME/KEY: misc_feature
<222> LOCATION: (1)...(2635)
<223> OTHER INFORMATION: n = A,T,C or G

<400> SEQUENCE: 57

```
tcttactcaa ggttcttctt tgtcatcttg ttgccgaatc cacaaagagg agaataaaga    60
ttcgaccttt attagatatt aacgactctg gattttgggg ttttggagt tggatccaca   120
tgggttctta tccggatgga ttccctggat ccatggacga gttggatttc aataaggact   180
ttgatttgcc tccctcctca aaccaaacct taggtttagc taatgggttc tatttagatg   240
acttagattt ctcatccttg gatcctccag aggcatatcc ctcccagaac aacaacaaca   300
acaacatcaa caacaaagct gtagcaggag atctgttatc atcttcatct gatgacgctg   360
atttctctga ttctgttttg aagtatataa gccaagttct tatggaagag gatatggaag   420
agaagccttg tatgtttcat gatgctttgg ctcttcaagc tgctgagaaa tctctctatg   480
aggctcttgg tgagaaagac ccttcttcgt cttctgcttc ttctgtggat catcctgaga   540
gattggctag tcatagccct gacggttctt gttcaggtgg tgcttttagt gattacgcta   600
gcaccactac cactacttcc tctgattctc actggagtgt tgatggtttg agaatagac    660
cttcttggtt acatacacct atgccgagta attttgtttt ccagtctact tctaggtcca   720
acagtgtcac cggtggtggt ggtggtggta atagtgcggt ttacggttca ggttttggcg   780
atgatttggt ttcgaatatg tttaaagatg atgaattggc tatgcagttc aagaaagggg   840
ttgaggaagc tagtaagttc cttcctaagt cttctcagct cttttattgat gtggatagtt   900
acatccctat gaattctggt tccaaggaaa atggttctga ggttttttgtt aagacggaga   960
```

```
agaaagatga gacagagcat catcatcatc atagctatgc accaccaccc aacagattaa   1020
ctggtaagaa aagccattgg cgcgacgaag atgaagattt cgttgaagaa agaagtaaca   1080
agcaatcagc tgtttatgtt gaggaaagcg agctttctga aatgtttgat aacatgttcc   1140
tatgtggccc tgggaaacct gtatgcattc ttaaccagaa ctttcctaca gaatccgcta   1200
aagtcgtgac cgcacagtca aatggagcaa agattcgtgg gaagaaatca acttctacta   1260
gtcatagtaa cgattctaag aaagaaactg ctgatttgag gactcttttg gtgttatgtg   1320
cacaagctgt atcagtggat gatcgtagaa ccgccaacgt ttagctaagg cagatacgag   1380
agcattcttc gcctctaggc aatggttcag agcggttggc tcattatttt gcaaatagtc   1440
ttgaagcacg cttagctggg accggtacac agatctacac cgctttatct tcgaagaaaa   1500
cgtctgcagc agacatgttg aaggcttacc agacatacat gtcggtctgc cctttcaaga   1560
aagctgctat catatttgct aaccacagca tgatgcgttt cactgcaaac gccaacacga   1620
tccacataat agatttcgga atatcttacg gttttcagtg gcctgctctg attcatcgcc   1680
tctcgctcag cagacctggt ggttcgccta agcttcgaat taccggtcnn nnnnnnnnnn   1740
nnnnnnnnnn nnnnnnnnnn nnngagttca ggagacaggt catcgcttgg ctcgatactg   1800
tcagcgacac aatgttccgt ttgagtacaa cgcaattgct cagaaatggg gaaacgatcc   1860
aagtcgaaga cttaaagctt cgacaaggag agtatgtggt tgtgaactct ttgttccgtt   1920
tcaggaacct tctagatgag accgttctgg taaacagccc gagagatgca gttttgaagc   1980
tgataagaaa aataaacccg aatgtcttca ttccagcgat cttaagcggg aattacaacg   2040
cgccattctt tgtcacgagg ttcagagaag cgttgtttca ttactcggct gtgtttgata   2100
tgtgtgactc gaagctagct agggaagacg agatgaggct gatgtatgtg tttgagtttt   2160
atgggagaga gattgtgaat gttgtggctt ctgaaggaac agagagagtg gagagccgag   2220
agacatataa gcagtggcag gcgagactga tccgagccgg atttagacag cttccgcttg   2280
agaaggaact gatgcagaat ctgaagttga aaatcgaaaa cgggtacgat aaaaacttcg   2340
atgttgatca aaacggtaac tggttacttc aagggtggaa aggtagaatc gtgtatgctt   2400
catctctatg ggttccttcg tcttcataga tgttgtttct tacgttctaa gcgactggga   2460
tttatgtagg gcttttctgt tgatagtctc tcgccaacac gagtggatta agttcagagt   2520
tagggttctt gaacactaga atgttgttat attatgcttg tgacatagcg tgtgtaagag   2580
tgtagcctaa gagatatagt actcattgca tgatcttttg ctatatgttn catgt        2635

<210> SEQ ID NO 58
<211> LENGTH: 809
<212> TYPE: PRT
<213> ORGANISM: Plant
<220> FEATURE:
<221> NAME/KEY: VARIANT
<222> LOCATION: (1)...(809)
<223> OTHER INFORMATION: Xaa = Any Amino Acid

<400> SEQUENCE: 58

Leu Leu Lys Val Leu Leu Cys His Leu Val Ala Glu Ser Thr Lys Arg
 1               5                  10                  15

Arg Ile Lys Ile Arg Pro Leu Asp Ile Asn Asp Ser Gly Phe Leu
            20                  25                  30

Gly Phe Trp Ser Trp Ile His Met Gly Ser Tyr Pro Asp Gly Phe Pro
        35                  40                  45

Gly Ser Met Asp Glu Leu Asp Phe Asn Lys Asp Phe Asp Leu Pro Pro
    50                  55                  60
```

-continued

```
Ser Ser Asn Gln Thr Leu Gly Leu Ala Asn Gly Phe Tyr Leu Asp Asp
 65                  70                  75                  80

Leu Asp Phe Ser Ser Leu Asp Pro Pro Glu Ala Tyr Pro Ser Gln Asn
                 85                  90                  95

Asn Asn Asn Asn Asn Ile Asn Asn Lys Ala Val Ala Gly Asp Leu Leu
            100                 105                 110

Ser Ser Ser Ser Asp Asp Ala Asp Phe Ser Asp Ser Val Leu Lys Tyr
            115                 120                 125

Ile Ser Gln Val Leu Met Glu Glu Asp Met Glu Glu Lys Pro Cys Met
            130                 135                 140

Phe His Asp Ala Leu Ala Leu Gln Ala Ala Glu Lys Ser Leu Tyr Glu
145                 150                 155                 160

Ala Leu Gly Glu Lys Asp Pro Ser Ser Ser Ala Ser Ser Val Asp
                165                 170                 175

His Pro Glu Arg Leu Ala Ser His Ser Pro Asp Gly Ser Cys Ser Gly
                180                 185                 190

Gly Ala Phe Ser Asp Tyr Ala Ser Thr Thr Thr Thr Ser Ser Asp
                195                 200                 205

Ser His Trp Ser Val Asp Gly Leu Glu Asn Arg Pro Ser Trp Leu His
210                 215                 220

Thr Pro Met Pro Ser Asn Phe Val Phe Gln Ser Thr Ser Arg Ser Asn
225                 230                 235                 240

Ser Val Thr Gly Gly Gly Gly Asn Ser Ala Val Tyr Gly Ser
                245                 250                 255

Gly Phe Gly Asp Asp Leu Val Ser Asn Met Phe Lys Asp Asp Glu Leu
                260                 265                 270

Ala Met Gln Phe Lys Lys Gly Val Glu Glu Ala Ser Lys Phe Leu Pro
                275                 280                 285

Lys Ser Ser Gln Leu Phe Ile Asp Val Asp Ser Tyr Ile Pro Met Asn
                290                 295                 300

Ser Gly Ser Lys Glu Asn Gly Ser Glu Val Phe Val Lys Thr Glu Lys
305                 310                 315                 320

Lys Asp Glu Thr Glu His His His His Ser Tyr Ala Pro Pro
                325                 330                 335

Asn Arg Leu Thr Gly Lys Lys Ser His Trp Arg Asp Glu Asp Glu Asp
                340                 345                 350

Phe Val Glu Glu Arg Ser Asn Lys Gln Ser Ala Val Tyr Val Glu Glu
                355                 360                 365

Ser Glu Leu Ser Glu Met Phe Asp Asn Met Phe Leu Cys Gly Pro Gly
370                 375                 380

Lys Pro Val Cys Ile Leu Asn Gln Asn Phe Pro Thr Glu Ser Ala Lys
385                 390                 395                 400

Val Val Thr Ala Gln Ser Asn Gly Ala Lys Ile Arg Gly Lys Lys Ser
                405                 410                 415

Thr Ser Thr Ser His Ser Asn Asp Ser Lys Lys Glu Thr Ala Asp Leu
                420                 425                 430

Arg Thr Leu Leu Val Leu Cys Ala Gln Ala Val Ser Val Asp Asp Arg
                435                 440                 445

Arg Thr Ala Asn Val Xaa Leu Arg Gln Ile Arg Glu His Ser Ser Pro
                450                 455                 460

Leu Gly Asn Gly Ser Glu Arg Leu Ala His Tyr Phe Ala Asn Ser Leu
465                 470                 475                 480
```

-continued

```
Glu Ala Arg Leu Ala Gly Thr Gly Thr Gln Ile Tyr Thr Ala Leu Ser
                485                 490                 495
Ser Lys Lys Thr Ser Ala Ala Asp Met Leu Lys Ala Tyr Gln Thr Tyr
            500                 505                 510
Met Ser Val Cys Pro Phe Lys Lys Ala Ile Ile Phe Ala Asn His
        515                 520                 525
Ser Met Met Arg Phe Thr Ala Asn Ala Asn Thr Ile His Ile Ile Asp
    530                 535                 540
Phe Gly Ile Ser Tyr Gly Phe Gln Trp Pro Ala Leu Ile His Arg Leu
545                 550                 555                 560
Ser Leu Ser Arg Pro Gly Gly Ser Pro Lys Leu Arg Ile Thr Gly Xaa
                565                 570                 575
Xaa Xaa Xaa Xaa Xaa Xaa Xaa Xaa Xaa Glu Phe Arg Arg Gln
            580                 585                 590
Val Ile Ala Trp Leu Asp Thr Val Ser Asp Thr Met Phe Arg Leu Ser
        595                 600                 605
Thr Thr Gln Leu Leu Arg Asn Gly Glu Thr Ile Gln Val Glu Asp Leu
    610                 615                 620
Lys Leu Arg Gln Gly Glu Tyr Val Val Asn Ser Leu Phe Arg Phe
625                 630                 635                 640
Arg Asn Leu Leu Asp Glu Thr Val Leu Val Asn Ser Pro Arg Asp Ala
                645                 650                 655
Val Leu Lys Leu Ile Arg Lys Ile Asn Pro Asn Val Phe Ile Pro Ala
        660                 665                 670
Ile Leu Ser Gly Asn Tyr Asn Ala Pro Phe Phe Val Thr Arg Phe Arg
    675                 680                 685
Glu Ala Leu Phe His Tyr Ser Ala Val Phe Asp Met Cys Asp Ser Lys
690                 695                 700
Leu Ala Arg Glu Asp Glu Met Arg Leu Met Tyr Val Phe Glu Phe Tyr
705                 710                 715                 720
Gly Arg Glu Ile Val Asn Val Val Ala Ser Glu Gly Thr Glu Arg Val
                725                 730                 735
Glu Ser Arg Glu Thr Tyr Lys Gln Trp Gln Ala Arg Leu Ile Arg Ala
        740                 745                 750
Gly Phe Arg Gln Leu Pro Leu Glu Lys Glu Leu Met Gln Asn Leu Lys
    755                 760                 765
Leu Lys Ile Glu Asn Gly Tyr Asp Lys Asn Phe Asp Val Asp Gln Asn
770                 775                 780
Gly Asn Trp Leu Leu Gln Gly Trp Lys Gly Arg Ile Val Tyr Ala Ser
785                 790                 795                 800
Ser Leu Trp Val Pro Ser Ser Xaa
                805
```

<210> SEQ ID NO 59
<211> LENGTH: 90
<212> TYPE: PRT
<213> ORGANISM: Plant
<220> FEATURE:
<221> NAME/KEY: VARIANT
<222> LOCATION: (1)...(90)
<223> OTHER INFORMATION: Xaa = Any Amino Acid

<400> SEQUENCE: 59

```
Gln Glu Ala Asp His Asn Lys Thr Gly Phe Leu Asp Arg Phe Thr Glu
1               5                   10                  15
Ala Leu Phe Tyr Tyr Ser Ala Val Phe Asp Ser Leu Asp Ala Ala Asn
```

```
                    20                  25                  30

Asn Asn Asn Asn Asn Asn Asn Gln Arg Met Glu Ala Glu Tyr Leu Gln
            35                  40                  45

Arg Glu Ile Cys Asp Ile Val Cys Gly Glu Gly Ala Ala Arg Xaa Glu
    50                  55                  60

Arg His Glu Pro Leu Ser Arg Trp Arg Asp Arg Leu Thr Arg Ala Gly
65                  70                  75                  80

Leu Ser Ala Val Pro Leu Gly Ser Asn Ala
                85                  90

<210> SEQ ID NO 60
<211> LENGTH: 199
<212> TYPE: DNA
<213> ORGANISM: Plant
<220> FEATURE:
<221> NAME/KEY: misc_feature
<222> LOCATION: (1)...(199)
<223> OTHER INFORMATION: n = A,T,C or G

<400> SEQUENCE: 60
tctgcagaca attttnagga ggccaatacc atgctattgg aaatttcaga actgtccaca      60
cctnnnnnnn nnnnnnnnnn nnnnnnnnnn nnngtacttc tcagaggnaa tgtcggnnag     120
attagttagc tcctgcttag gaatctatgc ttctcttccn gcaacagtgg tgcctcctca     180
tggtcagaaa gtggcctca                                                   199

<210> SEQ ID NO 61
<211> LENGTH: 66
<212> TYPE: PRT
<213> ORGANISM: Plant
<220> FEATURE:
<221> NAME/KEY: VARIANT
<222> LOCATION: (1)...(66)
<223> OTHER INFORMATION: Xaa = Any Amino Acid

<400> SEQUENCE: 61

Ser Ala Asp Asn Phe Xaa Glu Ala Asn Thr Met Leu Leu Glu Ile Ser
1               5                   10                  15

Glu Leu Ser Thr Pro Xaa Xaa Xaa Xaa Xaa Xaa Xaa Xaa Xaa Xaa Tyr
            20                  25                  30

Phe Ser Glu Xaa Met Ser Xaa Arg Leu Val Ser Ser Cys Leu Gly Ile
        35                  40                  45

Tyr Ala Ser Leu Pro Ala Thr Val Val Pro Pro His Gly Gln Lys Val
    50                  55                  60

Ala Ser
65

<210> SEQ ID NO 62
<211> LENGTH: 321
<212> TYPE: DNA
<213> ORGANISM: Plant
<220> FEATURE:
<221> NAME/KEY: misc_feature
<222> LOCATION: (1)...(321)
<223> OTHER INFORMATION: n = A,T,C or G

<400> SEQUENCE: 62
tcaactgaga atctagaaga tgccaacaag atgcttctgg agatttctca gttatcaaca      60
ccgttcnnca cttcagcaca gcgtgtggca gcatatttct cagaagccat atcagcaagg    120
ttggtgagtt catgtctagg gatatacgca actttgccac acacacacca aagccacaag    180
```

```
gtagcttcag cttttcaagt gttcaatggt attagtcctt tagtggagtt ctcacacttc      240
acagcaaacc aagcaattca agaagccttc gaaagagaag agagggtgca catcatagat      300
cttgatataa tgcaagggtt g                                                321
```

<210> SEQ ID NO 63
<211> LENGTH: 107
<212> TYPE: PRT
<213> ORGANISM: Plant
<220> FEATURE:
<221> NAME/KEY: VARIANT
<222> LOCATION: (1)...(107)
<223> OTHER INFORMATION: Xaa = Any Amino Acid

<400> SEQUENCE: 63

```
Ser Thr Glu Asn Leu Glu Asp Ala Asn Lys Met Leu Leu Glu Ile Ser
 1               5                  10                  15

Gln Leu Ser Thr Pro Phe Xaa Thr Ser Ala Gln Arg Val Ala Ala Tyr
             20                  25                  30

Phe Ser Glu Ala Ile Ser Ala Arg Leu Val Ser Ser Cys Leu Gly Ile
         35                  40                  45

Tyr Ala Thr Leu Pro His Thr His Gln Ser His Lys Val Ala Ser Ala
     50                  55                  60

Phe Gln Val Phe Asn Gly Ile Ser Pro Leu Val Glu Phe Ser His Phe
 65                  70                  75                  80

Thr Ala Asn Gln Ala Ile Gln Glu Ala Phe Glu Arg Glu Glu Arg Val
                 85                  90                  95

His Ile Ile Asp Leu Asp Ile Met Gln Gly Leu
            100                 105
```

<210> SEQ ID NO 64
<211> LENGTH: 195
<212> TYPE: DNA
<213> ORGANISM: Plant
<220> FEATURE:
<221> NAME/KEY: misc_feature
<222> LOCATION: (1)...(195)
<223> OTHER INFORMATION: n = A,T,C or G

<400> SEQUENCE: 64

```
tctgcagaca acttgaaga agccaataca atactgcctc agatcacaga actctccacc       60
ccctatngca actcggtgca acgagtggct gcctatnnnn nnnnnnnnn nnnnnnnnnn      120 nnnnnnnnnn nntgcatagg aatgtattct cctctccctc ctattcacat gtcccagagc     180
cagaaaattg tgaat                                                      195
```

<210> SEQ ID NO 65
<211> LENGTH: 65
<212> TYPE: PRT
<213> ORGANISM: Plant
<220> FEATURE:
<221> NAME/KEY: VARIANT
<222> LOCATION: (1)...(65)
<223> OTHER INFORMATION: Xaa = Any Amino Acid

<400> SEQUENCE: 65

```
Ser Ala Asp Asn Phe Glu Glu Ala Asn Thr Ile Leu Pro Gln Ile Thr
 1               5                  10                  15

Glu Leu Ser Thr Pro Tyr Xaa Asn Ser Val Gln Arg Val Ala Ala Tyr
             20                  25                  30

Xaa Xaa Xaa Xaa Xaa Xaa Xaa Xaa Xaa Xaa Xaa Cys Ile Gly Met
         35                  40                  45
```

Tyr Ser Pro Leu Pro Pro Ile His Met Ser Gln Ser Gln Lys Ile Val
            50                  55                  60

Asn
65

<210> SEQ ID NO 66
<211> LENGTH: 2151
<212> TYPE: DNA
<213> ORGANISM: Plant

<400> SEQUENCE: 66

| | | | | | |
|---|---|---|---|---|---|
| gatatcagca | tcatcaattt | taaatgtaag | ttggcaaaag | atcatgaggg | ttctcatagt | 60 |
| aatttggcca | caaggtatga | cactgtctca | attgagcaat | ctagtagaga | aactgatcca | 120 |
| tcatatattg | ctcatattga | aagtgaaaaa | gatatgctca | agaacctagt | agagaagcta | 180 |
| aaaattgaaa | atctagctc | tactagaaaa | atatgatagg | ttgcctgttt | ctcatgaaaa | 240 |
| tttattagat | aatcatatca | tggctagatg | tcgctcatga | ggttgttctt | gctagtttag | 300 |
| attcctgtgg | gcattcatct | cttttagatg | cactaacatg | ataggaagtt | tctaatctgg | 360 |
| tgcttcacaa | ttctggtgat | tcatgcttcc | ttcattgcaa | ttgatattga | tgcttgattc | 420 |
| atgcttcagt | cactttgtgc | gtttaattgg | tattgtatgt | atcactagat | tgtagggtgt | 480 |
| ctgcaactag | tgtttcacca | tgtggttttt | tagtatcatt | cgtattagtt | tctaactttc | 540 |
| tattgatata | ttaaagtgat | aactagtttt | agaaatattc | tcttgtgcca | ttaatgctac | 600 |
| aacttgtttt | tagcgtgtac | gttagcatta | taatatttcc | ttattatgaa | agcggaagag | 660 |
| aaacgcgccc | aaccagagca | tccacgtcgt | ctcatttcac | cttcatcgtt | ggatcataga | 720 |
| tgagcggtcc | acggtgaact | ccgtttgcct | gcaaaaccac | gtcctctacg | cgctgttaag | 780 |
| tagcttctag | aaacatcacg | atgtgtcccg | tccattcctt | taggaggagc | cggatccggc | 840 |
| gccgcagtcg | cccaaggtcc | cgaccgccgc | ggcctcggcc | gccgccgcca | aggagcggaa | 900 |
| ggaggtgcag | cggcggaagc | agcgcgacga | ggagggcctc | cacctgctga | gtgctgacgc | 960 |
| tgctgctgca | gtgcgcggag | gccgtgaacg | cggacaacct | cgacgacgcg | caccagacgc | 1020 |
| tgctggagat | cgcggagctg | gccacgccgt | tcggcacctc | gacccagcgc | gtggccgcct | 1080 |
| acttcgcgga | ggccatgtcg | gcgcgcgtcg | tcagctcctg | cctaggcctg | tacgcgccgc | 1140 |
| tgccgccggg | ctcccccgcc | gcggcgcgcc | tccacggccg | cgtggccgcc | gcgttccagg | 1200 |
| tgttcaacgg | catcagcccc | ttcgtcaagt | tctcgcactt | caccgccaac | caggccatcc | 1260 |
| aggaggcgtt | cgagcgggag | gagcgtgtgc | acatcatcga | cctcgacatc | atgcaggggc | 1320 |
| tgcagtggcc | gggcctcttc | cacatccttg | tctcccgccc | cggcggcccg | cccagggtca | 1380 |
| ggctcaccgg | cctgggggcg | tccatggacg | cgctcgaggc | gacggggaag | cgcctctccg | 1440 |
| acttcgccga | cacgctcggc | ctgccccttcg | agttctgcgc | cgtcgccgag | aaggccggca | 1500 |
| acgttgaccc | gcagaagctg | ggcgtcacgc | ggcgggaggc | cgtcgccgtc | cactggccgc | 1560 |
| accactcgct | ttacgacgtc | atcggctccg | actccaacac | gctctggctc | atccaaaggt | 1620 |
| cctccatttt | ccttctctgc | ctttcttcca | tgtcaaatct | tgatgcaatc | atgaccactt | 1680 |
| ttcagctgct | gacattggat | aatgtgagct | ttacggcaag | catcaagtcg | tggtagtaca | 1740 |
| tccattacag | ctatttctaa | aatattcttc | ggaggtttcc | tgctcatagt | aaaaaaaaat | 1800 |
| cgcgttttga | agctcaaaag | gcgatttctt | ccgaggtttg | ctgttgagcg | ctattttgga | 1860 |
| aaccccattt | tctcaattga | tttttatttt | ttaaagaaaa | attagttcat | ttttctcttg | 1920 |

```
tgaaatggag tcccaaacta accctaatat taaaaaaaac gcgctttgga gctcaaaacg   1980
ctcgttgtta tgaccaacca gctttatagg tttaaaaagg ttgaatcttg acaatgcttt   2040
tgaaaaggtt gaatcttgac aatgcttttg agatgatact gtagtgtagt ctgtagtgga   2100
gcatcctcca tggtctttgg tgatcgagaa ttcctgcagc ccgggggatc c            2151
```

<210> SEQ ID NO 67
<211> LENGTH: 716
<212> TYPE: PRT
<213> ORGANISM: Plant
<220> FEATURE:
<221> NAME/KEY: VARIANT
<222> LOCATION: (1)...(716)
<223> OTHER INFORMATION: Xaa = Any Amino Acid

<400> SEQUENCE: 67

```
Tyr Gln His His Gln Phe Xaa Met Xaa Val Gly Lys Arg Ser Xaa Gly
  1               5                  10                  15

Phe Ser Xaa Xaa Phe Gly His Lys Val Xaa His Cys Leu Asn Xaa Ala
             20                  25                  30

Ile Xaa Xaa Arg Asn Xaa Ser Ile Ile Tyr Cys Ser Tyr Xaa Lys Xaa
         35                  40                  45

Lys Arg Tyr Ala Gln Glu Pro Ser Arg Glu Ala Lys Asn Xaa Lys Ile
 50                  55                  60

Xaa Leu Tyr Xaa Lys Asn Met Ile Gly Cys Leu Phe Leu Met Lys Ile
 65                  70                  75                  80

Tyr Xaa Ile Ile Ile Ser Trp Leu Asp Val Ala His Glu Val Val Leu
                 85                  90                  95

Ala Ser Leu Asp Ser Cys Gly His Ser Ser Leu Leu Asp Ala Leu Thr
            100                 105                 110

Xaa Xaa Glu Val Ser Asn Leu Val Leu His Asn Ser Gly Asp Ser Cys
        115                 120                 125

Phe Leu His Cys Asn Xaa Tyr Xaa Cys Leu Ile His Ala Ser Val Thr
130                 135                 140

Leu Cys Val Xaa Leu Val Leu Tyr Val Ser Leu Asp Cys Arg Val Ser
145                 150                 155                 160

Ala Thr Ser Val Ser Pro Cys Gly Phe Leu Val Ser Phe Val Leu Val
                165                 170                 175

Ser Asn Phe Leu Leu Ile Tyr Xaa Ser Asp Asn Xaa Phe Xaa Lys Tyr
            180                 185                 190

Ser Leu Val Pro Leu Met Leu Gln Leu Val Phe Ser Val Tyr Val Ser
        195                 200                 205

Ile Ile Ile Phe Pro Tyr Tyr Glu Ser Gly Arg Glu Thr Arg Pro Thr
    210                 215                 220

Arg Ala Ser Thr Ser Ser His Phe Thr Phe Ile Val Gly Ser Xaa Met
225                 230                 235                 240

Ser Gly Pro Arg Xaa Thr Pro Phe Ala Cys Lys Thr Ser Ser Thr
                245                 250                 255

Arg Cys Xaa Val Ala Ser Arg Asn Ile Thr Met Cys Pro Val His Ser
            260                 265                 270

Phe Arg Arg Ser Arg Ile Arg Arg Ser Arg Pro Arg Ser Arg Pro
        275                 280                 285

Pro Arg Pro Arg Pro Pro Pro Arg Ser Gly Arg Arg Cys Ser Gly
    290                 295                 300

Gly Ser Ser Ala Thr Arg Arg Ala Ser Thr Cys Xaa Val Leu Thr Leu
305                 310                 315                 320
```

-continued

```
Leu Leu Gln Cys Ala Glu Ala Val Asn Ala Asp Asn Leu Asp Asp Ala
                325                 330                 335
His Gln Thr Leu Leu Glu Ile Ala Glu Leu Ala Thr Pro Phe Gly Thr
            340                 345                 350
Ser Thr Gln Arg Val Ala Ala Tyr Phe Ala Glu Ala Met Ser Ala Arg
                355                 360                 365
Val Val Ser Ser Cys Leu Gly Leu Tyr Ala Pro Leu Pro Pro Gly Ser
            370                 375                 380
Pro Ala Ala Ala Arg Leu His Gly Arg Val Ala Ala Phe Gln Val
385                 390                 395                 400
Phe Asn Gly Ile Ser Pro Phe Val Lys Phe Ser His Phe Thr Ala Asn
                405                 410                 415
Gln Ala Ile Gln Glu Ala Phe Glu Arg Glu Arg Val His Ile Ile
            420                 425                 430
Asp Leu Asp Ile Met Gln Gly Leu Gln Trp Pro Gly Leu Phe His Ile
                435                 440                 445
Leu Val Ser Arg Pro Gly Gly Pro Pro Arg Val Arg Leu Thr Gly Leu
            450                 455                 460
Gly Ala Ser Met Asp Ala Leu Glu Ala Thr Gly Lys Arg Leu Ser Asp
465                 470                 475                 480
Phe Ala Asp Thr Leu Gly Leu Pro Phe Glu Phe Cys Ala Val Ala Glu
                485                 490                 495
Lys Ala Gly Asn Val Asp Pro Gln Lys Leu Gly Val Thr Arg Arg Glu
            500                 505                 510
Ala Val Ala Val His Trp Pro His His Ser Leu Tyr Asp Val Ile Gly
            515                 520                 525
Ser Asp Ser Asn Thr Leu Trp Leu Ile Gln Arg Ser Ser Ile Phe Leu
530                 535                 540
Leu Cys Leu Ser Ser Met Ser Asn Leu Asp Ala Ile Met Thr Thr Phe
545                 550                 555                 560
Gln Leu Leu Thr Leu Asp Asn Val Ser Phe Thr Ala Ser Ile Lys Ser
                565                 570                 575
Trp Xaa Tyr Ile His Tyr Ser Tyr Phe Xaa Asn Ile Leu Arg Arg Phe
            580                 585                 590
Pro Ala His Ser Lys Lys Lys Ser Arg Phe Glu Ala Gln Lys Ala Ile
            595                 600                 605
Ser Ser Glu Val Cys Cys Xaa Ala Leu Phe Trp Lys Pro His Phe Leu
            610                 615                 620
Asn Xaa Phe Leu Phe Phe Lys Glu Lys Leu Val His Phe Ser Leu Val
625                 630                 635                 640
Lys Trp Ser Pro Lys Leu Thr Leu Ile Leu Lys Lys Thr Arg Phe Gly
                645                 650                 655
Ala Gln Asn Ala Arg Cys Tyr Asp Gln Pro Ala Leu Xaa Val Xaa Lys
                660                 665                 670
Gly Xaa Ile Leu Thr Met Leu Leu Lys Arg Leu Asn Leu Asp Asn Ala
            675                 680                 685
Phe Glu Met Ile Leu Xaa Cys Ser Leu Xaa Trp Ser Ile Leu His Gly
            690                 695                 700
Leu Trp Xaa Ser Arg Ile Pro Ala Ala Arg Gly Ile
705                 710                 715
```

<210> SEQ ID NO 68
<211> LENGTH: 23

```
<212> TYPE: DNA
<213> ORGANISM: Artificial Sequence
<220> FEATURE:
<221> NAME/KEY: CDS
<222> LOCATION: (1)...(23)
<223> OTHER INFORMATION: Primer
<221> NAME/KEY: misc_feature
<222> LOCATION: (1)...(23)
<223> OTHER INFORMATION: n = A,T,C or G
<221> NAME/KEY: modified_base
<222> LOCATION: (9)...(12)
<223> OTHER INFORMATION: n = I = inosine

<400> SEQUENCE: 68 cay tty acn gcn aay car gcn at                                  23

<210> SEQ ID NO 69
<211> LENGTH: 8
<212> TYPE: PRT
<213> ORGANISM: Artificial Sequence
<220> FEATURE:
<223> OTHER INFORMATION: primer

<400> SEQUENCE: 69

His Phe Thr Ala Asn Gln Ala Ile
 1               5

<210> SEQ ID NO 70
<211> LENGTH: 29
<212> TYPE: DNA
<213> ORGANISM: Artificial Sequence
<220> FEATURE:
<221> NAME/KEY: CDS
<222> LOCATION: (10)...(29)
<223> OTHER INFORMATION: Primer
<221> NAME/KEY: misc_feature
<222> LOCATION: (1)...(29)
<223> OTHER INFORMATION: n = A,T,C or G
<221> NAME/KEY: modified_base
<222> LOCATION: (12)...(12)
<223> OTHER INFORMATION: n = I = inosine

<400> SEQUENCE: 70 acgtctcga gtn cay ath ath gay ttn ga                            29

<210> SEQ ID NO 71
<211> LENGTH: 7
<212> TYPE: PRT
<213> ORGANISM: Artificial Sequence
<220> FEATURE:
<221> NAME/KEY: VARIANT
<222> LOCATION: (1)...(7)
<223> OTHER INFORMATION: Xaa = Any Amino Acid
<223> OTHER INFORMATION: Primer

<400> SEQUENCE: 71

Val His Ile Ile Asp Xaa Asp
 1               5

<210> SEQ ID NO 72
<211> LENGTH: 20
<212> TYPE: DNA
<213> ORGANISM: Artificial Sequence
<220> FEATURE:
<221> NAME/KEY: CDS
<222> LOCATION: (1)...(20)
<223> OTHER INFORMATION: Primer
<221> NAME/KEY: misc_feature
<222> LOCATION: (1)...(20)
<223> OTHER INFORMATION: n = A,T,C or G
<221> NAME/KEY: modified_base
```

```
<222> LOCATION: (3)...(12)
<223> OTHER INFORMATION: n = I = inosine

<400> SEQUENCE: 72 ytn car tgy gcn gar gcn gt                                          20

<210> SEQ ID NO 73
<211> LENGTH: 7
<212> TYPE: PRT
<213> ORGANISM: Artificial Sequence
<220> FEATURE:
<223> OTHER INFORMATION: Primer

<400> SEQUENCE: 73

Leu Gln Cys Ala Glu Ala Val
 1               5

<210> SEQ ID NO 74
<211> LENGTH: 23
<212> TYPE: DNA
<213> ORGANISM: Artificial Sequence
<220> FEATURE:
<221> NAME/KEY: CDS
<222> LOCATION: (3)...(23)
<223> OTHER INFORMATION: Primer
<221> NAME/KEY: misc_feature
<222> LOCATION: (1)...(23)
<223> OTHER INFORMATION: n = A,T,C or G
<221> NAME/KEY: modified_base
<222> LOCATION: (12)...(15)
<223> OTHER INFORMATION: n = I = inosine

<400> SEQUENCE: 74 ck ccm gtk tgg ngg ncc ncc ngg                                      23

<210> SEQ ID NO 75
<211> LENGTH: 8
<212> TYPE: PRT
<213> ORGANISM: Artificial Sequence
<220> FEATURE:
<221> NAME/KEY: VARIANT
<222> LOCATION: (1)...(8)
<223> OTHER INFORMATION: Xaa = Any Amino Acid
<223> OTHER INFORMATION: Primer

<400> SEQUENCE: 75

Pro Gly Gly Pro Pro Xaa Xaa Arg
 1               5

<210> SEQ ID NO 76
<211> LENGTH: 23
<212> TYPE: DNA
<213> ORGANISM: Artificial Sequence
<220> FEATURE:
<221> NAME/KEY: CDS
<222> LOCATION: (3)...(23)
<223> OTHER INFORMATION: Primer
<221> NAME/KEY: misc_feature
<222> LOCATION: (1)...(23)
<223> OTHER INFORMATION: n = A,T,C or G
<221> NAME/KEY: modified_base
<222> LOCATION: (3)...(12)
<223> OTHER INFORMATION: n = I = inosine

<400> SEQUENCE: 76 at ncc rtt raa nac ytg raa ngc                                      23

<210> SEQ ID NO 77
<211> LENGTH: 8
```

```
<212> TYPE: PRT
<213> ORGANISM: Artificial Sequence
<220> FEATURE:
<223> OTHER INFORMATION: Primer

<400> SEQUENCE: 77

Ala Phe Gln Val Phe Asn Gly Ile
 1               5

<210> SEQ ID NO 78
<211> LENGTH: 23
<212> TYPE: DNA
<213> ORGANISM: Artificial Sequence
<220> FEATURE:
<221> NAME/KEY: CDS
<222> LOCATION: (3)...(23)
<223> OTHER INFORMATION: Primer
<221> NAME/KEY: misc_feature
<222> LOCATION: (1)...(23)
<223> OTHER INFORMATION: n = A,T,C or G
<221> NAME/KEY: modified_base
<222> LOCATION: (9)...(9)
<223> OTHER INFORMATION: n = I = inosine
<221> NAME/KEY: modified_base
<222> LOCATION: (15)...(15)
<223> OTHER INFORMATION: n = I = inosine

<400> SEQUENCE: 78 at rtg raa nar ncc ngg cca ytg                                       23

<210> SEQ ID NO 79
<211> LENGTH: 8
<212> TYPE: PRT
<213> ORGANISM: Artificial Sequence
<220> FEATURE:
<223> OTHER INFORMATION: Primer

<400> SEQUENCE: 79

Gln Trp Pro Gly Leu Phe His Ile
 1               5
```

SCARECROW GENE, PROMOTER AND USES THEREOF

This application is a division of Application Ser. No. 08/842,445 filed on Apr. 24, 1997, which is a continuation-in-part of application Ser. No. 08/638,617, filed Apr. 26, 1996, abandoned each of which is hereby incorporated by reference in its entirety.

This invention was made with government support under grant number: GM43778 awarded by the National Institute of Health. The government may have certain rights in the invention.

TABLE OF CONTENTS

1. INTRODUCTION
2. BACKGROUND OF THE INVENTION
   2.1. ROOT DEVELOPMENT
   2.2. GENES REGULATING ROOT STRUCTURE
   2.3. GEOTROPISM
3. SUMMARY OF THE INVENTION
3. 1. DEFINITIONS
4. BRIEF DESCRIPTION OF THE FIGS.
5. DETAILED DESCRIPTION OF THE INVENTION
   5.1. SCRGENES
      5.1.1. ISOLATION OF SCR GENES
      5.1.2. EXPRESSION OF SCR GENE PRODUCTS
      5.1.3. ANTIBODIES TO SCR PROTEINS AND POLYPEPTIDES
      5.1.4. SCR GENE OR GENE PRODUCTS AS MARKERS FOR QUALITATIVE TRAIT LOCI
   5.2. SCR PROMOTERS
      5.2.1. CIS-REGULATORY ELEMENTS OF SCR PROMOTERS
      5.2.2. SCR PROMOTER-DRIVEN EXPRESSION VECTORS
   5.3. PRODUCTION OF TRANSGENIC PLANTS AND PLANT CELLS
      5.3.1. TRANSGENIC PLANTS THAT ECTOPICALLY EXPRESS SCR
      5.3.2. TRANSGENIC PLANTS THAT SUPPRESS ENDOGENOUS SCR EXPRESSION
      5.3.3. TRANSGENIC PLANTS THAT EXPRESS A TRANSGENE CONTROLLED BY THE SCR PROMOTER
      5.3.4. SCREENING OF TRANSFORMED PLANTS FOR THOSE HAVING DESIRED ALTERED TRAITS
6. EXAMPLE 1: ARABIDOPSIS SCR GENE
   6.1. MATERIALS AND METHODS
      6.1.1. PLANT CULTURE
      6.1.2. GENETIC ANALYSIS
      6.1.3. MAPPING
      6.1.4. PHENOTYPIC ANALYSIS
      6.1.5. MOLECULAR TECHNIQUES
      6.1.6. IN SITU HYBRIDIZATION
   6.2. RESULTS
      6.2.1. CHARACTERIZATION OF THE SCR PHENOTYPE
      6.2.2. CHARACTERIZATION OF CELL IDENTITY IN SCR ROOTS
      6.2.3. MOLECULAR CLONING OF THE SCR GENE
      6.2.4. THE SCR GENE HAS MOTIFS THAT INDICATE IT IS A TRANSCRIPTION FACTOR
      6.2.5. SCR IS A MEMBER OF A NOVEL PROTEIN FAMILY
      6.2.6. SCR IS EXPRESSED IN THE CORTEX/ENDODERMAL INITIALS AND IN THE ENDODERMIS
   6.3. DISCUSSION
      6.3.1. THE SCR GENE REGULATES AN ASYMMETRIC DIVISION REQUIRED FOR ROOT RADIAL ORGANIZATION
      6.3.2. SCR INVOLVEMENT IN CELL SPECIFICATION OR CELL DIVISION
      6.3.3. A ROLE FOR SCR IN EMBRYONIC DEVELOPMENT
      6.3.4. TISSUE-SPECIFIC EXPRESSION OF SCR IS REGULATED AT THE TRANSCRIPTIONAL LEVEL
      6.3.5. A NEW FAMILY OF TRANSCRIPTIONAL REGULATORS
7. EXAMPLE 2: ENHANCER TRAP ANALYSIS OF ROOT DEVELOPMENT
   7.1. MATERIALS AND METHODS
      7.1.1. PLANT GROWTH CONDITIONS
      7.1.2. HISTOLOGY AND GUS STAINING
      7.1.3. CONSTRUCTION OF ENHANCER TRAP LINES
   7.2. RESULTS
      7.2.1. DIFFERENTIATION IN THE LRP
      7.2.2. MARKER LINES
      7.2.3. ET199 PROVIDES EVIDENCE FOR THE ROLE OF SCR IN PLANT DEVELOPMENT
8. EXAMPLE 3: ACTIVITY OF ARABIDOPSIS SCR PROMOTER IN TRANSGENIC ROOTS
9. EXAMPLE 4: ISOLATION SCR SEQUENCES USING PCR-CLONING STRATEGY
10. EXAMPLE 5. EXPRESSION PATTERN OF MAIZE ZCR GENE IN ROOT TISSUE
11. EXAMPLE 6. EXPRESSION PATTERN OF ZCR GENE IN SOYBEAN ROOTS AND ROOT NODULES
12. EXAMPLE 7. SCR EXPRESSION AFFECTS GRAVITROPISM OF AERIAL STRUCTURES
13. DEPOSIT OF MICROORGANISMS

1. INTRODUCTION

The present invention generally relates to the SCARECROW (SCR) gene family and their promoters. The invention more particularly relates to ectopic expression of members of the SCARECROW gene family in transgenic plants to artificially modify plant structures. The invention also relates to utilization of SCARECROW promoter for tissue and organ specific expression of heterologous gene products.

2. BACKGROUND OF THE INVENTION

Asymmetric cell divisions, in which a cell divides to give two daughters with different fates, play an important role in the development of all multicellular organisms. In plants, because there is no cell migration, the regulation of asymmetric cell divisions is of heightened importance in determining organ morphology. In contrast to animal embryogenesis, most plant organs are not formed during embryogenesis. Rather, cells that form the apical meristems are set aside at the shoot and root poles. These reservoirs of stem cells are considered to be the source of all post-embryonic organ development in plants. A fundamental question in developmental biology is how meristems function to generate plant organs.

2.1. ROOT DEVELOPMENT

Root organization is established during embryogenesis. This organization is propagated during postembryonic development by the root meristem. Following germination, the development of the postembryonic root is a continuous process, a series of initials or stem cells continuously divide to perpetuate the pattern established in the embryonic root (Steeves & Sussex, 1972, *Patterns in Plant Development*, Englewood Cliffs, NJ: Prentice-Hall, Inc.).

Figure 1B:
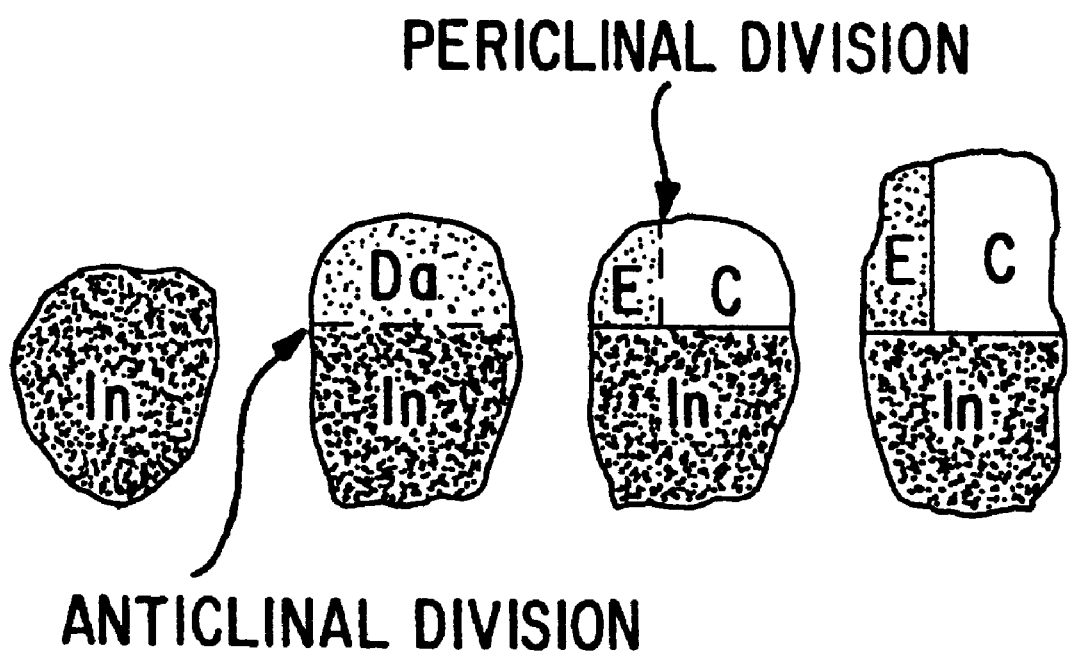

Due to the organization of the Arabidopsis root it is possible to follow the fate of cells from the meristem to maturity and identify the progenitors of each cell type (Dolan et al., 1993, Development 119:71–84). The Arabidopsis root is a relatively simple and well characterized organ. The radial organization of the mature tissues in the Arabidopsis root has been likened to tree rings with the epidermis, cortex, endodermis and pericycle forming radially symmetric cell layers that surround the vascular cylinder (FIG. 1A). See also Dolan et al., 1993, Development 119:71–84. These mature tissues are derived from four sets of stem cells or initials: i) the columella root cap initial; ii) the pericycle/vascular initial; iii) the epidermal/lateral root cap initial; and iv) the cortex/endodermal initial (Dolan et al., 1993, Development 119:71–84). It has been shown that these initials undergo asymmetric divisions (Scheres et al., 1995, Development 121:53–62). The cortex/endodermal initial, for example, first divides anticlinally (in a transverse orientation) (FIG. 1B). This asymmetric division produces another initial and a daughter cell. The daughter cell, in turn, expands and then divides periclinally (in the longitudinal orientation) (FIG. 1B). This second asymmetric division produces the progenitors of the endodermis and the cortex cell lineages (FIG. 1B).

2.2. GENES REGULATING ROOT STRUCTURE

Mutations that disrupt the asymmetric divisions of the cortex/endodermal initial have been identified and characterized (Benfey et al., 1993, Development 119:57–70; Scheres et al., 1995, Development 121:53–62). short-root (shr) and scarecrow (scr) mutants are missing a cell layer between the epidermis and the pericycle. In both types of mutants the cortex/endodermal initial divides anticlinally, but the subsequent periclinal division that increases the number of cell layers does not take place (Benfey et al., 1993, Development 119:57–70; Scheres et al., 1995, Development 121:53–62). The defect is first apparent in the embryo and it extends throughout the entire embryonic axis which includes the embryonic root and hypocotyl (Scheres et al., 1995, Development 121:53–62). This is also true for the other radial organization mutants characterized to date, suggesting that radial patterning that occurs during embryonic development may influence the post-embryonic pattern generated by the meristematic initials (Scheres et al., 1995, Development 121:53–62).

Characterization of the mutant cell layer in shr indicated that two endodermal-specific markers were absent (Benfey et al., 1993, Development 119:57–70). This provided evidence that the wild-type SHR gene may be involved in specification of endodermis identity.

2.3. GEOTROPISM

In plants, the capacity for gravitropism has been correlated with the presence of amyloplast sedimentation. See, e.g., Volkmann and Sievers, 1979, Encyclopedia Plant Physiol., N.S. vol 7, pp. 573–600; Sack, 1991, Intern. Rev. Cytol. 127:193–252; Björkmann, 1992, Adv. Space Res. 12:195–201; Poff et al., in *The Physiology of Tropisms*, Meyerowitz & Somerville (eds); Cold Spring Harbor Laboratory Press, Plainview, NY (1994) pp. 639–664; Barlow, 1995, Plant Cell Environ. 18:951–962. Amyloplast sedimentation only occurs in cells in specific locations at distinct developmental stages. That is, when and where sedimentation occurs is precisely regulated (Sack, 1991, Intern. Rev. Cytol. 127:193–252). In roots, amyloplast sedimentation only occurs in the central (columella) cells of the rootcap; as these cells mature into peripheral cap cells, the amyloplasts no longer sediment (Sack & Kiss, 1989, Amer. J. Bot. 76:454–464; Sievers & Braun, in *The Root Cap: Structure and Function*, Wassail et al. (eds.), New York: M. Dekker (1996) pp. 31–49). In stems of many plants, including Arabidopsis, amyloplast sedimentation occurs in the starch sheath (endodermis) especially in elongating regions of the stem (von Guttenberg, *Die Physiologischen Scheiden*, Handbuch der Pflanzenanatomie; K. Linsbauer (ed.), Berlin: Gebruder Borntraeger, vol. 5 (1943) p. 217; Sack, 1987, Can. J. Bot. 65:1514–1519; Sack, 1991, Intern. Rev. Cytol. 127:193–252; Caspar & Pickard, 1989, Planta 177:185–197; Volkmann et al., 1993, J. Pl. Physiol. 142:710–6).

Gravitropic mutants have been studied for evidence that proves the role of amyloplast sedimentation in gravity sensing. However, many gravitropic mutations affect downstream events such as auxin sensitivity or metabolism (Masson, 1995, BioEssays 17:119–127). Other mutations seem to affect gene products that process information from gravity sensing. For example, the lazy mutants of higher plants and comparable mutants in mosses can clearly sense and respond to gravity, but the mutations reverse the normal polarity of the gravitropic response (Gaiser & Lomax, 1993, Plant Physiol. 102:339–344; Jenkins et al., 1986, Plant Cell Environ 9:637–644). Other mutations appear to affect gravitropism of specific organs. For example, sgr mutants have defective shoot gravitropism (Fukaki et al., 1996, Plant Physiol. 110:933–943; Fukaki et al., 1996, Plant Physiol. 110:945–955; Fukaki et al., 1996, Plant Res. 109:129–137).

Citation or identification of any reference herein shall not be construed as an admission that such reference is available as prior art to the present invention.

3. SUMMARY OF THE INVENTION

The structure and function of a regulatory gene, SCARECROW (SCR), is described. The SCR gene is expressed specifically in root progenitor tissues of embryos, and in certain tissues of roots and stems. SCR expression controls cell division of certain cell types in roots, and affects the organization of root and stem. The invention relates to the SCARECROW (SCR) gene (which encompasses the Arabidopsis SCR gene and its orthologs and paralogs), SCR gene products, (including but not limited to transcriptional products such as mRNAs, antisense and ribozyme molecules, and translational products such as the SCR protein, polypeptides, peptides and fusion proteins related thereto), antibodies to SCR gene products, SCR regulatory regions and the use of the foregoing to improve agronomically valuable plants.

The invention is based, in part, on the discovery, identification and cloning of the gene responsible for the scarecrow phenotype. In contrast to the prevailing view that the SCR gene was likely to be involved in the specification of endodermis, the inventors have determined that the mutant cell layer in roots of scr mutants has differentiated characteristics of both cortex and endodermis. This is consistent with a role for SCR in the regulation of the asymmetric cell division rather than in specification of the identity of either cortex or endodermis. The inventors have also determined that SCR expression affects the gravitropism of plant aerial structures such as the stem.

One aspect of the invention relates to the heterologous expression of SCR genes and related nucleotide sequences, and specifically the Arabidopsis SCR genes, in stably transformed higher plant species. Modulation of SCR expression levels can be used to advantageously modify root and aerial structures of transgenic plants and enhance the agronomic properties of such plants.

Another aspect of the invention relates to the use of promoters of SCR genes, and specifically the use of Arabidopsis SCR promoter to control the expression of protein and RNA products in plants. Plant SCR promoters have a variety of uses, including but not limited to expressing heterologous genes in the embryo, root, root nodule, and stem of transformed plants.

The invention is illustrated by working examples described infra which demonstrate the isolation of the Arabidopsis SCR gene using insertion mutagenesis. More specifically, T-DNA tagging of genomic and cDNA clones of the Arabidopsis SCR gene are described. Additional working examples include the isolation of SCR sequences from plant genomes using PCR amplification in combination with screening of genomic libraries, and heterologous gene expression in transgenic plants using SCR promoter expression constructs.

Structural analysis of the deduced amino acid sequence of Arabidopsis SCR protein indicates that SCR encodes a transcription factor. Northern analysis, in situ hybridization analysis and enhancer trap analysis show highly localized expression of Arabidopsis SCR in embryos and roots. Genetic analysis shows SCR expression also affects gravitropism of aerial structures (e.g., stems). This indicates that SCR is also expressed in those structures.

Computer analysis of the deduced amino acid sequence of Arabidopsis SCR protein with those of Expressed Sequence Tag (EST) sequences in GenBank reveals the existence of at least thirteen SCR genes in Arabidopsis, one SCR gene in maize, four SCR genes in rice, and one SCR gene in Brassica. A further aspect of the invention relates to the use of such EST sequences to obtain larger and/or complete clones of the corresponding SCR gene.

The various embodiments of the claimed invention presented herein are by the way of illustration and are not meant to limit the invention.

3.1. DEFINITIONS

As used herein, the terms listed below will have the meanings indicated.

35S=cauliflower mosaic virus promoter for the 35S transcript
cDNA=complementary DNA
cis-regulatory element=A promoter sequence 5' upstream of the TATA box that confers specific regulatory response to a promoter containing such an element. A promoter may contain one or more cis-regulatory elements, each responsible for a particular regulatory response
coding sequence=sequence that encodes a complete or partial gene product (e.g., a complete protein or a fragment thereof)
DNA=deoxyribonucleic acid
EST=expression tagged
functional portion=a functional portion of a promoter is any portion of a promoter that is capable of causing transcription of a linked gene sequence, e.g., a truncated promoter
gene fusion=a gene construct comprising a promoter operably linked to a heterologous gene, wherein said promoter controls the transcription of the heterologous gene
gene product=the RNA or protein encoded by a gene sequence
gene sequence=sequence that encodes a complete gene product (e.g., a complete protein)
GUS=1,3-β-Glucuronidase
gDNA=genomic DNA
heterologous gene=In the context of gene constructs, a heterologous gene means that the gene is linked to a promoter that said gene is not naturally linked to. The heterologous gene may or may not be from the organism contributing said promoter. The heterologous gene may encode messenger RNA (mRNA), antisense RNA or ribozymes
homologous promoter=a native promoter of a gene that selectively hybridizes to the sequence of a SCR gene described herein
mRNA=messenger RNA
operably linked=A linkage between a promoter and gene sequence such that the transcription of said gene sequence is controlled by said promoter
ortholog=related gene in a different plant (e.g., maize ZCARECROW gene is an ortholog of the Arabidopsis SCR gene)
paralog=related gene in the same plant (e.g., Arabidopsis SRPa1 is a paralog of Arabidopsis SCR gene)
RNA=ribonucleic acid
RNase=ribonuclease
SCR=SCARECROW gene or gene product, encompasses (italic) SCR and ZCR genes and their orthologs and paralogs
SCR=SCARECROW protein
scr=scarecrow mutant (e.g., scr1) (lower case)
ZCR=maize ZCARECROW gene, a paralog of, for example, the Arabidopsis SCR gene SCR protein means a protein containing sequences or a domain substantially similar to one or more motifs (i.e., Motif I-VI), preferably MOTIF III (amino acid residues 373–435 of SEQ ID NO:2) (VHIID) amino acid residues 8–12 of SEQ ID NO:12), of Arabidopsis SCR protein as shown in FIGS. 13A–F and FIGS. 15A–S. SCR proteins include SCR ortholog and paralog proteins having the structure and activities described herein.

SCR polypeptides and peptides include deleted or truncated forms of the SCR protein, and fragments corresponding to the SCR motifs described herein.

SCR fusion proteins encompass proteins in which the SCR protein or an SCR polypeptide or peptide is fused to a heterologous protein, polypeptide or peptide.

SCR gene, nucleotides or coding sequences means nucleotides, e.g., gDNA or cDNA encoding SCR protein, SCR polypeptides or peptides, or SCR fusion proteins.

SCR gene products include transcriptional products such as mRNAs, antisense and ribozyme molecules, as well as translational products of the SCR nucleotides described herein including but not limited to the SCR protein, polypeptides, peptides and/or SCR fusion proteins.

SCR promoter means the regulatory region native to the SCR gene in a variety of species, which promotes the organ and tissue specific pattern of SCR expression described herein.

4. BRIEF DESCRIPTION OF THE FIGURES

FIGS. 1A–B. Schematic of Arabidopsis root anatomy. FIG. 1A. Transverse section showing the four tissues, epidermis, cortex, endodermis and pericycle that surround the vascular tissue. In the longitudinal section, the epidermal/lateral root cap initials and the cortex/endodermal initials are shown at the base of their respective cell files. FIG. 1B. Schematic of division pattern of the cortex/ endodermal initial. The initial expands then divides anticlinally to reproduce itself and a daughter cell. The daughter then divides periclinally to produce the progenitors of the endodermis and cortex cell lineages. Abbreviations: C, cortex; Da, daughter cell; E, endodermis; In, initial.

Figure 2A:
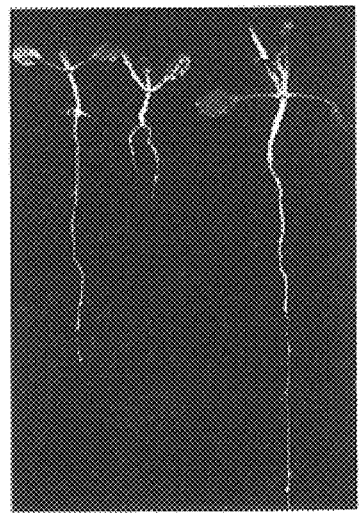
Figure 2B:
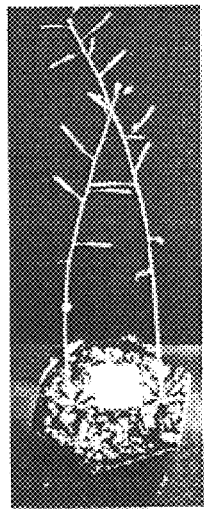
Figure 2C:
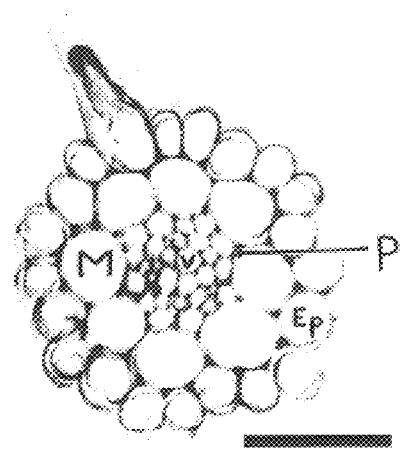
Figure 2D:
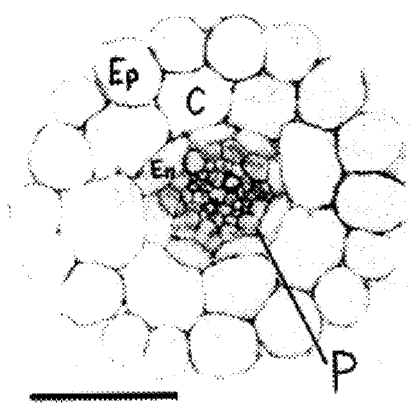
Figure 2E:
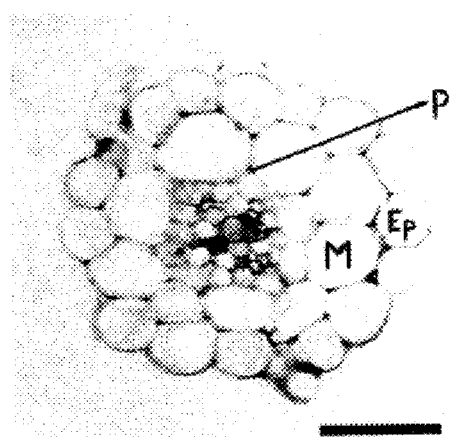
Figure 2F:
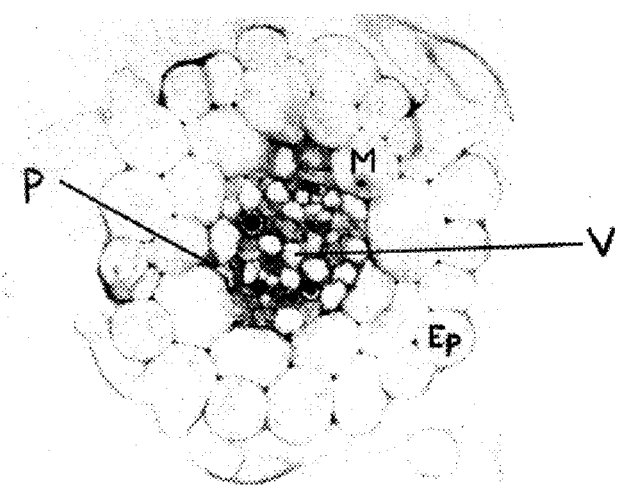

FIGS. 2A–F. Phenotype of scr mutant plants. FIG. 2A. Shown left to right are 12-day scr-2, scr-1 and wild-type seedlings grown vertically on nutrient agar medium. FIG. 2B. 21-day scr-2 mutant plants in soil. FIG. 2C. Transverse section through primary root of 7-day scr-2. FIG. 2D. Transverse section through primary root of 7-day wild-type (WT). FIG. 2E. Transverse section through lateral root of 12-day scr-1 mutant seedling. FIG. 2F. Transverse section through root regenerated from scr-1 callus. Bar, 50 µm. Abbreviations: C, cortex; En, endodermis; Ep, epidermis; M, mutant cell layer; P, pericycle; V, vascular tissue.

Figure 3A:
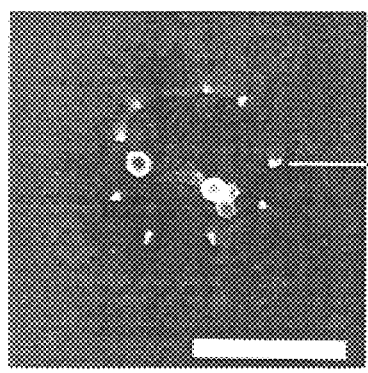
Figure 3D:
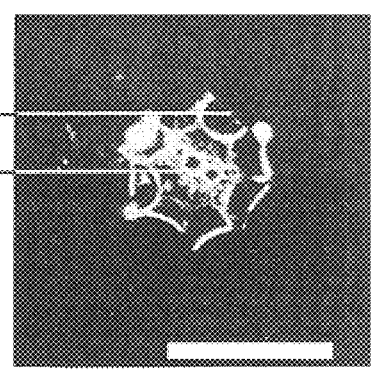
Figure 3B:
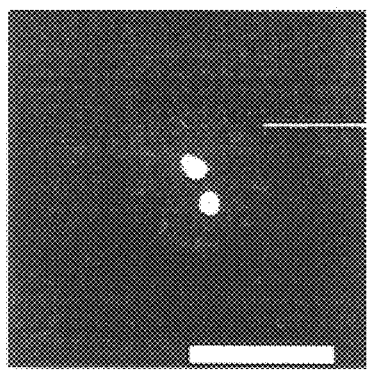
Figure 3E:
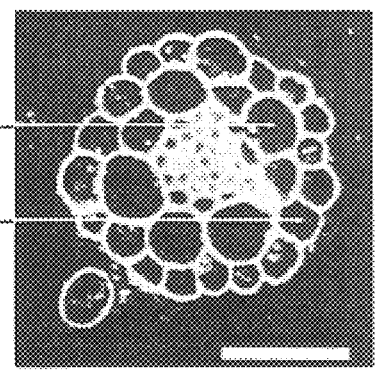
Figure 3C:
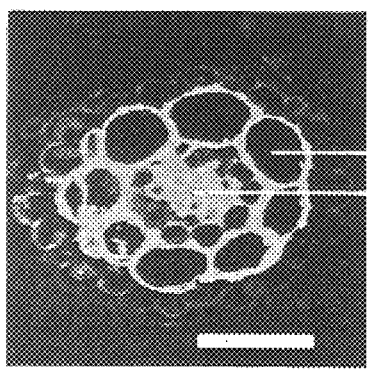
Figure 3F:
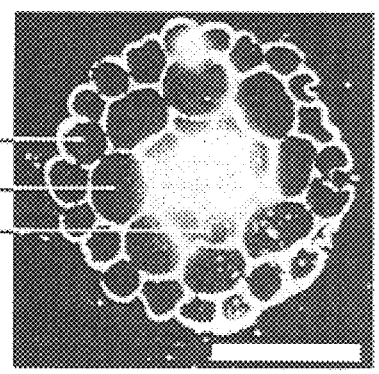

FIGS. 3A–F. Characterization of the cellular identity of the mutant cell layer. FIG. 3A. Endodermis-specific Casparian band staining of transverse sections through the primary root of 7-day scr-1 mutant. (Note: the histochemical stain also reveals xylem cells in the vascular cylinder.) FIG. 3B. Casparian band staining of transverse sections through the primary root of 7-day wild-type (WT). FIG. 3C. Immunostaining with the endodermis (and a subset of vascular tissue) specific JIM13 monoclonal antibodies on transverse root sections of scr-2 mutant. FIG. 3D. Immunostaining with JIM13 monoclonal antibodies on transverse root sections of WT. FIG. 3E. Immunostaining with the JIM7 monoclonal antibody that stains all cell walls on transverse root sections of scr-2 mutant. FIG. 3F. Immunostaining with JIM7 monoclonal antibodies on transverse root sections of WT. Bar, 25 µm. Abbreviations are same as those for description of FIGS. 2A–2F and: Ca, casparian strip.

Figure 4A:
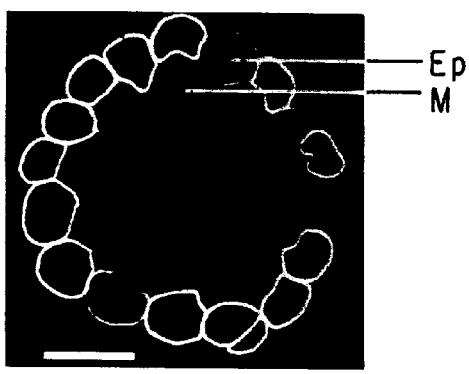
Figure 4D:
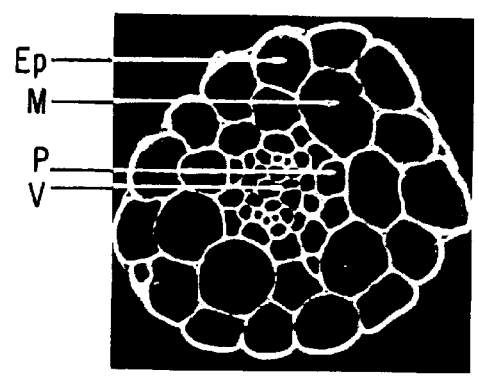
Figure 4B:
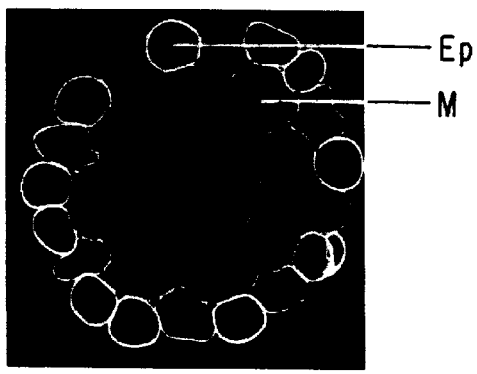
Figure 4E:
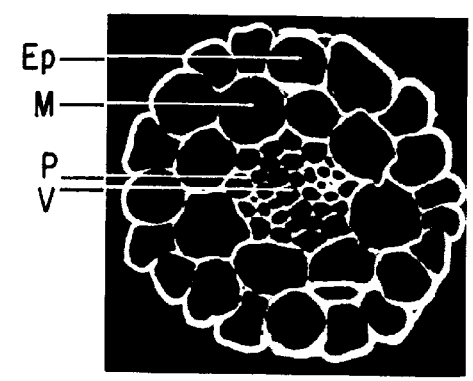
Figure 4C:
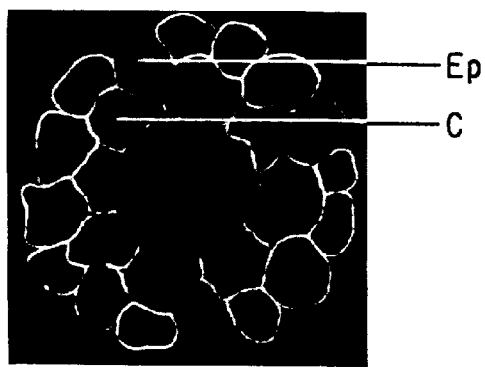
Figure 4F:
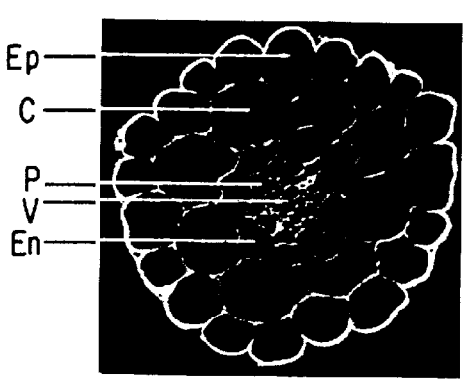

FIGS. 4A–F. Immunostaining. FIG. 4A. Immunostaining with the cortex (and epidermis) specific CCRC-M2 monoclonal antibodies on transverse root sections of scr-1 mutant. FIG. 4B. Immunostaining with CCRC-M2 antibodies on transverse root sections of scr-2 mutant. FIG. 4C. Immunostaining with CCRC-M2 antibodies on transverse root sections of wild-type (WT). FIG. 4D. Immunostaining with the CCRC-M1 monoclonal antibodies (specific to a cell wall epitope found on all cells) on transverse root sections of scr-1. FIG. 4E. Immunostaining with CCRC-M1 antibodies on transverse root sections of scr-2. FIG. 4F. Immunostaining with CCRC-M1 antibodies on transverse root sections of WT. Bar, 30 µm. Abbreviations are same as those for description of FIGS. 2A–2F.

Figure 5A-1:
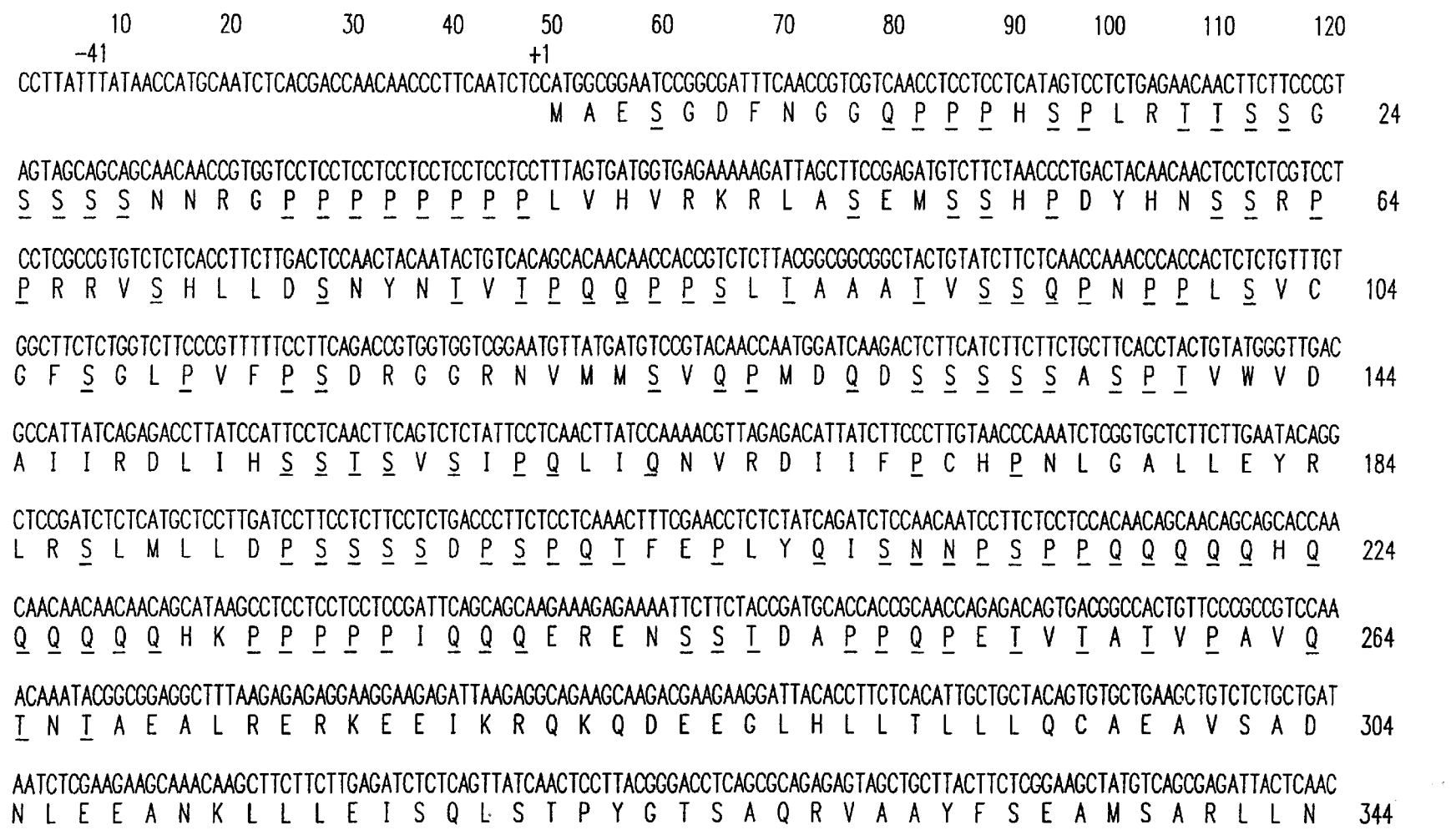
Figure 5B:
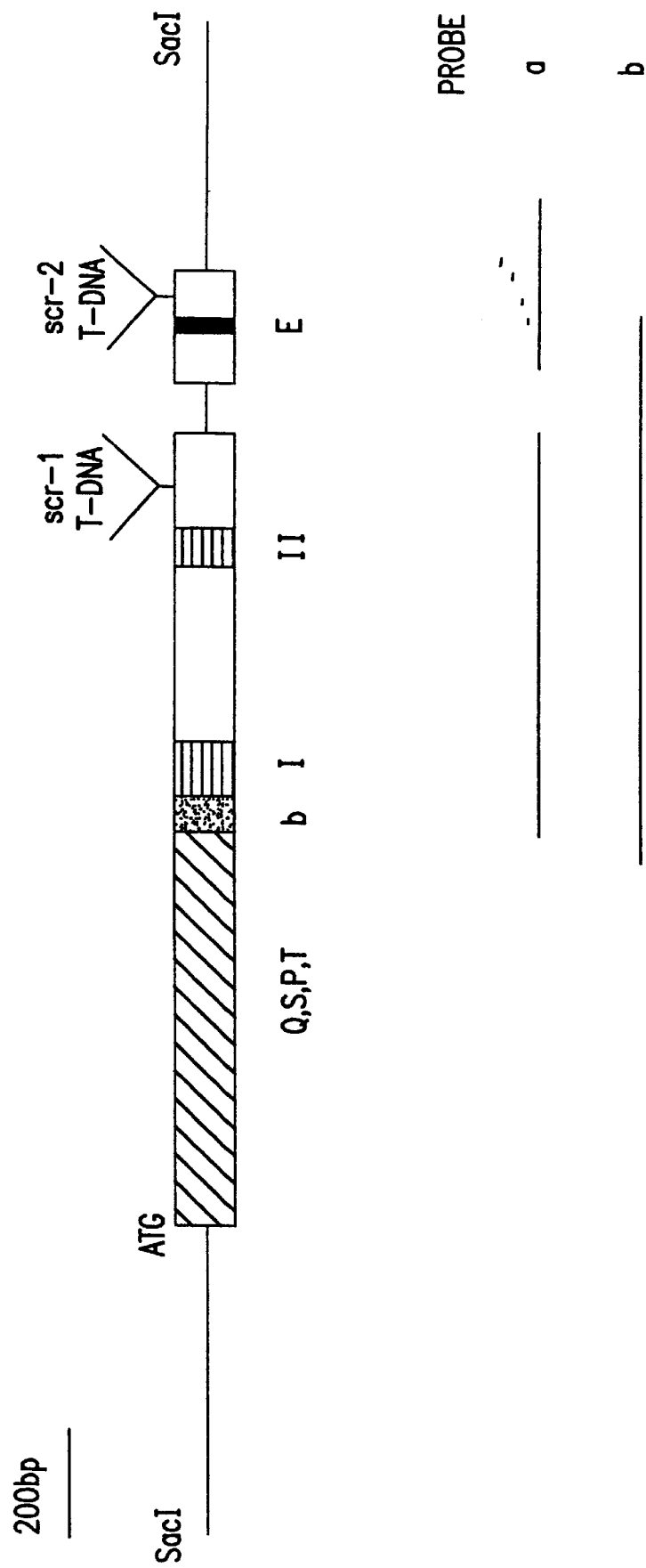

FIGS. 5A–E. Structure of the Arabidopsis SCARECROW gene. FIG. 5A. Nucleic acid sequence and deduced amino acid sequence of the Arabidopsis SCR genomic region (SEQ ID NO:1) and (SEQ ID NO:2), respectively. Regulatory sequences including: (i) TATA box, (ii) ATG start codon, and (iii) potential polyadenylation sequence are underlined. Within the deduced amino acid sequence homopolymeric repeats are underlined. FIG. 5B. Schematic diagram of genomic clone indicating possible functional motifs, T-DNA insertion sites and subclones used as probes. Abbreviations: Q,S,P,T, region with homopolymeric repeats of these amino acids; b, region with similarity to the basic region of bZIP factors; I and II, regions with leucine heptad repeats; E, acidic region. FIG. 5C. comparison of the charged region found in Arabidopsis SCR protein with that found in bZIP transcription factors, SCR bZIP-like domain (SEQ ID NO:3), GCN4 (SEQ ID NO:4), TGAl (SEQ ID NO:5), C-Fos (SEQ ID NO:6), c-JUN (SEQ ID NO:7), CREB (SEQ ID NO:8), Opaque-2 (SEQ ID NO:9), OBF2 (SEQ ID NO:10), RAF-1 (SEQ ID NO:11). FIG. 5D. Translations of EST clones encoding putative peptide having similarities to the VHIID domain region of Arabidopsis SCR protein (SEQ ID NO:12), F13896 (SEQ ID NO:13), Z37192 (SEQ ID NO:14), and Z25645 (SEQ ID NO:15) are from Arabidopsis, T18310 (SEQ ID NO:17) is from maize and D41474 (SEQ ID NO:16) is from rice. FIG. 5E. The deduced amino acid sequence of the Arabidopsis SCARECROW gene (SEQ ID NO:2).

Figure 6A:
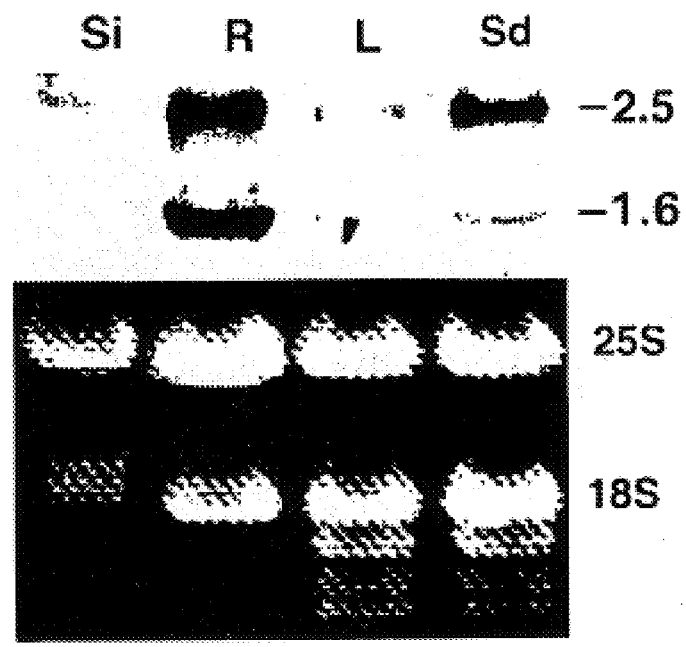
Figure 6B:
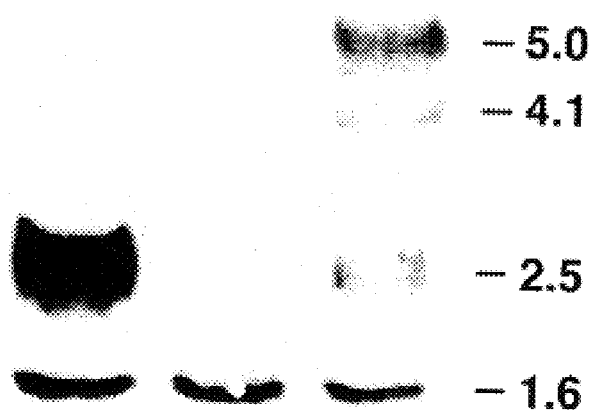

FIGS. 6A–B. Expression of the Arabidopsis SCARECROW gene. FIG. 6A. Northern blot of total RNA from wild-type siliques (Si), roots (R), leaves (L) and whole seedlings (Sd) hybridized with Arabidopsis SCR probe a and with a probe from the Arabidopsis glutamine dehydrogenase (GDH) gene (Melo-Oliveira et al., 1996, Proc. Natl. Acad. Sci. USA 93:4718–4723) as a control for RNA integrity. (GDH expression is lower in siliques than in vegetative tissues.) The 1.6 kb band corresponds to the GDH gene and the approximately 2.5 kb band corresponds to SCR. Ribosomal RNA is shown as a loading control. FIG. 6B. Northern blot of Arabidopsis wild-type, scr-1 and scr-2 total RNA, probed with Arabidopsis SCR probe "aa" corresponding to a cDNA sequence shown in FIG. 5B, and with the GDH probe. In scr-2 mutant additional bands of 4.1 kb and 5.0 kb were detected.

Figure 7A:
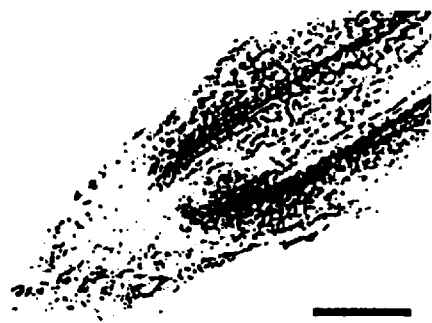
Figure 7B:
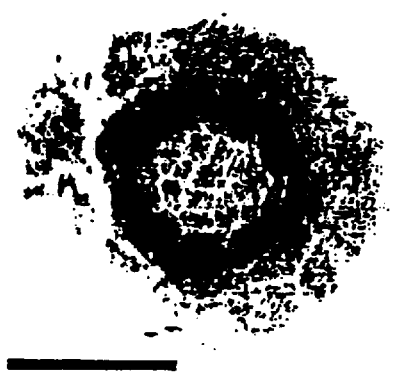
Figure 7C:
Figure 7D:
Figure 7E:
Figure 7F:
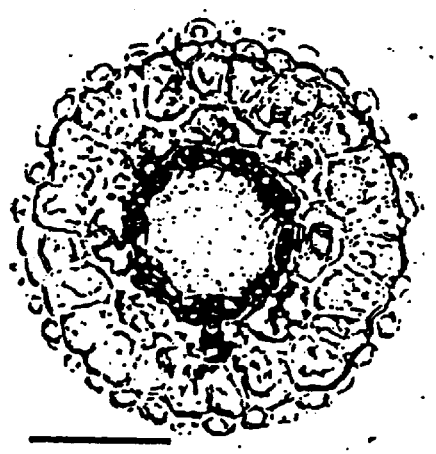
Figure 7G:
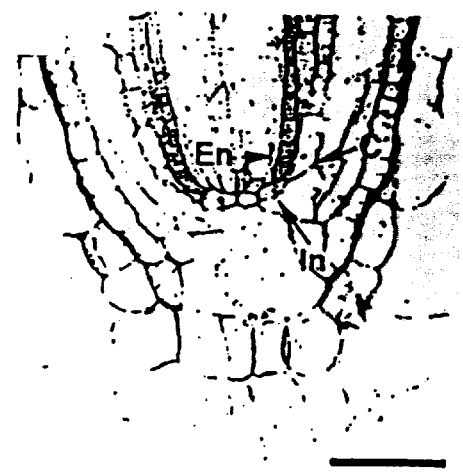

FIGS. 7A–G. In situ hybridization and enhancer trap analyses of Arabidopsis SCR expression. FIG. 7A. SCR RNA expression detected by in situ hybridization of SCR antisense probe to a longitudinal section through the root meristem. FIG. 7B. In situ hybridization of SCR antisense probe to a transverse section in the meristematic region. FIG. 7C. In situ hybridization of SCR antisense probe to late torpedo stage embryo. FIG. 7D. Negative control in situ hybridization using a SCR sense probe to a longitudinal section through the root meristem. FIG. 7E. GUS expression in a whole mount in the enhancer trap line, ET199 in primary root tip. FIG. 7F. GUS expression in the ET199 line in transverse root section in the meristematic region. FIG. 7G. GUS expression in ET199 detected in a section through the root meristem. GUS expression is observed in the cortex/endodermal initial, and in the first cell in the endodermal cell lineage but not in the first cell of the cortex lineage. Expression in two endodermal layers is observed higher up in the root because the section was not median at that point. Bar, 50 µm. Abbreviations are same as those in the description of FIGS. 2A–2F.

FIG. 8. Partial nucleotide sequence (SEQ ID NO:18) and deduced amino acid sequence (SEQ ID NO:19) of the Arabidopsis SRPa4 gene.

FIG. 9. Partial nucleotide sequence (SEQ ID NO:20) and deduced amino acid sequence (SEQ ID NO:21) of the Arabidopsis SRPa3 gene.

FIG. 10. Partial nucleotide sequence (SEQ ID NO:22) of the Arabidopsis SRPa1 gene.

FIG. 11A. Nucleotide sequence (SEQ ID NO:24) and deduced amino acid sequence (SEQ ID NO:25) of the maize Zm-Scl1 fragment.

FIG. 11B. Partial nucleotide sequence (SEQ ID NO:25) and deduced amino acid sequence (SEQ ID NO:26) of the maize SRPm1 gene (Zm-Scl2).

FIGS. 12A–B. Nucleotide sequence of rice SRPo3 EST clone. FIG. 12A. Sequence of 5' end of EST clone (SEQ ID NO:28). FIG. 12B. Sequence of 3' end of EST clone. (SEQ ID NO:29).

FIGS. 13A–F. Comparison of the amino acid sequence of members of the SCARECROW family of genes. Conserved Motifs I through VI are indicated by dashed line above the aligned sequences. Consensus sequences are shown in bold. See Table 1 for the identity and sequence identifier number of each of the sequences shown in this Figure. Hu-scr-1= Human SCR paralog (SEQ ID NO:40).

Figure 14:
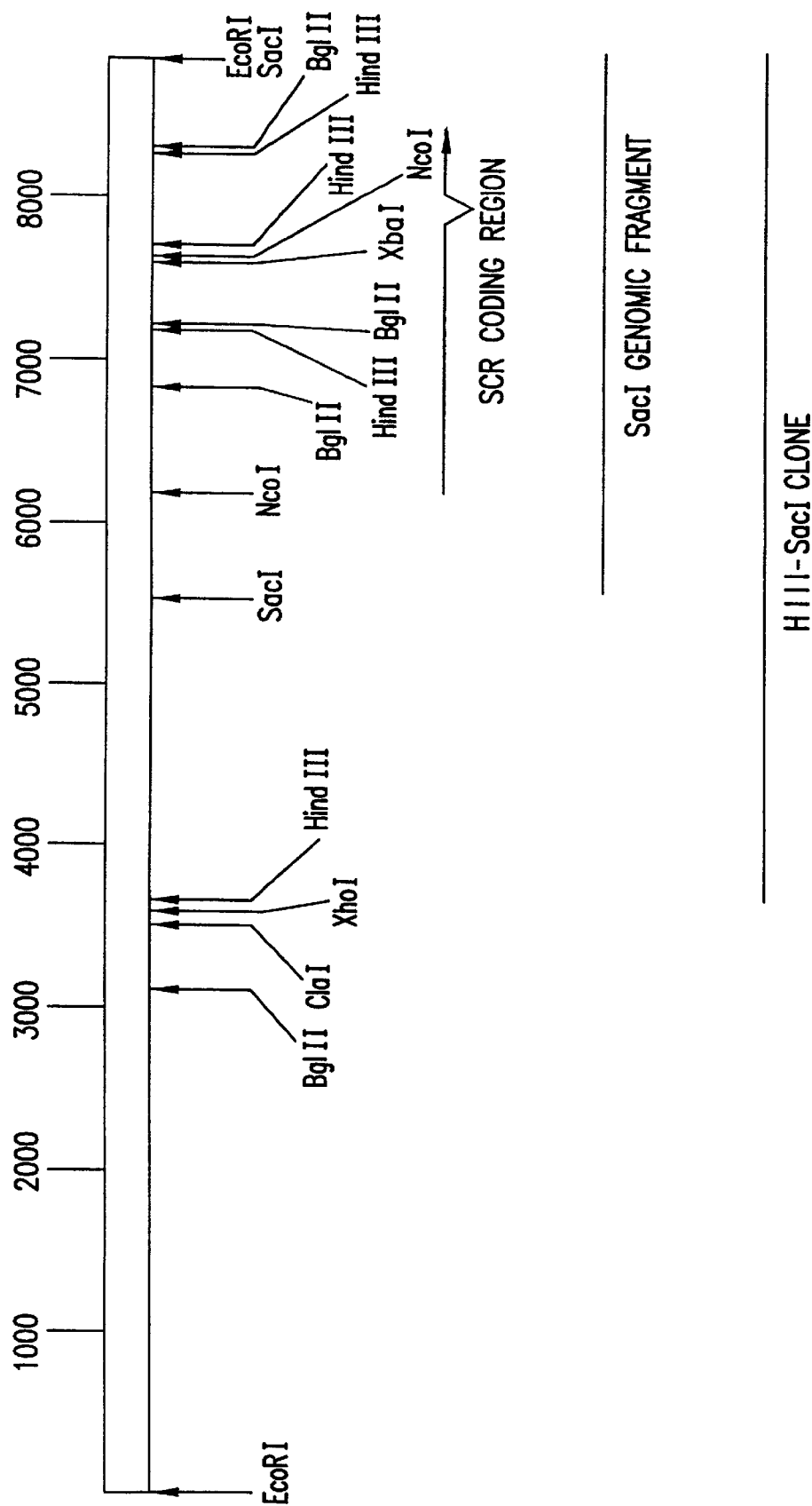
Figure 19A:
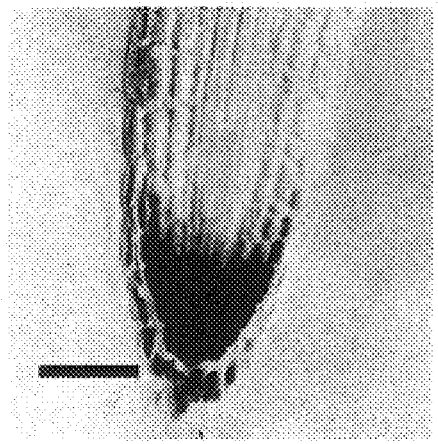
Figure 19C:
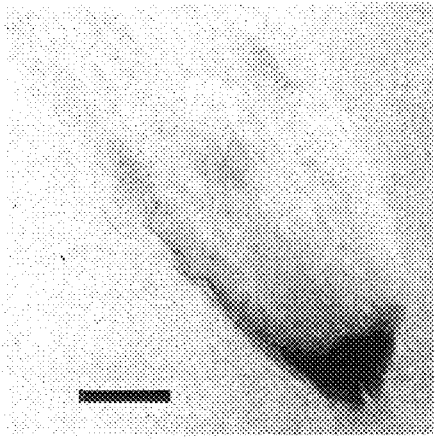
Figure 19B:
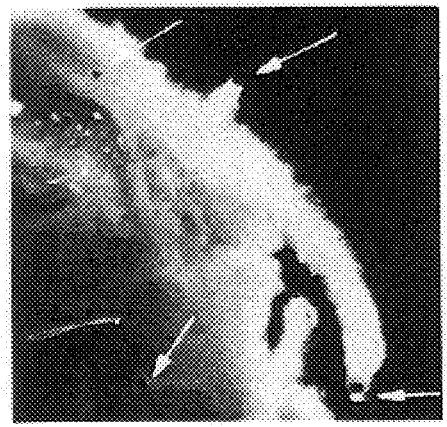
Figure 19D:
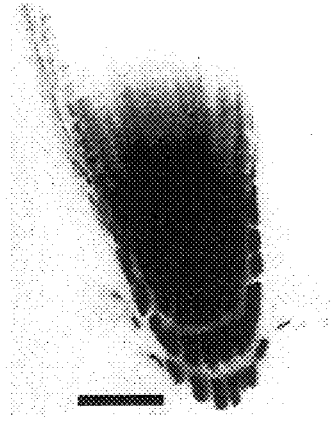
Figure 19E:
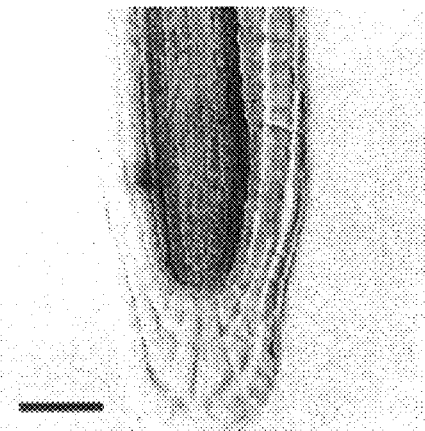
Figure 19F:
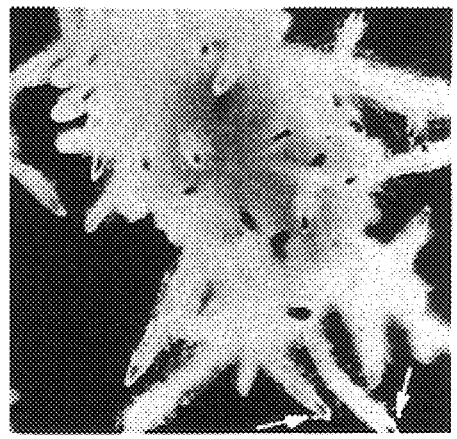
Figure 19G:
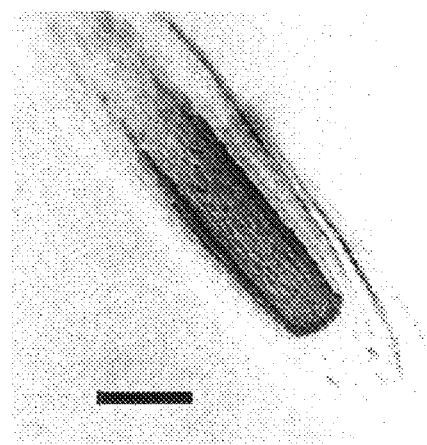
Figure 21A:
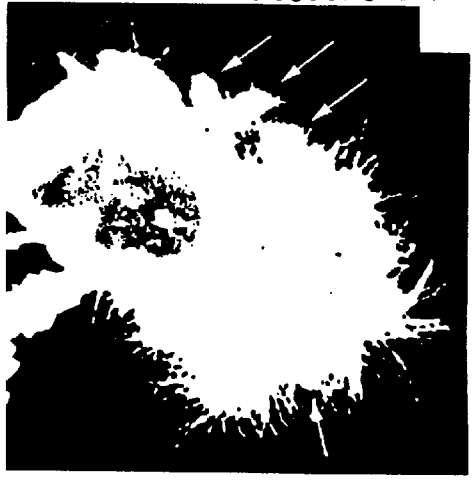
Figure 21B:
Figure 21C:
Figure 21D:
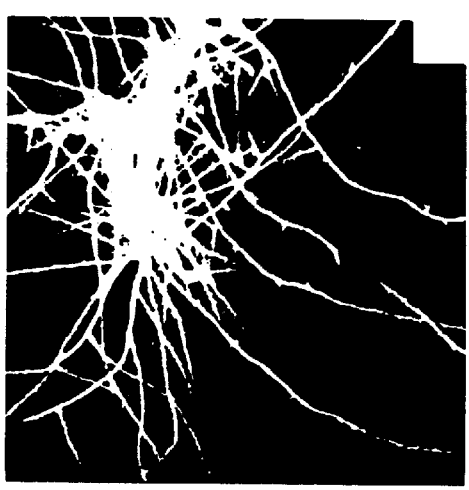
Figure 21E:
Figure 21F:
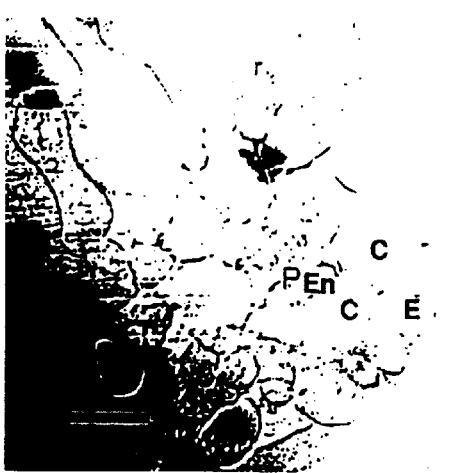

FIG. 14. Restriction map of the approximately 8.8 kb Eco RI insert DNA of lambda clone, t643, containing the Arabidopsis SCR gene. The locations of the approximately 5.6 kb HindIII-SacI fragment subcloned in plasmid LIG 1–3/SAC+MoB$_2$ 1SAC, and the SCR coding region are indicated below the restriction map. The location of the translational initiation site of the SCR gene is at the Nco I site at the left end of the indicated coding region. The SCR coding sequence begins at the translation initiation site and extends approximately 1955 nucleotides to its right. E. coli DH5α containing plasmid pLIG1–3/SAC+MoB$_2$ 1SAC, has the ATCC accession number 98031.

FIGS. 15A–S. Comparison of the partial and complete amino acid sequences of several plant members of the SCARECROW family of genes. The amino acid sequences are aligned in a manner that maximizes amino acid sequence similarity and identity among SCR family members. Each sequence shown is continuous except where noted otherwise; the dots are inserted between two sequence segments in order to align homologous segments. "X" in the middle of a sequence indicates ambiguity in the corresponding nucleotide sequence and, possible termination of the ORF at the "X" residue site. "X" at the end of a sequence indicates termination of the ORF at the "X" residue site. The numbering of the amino acid residues is shown at the bottom of each figure and is based on the Arabidopsis SCR amino acid sequence. Conserved Motifs I through VI are indicated by the various dashed lines above the figures. The new and old names of the family members are shown in FIG. 15A. The sequences of SCR, Tf1 and Tf4 are of the complete SCR protein. See Table 1 for the identity and the sequence identifier number of each sequence shown in these figures.

FIGS. 16A–M. The partial nucleotide sequences of several plant members of the SCARECROW family of genes. "N" indicates an unknown base. See Table 1 for the identity and the sequence identifier number of each sequence shown in these figures.

FIG. 17A. The partial nucleotide sequence (SEQ ID NO:66) of the maize ZCR gene.

FIG. 17B. The partial amino acid sequence (SEQ ID NO:67) of the maize ZCR gene. The underlined sequence shares approximately 80% sequence identity with a corresponding sequence of Arabidopsis SCR protein.

FIG. 18. Comparison of the partial amino acid sequences of several SCR ortholog sequences amplified from the genomes of carrot, soybean and spruce. The SRPdl and SRPpl sequences each were obtained by PCR amplification using a combination of 1F and 1R primers. The SRPg1 sequence was obtained by PCR amplification using a combination of 1F and WP primers. The amino acid sequences are aligned in a manner that maximizes amino acid sequence identity and similarity amongst these sequences. Each sequence shown is continuous except where noted otherwise; the dashes are inserted between two sequence segments in order to allow alignment of homologous segments. "x" in the middle of a sequence indicates ambiguity in the corresponding nucleotide sequence and, possible termination of the ORF or existence of an intron at the "x" residue site. See Table 1 for the identity and the sequence identifier number of each sequence shown in this figure.

FIG. 19. Comparison of promoter activities in transgenic lines and roots. Panel a. A stably transformed line containing four copies of the B2 subdomain of the 35S promoter of CaMV upstream of GUS (Benfey et al., 1990). GUS is expressed in the root tip. Panel b. Roots emerging from callus transformed with four copies of the B2 subdomain of the 35S promoter fused to GUS. GUS expression can be seen in the emerging root tips (arrows). Panel c. Higher magnification of a root emerging from the callus in panel b. GUS is clearly restricted to the root tip. The morphology of roots regenerated from calli often appears abnormal. Panel d. A transgenic plant regenerated from the calli and roots shown in panel b. GUS expression in this plants appears to be similar to that of the original line shown in panel a. Panel e. ET199, a stably transformed line that contains an enhancer trapping construct with a minimal promoter fused to the GUS coding region inserted 1 kb upstream from the SCR coding region. GUS expression is primarily in the endodermal layer of the root. Panel f. Roots emerging from calli transformed with the SCR promoter::GUS construct. Expression of the GUS gene appears to be limited to an internal layer (arrows). Panel g. SCR promoter::GUS transformed root in liquid culture. Roots shown in panel f were excised and transferred to liquid cultures. GUS expression is primarily found in the endodermal layer as in ET199. The expression of GUS in the quiescent center, as seen here, is also sometimes observed in ET199. Bar, 50 μm.

FIG. 20. Analysis of SCR promoter activity in the scr mutant background. Panel a. Roots emerging from scr calli transformed with the SCR promoter::GUS construct. Roots regenerated from scr calli are very short. GUS expression appears to be limited to an internal layer of the root (arrows). Panel b. Root regenerated from transformed scr calli and transferred to liquid culture. The scr phenotype, a single layer between the epidermis and pericycle, is easily seen. GUS expression is limited to this mutant layer. E, Epidermis. M, Mutant Layer. P, Pericycle. Bar, 50 μm.

FIG. 21. Molecular Complementation of the scr mutant. Panels a, c and e. scr transformed with the SCR promoter-::GUS construct. Panels b, d and f. scr transformed with the SCR promoter::SCR coding region construct. Panels a and b. Roots emerging from scr calli. Arrows point to several very short roots among many fine root hairs in the scr calli transformed with the SCR promoter::GUS construct. In contrast, roots from scr calli transformed with the SCR promoter::SCR coding region construct appeared to be wild-type in length, suggesting molecular complementation by the transgene. Panels c and d. Transgenic roots in liquid culture. The scr roots transformed with the SCR promoter-::GUS construct appeared short, while those transformed with the SCR promoter::SCR coding region construct appeared of wild-type length. Panels e and f. Transverse sections through roots emerging from calli. Whereas there is only a single cell layer between the epidermis and stele in the SCR promoter::GUS transformed root, the radial organization of the root transformed with the SCR promoter-::SCR coding region appeared identical to wild-type, with both cortex and endodermal layers. E, epidermis. M, mutant layer. C, cortex. En, Endodermis. P, Pericycle. Bar, 50 μm FIG. 22. Expression of ZCR in maize root tips. Left Panel. Expression of ZCR is in the endodermal layer and extends down through the region of the quiescent center. Right Panel. Higher magnification showing expression in a single cell layer through the quiescent center.

5. DETAILED DESCRIPTION OF THE INVENTION

The invention relates to the SCARECROW (SCR) gene, SCR gene products, including but not limited to transcriptional products such as mRNAs, antisense and ribozyme molecules, and translational products such as the SCR protein, polypeptides, peptides and fusion proteins related thereto; antibodies to SCR gene products; SCR regulatory regions; and the use of the foregoing to improve agronomically valuable plants.

In summary, the data described herein show the identification of SCR, a gene involved in the regulation of a specific asymmetric division, in controlling gravitropic response in aerial structures, and in controlling pattern formation in roots. Sequence analysis shows that the SCR protein has many hallmarks of transcription factors. In situ and marker line expression studies show that SCR is expressed in the cortex/endodermal initial of roots before asymmetric division occurs, and in quiescent center of regenerating roots. Together, these findings indicate that SCR gene regulates key events that establish the asymmetric division that generates separate cortex and endodermal cell lineages, and that affect tissue organization of roots. The establishment of these lineages is not required for cell differentiation to occur, because in the absence of division the resulting cell acquires mature characteristics of both cortex and endodermal cells. However, it is possible that SCR functions to establish the polarity of the initial before cell division, or that it is involved in generating an external polarity that has an effect on asymmetric cell division.

Genetic analysis indicates that SCR expression affects gravitropism of plant stems and hypocotyls. This indicates that SCR is also expressed in these aerial structures of plants.

The SCR genes and promoters of the present invention have a number of important agricultural uses. The SCR promoters of the invention may be used in expression constructs to express desired heterologous gene products in the embryo, root, root nodule, and starch sheath layer in stem of transgenic plants transformed with such constructs. For example, SCR promoters may be used to express disease resistance genes such as lysozymes, cecropins, maganins, or thionins for anti-bacterial protection or the pathogenesis-related (PR) proteins such as glucanases and chitinases for anti-fungal protection. SCR promoters also may be used to express a variety of pest resistance genes in the aforementioned plant structures and tissues. Examples of useful gene products for controlling nematodes or insects include *Bacillus thuringiensis* endotoxins, protease inhibitors, collagenases, chitinase, glucanases, lectins, and glycosidases.

Gene constructs that express or ectopically express SCR, and the SCR-suppression constructs of the invention may be used to alter the root and/or stem structure, and the gravitropism of aerial structures of transgenic plants. Since SCR regulates root cell divisions, overexpression of SCR can be used to increase division of certain cells in roots and thereby form thicker and stronger roots. Thicker and stronger roots are beneficial in preventing plant lodging. Conversely, suppression of SCR expression can be used to decrease cell division in roots and thereby form thinner roots. Thinner roots are more efficient in uptake of soil nutrients. Since SCR affects gravitropism of aerial structures, overexpression of SCR may be used to develop "straighter" transgenic plants that are less susceptible to lodging.

Further, SCR gene sequence may be used as a molecular marker for a qualitative trait, e.g., a root or gravitropism trait, in molecular breeding of crop plants.

For purposes of clarity and not by way of limitation, the invention is described in the subsections below in terms of (a) SCR genes and nucleotides; (b) SCR gene products; (c) antibodies to SCR gene products; (d) SCR promoters and promoter elements; (e) transgenic plants which ectopically express SCR; (f) transgenic plants in which endogenous SCR expression is suppressed; and (g) transgenic plants in which expression of a transgene of interest is controlled by SCR promoter.

5.1. SCR GENES

The SCARECROW genes and nucleotide sequences of the invention include: (a) a gene listed below in Table 1 (hereinafter, a gene comprising any one of the nucleotide sequences shown in FIG. 5A, FIG. 8, FIG. 9, FIG. 10, FIGS. 11A–B, FIGS. 12A–B, FIGS. 16A–M, or FIG. 17A, or a segment of such nucleotide sequences), or as contained in the clones described herein and deposited with the ATCC (see Section 13, infra); (b) nucleotide sequence that encodes a protein comprising any one of the amino acid sequences shown in FIG. 5A, FIG. 5D, FIG. 5E, FIG. 8, FIG. 9, FIGS. 11A–B, FIGS. 13A–F, FIGS. 15A–S, FIG. 17B or FIG. 18 or a segment of such amino acid sequences, or that is encoded by any one of the genes and/or nucleotide sequences listed by their sequence identifier numbers in Table 1, or any segment of such genes and/or nucleotide sequences, or contained in any one of the clones described herein and deposited with the ATCC (see Section 13, infra); (c) any gene comprising nucleotide sequence that hybridizes to the complement of any one of the genes and/or nucleotide sequences listed by their sequence identifier numbers in Table 1, or any segment of such genes and/or nucleotide sequences, or as contained in any one of the clones described herein and deposited with the ATCC, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and that encodes a gene product functionally equivalent to SCR gene product encoded completely or partly by any one of the genes and/or sequences listed in Table 1 or any segment of such genes and nucleotide sequences, or as contained in any one of the clones deposited with the ATCC; (d) any gene comprising nucleotide sequence that hybridizes to the complement of any one of the sequences listed by their sequence identifier numbers in Table 1, or any segment of such nucleotide sequences, or as contained in any one of the clones described herein and deposited with the ATCC, under less stringent conditions, such as moderately stringent conditions, e.g., washing in 0.2×SSC/0.1% SDS at 42° C. (Ausubel et al., 1989, supra), and which encodes a functionally equivalent SCR gene product; (e) any gene comprising nucleotide sequence that hybridizes to the complement of any one of the sequences listed by their sequence identifier numbers in Table 1 or any segment of such nucleotide sequences, or as contained in any one of the clones described herein and deposited with the ATCC, under the following low stringency conditions: pre-hybridization in hybridization solution (HS) containing 43% formamide, 5×SSC, 1% SDS, 10% dextran sulfate, 0.1% sarkosyl, 2% block (Genius kit, Boehringer-Mannheim), followed by hybridization overnight at 30 to 33° C. using as a probe a DNA molecule of approximately 1.6 kb of SEQ ID NO:1 at a concentration of 20 ng/ml, followed by washing in 2×SSC/ 0.1% SDS two times for 15 minutes at room temperature and then two times at 50° C., and which encodes a functionally equivalent SCR gene product; and/or (f) any gene comprising nucleotide sequence that encodes a polypeptide or protein containing the consensus sequence for SCR (i.e., MOTIF III (amino acid residues 373–435 of SEQ ID NO:2) or VHIID (amino acid residues 8–12 of SEQ ID NO:12)) shown in FIGS. 13B–D or a segment of such polypeptide or protein. The partial and complete nucleotide and amino acid sequences of SCR genes and encoded proteins and polypeptides included in the invention are listed in Table 1 below.

TABLE 1

SCR ORTHOLOGS AND PARALOGS

| New Name | Old Name | EST Clone[1] | SEQ ID NOs | |
|---|---|---|---|---|
| | | | Nucleotide[3] | Amino Acid |
| ARABIDOPSIS | | | | |
| SRPa1 | 1110 | Z25645/33772 | 22 | 23 |
| SRPa2 | Tf4 | Z34599 | — | 35* |
| SRPa3 | 3935 | Z37192/1 N96166 | 20 | 21 |
| SRPa4 | 4818 | F13896/7 | 18 | 19 |
| SRPa5 | 4871 | F13949 | 45 | 46 |
| SRPa6 | 12398 | R29793 | 51 | 52 |
| SRPa7 | 3635 | T21627 H76979 N96767 | 55 | 56 |
| SRPa8 | Tf1 | T46205 (9468) N96653 (21711) | — | 34* |
| SRPa9 | 10964 | T78186 T44774 | 47 | 48 |
| SRPa10 | 11261 | T76483 | 49 | 50 |
| SRPa11 | 18652 | N37425 | 53 | 54 |
| SRPa12 | 23196 | W43803 W435138 AA042397 | 57 | 58 |
| SRPa13 | 33/08 | T46008 | — | 41 |
| SCR | Scr | N.A.[2] | 1[+] | 2* |
| RICE | | | | |
| SRPo1 | 713 | D15490 | — | 43 |
| SRPo2 | 2504 | D40482 D40607 D40800 D41389 | — | 44 |
| SRPo3 | 3989 | D41474 | — | 36 |
| SRPo4 | 11846 | C20324 | — | 59 |
| MAIZE | | | | |
| SRPm1 | 18310 | T18310 | — | 37 |
| BRASSICA | | | | |
| SRPb1 | 174 | H74669 | — | 42 |
| CARROT | | | | |
| SRPd1 | N.A. | N.A. | 60 | 61 |
| SOYBEAN | | | | |
| SRPg1 | N.A. | N.A. | 62 | 63 |
| SPRUCE | | | | |
| SRPp1 | N.A. | N.A. | 64 | 65 |

[1]Each EST clone is identified by its GenBank accession number. Each EST clone corresponds to a deposit of a cDNA sequence that matches a part of the nucleotide sequence of the corresponding SCR ortholog or paralog.
[2]N.A. = not applicable.
[3]The partial or complete nucleotide sequence of the SCR orthologs and paralogs listed here are shown in FIGS. 5A, 8, 9, 10, 11A–B, 12A–B, 16A–M and 17A.
[+]Contains the complete coding sequence of Arabidopsis SCR gene.
*Contains the complete amino acid sequence of Arabidopsis SRPa2, SRPa8, or SCR protein.

Functional equivalents of the SCR gene product include any plant gene product that regulates plant embryo or root development, or, preferably, that regulates root cell division or root tissue organization, or affects gravitropism of plant aerial structures (e.g., stems and hypocotyls). Functional equivalents of the SCR gene product include naturally occurring SCR gene products, and mutant SCR gene products, whether naturally occurring or engineered.

The invention also includes nucleic acid molecules, preferably DNA molecules, that hybridize to, and are therefore the complements of the nucleotide sequences (a) through (f), in the first paragraph of this section. Such hybridization conditions may be highly stringent, less highly stringent, or low stringency as described above. In instances wherein the nucleic acid molecules are oligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as SCR antisense molecules, useful, for example, in SCR gene regulation and/or as antisense primers in amplification reactions of SCR gene and/or nucleic acid sequences. Further, such sequences may be used as part of ribozyme and/or triple helix sequences, also useful for SCR gene regulation. Still further, such molecules may be used as components in probing methods whereby the presence of a SCARECROW allele may be detected.

The invention also includes nucleic acid molecules, preferably DNA molecules, which are amplified using the polymerase chain reaction under conditions described in Section 5.1.1., infra, and that encode a gene product functionally equivalent to a SCR gene product encoded by any one of the genes and sequences listed in Table 1 or as contained in any one of the clones described herein and deposited with the ATCC.

The invention also encompasses (a) DNA vectors that contain any of the foregoing gene and/or coding sequences and/or their complements (i.e., antisense or ribozyme molecules); (b) DNA expression vectors that contain any of the foregoing gene and/or coding sequences operatively associated with a regulatory element that directs the expression of the gene and/or coding sequences; and (c) genetically engineered host cells that contain any of the foregoing gene and/or coding sequences operatively associated with a regulatory element that directs the expression of the gene and/or coding sequences in the host cell. As used herein, regulatory elements include but are not limited to inducible and non-inducible promoters, enhancers, operators and other elements known to those skilled in the art that drive and regulate expression.

The invention also encompasses nucleotide sequences that encode mutant SCR gene products, peptide fragments of the SCR gene product, truncated SCR gene products, and SCR fusion proteins. These gene products include, but are not limited to, nucleotide sequences encoding mutant SCR gene products; polypeptides or peptides corresponding to one or more of the Motifs I–VI as shown in FIGS. 13A–F and FIGS. 15A–S, or the bZIP, VHIID (amino acid residues 8–12 of SEQ ID NO:12), or leucine heptad domains of the SCR, or portions of these motifs and domains; truncated SCR gene products in which one or more of the motifs or domains is deleted, e.g., a truncated, nonfunctional SCR lacking all or a portion of the Motifs I–VI as shown in FIGS. 13A–F and FIGS. 15A–S, or the bZIP, VHIID (amino acid residues 373–435 of SEQ ID NO:2), or leucine heptad domains of the SCR. Nucleotides encoding fusion proteins may include but are not limited to full length SCR, truncated SCR or peptide fragments of SCR fused to an unrelated protein or peptide, such as for example, an enzyme, fluorescent protein, or luminescent protein which can be used as a marker.

In particular, the invention includes, for example, fragments of SCR genes encoding one or more of the following domains as shown in FIG. 5E: amino acids 1–264, 265–283, 287–316, 410–473, 436–473, and 473–653.

In addition to the gene and/or coding sequences described above, homologous SCR genes, and other genes related by DNA sequence, may be identified and may be readily isolated, without undue experimentation, by molecular biological techniques well known in the art. More specifically, such homologs include, for example, paralogs (i.e., members of the SCR gene family occurring in the same plant) as well as orthologs (i.e., members of the SCR gene family which occur in a different plant species) of the Arabidopsis SCR gene.

A specific embodiment of a SCR gene and coding sequence of the invention is Arabidopsis SCR (FIGS. 5A and 5E). Other specific embodiments include the various SCR genes and coding sequences listed in Table 1, supra.

Methods for isolating SCR genes and coding sequences are described in detail in Section 5.2, below.

SCR genes share substantial amino acid sequence similarities at the protein level and nucleotide sequence similarities in their encoding genes. The term "substantially similar" or "substantial similarity" when used herein with respect to two amino acid sequences means that the two sequences have at least 75% identical residues, preferably at least 85% identical residues and most preferably at least 95% identical residues. The same term when used herein with respect to two nucleotide sequences means that the two sequences have at least 70% identical residues, preferably at least 85% identical residues and most preferably at least 95% identical residues. Determining whether two sequences are substantially similar may be carried out using any methodologies known to one skilled in the art, preferably using computer assisted analysis. For example, the alignments showed herein were initially accomplished by a BLAST search (NCBI using the BLAST network server). The final alignments of SCR family members were done manually.

Moreover, SCR genes show highly localized expression in embryos and, particularly, roots. Such expression patterns may be ascertained by Northern hybridizations and in situ hybridizations using antisense probes.

5.1.1. ISOLATION OF SCR GENES

The following methods can be used to obtain SCR genes and coding sequences from a wide variety of plants, including but not limited to *Arabidopsis thaliana, Zea says, Nicotiana tabacum, Daucus carota,* Oryza, *Glycine max, Lemna gibba,* and *Picea abies.*

Nucleotide sequences encoding an SCR gene or a portion thereof may be obtained by PCR amplification of plant genomic DNA or cDNA. Useful cDNA sources include "free" cDNA preparations (i.e., the products of cDNA synthesis) and cloned cDNA in cDNA libraries. Root cDNA preparations or libraries are particularly preferred.

The amplification may use, as the 5'-primer (i.e., forward primer), a degenerate oligonucleotide that corresponds to a segment of a known SCR amino acid sequence, preferably from the amino-terminal region. The 3'-primer (i.e., reverse primer) may be a degenerate oligonucleotide that corresponds to a distal segment of the same known SCR amino acid sequence (i.e., carboxyl to the sequence that corresponds to the 5'-primer). For example, the amino acid sequence of the Arabidopsis SCR protein (SEQ ID NO:2) may be used to design useful 5' and 3' primers. Preferably, the primers corresponds to segments in the Motif III (amino acid residues 373–435 of SEQ ID NO:2)or VHIID (amino acid residues 8–12 of SEQ ID NO:12) domain of SCR protein (see FIGS. 13B–D and FIGS. 15K–L). The sequence of the optimal degenerate oligonucleotide probe corresponding to a known amino acid sequence may be determined by standard algorithms known in the art. See for example, Sambrook et al., *Molecular Cloning: A Laboratory Manual,* 2nd ed., Cold Spring Harbor Laboratory Press, Cold Spring Harbor, NY, Vol 2 (1989).

Further, for amplification from CDNA sources, the 3'-primer may be an oligonucleotide comprising an 3' oligo (dT) sequence. The amplification may also use as primers nucleotide sequences of SCR genes or coding sequences (e.g., any one of the scr sequences and EST sequences listed in Table 1).

PCR amplification can be carried out, e.g., by use of a Perkin-Elmer Cetus thermal cycler and Taq polymerase (Gene Amp ). One can choose to synthesize several different degenerate primers for use in the PCR reactions. It is also possible to vary the stringency of hybridization conditions used in priming the PCR reactions, to allow for greater or lesser degrees of nucleotide sequence similarity between the degenerate primers and the corresponding sequences in the cDNA library. One of ordinary skill in the art will know that the appropriate amplification conditions and parameters depend, in part, on the length and base composition of the primers and that such conditions may be determined using standard formulae. Protocols for executing all PCR procedures discussed herein are well known to those skilled in the art, and may be found in references such as Gelfand, 1989, *PCR Technoloqy, Principles and Applications for DNA Amplification,* H. A. Erlich, ed., Stockton Press, New York; and *Current Protocols In Molecular Biology,* Vol. 2, Ch. 15, Ausubel et al., eds 1988, New York, Wiley & Sons, Inc.

A PCR amplified sequence may be molecularly cloned and sequenced. The amplified sequence may utilized as a probe to isolate genomic or cDNA clones of a SCR gene, as described below. This, in turn, will permit the determination of a SCR gene's complete nucleotide sequence, including its promoter, the analysis of its expression, and the production of its encoded protein, as described infra.

In a preferred embodiment, PCR amplification of SCR gene and/or coding sequences can be carried out according to the following procedure:

PRIMERS:

Forward:

Name: SCR5AII (23-mer, 2 inosines, 64-mix) A.A. code: HFTANQAI (SEQ ID NO:69) DNA Sequence: 5' CAT/C TTT/C ACI GCI AAT/C CAA/G GCN AT 3' (SEQ ID NO:68)

Name: SCR5B (29-mer, 1 inosine, 144-mix) A.A. code: VHIID(L/F)D (SEQ ID NO:71) DNA Sequence: 5' ACGTCTCGA GTI CAT/C ATA/C/T ATA/C/T GAT/C TTN GA 3' (SEQ ID NO:70)

Name: 1F A.A. code: LQCAEAV (SEQ ID NO:73) DNA Sequence: (T/C)TI CA(A/G) TG(T/C GCI GA(A/G) GCN GT (SEQ ID NO:72)

Reverse:

Name: SCR3AII (23-mer, 2 inosines, 128-mix) A.A. code: PGGPP(H/N/K)(V/L/F)R' (SEQ ID NO:75) DNA Sequence: 5' CG/T CCA/C GTG/T TGG IGG ICC NCC NGG 3' (SEQ ID NO:74)

Name: 1R A.A. code: AFQVFNGI (SEQ ID NO:77) DNA Sequence: AT ICC (A/G)TT (A/G)AA IAC (C/T)TG (A/G)AA NGC (SEQ ID NO:76)

Name: 4R A.A. code: QWPGLFHI (SEQ ID NO:79) DNA Sequence: AT (A/G)TG (A/G)AA IA(A/G) NCC IGG CCA (C/T)TG (SEQ ID NO:78)

I=inosine

N=A/C/G/T

Useful primer combinations include the following: SCR5AII+SCR3AII; SCR5B+SCR3AII; IF+IR; and IF+4R

PCR:

Reaction mixture (volume 50 µl ):

5 µl 10× amplification buffer containing Mg (Boehringer-Mannheim)

1 µl 10 mM dNTP's

1 µl forward primer (stock concentration: 80 pmol/µl)

1 µl reverse primer (80 pmol/µl)

DNA (100–300 ng).

Begin reaction with "hot start" in which the enzyme is added to the mix only after a brief denaturation at a high temperature (80° C.)

Cycles:

94° C. 30 sec—brief denaturation (to prevent non-specific priming)

80° C. 5 min—apply the enzyme to the tubes (30 tubes/round at maximum)

94° C. 5 min—thorough denaturation 2 times: 94° C. 1 min 64° C. 5 min 72° C. 2 min 2 times: 94° C. 1 min 62° C. 5 min 72° C. 2 min 2 times: 94° C. 1 min 60° C. 5 min 72° C. 2 min (reduce the annealing temperature 2° C. in every second round), until 44° C. is reached after that:

40 times: 94° C. 20 sec 48° C. 1 min 72° C. 2 min finally, let cool down to 15° C.

A SCR gene coding sequence may also be isolated by screening a plant genomic or cDNA library using a SCR nucleotide sequence (e.g., the sequence of any of the SCR genes and sequences and EST clone sequences listed in Table 1.) as hybridization probe. For example, the whole or a segment of the Arabidopsis SCR nucleotide sequence (FIG. 5A) may be used. Alternatively, a SCR gene may be isolated from such libraries using as probe a degenerate oligonucleotide that corresponds to a segment of a SCR amino acid sequence. For example, degenerate oligonucleotide probe corresponding to a segment of the Arabidopsis SCR amino acid sequence (FIG. 5E) may be used.

In preparation of CDNA libraries, total RNA is isolated from plant tissues, preferably roots. Poly(A)+RNA is isolated from the total RNA, and cDNA prepared from the poly(A)+RNA, all using standard procedures. See, for example, Sambrook et al., *Molecular Cloning: A Laboratory Manual*, 2d ed., Vol. 2 (1989). The cDNAs may be synthesized with a restriction enzyme site at their 3'-ends by using an appropriate primer and further have linkers or adaptors attached at their 5'-ends to facilitate the insertion of the cDNAs into suitable CDNA cloning vectors. Alternatively, adaptors or linkers may be attached to the cDNAs after the completion of cDNA synthesis.

In preparation of genomic libraries, plant DNA is isolated and fragments are generated, some of which will encode parts of the whole SCR protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation.

The genomic DNA or cDNA fragments can be inserted into suitable vectors, including but not limited to, plasmids, cosmids, bacteriophages lambda or $T_4$, and yeast artificial chromosome (YAC) [See, for example, Sambrook et al., *Molecular Cloning: A Laboratory Manual*, 2d ed., Cold Spring Harbor Laboratory Press, Cold Spring Harbor, New York (1989); Glover, D. M(ed.), *DNA Cloning: A Practical Approach*, MRL Press, Ltd., Oxford, U. K., Vols. I and II (1985)].

The SCR nucleotide probe, DNA or RNA, should be at least 17 nucleotides, preferably at least 26 nucleotides, and most preferably at least 50 nucleotides in length. The nucleotide probe is hybridized under moderate stringency conditions and washed under moderate, preferably high stringency conditions. Clones in libraries with insert DNA having substantial homology to the SCR probe will hybridize to the probe. Hybridization of the nucleotide probe to genomic or cDNA libraries is carried out using methods known in the art. One of ordinary skill in the art will know that the appropriate hybridization and wash conditions depend on the length and base composition of the probe and that such conditions may be determined using standard formulae. See, for example, Sambrook et al., *Molecular Cloning: A Laboratory Manual*, 2nd ed., Cold Spring Harbor Laboratory Press, Cold Spring Harbor, NY, Vol. 2, (1989) pp 11.45–11.57 and 15.55–15.57.

The identity of a cloned or amplified SCR gene sequence can be verified by comparing the amino acid sequences of its three open reading frames with the amino acid sequence of a SCR gene (e.g., Arabidopsis SCR protein [SEQ ID No:2]). A SCR gene or coding sequence encodes a protein or polypeptide whose amino acid sequence is substantially similar to that of a SCR protein or polypeptide (e.g., the amino acid sequence of any one of the SCR proteins and/or polypeptides shown in FIG. 5A, 5E, FIG. 8, FIG. 9, FIGS. 11A–B, FIGS. 15A–S, FIG. 17B and FIG. 18). The identity of the cloned or amplified SCR gene sequence may be further verified by examining its expression pattern, which should show highly localized expression in the embryo and/or root of the plant from which the SCR gene sequence was isolated.

Comparison of the amino acid sequences encoded by a cloned or amplified sequence may reveal that it does not contain the entire SCR gene or its promoter. In such a case the cloned or amplified SCR gene sequence may be used as a probe to screen a genomic library for clones having inserts that overlap the cloned or amplified SCR gene sequence. A complete SCR gene and its promoter may be reconstructed by splicing the overlapping SCR gene sequences.

5.1.2. EXPRESSION OF SCR GENE PRODUCTS

SCR proteins, polypeptides and peptide fragments, mutated, truncated or deleted forms of SCR and/or SCR fusion proteins can be prepared for a variety of uses, including but not limited to the generation of antibodies, as reagents in assays, the identification of other cellular gene products involved in regulation of root development; etc.

SCR translational products include, but are not limited to those proteins and polypeptides encoded by the SCR gene sequences described in Section 5.1, above. The invention encompasses proteins that are functionally equivalent to the SCR gene products described in Section 5.1. Such a SCR gene product may contain one or more deletions, additions or substitutions of SCR amino acid residues within the amino acid sequence encoded by any one of the SCR gene sequences described, above, in Section 5.1, but which result in a silent change, thus producing a functionally equivalent SCR gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous SCR gene products encoded by the SCR gene sequences described in Section 5.1, above. Alternatively, "functionally equivalent" may refer to peptides capable of regulating gene expression in a manner substantially similar to the way in which the corresponding portion of the endogenous SCR gene product would.

The invention also encompasses mutant SCR proteins and polypeptides that agree not functionally equivalent to the gene products described in Section 5.1. Such a mutant SCR protein or polypeptide may contain one or more deletions, additions or substitutions of SCR amino acid residues within the amino acid sequence encoded by any one the SCR gene sequences described above in Section 5.1., and which result in loss of one or more functions of the SCR protein (e.g., recognition of a specific nucleic sequence, binding of an transcription factor, etc.), thus producing a SCR gene product not functionally equivalent to the wild-type SCR protein.

While random mutations can be made to SCR DNA (using random mutagenesis techniques well known to those skilled in the art) and the resulting mutant SCRs tested for activity, site-directed mutations of the SCR gene and/or coding sequence can be engineered (using site-directed mutagenesis techniques well known to those skilled in the art) to generate mutant SCRs with increased function, (e.g., resulting in improved root formation), or decreased function (e.g., resulting in suboptimal root function). In particular, mutated SCR proteins in which any of the domains shown in FIGS. 13A–F are deleted or mutated are within the scope of the invention. Additionally, peptides corresponding to one or more domains of the SCR (e.g., shown in FIGS. 13A–F), truncated or deleted SCRS, as well as fusion proteins in which the full length SCR, a SCR polypeptide or peptide fused to an unrelated protein are also within the scope of the invention and can be designed on the basis of the SCR nucleotide and SCR amino acid sequences disclosed in Section 5.1. above.

While the SCR polypeptides and peptides can be chemically synthesized (e.g., see Creighton, 1983, Proteins: Structures and Molecular Principles, W. H. Freeman & Co., N.Y.) large polypeptides derived from SCR and the full length SCR may advantageously be produced by recombinant DNA technology using techniques well known to those skilled in the art for expressing nucleic acid sequences.

Methods which are well known to those skilled in the art can be used to construct expression vectors containing SCR protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding SCR protein sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express the SCR gene products of the invention. Such host-expression systems represent vehicles by which the CR gene products of interest may be produced and subsequently recovered and/or purified from the culture or plant (using purification methods well known to those skilled in the art), but also represent cells which may, when transformed or transfected with the appropriate nucleotide coding sequences, exhibit the SCR protein of the invention in situ. These include but are not limited to microorganisms such as bacteria (e.g., *E. coli, B. subtilis*) transformed with recombinant bacteriophage DNA, plasmid DNA or cosmid DNA expression vectors containing SCR protein coding sequences; yeast (e.g., *Saccharomyces, Pichia*) transformed with recombinant yeast expression vectors containing the SCR protein coding sequences; insect cell systems infected with recombinant virus expression vectors (e.g., baculovirus) containing the SCR protein coding sequences; plant cell systems infected with recombinant virus expression vectors (e.g., cauliflower mosaic virus, caMV; tobacco mosaic virus, TMV) or transformed with recombinant plasmid expression vectors (e.g., Ti plasmid) containing SCR protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; the cytomegalovirus promoter/enhancer; etc.).

In bacterial systems, a number of expression vectors may be advantageously selected depending upon the use intended for the SCR protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the SCR coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with gluta-thione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene protein can be released from the GST moiety.

In one such embodiment of a bacterial system, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labelling and glutathione S-transferase sequences at the carboxyl terminus for affinity purification (Nilsson, et al., 1985, EMBO J. 4: 1075; Zabeau and Stanley, 1982, *EMBO J.* 1:1217.

The recombinant constructs of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible, selectable, or screenable marker genes for isolating, identifying or tracking plant cells transformed by these constructs. Selectable markers include, but are not limited to, genes that confer antibiotic resistance, (e.g., resistance to kanamycin or hygromycin) or herbicide resistance (e.g., resistance to sulfonylurea, phosphinothricin, or glyphosate). Screenable markers include, but are not be limited to, genes encoding β-glucuronidase (Jefferson, 1987, Plant Mol. Biol. Rep. 5:387–405), luciferase (Ow et al., 1986, Science 234:856–859), B protein that regulates anthocyanin pigment production (Goff et al., 1990, EMBO J 9:2517–2522).

In embodiments of the present invention which utilize the *Agrobacterium tumefacien* system for transforming plants (see infra), the recombinant constructs may additionally comprise at least the right T-DNA border sequences flanking the DNA sequences to be transformed into the plant cell. Alternatively, the recombinant constructs may comprise the right and left T-DNA border sequences flanking the DNA sequence. The proper design and construction of such T-DNA based transformation vectors are well known to those skilled in the art.

5.1.3. ANTIBODIES TO SCR PROTEINS AND POLYPEPTIDES

Antibodies that specifically recognize one or more epitopes of SCR, or epitopes of conserved variants of SCR, or peptide fragments of the SCR are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

For the production of antibodies, various host animals may be immunized by injection with the SCR protein, an SCR peptide (e.g., one corresponding to a functional domain of the protein), a truncated SCR polypeptide (SCR in which one or more domains has been deleted), functional equivalents of the SCR protein, or mutants of the SCR protein. Such SCR proteins, polypeptides, peptides or fusion proteins can be prepared and obtained as described in Section 5.1.2. supra. Host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (Nature 256:495–497 [1975]; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

In addition, techniques have been developed for the production of humanized antibodies. (See, e.g., Queen, U.S. Pat. No. 5,585,089.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against SCR proteins or polypeptides. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a SCR protein and/or polypeptide can, in turn, be utilized to generate anti-idiotype antibodies that "mimic" SCR, using techniques well known to those skilled in the art. (See, e.g., Greenspan & Bona, 1993, FASEB J 7(5):437–444; and Nissinoff, 1991, J. Immunol. 147(8): 2429–2438).

5.1.4. SCR GENE OR GENE PRODUCTS AS MARKERS FOR QUALITATIVE TRAIT LOCI

Any of the nucleotide sequences (including EST clone sequences) described in §§ 5.1 and 5.1.1. and/or listed in Table 1, and/or polypeptides and proteins described in §§ 5.1.2. and/or listed in Table 1, can be used as markers for qualitative trait loci in breeding programs for crop plants. To this end, the nucleic acid molecules, including but not limited to full length SCR coding sequences, and/or partial sequences (ESTs), can be used in hybridization and/or DNA amplification assays to identify the endogenous SCR genes, scr mutant alleles and/or SCR expression products in cultivars as compared to wild-type plants. They can also be used as markers for linkage analysis of qualitative trait loci. It is also possible that the SCR gene may encode a product responsible for a qualitative trait that is desirable in a crop breeding program. Alternatively, the SCR protein, peptides and/or antibodies can be used as reagents in immunoassays to detect expression of the SCR gene in cultivars and wild-type plants.

5.2. SCR PROMOTERS

According to the present invention, SCR promoters and functional portions thereof described herein refer to regions of the SCR gene which are capable of promoting tissue-specific expression in embryos and/or roots of an operably linked coding sequence in plants. The SCR promoter described herein refers to the regulatory elements of SCR genes, i.e., regulatory regions of genes which are capable of selectively hybridizing to the nucleic acids described in Section 5.1, or regulatory sequences contained, for example, in the region between the translational start site of the Arabidopsis SCR gene and the HindIII site approximately 2.5 kb upstream of the site in plasmid pLIG1-3/SAC+Mob21SAC (see FIGS. 5A and 14) in hybridization assays, or which are homologous by sequence analysis (containing a span of 10 or more nucleotides in which at least 50 percent of the nucleotides are identical to the sequences presented herein). Homologous nucleotide sequences refer to nucleotide sequences including, but not limited to, SCR promoters in diverse plant species (e.g., promoters of orthologs of Arabidopsis SCR) as well as genetically engineered derivatives of the promoters described herein.

Methods which could be used for the synthesis, isolation, molecular cloning, characterization and manipulation of SCR promoter sequences are well known to those skilled in the art. See, e.g., the techniques described in Sambrook et al., Molecular Cloning: A Laboratory Manual, 2nd. ed., Cold Spring Harbor Laboratory, Cold Spring Harbor, New York (1989).

According to the present invention, SCR promoter sequences or portions thereof described herein may be obtained from appropriate plant or mammalian sources from cell lines or recombinant DNA constructs containing SCR promoter sequences, and/or by chemical synthetic methods. SCR promoter sequences can be obtained from genomic clones containing sequences 5' upstream of SCR coding sequences. Such 5' upstream clones may be obtained by screening genomic libraries using SCR protein coding sequences, particularly those encoding SCR N-terminal sequences, from SCR gene clones obtained as described in Sections 5.1. and 5.2. Standard methods that may used in such screening include, for example, the method set forth in Benton & Davis, 1977, Science 196:180 for bacteriophage libraries; and Grunstein & Hogness, 1975, Proc. Nat. Acad. Sci. U.S.A. 72:3961–3965 for plasmid libraries.

The full extent and location of SCR promoters within such 5' upstream clones may be determined by the functional assay described below. In the event a 5' upstream clone does not contain the entire SCR promoter as determined by the functional assay, the insert DNA of the clone may be used to isolate genomic clones containing sequences further 5' upstream of the SCR coding sequences. Such further upstream sequences can be spliced on to existing 5' upstream sequences and the reconstructed 5' upstream region tested for functionality as a SCR promoter (i.e., promoting tissue-specific expression in embryos and/or roots of an operably linked gene in plants). This process may be repeat until the complete SCR promoter is obtained.

The location of the SCR promoter within genomic sequences 5' upstream of the SCR gene isolated as described above may be determined using any method known in the art. For example, the 3'-end of the promoter may be identified by locating the transcription initiation site, which may be determined by methods such as RNase protection (e.g., Liang et al., 1989, J. Biol. Chem. 264:14486–14498), primer extension (e.g., Weissenborn & Larson, 1992, J. Biol. Chem. 267:6122–6131), and/or reverse transcriptase/PCR. The location of the 3'-end of the promoter may be confirmed by sequencing and computer analysis, examining for the canonical AGGA or TATA boxes of promoters that are typically 50–60 base pairs (bp) and 25–35 bp 5'-upstream of the transcription initiation site. The 5'-end promoter may be defined by deleting sequences from the 5'-end of the promoter containing fragment, constructing a transcriptional or translational fusion of the resected fragment and a reporter gene, and examining the expression characteristics of the chimeric gene in transgenic plants. Reporter genes that may be used to such ends include, but are not limited to, GUS, CAT, luciferase, β-galactosidase and C1 and R gene controlling anthocyanin production.

According to the present invention, a SCR promoter is one that confers to an operably linked gene in a transgenic plant tissue-specific expression in roots, root nodules, stems and/or embryos. A SCR promoter comprises the region between about −5,000 bp and +1 bp upstream of the transcription initiation site of SCR gene. In a particular embodiment, the Arabidopsis SCR promoter comprises the region between positions −2.5 kb and +1 in the 5' upstream region of the Arabidopsis SCR gene (see FIGS. 5A and 14).

5.2.1. CIS-REGULATORY ELEMENTS OF SCR PROMOTERS

According to the present invention, the cis-regulatory elements within a SCR promoter may be identified using any method known in the art. For example, the location of cis-regulatory elements within an inducible promoter may be identified using methods such as DNase or chemical footprinting (e.g., Meier et al., 1991, Plant Cell 3:309–315) or gel retardation (e.g., Weissenborn & Larson, 1992, J. Biol. Chem. 267–6122–6131; Beato, 1989, Cell 56:335–344; Johnson et al., 1989, Ann. Rev. Biochem. 58:799–839). Additionally, resectioning experiments may also be employed to define the location of the cis-regulatory elements. For example, an inducible promoter-containing fragment may be resected from either the 5' or 3'-end using restriction enzyme or exonuclease digests.

To determine the location of cis-regulatory elements within the sequence containing the inducible promoter, the 5'- or 3'-resected fragments, internal fragments to the inducible promoter containing sequence, or inducible promoter fragments containing sequences identified by footprinting or gel retardation experiments may be fused to the 5'-end of a truncated plant promoter, and the activity of the chimeric promoter in transgenic plant examined. Useful truncated promoters to these ends comprise sequences starting at or about the transcription initiation site and extending to no more than 150 bp 5' upstream. These truncated promoters generally are inactive or are only minimally active. Examples of such truncated plant promoters may include, among others, a "minimal" CaMV 35S promoter whose 5' end terminates at position −46 bp with respect to the transcription initiation site (Skriver et al., Proc. Natl. Acad. Sci. USA 88:7266–7270); the truncated "−90 35S" promoter in the X-GUS-90 vector (Benfey & Chua, 1989, Science 244:174–181); a truncated "−101 nos" promoter derived from the nopaline synthase promoter (Aryan et al., 1991, Mol. Gen. Genet. 225:65–71); and the truncated maize Adh-1 promoter in pADcat 2 (Ellis et al., 1987, EMBO J. 6:11–16).

According to the present invention, a cis-regulatory element of a SCR promoter is a sequence that confers to a truncated promoter tissue-specific expression in embryos, stems, root nodules and/or roots.

5.2.2. SCR PROMOTER-DRIVEN EXPRESSION VECTORS

The properties of the nucleic acid sequences are varied as are the genetic structures of various potential host plant cells. In the preferred embodiments of the present invention, described herein, a number of features which an artisan may recognize as not being absolutely essential, but clearly advantageous are used. These include methods of isolation, synthesis or construction of gene constructs, the manipulation of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The present invention provides for use of recombinant DNA constructs which contain tissue-specific and developmental-specific promoter fragments and functional portions thereof. As used herein, a functional portion of a SCR promoter is capable of functioning as a tissue-specific promoter in the embryo, stem, root nodule and/or root of a plant. The functionality of such sequences can be readily established by any method known in the art. Such methods include, for example, constructing expression vectors with such sequences and determining whether they confer tissue-specific expression in the embryo, stem, root nodule and/or root to an operably linked gene. In a particular embodiment, the invention provides for the use of the Arabidopsis SCR promoter contained in the sequences depicted in FIGS. 5A and 14 and the insert DNA of plasmid pGEX-2TK⁺.

The SCR promoters of the invention may be used to direct the expression of any desired protein, or to direct the expression of a RNA product, including, but not limited to, an "antisense" RNA or ribozyme. Such recombinant constructs generally comprise a native SCR promoter or a recombinant SCR promoter derived therefrom, ligated to the nucleic acid sequence encoding a desired heterologous gene product.

A recombinant SCR promoter is used herein to refer to a promoter that comprises a functional portion of a native SCR promoter or a promoter that contains native promoter sequences that is modified by a regulatory element from a SCR promoter. Alternatively, a recombinant inducible promoter derived from the scr promoter may be a chimeric promoter, comprising a full-length or truncated plant promoter modified by the attachment of one or more SCR cis-regulatory elements.

The manner of chimeric promoter constructions may be any well known in the art. For examples of approaches that can be used in such constructions, see Section 5.1.2., above and Fluhr et al., 1986, Science 232:1106–1112; Ellis et al., 1987, EMBO J. 6:11–16; Strittmatter & Chua, 1987, Proc. Natl. Acad. Sci. USA 84:8986–8990; Poulsen & Chua, 1988, Mol. Gen. Genet. 214:16–23; Comai et al., 1991, Plant Mol. Biol. 15:373–381; Aryan et al., 1991, Mol. Gen. Genet. 225:65–71.

According to the present invention, where a SCR promoter or a recombinant SCR promoter is used to express a desired protein, the DNA construct is designed so that the protein coding sequence is ligated in phase with the translational initiation codon downstream of the promoter. Where the promoter fragment is missing 5' leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria, or vacuole).

5.3. PRODUCTION OF TRANSGENIC PLANTS AND PLANT CELLS

According to the present invention, a desirable plant or plant cell may be obtained by transforming a plant cell with the nucleic acid constructs described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium is employed to introduce the gene constructs into plants. Such transformations preferably use binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet. 16:357–384; Rogers et al., 1986, Methods Enzymol. 118:627–641). The Agrobacterium transformation system may also be used to transform, as well as transfer, DNA to monocotyledonous plants and plant cells (see Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al., 1985, Mol. Gen. Genet. 199:169–177; Fromm et al., 1985, Proc. Natl. Acad. Sci. USA 82:5824–5828; Shimamoto, 1989, Nature 338:274–276), and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Natl. Acad. Sci. USA 85:4305–4309; Gordon-Kamm et al., 1990, Plant Cell 2:603–618).

According to the present invention, a wide variety of plants may be engineered for the desired physiological and agronomic characteristics described herein using the nucleic acid constructs of the instant invention and the various transformation methods mentioned above. In preferred embodiments, target plants for engineering include, but are not limited to, crop plants such as maize, wheat, rice, soybean, tomato, tobacco, carrots, peanut, potato, sugar beets, sunflower, yam, Arabidopsis, rape seed, and petunia; and trees such as spruce.

According to the present invention, desired plants and plant cells may be obtained by engineering the gene constructs described herein into a variety of plant cell types, including but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene construct(s)) following the approaches and methods described below. An isolated transformant may then be regenerated into a plant. Alternatively, the engineered plant material may be regenerated into a plant, or plantlet, before subjecting the derived plant, or plantlet, to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods may also be used to identify a plant or plant cell transformant containing the gene constructs of the present invention. These methods include but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, may also be used to detect the presence or expression of the recombinant construct in specific plant organs and tissues. The methods for doing all these assays are well known to those skilled in the art.

5.3.1. TRANSGENIC PLANTS THAT ECTOPICALLY EXPRESS SCR

In accordance to the present invention, a plant that expresses a recombinant SCR gene may be engineered by transforming a plant cell with a gene construct comprising a plant promoter operably associated with a sequence encoding SCR protein or a fragment thereof. (Operably associated is used herein to mean that transcription controlled by the "associated" promoter would produce a functional messenger RNA, whose translation would produce the enzyme.) The plant promoter may be constitutive or inducible. Useful constitutive promoters include, but are not limited to, the CaMV 35S promoter, the T-DNA mannopine synthetase promoter, and their various derivatives. Useful inducible promoters include but are not limited to the promoters of ribulose bisphosphate carboxylase (RUBISCO) genes, chlorophyll a/b binding protein (CAB) genes, heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, PR-1 genes etc.), dark-inducible genes (e.g., asparagine synthetase gene (Coruzzi and Tsai, U.S. Pat. No. 5,256,558, Oct. 26, 1993, Gene Encoding Plant Asparagine Synthetase) developmentally regulated genes (e.g., Shoot Meristemless gene) to name just a few.

In yet another embodiment of the present invention, it may be advantageous to transform a plant with a gene construct operably linking a modified or artificial promoter to a sequence encoding SCR protein or a fragment thereof. Typically, such promoters, constructed by recombining structural elements of different promoters, have unique expression patterns and/or levels not found in natural promoters. See, e.g., Salina et al., 1992, Plant Cell 4:1485–1493, for examples of artificial promoters constructed from combining cis-regulatory elements with a promoter core.

In a preferred embodiment of the present invention, the associated promoter is a strong and root, root nodule, stem and/or embryo-specific plant promoter such that the SCR protein is overexpressed in the transgenic plant. Examples of root- and root nodules-specific promoters include but are not limited to the promoters of SCR genes, SHR genes, legehemoglobin genes, nodulin genes and root-specific glutamine synthetase genes (See e.g., Tingey et al., 1987, EMBO J. 6:1–9; Edwards et al., 1990, Proc. Nat. Acad. Sci. USA 87:3459–3463).

In yet another preferred embodiment of the present invention, the overexpression of SCR protein in roots may be engineered by increasing the copy number of the SCR gene. One approach to producing such transgenic plants is to transform with nucleic acid constructs that contain multiple copies of the complete SCR gene (i.e., with its own native scr promoter). Another approach is repeatedly transform successive generations of a plant line with one or more copies of the complete SCR gene. Yet another approach is to place a complete SCR gene in a nucleic acid construct containing an amplification-selectable marker (ASM) gene such as the glutamine synthetase or dihydrofolate reductase gene. Cells transformed with such constructs is subjected to culturing regimes that select cell lines with increased copies of complete SCR gene. See, e.g., Donn et al., 1984, J. Mol. Appl. Genet. 2:549–562, for a selection protocol used to isolate of a plant cell line containing amplified copies of the GS gene. Because the desired gene is closely linked to the ASM, cell lines that amplified the ASM gene are also likely to have amplified the SCR gene. Cell lines with amplified copies of the SCR gene can then be regenerated into transgenic plants.

5.3.2. TRANSGENIC PLANTS THAT SUPPRESS ENDOGENOUS SCR EXPRESSION

In accordance with the present invention, a desired plant may be engineered by suppressing SCR activity. In one embodiment, the suppression may be engineered by transforming a plant with a gene construct encoding an antisense RNA or ribozyme complementary to a segment or the whole of SCR RNA transcript, including the mature target mRNA. In another embodiment, SCR gene suppression may be engineered by transforming a plant cell with a gene construct encoding a ribozyme that cleaves the SCR MRNA transcript. Alternatively, the plant can be engineered, e.g., via targeted homologous recombination to inactive or "knock-out" expression of the plant's endogenous SCR.

For all of the aforementioned suppression constructs, it is preferred that such gene constructs express specifically in the root, root nodule, stem and/or embryo tissues. Alternatively, it may be preferred to have the suppression constructs expressed constitutively. Thus, constitutive promoters, such as the nopaline, CaMV 35S promoter, may also be used to express the suppression constructs. A most preferred promoter for these suppression constructs is a SCR or SHR promoter.

In accordance with the present invention, desired plants with suppressed target gene expression may also be engineered by transforming a plant cell with a co-suppression construct. A co-suppression construct comprises a functional promoter operatively associated with a complete or partial SCR gene sequence. It is preferred that the operatively associated promoter be a strong, constitutive promoter, such as the CaMV 35S promoter. Alternatively, the co-suppression construct promoter can be one that expresses with the same tissue and developmental specificity as the scr gene.

According to the present invention, it is preferred that the co-suppression construct encodes a incomplete SCR mRNA, although a construct encoding a fully functional SCR mRNA or enzyme may also be useful in effecting co-suppression.

In accordance with the present invention, desired plants with suppressed target gene expression may also be engineered by transforming a plant cell with a construct that can effect site-directed mutagenesis of the SCR gene. (See, e.g., Offringa et al., 1990, EMBO J. 9:3077–84; and Kanevskii et al., 1990, Dokl. Akad. Nauk. SSSR 312:1505–1507) for discussions of nucleic constructs for effecting site-directed mutagenesis of target genes in plants.) It is preferred that such constructs effect suppression of SCR gene by replacing the endogenous SCR gene sequence through homologous recombination with none or inactive SCR protein coding sequence.

5.3.3. TRANSGENIC PLANTS THAT EXPRESS A TRANSGENE CONTROLLED BY THE SCR PROMOTER

In accordance with the present invention, a desired plant may be engineered to express a gene of interest under the control of the SCR promoter. SCR promoters and functional portions thereof refer to regions of the nucleic acid sequence which are capable of promoting tissue-specific transcription of an operably linked gene of interest in the embryo, stem, root nodule and/or root of a plant. The SCR promoter described herein refers to the regulatory elements of SCR genes as described in Section 5.2.

Genes that may be beneficially expressed in the roots and/or root nodules of plants include genes involved in nitrogen fixation or cytokines or auxins, or genes which regulate growth, or growth of roots. In addition, genes encoding proteins that confer on plants herbicide, salt, or pest resistance may be engineered for root specific expression. The nutritional value of root crops may also be enhanced through SCR promoter driven expression of nutritional proteins. Alternatively, therapeutically useful proteins may be expressed specifically in root crops.

Genes that may be beneficially expressed in the stems of plants include those involved in starch lignin or cellulose biosynthesis.

In accordance with the present invention, desired plants which express a heterologous gene of interest under the control of the SCR promoter may be engineered by transforming a plant cell with SCR promoter driven constructs using those techniques described in Section 5.2.2. and 5.3., supra.

5.3.4. SCREENING OF TRANSFORMED PLANTS FOR THOSE HAVING DESIRED ALTERED TRAITS

It will be recognized by those skilled in the art that in order to obtain transgenic plants having the desired engineered traits, screening of transformed plants (i.e., those having an gene construct of the invention) having those traits may be required. For example, where the plants have been engineered for ectopic overexpression of SCR gene, transformed plants are examined for those expressing the SCR gene at the desired level and in the desired tissues and developmental stages. Where the plants have been engineered for suppression of the SCR gene product, transformed plants are examined for those expressing the SCR gene product (e.g., RNA or protein) at reduced levels in various tissues. The plants exhibiting the desired physiological changes, e.g., ectopic SCR overexpression or SCR suppression, may then be subsequently screened for those plants that have the desired structural changes at the plant level (e.g., transgenic plants with overexpression or suppression of SCR gene having the desired altered root structure). The same principle applies to obtaining transgenic plants having tissue-specific expression of a heterologous gene in embryos and/or roots by the use of a SCR promoter driven expression construct.

Alternatively, the transformed plants may be directly screened for those exhibiting the desired structural and functional changes. In one embodiment, such screening may be for the size, length or pattern of the root of the transformed plants. In another embodiment, the screening of the transformed plants may be for altered gravitropism or decreased susceptibility to lodging. In other embodiments, the screening of the transformed plants may be for improved agronomic characteristics (e.g., faster growth, greater vegetative or reproductive yields, or improved protein contents, etc.), as compared to unengineered progenitor plants, when cultivated under various growth conditions (e.g., soils or media containing different amount of nutrients, water content).

According to the present invention, plants engineered with SCR overexpression may exhibit improved vigorous growth characteristics when cultivated under conditions where large and thicker roots are advantageous. Plants engineered for SCR suppression may exhibit improved vigorous growth characteristics when cultivated under conditions where thinner roots are advantageous.

Engineered plants and plant lines possessing such improved agronomic characteristics may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

6. EXAMPLE 1: ARABIDOPSIS SCR GENE

This example describes the cloning and structure of the Arabidopsis SCR gene and its expression. The deduced amino acid sequence of the Arabidopsis SCR gene product contains a number of potential functional domains similar to those found in transcription factors. Closely related sequences have been found in both dicots and monocots indicating that Arabidopsis SCR is a member of a new protein family. The expression pattern of the SCR gene was characterized by means of in situ hybridization and by an enhancer trap insertion upstream of the SCR gene (described in more detail in Section 7). The expression pattern is consistent with a key role for Arabidopsis SCR in regulating the asymmetric division of the cortex/endodermis initial which is essential for generating the radial organization of the root.

6.1. MATERIALS AND METHODS

6.1.1. PLANT CULTURE

Arabidopsis ecotypes Wassilewskija (Ws), Columbia (Col), and Landsberg erecta (Ler) were obtained from Lehle. Arabidopsis seeds were surface sterilized and grown as described previously (Benfey et al., 1993, Development 119:57–70). Generation of the enhancer trap lines is described in Section 7.

6.1.2. GENETIC ANALYSIS

For the scr-1 allele, co-segregation of the mutant phenotype and kanamycin resistance conferred by the inserted T-DNA was determined as described previously (Aeschbacher et al., 1995, Genes & Development 9:330–340). Because kanamycin affects root growth, 1557 seeds from heterozygous lines were germinated on non-selective media, scored for the appearance of the mutant phenotype, and subsequently transferred to selective media. All (284) phenotypically mutant seedlings showed resistance to the antibiotic, whereas 834 of 1273 phenotypically wild-type seedlings showed resistance to kanamycin, respectively. Phenotypically wild type plants (83) were also transferred to soil and allowed to set seeds. The progeny of these plants were plated on selective and non-selective media, and scored for the co-segregation of the mutant phenotype and antibiotic resistance. A majority (48) of the plants segregated for the mutant phenotype and for kanamycin resistance, whereas 35 were wild-type and sensitive to kanamycin. Due to a mis-identified cross, scr-2 was originally thought to be non-allelic and was named pinocchio (Scheres et al., 1995, Development 121:53–62). Subsequent mapping results placed it in an identical chromosomal location as scr-1. The original scr-2 line contained at least two T-DNA inserts. Co-segregation analysis revealed a lack of linkage between the antibiotic resistance marker carried by the T-DNA and the mutant phenotype. Antibiotic sensitive lines were identified that segregated for mutants. These lines were crossed to scr-1. All F1 antibiotic resistant progeny exhibited a mutant phenotype. All F2 progeny (from independent lines) were mutant, and there was a 3:1 segregation for antibiotic resistance indicating that the two mutations were allelic. Antibiotic sensitive lines of scr-2 were found to contain a rearranged T-DNA insert as determined by Southern blots and PCR using T-DNA specific probes and primers respectively. The presence of this T-DNA in the SCR gene was confirmed by Southern blots using SCR probes. A combination of T-DNA and SCR specific primers was used to amplify T-DNA/SCR junctions. The PCR fragments were cloned using the TA cloning kit (Invitrogen) and sequenced. The insertion points were determined for both 5' and 3' T-DNA/SCR junctions.

6.1.3. MAPPING

Mutant plants of scr-2 (WS background) were crossed to Col WT. DNA from mutant F2 individual plants were analyzed for co-segregation with microsatellite (Bell & Ecker, 1994, Genomics 18:137–144) and CAPS markers (Konieczny & Ausubel, 1993, Plant J. 4:403–410). The closest linkage was found to two CAPS markers located at the bottom of chromosome III. Only one out of 238 mutant chromosomes was recombinant for the BGL1 marker (Konieczny & Ausubel, 1993, Plant J. 4:403–410) and one out of 210 chromosomes was recombinant for the cdc2b marker.

A RFLP for the SCR gene was identified between Col and Ler ecotypes with Xho I endonuclease. Genomic DNAs from independent R1 lines (Jarvis et al., 1994, Plant Mol. Biol. 24:685–687) were digested with Xho I and blots were hybridized to SCR. Using the segregation data obtained for 25 R1 lines, the SCR gene was mapped relative to molecular markers by CLUSTER. The SCR gene was assigned to the bottom of chromosome III closest to BGL1.

6.1.4. PHENOTYPIC ANALYSIS

Morphological characterization of the mutant roots was performed as follows: 7 to 14 days post-germination phenotypically mutant seedlings were fixed in 4.0% formaldehyde in PIPES buffer pH 7.2. After fixation the samples were dehydrated in ethanol followed by infiltration with Historesin (Jung-Leica, Heidelberg, Germany). Plastic sections were mounted on superfrost slides (Fisher). The sections were either stained with 0.05% toluidine blue and photographed using Kodak 160T film or used for Casparian strip detection or antibody staining.

Casparian strip detection was performed as described previously (Scheres et al., 1995, Development 121:53–62), with the following modifications. Plastic sections were used and the counterstaining was done in 0.1% aniline blue for 5 to 15 min. The sections were visualized with a Leitz fluorescent microscope with FITC filter. Pictures were taken using a Leitz camera attached to the microscope and Kodak HC400 film. Slides were digitized with a Nikon slide scanner and manipulated in Adobe Photoshop.

For antibody staining, sections were blocked for 2 hours at room temperature in 1% BSA in PBS containing 0.1% Tween 20 (PBT). Samples were incubated with primary antibodies at 4° C. in 1% BSA in PBT overnight, and then washed 3 times 5 minutes each with PBT. Samples were incubated for two hours with biotinylated secondary antibodies (Vector Laboratories) in PBT, and washed as above. Samples were incubated with Texas Red conjugated avidin D for 2 hours at room temperature, washed as before, and mounted in Citifluor. Immunofluorescence was observed with a fluorescent microscope equipped with a Rhodamine filter. Staining with the CCRC antibodies was performed as described previously (Freshour et al., 1996, Plant Physiol. 110:1413–1429).

6.1.5. MOLECULAR TECHNIQUES

Genomic DNA preparation was performed using the Elu-Quik kit (Schleicher & Schuell) protocol. Radioactive and non-radioactive DNA probes were labeled with either random primed labeling or PCR-mediated synthesis according to the Genius kit manual (Boehringer Mannheim). *E. coli* and *Agrobacterium tumefaciens* cells were transformed using a BIO-RAD gene pulser. Plasmid DNA was purified using the alkaline lysis method (Maniatis et al., Molecular Cloning: A Laboratory Manual, Cold Spring Harbor, New York:Cold Spring Harbor Laboratory, 1982).

A probe made from a rescued fragment of 1.2 kb was used to screen a wild-type genomic library made from WS plants. One genomic clone containing an insert of approximately 23 kb was isolated. A 3.0 kb Sac I fragment from the genomic clone, which hybridized to the 1.2 kb probe, was subcloned and sequenced (FIG. 5A). Comparison of the nucleotide sequence between the genomic clone and the rescued plasmid revealed the site of the T-DNA insertion. Approximately 600,000 plaques from a CDNA library, obtained from inflorescences and siliques (Col ecotype), and therefore enriched in embryos, were screened with the 1.2 kb probe. Four cDNA clones were isolated. The dideoxy sequencing method was performed using the Sequenase kit (United States Biochemical Corp.). Sequence-specific internal primers were synthesized and used to sequence the Sac I genomic as well the CDNA clones. Total RNA from plant tissues was obtained using phenol/chloroform extractions as described in (Berry et al., 1985, Mol. Cell. Biol. 5:2238–2246) with minor modifications. Northern hybridization and detection were performed according to the Genius kit manual (Boehringer Mannheim).

To identify the site of insertion of the enhancer-trap T-DNA, genomic DNA from ET199 homozygous plants was amplified using primers specific for the T-DNA left border and the SCR gene. An approximately 2.0 kb fragment was amplified. This fragment was sequenced and the site of insertion was found to be approximately 1 kb from the ATG start codon.

6.1.6. IN SITU HYBRIDIZATION

Antisense and sense SCR riboprobes were labeled with digoxigenin-11-UTP (Boehringer Mannheim) using T7 polymerase following the manufacturer's protocol. Probes contained a 1.1 kb 3' portion of the cDNA. Probe purification, hydrolysis and quantification were performed as described in the Boehringer Mannheim Genius System user's guide.

Tissue samples were fixed in 4% formaldehyde overnight at 4° C. and rinsed two times in PBS (Jackson et al., 1991, P1. Cell 3:115–125). They were subsequently pre-embedded in 1% agarose in PBS. The fixed tissue was dehydrated in ethanol, cleared in Hemo-De (Fisher Scientific, Pittsburgh, Pa.) and embedded in ParaplastPlus (Fisher Scientific). Tissue sections (10 μm thick) were mounted on Superfrost-Plus slides (Fisher Scientific). Section pretreatment and hybridization were performed according to (Lincoln et al., 1994, Plant Cell 6:1859–1876) except that proteinase K was used at 30 mg/ml and a two hour prehybridization step was included. Probe concentration of 50 ng/ml/kb was used in the hybridization.

Slides were washed and the immunological detection was performed according to (Coen et al., 1990, Cell 63:1311–1322) with the following modifications. Slides were first washed 5 h in 5xSSC, 50% formamide. After RNase treatment slides were rinsed three times (20 min each) in the buffer (0.5 M NaCl, 10 mM Tris-HCl pH 8.0, 5.0 mM EDTA). In the immunological detection, antibody was diluted 1:1000, levamisole (240 ng/ml) was included in the detection buffer, and after stopping the reaction in 10 mM Tris, 1 mM EDTA, sections were mounted directly to Aqua-Poly/Mount (Polysciences, Warrington, Pa.).

6.2. RESULTS

6.2.1. CHARACTERIZATION OF THE SCR PHENOTYPE

The scarecrow mutant scr-1 was isolated in a screen of T-DNA transformed Arabidopsis lines (Feldmann, K.A., 1991, Plant J. 1:71–82), as a seedling with greatly reduced root length compared to wild-type (Scheres et al., 1995, Development 121:53–62). A second mutant scr-2 with a similar phenotype was subsequently identified among T-DNA transformed lines. Analysis of co-segregation between the mutant phenotype and antibiotic resistance carried by the T-DNA indicated tight linkage for scr-1 and no linkage for scr-2 (see Experimental Procedures). An antibiotic sensitive line of scr-2 was isolated and crossed with scr-1. The F2 progeny of this cross were all mutant and segregated 3:1 for antibiotic resistance confirming allelism (see Materials & Methods). The principal phenotypic difference between the two alleles was that scr-1 root growth was more retarded than that of scr-2, suggesting that it is the stronger allele (FIG. 2A). For both alleles the aerial organs appeared similar to wild-type and the flowers were fertile (FIGS. 2A and 2B). The progeny of backcrosses of scr-1 or scr-2 to wild-type plants segregated 3:1 for the root phenotype for both alleles, indicating that each mutation is monogenic and recessive.

Analysis of transverse sections through the primary root of seedlings revealed only a single cell layer between the epidermis and the pericycle (FIG. 2C) instead of the normal radial organization consisting of cortex and endodermis (FIG. 2D). This radial organization defect was not limited to the primary root, but was also present in secondary roots (FIG. 2E) and in roots regenerated from calli (FIG. 2F). Occasionally defects were observed in the number of cells in the remaining cell layer (more than the invariant 8 found in wild-type). Abnormal placement or numbers of epidermal cells were also observed (see FIG. 2E). These abnormalities were more frequently observed in scr-1 than in scr-2. Nevertheless, organization of the mutant root closely resembles that of wild-type except for the consistent reduction in the number of cell layers. Because the endodermis and cortex are normally generated by an asymmetric division of the cortex/endodermal initial, this indicates that the primary defect in scr is disruption of this asymmetric division.

It has been shown that the radial organization defect in scr-1 first appears in the developing embryo at the early torpedo stage and manifests itself as a failure of the embryonic ground tissue to undergo the asymmetric division into cortex and endodermis (Scheres et al., 1995, Development 121:53–62). This defect extends the length of the embryonic axis which encompasses the embryonic root and hypocotyl. Other embryonic tissues appear similar to wild-type (Scheres et al., 1995, Development 121:53–62). In seedling hypocotyls of the scarecrow phenotype, two cell layers instead of the normal three layers (two cortex and one endodermis) between epidermis and stele were found. This would be the expected result of the lack of the division of the embryonic ground tissue. Similar results were obtained for scr-2. Hence, this mutant identifies a gene involved in the asymmetric division that produces cortex and endodermis from ground tissue in the embryonic root and hypocotyl and from the cortex/endodermal initials in primary and secondary roots.

6.2.2. CHARACTERIZATION OF CELL IDENTITY IN SCR ROOTS

To understand the role of the Arabidopsis SCR gene in regulating this asymmetric division, it was necessary to determine the identity of the mutant cell layer. Tissue-specific markers were used to distinguish between several possibilities. The cell layer could have differentiated attributes of either cortex or endodermis. Alternatively, it could have an undifferentiated, initial-cell identity or it could have a chimeric identity with differentiated attributes of both endodermis and cortex in the same cell.

Transverse sections of scr-1 and scr-2 roots were assayed for the presence of tissue-specific markers. The casparian strip, a deposition of suberin between radial cell walls, is specific to the endodermal cells and is believed to act as a barrier to the entry of solutes into the vasculature (Esau, K. Anatomy of Seed Plants, New York: John Wiley & Sons, 1977, Ed. 2, pp. 1–550). Histochemical staining revealed the presence of a casparian strip in the mutant cell layer (FIG. 3A, compare to wild-type, FIG. 3B). It is noted that in the vascular cylinder, this histochemical stain also reveals the presence of lignin, indicating the presence of differentiated xylem cells in mutant (FIG. 3A) and wild-type (FIG. 3B). Another marker of the differentiated endodermis is the arabinogalactan epitope recognized by the monoclonal antibody, JIM13 (Knox et al., 1990, Planta 181:512–521). The mutant cell layer showed staining with this antibody (FIG. 3C, compare with wild-type, FIG. 3B). As a positive control, the JIM7 antibody that recognizes pectin epitopes in all cell walls was used (FIGS. 3E and 3F). These results indicate that the cell layer between the epidermis and the pericycle has differentiated attributes of the endodermis.

As a marker for the cortex, the CCRC-M2 monoclonal antibody was used. This antibody recognizes a cell wall oligosaccharide epitope, found only on differentiated cortex and epidermis cells. In sections from the differentiation zone of scr-1 and scr-2, both cortex and epidermal cells showed staining (FIGS. 4A and 4B) that was similar to that of wild-type (FIG. 4C). In scr-1, staining of both cell types was apparent, but staining of cortex was somewhat weaker than wild-type. The positive control used the CCRC-M1 monoclonal antibody which recognizes an oligosaccharide epitope found on all cells (FIGS. 4D–F).

With the CCRC-M2 antibody an interesting difference was observed between the staining pattern of the mutants as compared to wild-type. The appearance of this epitope correlates with differentiation in these two cell types. Normally, in sections close to the root tip there is no staining. In sections higher up in the root, atrichoblasts (epidermal cells that do not make root hairs) stain. In sections from more mature root tissue, all epidermal cells as well as cortex cells stain for this epitope. In both scr-1 and scr-2, sections could be found in which all epidermal cells stained while there was little detectable staining of cortex cells. Although not precisely identical to the wild-type staining pattern, the fact that the mutant cell layer clearly stains for this cortex marker indicates that there are cortex differentiated attributes expressed in these cells.

Taken together, these results indicate that the mutant cell layer has differentiated attributes of both the endodermis and cortex. The possibility that there has been a simple deletion of a cell type, or that the resulting cell type remains in an undifferentiated initial-like stage can be ruled out. This result is consistent with a role for the scr gene in regulating this asymmetric division rather than a role in directing cell specification.

6.2.3. MOLECULAR CLONING OF THE SCR GENE

To further elucidate the function of the Arabidopsis SCR gene the inserted T-DNA sequences were used to clone the gene. Plant DNA flanking the insertion site was obtained from scr-1 by plasmid rescue and used to isolate the corresponding wild-type genomic DNA. Several cDNA clones were isolated from a library made from silique tissue. Comparison of the sequence of the longest cDNA and the corresponding genomic region revealed an open reading frame (ORF) interrupted by a single small intron. (FIG. 5A). A potential TATA box and polyadenylation signal that matched the consensus sequences for plant genes were also identified (Joshi, C. P., 1987, Nucl. Acids Res. 15:6643–6653); Heidecker & Messing, 1986, Ann. Rev. Plant Physiol. 37:439–466); Mogen et al., 1990, Plant Cell 2:1261–1272).

Comparison of the nucleotide sequence between the genomic clone and the rescued plasmid placed the site of the T-DNA insertion in scr-1 at codon 470 (FIGS. 5A and 5B). For scr-2, although no linkage was found between the mutant phenotype and antibiotic resistance, DNA blot and PCR analysis of antibiotic sensitive lines revealed the presence of T-DNA sequences that co-segregated with the mutant phenotype. The insertion position in scr-2 was determined by cloning and sequencing the PCR products amplified from its genomic DNA using a combination of T-DNA and SCR specific primers at both sides of the insertion (FIG. 5B). In scr-2 the T-DNA insertion point is at codon 605 (FIG. 5A and 5B). To verify linkage between the cloned gene and the mutant phenotype, we identified the chromosomal location of both the scr locus and the SCR gene. To map the scr locus, molecular markers were used on F2 progeny of crosses between scr-2 (ecotype Wassilewskija, Ws) and Colombia (Col) WT. These placed the scr locus at the bottom of chromosome III, approximately 0.5 cM away from each of the two closest markers available, cdc2b and BGL1 (Konieczny and Ausubel, 1993, Plant J. 4:403–410). To map the SCR gene, we identified a polymorphism between Col and Landsberg (Ler) ecotypes using the SCR probe b (FIG. 5B). Southern analysis of 25 recombinant inbred lines (Jarvis et al., 1994, Plant Mol. Biol. 24:685–687) mapped the cloned gene to the same location as the SCR locus on chromosome III.

The determination of the molecular defects in two independent alleles and the co-localization of the cloned gene and the mutant locus confirms that we have identified the SCR gene.

6.2.4. THE SCR GENE HAS MOTIFS THAT INDICATE IT IS A TRANSCRIPTION FACTOR

The Arabidopsis SCR gene product is a 653 amino acid polypeptide that contains several domains (FIG. 5B). The amino-terminus has homopolymeric stretches of glutamine, serine, threonine, and proline residues, which account for 44% of the first 267 residues. Domains rich in these residues have been shown to activate transcription and may serve such a role in SCR (Johnson et al., 1993, J. Nutr. Biochem 4:386–398). A charged region between residues 265 and 283 has similarity to the basic domain of the bZIP family of transcriptional regulatory proteins (FIG. 5C) (Hurst, H. C., 1994, Protein Profile 1:123–168). The basic domains from several bZIP proteins have been shown to act as nuclear localization signals (Varagona et al., 1992, Plant Cell 4:1213–1227), and this region in SCR may act similarly. This charged region is followed by a leucine heptad repeat (residues 291–322). A second leucine heptad repeat is found toward the carboxy-terminus (residues 436 to 473). As leucine heptad repeats have been demonstrated to mediate protein-protein interactions in other proteins (Hurst, H. C., 1994, Protein Profile 1:123–168), the existence of these motifs suggests that SCR may function as a dimer or a multimer. The second leucine heptad repeat is followed by a small region rich in acidic residues, also present in a number of defined transcriptional activation domains (Johnson et al., 1993, J. Nutr Biochem 4:386–398). While each of these domains has been found within proteins that do not act as transcriptional regulators, the fact that all of them are found within the deduced SCR protein sequence indicates that SCR is a transcriptional regulatory protein.

6.2.5. SCR IS A MEMBER OF A NOVEL PROTEIN FAMILY

The Arabidopsis SCR protein sequence was compared with the sequences in the available databases. Eleven expressed sequence tags (ESTs), nine from Arabidopsis, one from rice and one from maize, showed significant similarity to residues 394 to 435 of the SCR sequence, a region immediately amino-terminal to the second leucine heptad repeat (FIGS. 15K–L). This region is designated the VHIID (amino acid residues 8–12 of SEQ ID NO:12) domain. Subsequent analysis of these EST sequences has revealed that the sequence similarity extends beyond this region; in fact, the similarity extends throughout the entire known gene products. The combination and order of the motifs found in these sequences do not show significant similarity to the general structures of other established regulatory protein families (i.e., bZIP, zinc finger, MADS-domain, and homeodomain), indicating that the SCR proteins comprise a novel family.

6.2.6. SCR IS EXPRESSED IN THE CORTEX/ENDODERMAL INITIALS AND IN THE ENDODERMIS

RNA blot analysis revealed expression of SCR in Arabidopsis siliques, leaves and roots of wild-type plants (FIG. 6A). No hybridization was detected to RNA from scr-1 plants (FIG. 6B, lane 2). This indicates that scr-1 has a reduced level of RNA expression and may represent the null phenotype. Hybridization to RNA species larger than the normal size were detected in scr-2. This indicates that abnormal SCR transcripts are made in this allele, suggesting that functional but possibly altered proteins may be produced.

To determine if expression was localized to any particular cell type, RNA in situ was hybridization performed on sections of root tissue. In mature roots, expression was localized primarily to the endodermis (FIGS. 7A and 7B). Expression appeared to start very close to or within the cortex/endodermal initials and continue up the endodermal cell file as far as the section extended. Expression was also detected in late-torpedo stage embryos in the endodermis throughout the embryonic axis (FIG. 7C). Sense strand controls showed only background hybridization (FIG. 7D).

To determine whether the localization of SCR RNA was regulated at the transcriptional or post-transcriptional level, enhancer trap (ET) lines were prepared and examined in which the β-glucuronidase (uid-A or GUS) coding sequence with a minimal promoter was expressed in the root endodermis. (See Section 7, infra). Restriction fragment length polymorphisms were observed when DNA from one of these lines, ET199 and wild-type were probed with SCR. PCR and sequence analysis confirmed that the enhancer-trap construct had inserted approximately 1 kb upstream of the SCR start site and in the same orientation as that of SCR transcription.

In mature roots, expression in ET199 whole mounts showed a similar pattern to that of the in situ hybridizations, with the strongest staining present in endodermal cells (FIG. 7E). Transverse sections indicated that expression was primarily in endodermal cells in the elongation zone (FIG. 7F). Longitudinal sections through the meristematic zone revealed that expression could be detected in the cortex/endodermal initial (FIG. 7G). Of particular interest was the restriction of expression to the endodermal daughter cell after the periclinal division (FIG. 7G). This indicated that the expression pattern observed in the in situ analysis was not due to post-transcriptional partitioning of SCR RNA. Rather, it suggests that after the periclinal division of the cortex/endodermis initial only one of the two cells is able to transcribe SCR RNA.

6.3. DISCUSSION

6.3.1. THE SCR GENE REGULATES AN ASYMMETRIC DIVISION REQUIRED FOR ROOT RADIAL ORGANIZATION

The formation of the cortex and endodermal layers in the Arabidopsis root requires two asymmetric divisions. In the first, an anticlinal division of the cortex/endodermal initial generates two cells with different developmental potentials. One will continue to function as an initial, while the other undergoes a periclinal division to generate the first cells in the endodermal and cortex cell files. This second asymmetric division is eliminated in the scarecrow mutant, resulting in a single cell layer instead of two. The scr mutation appears to have little effect on any other cell divisions in the root indicating that it is involved in regulating a single asymmetric division in this organ. Several other mutations have been characterized that appear to affect specific cell division pathways in Arabidopsis. These include knolle (kn) in which formation of the epidermis is impaired (Lukowitz et al., 1996, Cell 84:61–71), wooden leg (wol) in which vascular cell division is defective (Scheres et al., 1995, Development 121:53–62) and fass (fs) in which there are supernumerary cortex and vascular cells (Scheres et al., 1995, Development 121:53–62); Torres Ruiz & Jurgens, 1994, Development 120:2967–2978). Only in the case of scr and short-root (shr) mutants has it been shown that the defect is in a specific asymmetric division.

Mutational analyses in several organisms have revealed that the genes that regulate asymmetric divisions can be specific to a single type of division or can affect divisions that are not clonally related (Horvitz & Herskowitz, 1992, Cell 68:237–255). In most cases, these mutations result in the formation of two identical daughter cells with similar developmental potentials (Horvitz & Herskowitz, 1992, Cell 68:237–255). Both resulting cells have the identity of one or the other of the normal daughter cells, an example of which is the swi⁻ mutation in *S. cerevisiae* (Nasmyth et al., 1987, Cell 48:579–587). However, there are also examples of mutations that result in the formation of chimeric cell types such as the ham-1 mutation in *C. elegans* (Desai et al., 1988, Nature 336:638–646).

6.3.2. SCR INVOLVEMENT IN CELL SPECIFICATION OR CELL DIVISION

Genes that regulate asymmetric cell divisions can be divided into those that specify the differentiated fates of the daughter cells and those that function to effect the division of the mother cell (Horvitz & Herskowitz, 1992, Cell, 68:237–255). The aberrant cell layer formed in the scr mutant has differentiated features of both endodermal and cortex cells. Thus, scr is in the rare class of asymmetric division mutants in which a chimeric cell type is created. The ability to express differentiated characteristics of cortex and endodermal cells implies that the differentiation pathways for both these cell types are intact and do not require the functional SCR gene. This indicates that SCR is involved primarily in regulating a specific cell division, and that the correct occurrence of this division can be unlinked from cell specification. This is in contrast to the shr mutant, in which the periclinal division of the cortex/endodermal initial also fails to occur and the resulting cell lacks endodermal markers (Benfey et al., 1993, Development 119:57–70) and has cortex attributes. A genetic analysis was used to address the function of SHR and SCR in the asymmetric division of the cortex/endodermal initial. Placing mutants of each of these genes in a fs mutant background asked whether the supernumerary cell divisions characteristic of fs were sufficient to restore normal cell identities (Scheres et al., 1995, Development 121:53–62). In the shr,fs double mutant there were additional cell layers but no endodermal, indicating that the SHR gene has a role in specifying cell identity. In the scr,fs double mutant no alteration in cell identity was observed as compared to fs (Scheres et al., 1995, Development 121:53–62). Taken together with the cell marker analysis presented herein, these results are consistent with a role for SCR in generating the division of the mother cell while the SHR gene may be involved in specifying the fate of the endodermal daughter.

6.3.3. A ROLE FOR SCR IN EMBRYONIC DEVELOPMENT

At least one additional cell division appears to be affected in the scr mutant. During embryonic development, the ground tissue does not divide to form the endodermal and cortex layers of the embryonic root and hypocotyl. As shown herein, expression of SCR was detected in the endodermal tissue throughout the embryonic axis shortly after this division occurs. Thus, SCR may play a direct role in regulating both this division and the division of the cortex/endodermal initial in the root apical meristem. Alternatively, the radial organization established in the embryo may somehow act as a template that directs the division of the cortex/endodermal initial, thus perpetuating the pattern. This is consistent with the finding in the scr mutant that the aberrant pattern established in the embryo is perpetuated in the primary root. It is also consistent with a recent study in which the daughter cells of the cortex/endodermal initial were laser ablated (van den Berg et al., 1995, Nature 378:62–65). When a single daughter cell was ablated, it was replaced by a cell that followed the normal asymmetric division pattern. When three adjacent daughter cells were ablated, the central initial divided anticlinally but failed to perform the periclinal division (van den Berg et al., 1995, Nature 378:62–65). This provided evidence that information from mature cells is required for the correct division pattern of cortex/endodermal initials suggesting a "top down" transfer of information. However, the absence of a cell layer in lateral roots and callus-derived roots of the scr mutant suggests that embryo events are not unique in their ability to establish radial organization. Rather, these observations implicate SCR in regulating both embryonic and post-embryonic root radial organization.

6.3.4. TISSUE-SPECIFIC EXPRESSION OF SCR IS REGULATED AT THE TRANSCRIPTIONAL LEVEL

Although not intending to be limited to any theory or explanation regarding the mechanism of SCR action, the cloning of the gene and the expression pattern provide some clues as to the role of SCR in the regulation of a specific asymmetric division. The SCR gene is expressed in the cortex/endodermal initial, but immediately after division is restricted to the endodermal lineage. A similar pattern is seen in the ET199 enhancer trap line in which SCR regulatory elements are in proximity to a GUS gene, indicating that SCR restriction to the endodermal cell file is due to differential regulation of expression of the SCR gene in this cell and the first cell in the cortex file. Another marker line in which expression of GUS is detected only in the cortex daughter cell provides a control for differential degradation of GUS RNA or protein. Thus, partitioning of SCR RNA as a means of achieving this segregation of expression can be ruled out. What remains to be determined is whether this difference in transcriptional activity of the two daughter cells is due to internal polarity of the mother cell prior to division such that cytoplasmic determinants are unequally distributed, or to external polarity that influences cell fate after division. Since SCR is expressed prior to cell division, an attractive hypothesis is that it is involved in establishing polarity in the cortex/endodermal initial. The sequence of the SCR protein strongly suggests that it acts as a transcription factor. Hence, it may act to regulate the expression of other genes essential for the establishment of unequal division. Alternatively, it is conceivable that it could play a role in creating an external polarity that provides a signal to divide asymmetrically. Its expression in more mature endodermal cells is consistent with a role in "top-down" signaling.

6.3.5. A NEW FAMILY OF TRANSCRIPTIONAL REGULATORS

Analysis of eighteen EST clones found in the GenBank database reveals that the proteins they encode share a high degree of homology with Arabidopsis SCR protein. See Table 1 and FIGS. 15A–S. Further sequence analysis of the encoded proteins indicate that a high degree of sequence similarity extends from at least the highly conserved VHIID (amino acid residues 8–12 of SEQ ID NO:12) domain to the carboxy-terminus of the gene products. Comparison of the amino termini of these proteins is precluded by the fact that the ESTs are incomplete. The high degree of similarity among these proteins, in combination with the motifs observed in the SCR protein (homopolymeric motifs, two leucine heptad repeats and a bZIP-like basic domain that may also function as a nuclear localization sequence) indicates that these proteins form a novel class of regulatory proteins.

The insertion sites of the T-DNA in the two scr mutant alleles raised the possibility that the mutant phenotype was due to the production of truncated proteins. Northern blot analysis indicated SCR RNA is undetectable in scr-1. This suggests that the phenotype is either the null, or due to highly reduced RNA expression. In scr-2, an alteration in RNA size was detected which would be consistent with the presence of a functional and possibly truncated protein. This could provide an explanation for the observation that scr-2 appears to be the weaker allele.

7. EXAMPLE 2: ENHANCER TRAP ANALYSIS OF ROOT DEVELOPMENT

An enhancer trap system was used in order to provide a more detailed molecular analysis of gene expression in lateral root patterning and development in Arabidopsis thaliana. A new collection of marker lines that express β-glucuronidase (GUS) activity in a cell-type specific manner in each of the cells of the root was generated. These lines allow differentiation of cells to be monitored based on molecular characteristics. One of these marker lines, ET199, resulted from the integration of the GUS cassette in proximity to an SCR enhancer. The results described below demonstrate that transcriptional activation of the SCR gene plays an important role in root development in Arabidopsis, and that SCR gene transcriptional regulatory elements can express a transgene in a developmentally and tissue specific manner.

7.1. MATERIALS AND METHODS

7.1.1. PLANT GROWTH CONDITIONS:

Arabidopsis seeds from NO-O and Columbia ecotypes were sterilized and sown on MS plates containing 4.5% sucrose. Plates were oriented vertically and maintained under 18 hours light, 6 hours dark cycle.

7.1.2. HISTOLOGY AND GUS STAINING:

For observation of lateral roots, roots were removed from plates and infiltrated in 25% glycerol for several hours to overnight. Roots were then mounted in 50% glycerol. Whole seedlings were stained for GUS activity for up to three days in the following solution: 1X GUS buffer, 20% methanol, 0.5 mg/ml X-Glu. Addition of methanol greatly improves the specificity and reproducibility of staining. Staining solution was made fresh from a 10X buffer (1 M Tris pH7.5, 290 mg NaCl, 66 mg $K_3Fe(CN)_6$) that was stored for no more than one week. Stained roots were cleared in glycerol and mounted as above. All samples were observed using Nomarski optics on a Leitz Laborlux S microscope. Photographs were taken using a Leitz MPS52 camera, and images were scanned into Adobe Photoshop to create figures. In some cases the intensity of the blue color was increased.

7.1.3. CONSTRUCTION OF ENHANCER TRAP LINES:

Plant Cloning Vector (PCV) (Koncz et al., 1994, Specialized vectors for gene tagging and expression studies, in *Plant Molecular Biology Manual*, Gelvin & Schilperoort, eds., Vol. B2, pp. 1–2, Kluover Academic Press, Dordrecht, The Netherlands) contains a Bam HI site immediately adjacent to the T-DNA right border sequence. The β-glucuronidase gene fused to the TATA region (−46 to 78) of the CaMV 35S promoter was introduced into this site (Benfey et al., 1990, EMBO J. 9:1677–1684). 350 transgenic lines were generated by Agrobacterium mediated root transformation (Marton & Browse, 1991, Plant Cell Reports 10:235–239), and 4 independent lines from each transformant were screened for GUS activity in the root.

7.2. RESULTS

7.2.1. DIFFERENTIATION IN THE LRP

The marker lines described above reflect patterns of gene expression that are specific to individual root cell types. There are no readily apparent mutant phenotypes in any of these lines. Therefore, they can be used to analyze the differentiation state of the cells during normal development of the lateral root primordial (LRP). If there are stages at which the pericycle cells proliferate in the absence of patterning, it can be expected that all cells would be identical with none expressing differentiated characteristics. In contrast, organization of the LRP would be reflected in differential patterns of GUS gene expression, with certain cells beginning to turn on transcription from differentiated cell-type specific promoters (i.e., those that drive GUS expression in the enhancer trap lines).

The process of lateral root formation is divided into the following seven stages:

Stage I: The LRP is first visible as a set of pericycle cells that are clearly shorter in length than their neighbors, having undergone a series of anticlinal divisions. Laskowski et al., 1995, Dev. 121:3303–3310 predict that there are approximately 4 founder pericycle cells involved. In the longitudinal plane, these divisions result in the formation of 8–10 small cells, which enlarge in a radial direction.

Stage II: A periclinal division occurs that divides the LRP into two layers (Upper Layer (UL) and Lower Layer (LL)). Not all the small pericycle-derived cells appear to participate in this division—typically the most peripheral cells do not divide. Hence, as the UL and LL cells expand radially the domed shape of the LRP begins to appear.

Stage III: The UL divides periclinally, generating a three layer primordium comprised of UL1, UL2 and LL. Again, some peripheral cells do not divide, creating peripheral regions that are one and two cell layers thick. This further emphasizes the domed shape of the LRP.

Stage IV: The LL divides periclinally, creating a total of four cell layers (UL1, UL2, LL1, LL2). At this stage the LRP has penetrated the parent endodermal layer.

Stage V: The central cells in LL2 undergo a number of divisions that push the overlying layers up and distort the cells in LL1. These divisions are difficult to visualize at this stage, but clearly form a knot of mitotic activity. The LRP at this stage is midway through the parent cortex. The outer layer contains 10–12 cells.

Stage VI: This stage is characterized by several events. The four central cells of UL1 divide periclinally. This division is particularly useful in identifying the median longitudinal plane in the enlarging LRP. At this point there are a total of twelve cells in UL1, four in the middle that have undergone the periclinal division and four on either side. In addition, all but the most central cells of UL2 undergo a periclinal division. At this point the LRP has passed through the parent cortex layer and has penetrated the epidermis. The central cells apparently derived from LL2 have a distinct elongated shape characteristic of vascular elements.

Stage VII: As the primordium enlarges it becomes difficult to characterize the divisions in the internal layers. However, the cells in the outermost layer can still be seen very clearly. All of these cells undergo a anticlinal division, resulting in 16 central cells (8 cells in each of two layers) flanked by 8–10 cells on each side. We refer to this as the 8-8-8 cell pattern. The LRP appears to be just about to emerge from the parent root.

7.2.2. MARKER LINES

An enhancer trapping cassette was generated by fusing the GUS coding sequence to the minimal promoter of the 35S promoter from CaMV. This minimal promoter does not produce a detectable level of GUS expression. However, its presence allows other upstream elements to direct GUS expression in a developmental and/or cell-specific manner (Benfey et al., 1990, EMBO J. 9:1677–1684). The use of a minimal promoter instead of a promoterless construct allows GUS expression to occur even if the enhancer trap cassette inserts at a distance from the coding region. Since the insert does not have to be within the structural gene, there are often no mutations generated in the enhancer trap lines.

The minimal promoter:GUS construct was cloned immediately adjacent to the T-DNA right border sequence of PCV (Koncz et al., supra) and introduced into Arabidopsis. 350 independent lines were generated and analyzed for GUS activity in the root. The following lines most clearly define each cell type. All of the lines were generated through enhancer trapping, as described herein, below, except for CorAX92 (Dietrich et al., 1992, Plant Cell 4:1371–1382) and EpiGL2:GUS (Masucci et al., Dev. 122:1253–1260) which are transgenic plants that contain cell-type specific promoters fused to the GUS gene.

SteO5—expresses GUS in the stele including the pericycle layer throughout primary and lateral roots. At the root tip, staining becomes weaker in the elongation zone; therefore, it is likely that only differentiated stele cells express GUS activity. Stelar GUS expression is also seen in aerial parts of the plant. End195—expresses GUS in the endodermis of primary and lateral roots. Staining can be seen most clearly in the cells in the meristematic region of the root, although overstaining shows that more mature cells also express some GUS activity. It appears that there is no staining in the cortex/endodermal initial, but staining is evident in the first daughter cell of this initial. GUS expression is also seen at the base of young leaves and in the stipules.

ET199—expresses GUS in the endodermis of primary and lateral roots, again most clearly in cells in the meristematic region. Unlike Endl95, staining in ET199 appears to continue down to the cortex/endodermal initial and, in younger roots, even into the cells of the quiescent center. Expression in the aerial parts of the plant is detectable in the young leaf primordia.

CorAX92—This line was generated by fusing the 5' and 3' sequences from a cortex specific gene isolated from oilseed rape to the GUS reporter gene (Dietrich et al., Plant Cell 4:1371–1382). Expression is limited to the cortex layer, extending to but not including the cortex/endodermal initial. Staining is also apparent in the petioles and leaf blades of expanded leaves.

EpiGL2:GUS—This line was generated by fusing the GL2 promoter to the GUS gene (Masucci et al., Dev. 122:1253–1260). Expression is seen in the non-hair forming epidermal cells (atrichoblasts). Staining is seen near the root tip, but it is difficult to determine if it includes the epidermal initial. Staining is also seen in the trichomes, leaf primordia, and the epidermis of the hypocotyl and leaf petioles.

CRC219—This line shows staining in the columella root cap only.

LRC244—This line shows staining in the lateral root cap only.

RC162—This line shows staining in both the lateral and columella root caps.

Two marker lines show differential staining at very early stages of LRP development. One of these, ET199, presents a complex and dynamic pattern of expression. Staining is first apparent at stage II in only the four central cells of the UL. At stage III staining is strongest in the central cells of UL2. As the LRP reaches stage V the staining remains strongest in the central 2–4 cells of UL2. By stage VI staining also begins to extend into the newly formed endodermal layer, and staining in both the central cells and endodermis persists beyond emergence of the lateral root.

Another line, LRB10 (lateral root base), does not express GUS in the primary root tip. Staining in the LRP is seen at stage I, and at stage II all the cells of the UL and LL are stained. However, by stage IV and V only the cells at the periphery of the LRP are still expressing GUS. As the LRP develops, these cells continue to stain, although less intensely, resulting in a ring of GUS expressing cells at the base of the LR.

LRB10 and ET199 clearly demonstrate non-identity between the cells at very early stages, stage IV in the case of LRB10 and within the UL at stage II in ET199. In addition, although it is difficult to identify the nature of the cells that correspond to the observed staining pattern in LRB10 and the early staining cells of ET199, post-emergent lateral roots show analogous staining in these lines, suggesting that the stained cells are already expressing markers that reflect their differentiated cell fates. Hence, these observations suggest a very early onset of differentiation in the cells of the LRP.

7.2.3. ET199 PROVIDES EVIDENCE FOR THE ROLE OF SCR IN PLANT DEVELOPMENT

Fortuitously, it was discovered that the GUS cassette in ET199 described Section 7.2.2, above, is situated approximately 1 kb upstream from the SCR gene. The SCR cDNA was labelled and used to probe genomic DNA from WT and ET199 plants. The band pattern seen in the Southern was completely consistent with a T-DNA inserted 1 kb upstream of the putative SCARECROW start site. Subsequently, a DNA fragment was PCR amplified using a primer within the T-DNA and a primer within SCARECROW. The size of this fragment was also consistent with the predicted insertion site. Partial sequencing of the PCR fragment confirmed the presence of SCARECROW sequence. Mutants in the SCR gene are completely lacking one of the radial layers between the epidermis and pericycle in both primary and lateral roots, due to the absence of specific cell division during embryogenesis and of the cortex/endodermal initial during post-embryonic growth. The expression pattern (described in Section 7.2.2., above) that was observed in the central cells of the developing LRP of ET199 provide strong evidence that the cells in this region are involved in the establishment of the meristematic initials. More importantly, these results demonstrate that transcriptional activation of the SCR gene plays a major role in the development of the Arabidopsis LRP. Furthermore, these results demonstrate that a transgene can be expressed under the control of SCR gene transcriptional regulatory elements in a developmental and tissue-specific manner.

8. EXAMPLE 3: ACTIVITY OF ARABIDOPSIS SCR PROMOTER IN TRANSGENIC ROOTS

The expression pattern of Arabidopsis SCR has een determined by analysis of an enhancer trap line, ET199, in which a GUS coding region with a minimal promoter was fortuitously inserted 1 kb upstream of the SCR coding region (see supra). In ET199 plants, GUS expression is detected in the endodermis, endodermal initials and sometimes in the quiescent center (QC) of the root. See supra and Malamy and Benfey, 1997, Dev. 124:33–44. This expression pattern of SCR in the primary root has been confirmed by in situ analysis (See supra and Di Laurenzio et al., 1996, Cell 86:423–433).

The following experiments demonstrate that 2.5 kb of 5' sequence upstream of the Arabidopsis SCR coding region is sufficient to confer SCR expression pattern to a heterologous gene. The 5' sequence used in these studies starts from the Hind III site approximately 2.5 kb upstream of the ATG initiation site and extends 3' downstream to the base pair immediately upstream of the ATG initiation site (see FIG. 14). This 5' sequence was fused to a GUS coding sequence. The resulting SCR promoter::GUS construct was incorporate into an Agrobacterium vector, which was used to transform and generate transgenic roots using standard procedures.

A large number of roots were regenerated. They show GUS staining pattern that is similar to the SCR expression pattern in ET199 plants (FIG. 19, Panel f). Since organs regenerated from callus often have an abnormal morphology, transgenic roots were transferred to liquid culture. Roots grown in liquid culture appeared morphologically normal and showed GUS expression in the endodermis, endodermal initial and QC (FIG. 19, Panel g), similar to the expression pattern of SCR seen in the enhancer trap line ET199. These results indicate that the 2.5 kb region upstream of the SCR start site is sufficient to confer the SCR expression pattern in the root.

The expression of the SCR promoter::GUS construct was also examined in scr mutant background. The scr mutant has an altered root organization (see, supra). Whereas the wild-type root of Arabidopsis has four distinct cell layers surrounding the vascular tissue, the roots of scr mutant have only three.

Transgenic roots of the scr mutant were generated that contained a SCR promoter::GUS construct. As in the wild-type, a large number of transgenic roots were formed that had detectable GUS expression (FIG. 20, Panel a). These roots were shorter than wild-type regenerated roots, consistent with the shorter root phenotype of the scr mutant.

Additional transgenic root experiments demonstrated that the SCR gene under control of its own promoter can rescue the scr mutant phenotype. Transgenic scr roots were generated that contained the full length SCR gene under the control of its own promoter. The length of transgenic roots containing the construct were longer than those of the scr mutant, indicating that the introduced SCR gene partially rescued the mutant. Whereas scr regenerated roots that carried the SCR promoter::GUS construct were very short (FIG. 21, Panel a; and FIG. 20, Panel a), roots transformed with the SCR promoter and coding region were noticeably longer (FIG. 21, Panel b). The difference was even more obvious in liquid culture, in which scr mutant roots remained short (FIG. 21, Panel c), while SCR gene complemented scr mutant roots were long and resembled wild-type roots (FIG. 21, Panel d).

Anatomical studies of the regenerated roots confirmed the ability of the SCR promoter::SCR gene construct to rescue the scr mutant phenotype. Whereas regenerated roots of scr mutant were missing an internal layer (FIG. 21, Panel e), the scr mutant roots that were transformed with the SCR promoter::SCR gene construct had a radial organization that resembled wild-type root (FIG. 21, Panel f).

9. EXAMPLE 4: ISOLATION SCR SEQUENCES USING PCR-CLONING STRATEGY

Based on the comparison of the sequences of SCR paralogs in Arabidopsis, degenerate primers SCR3AII, SCR5AII and SCR5B were designed and used in PCR amplification of SCR sequences from genomic DNA of various plant species. The amplification was performed according to condition described in Section 5.1.1., supra, using DNA isolated from maize plants grown from a commercial seed mixture. Amplification products (104 bp fragment for the SCR5B+SCR3AII primer combination; 146 bp fragment for the SCR5AII+SCR3AII primer combination) were obtained, and each cloned into a T/A vector (Invitrogen, San Diego, Calif.) and sequenced. Two of the three different types of clones obtained had deduced amino acid sequences that were very similar to a part of the Arabidopsis SCR protein (i.e., approximately 90% identity), suggesting that they represent parts from two different alleles of the maize SCR gene (i.e., ZCR gene). The two clones each had only two conservative changes in their nucleotide sequence.

The 146 bp amplification product, ZmScl1, was subsequently used as a probe for screening of a genomic library generated in lambda BlueSTAR vector (NOVAGEN) from maize (HII line) genomic DNA. The screening was performed according to the standard procedures described in *Genius*™ *System User's Guide For Membrane Hybridization* (Boehringer-Mannheim): The probe was a single-strand DNA molecule corresponding to the ZmScl1 fragment produced by PCR (Genius, Boehringer-Mannheim). Hybridization was performed according to recommendations of the manufacturer's manual (Boehringer-Mannheim). Prehybridization was for 2 hr in 50% formamide hybridization solution at 42° C. Hybridization was overnight at 42° C. with 200 ng/ml probe concentration. Filters were washed twice at room temperature in 2×SSC, 0.1% SDS for 5 min, and for stringent washing at 65° C. in 0.5×SSC,0.1% SDS twice for 15 min.

A positive clone was identified. The clone contained a 13 kb insert, which was subcloned into a plasmid vector. The resulting plasmid was designated pZCR. A 5 kb Eco RI fragment containing the maize SCR (ZCR) sequence was subcloned and sequenced. The nucleotide sequence of the region containing a partial ZCR coding sequence is shown in FIG. 17A and the corresponding deduced amino acid sequence is shown in FIG. 17B. The ZCR protein contain a segment that is highly homologous to a corresponding segment in the Arabidopsis SCR protein (FIG. 17B). This segment is flanked by segments of low homology. Thus, it is possible that the genomic clone of ZCR is a composite clone, containing sequences that are not ZCR sequences.

The deduced ZCR protein sequence was aligned with that of Arabidopsis SCR protein. The comparison revealed new conserved sites in the SCR coding sequence which were used to design new, more specific PCR primers (i.e., iF, 1R, and 4R) for use in amplification of SCR sequences from yet other plant species.

Using combinations of primers 1F+1R and 1F+4R, PCR amplification were performed as described in section 5.1.1. Two DNA of expected size were obtain from soybean: a 247 bp DNA from the 1F+1R primer combination and a 379 bp DNA from the 1F+4R primer combination. A DNA of expected size (247 kb) was obtained from carrot and spruce when their genomic DNA was amplified using 1F+4R primer combination. The nucleotide sequences of the 379 kb soybean DNA (SRPg1), the 247 kb DNA from carrot (SRPd1) and spruce (SRPp1) are shown in FIGS. 16K–M. The corresponding deduced amino acid sequences of these amplified sequences are shown in FIG. 18. Comparison of these partial SCR coding sequences indicate this approach isolated DNA sequences that encode SCR proteins with amino acid sequences that are very similar but not identical to a segment of Arabidopsis SCR protein (see FIG. 18).

10. EXAMPLE 5. EXPRESSION PATTERN OF MAIZE ZCR GENE IN ROOT TISSUE

These experiments examined the expression pattern of ZCR in the primary root and quiescent centers of maize root. The expression pattern was determined by in situ hybridization using a ZCR RNA probe, corresponding to an amino acid segment region that is highly homologous to a corresponding segment of the Arabidopsis SCR protein. The experiment was carried out as follows. Restriction fragments containing the maize ZCR sequence were isolated from pZCR and subcloned into a pBluescript vector for in vitro transcription. The probe was synthesized using conditions described in the Genius Dig RNA labeling kit. The pBluescript plasmid was linearized, and 1 µg was used as a template to synthesize digoxigenin-labeled RNA using the T7 polymerase. The RNA probe was subjected to mild alkali hydrolysis by heated at 60° C. for 1 hr in 100 mM carbonate buffer (pH 10.2) to yield a probe size of approximately 0.15 kb. Probe concentration for hybridization was optimized at 1 μg/ml/kb. In situ hybridization of root tips from 48 to 72 hr-old maize seedlings or excised quiescent centers (QCs) of roots were carried out following procedures described in Section 6.1.6., supra.

Figure 22A:
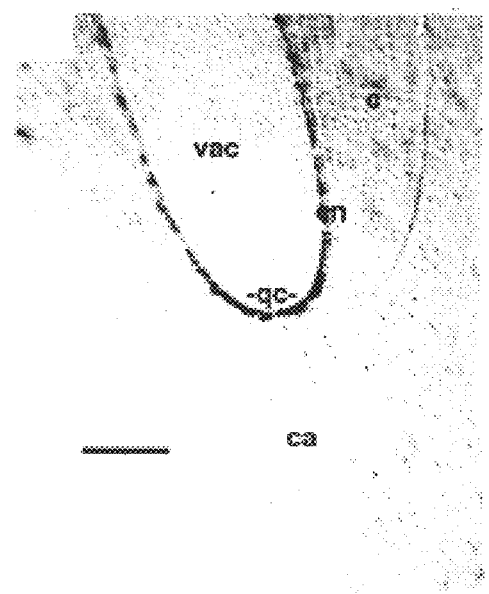
Figure 22B:
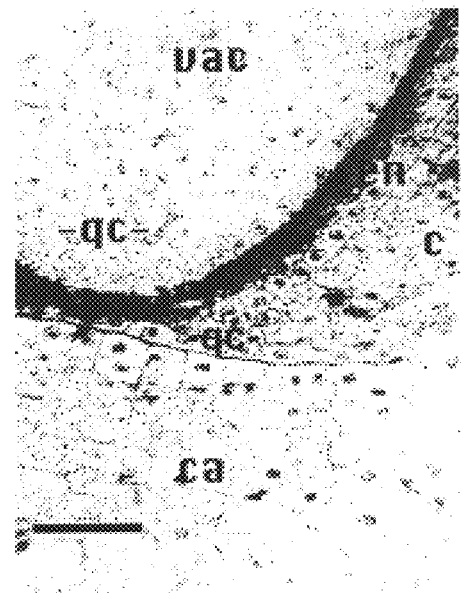

The results show that ZCR expression in maize primary roots is localized to a file of cells that is identified as the endodermal layer. The expression pattern continues in a single uninterrupted file through the QC which consists of approximately 1000–1500 cells (FIG. 22).

In two-week old regenerating QCs, ZCR expression is found in a file of cells extending through the newly formed apex. Thus, the regenerated roots exhibits a ZCR expression pattern that is similar to that seen in the primary root, even though the root apex does not contain the normal arrangement of cell files at this stage.

ZCR expression during regeneration of the root apex was also examined. In the initial stages of regeneration, cell proliferation occurs to fill in the removed tissue and begins to regenerate the basic shape of the root tip. All cells on the blunt edge of the root appears to contribute to the new population of cells. The ZCR expression pattern indicates that molecular signals are differentially present in these cells at an early stage in regeneration. The gene appears to be diagnostic of cells that are preparing to undergo asymmetrical division in order to re-establish the normal organization of the root apex from the large undifferentiated cells. The results indicate that ZCR expression is required for pattern formation since it is expressed prior to the generation of any specific anatomical pattern in the newly formed not tissue.

11. EXAMPLE 6. EXPRESSION PATTERN OF ZCR GENE IN SOYBEAN ROOTS AND ROOT NODULES

SCR expression in soybean roots and nodules was examined using in situ hybridization with a SCR probe. The procedure used were as described in Sections 6.1.6. and 11.

In primary roots, SCR is expressed in the endodermis. Expression was also found in cells at the root tip that are located at the distal end of the endodermal cell files. In soybean nodules, expression of SCR was detected in the peripheral tissue at the site of developing vascular strands. At later stages of vascular development within the nodule, SCR expression was found flanking the vascular tissue. These results indicate that SCR is involved in regulating vascularization in the nodule by contributing to the radial organization that is required to generate endodermis. These findings indicate that SCR promoter may be used to express proteins in a highly tissue-specific manner in soybean nodules. One application is to use SCR promoter to engineer nodules through production of components in a tissue-specific manner. Another application is that modification of the expression of SCR could enhance nodule activity by improving vascularization and/or the number of endodermal layers.

12. EXAMPLE 7. SCR EXPRESSION AFFECTS GRAVITROPISM OF AERIAL STRUCTURES

In addition to being defective in specific embryonic and postembryonic meristematic divisions, both the scr and the shr mutants have shoots that exhibit severely defective gravitropism. Complementation analysis showed that scr is allelic to a sgr (shoot gravitropism) mutant, sgr1. Four mutant alleles of SCR (i.e., scr1, scr2, sgr1-1 and sgr1-2) have been identified. All four of these mutants have normal root gravitropism and defective shoot gravitropism.

Etiolated hypocotyls of scr mutants placed on their sides do not respond to gravity even after 3 hr. Similar behaviors were observed with the inflorescence stems of sgr1-1 mutant, which do not curve upwards even after two days on their sides. In contrast, the roots of these plants respond rapidly to the change in orientation with the same kinetics as the wild type. Thus, mutations in the SCR gene lead to a radial pattern deficiency in the root but have no effect on root gravitropism.

Comparable results were also obtained for shr roots and for hypocotyls and inflorescence stems, i.e., data indicate that shr shows normal root gravitropism but almost no stem gravitropism.

13. DEPOSIT OF MICROORGANISMS

The following microorganisms have been deposited in accordance with the terms of the Budapest Treaty with the American Type Culture Collection; 10801 University Boulevard Manassas, Va. 20110-2209, U.S.A., on the dates indicated:

| Microorganism | Clone | Accession No. | Date |
|---|---|---|---|
| DH5α | pGEX-2TK+ (pLIG 1-3/Sac+MOB1Sac) | 98031 | April 26, 1996 |
| DH5α | pNYH1 (Zm-sc11b) | 98032 | April 26, 1996 |
| DH5α | pNYH2 (Zm-sc11) | 98033 | April 26, 1996 |
| DH5α | pNYH3 (Zm-sc12) | 98034 | April 26, 1996 |
| DH5α | pZCR | | April 18, 1997 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings such modifications are intended to fall within the scope of the appended claims.

Various publications are cited herein, each of the disclosures of which is incorporated by reference in its entirety.

What is claimed is:

1. An isolated polypeptide encoded by a nucleic acid molecule which hybridizes over its full length to the complement of the nucleic acid molecule of SEQ ID NO:1 under highly stringent conditions, wherein said highly stringent conditions consist of hybridization to filter-bound DNA in 0.5 M NaHPO4, 7% sodium dodecyl sulfate (SDS), 1 mM EDTA at 65° C., and washing in 0.1×SSC/0.1% SDS at 68° C., which nucleic acid molecule encodes a SCARECROW protein that has the property of SEQ ID NO:2 of directing the asymmetric division of the cortex/endodermal initial of a plant.

2. The isolated polypeptide of claim 1, wherein the nucleic acid molecule is expressed in the endodermis, cortex/endodermal initial, or quiescent center of a wild-type plant.

3. The isolated polypeptide of claim 1, wherein the nucleic acid molecule is expressed in the cortex/endodermal initial before asymmetric division of the cortex/endodermal initial and is expressed after the asymmetric division in endodermis cells, with no detectable expression in cortex cells as assessed using in situ hybridization in a wild-type plant under highly stringent conditions, wherein said highly stringent conditions, after the in situ hybridization step, consist of (i) washing twice in 0.2×SSC, at 55° C., (ii) rinsing twice in NTE (0.5 M NaCl, 10 mM Tris-HCl, pH 7.5, 1 mM EDTA) at 37° C., (iii) incubating at 37° C. in NTE containing 20 mg/ml RNase A for 30 min followed by several rinses in NTE, and (iv) washing in 0.2×SSC at 55° C.

4. An isolated polypeptide encoded by a nucleic acid molecule wherein the nucleic acid molecule comprises SEQ ID NO:1.

5. An isolated polypeptide comprising the amino acid sequence of SEQ ID NO:2.

6. A fusion protein comprising the polypeptide of any one of claims 1, 4, or 5 linked to a heterologous polypeptide.

* * * * *

UNITED STATES PATENT AND TRADEMARK OFFICE
CERTIFICATE OF CORRECTION

PATENT NO.    : 6,455,672 B1
DATED         : September 24, 2002
INVENTOR(S)   : Benfey et al.

It is certified that error appears in the above-identified patent and that said Letters Patent is hereby corrected as shown below:

<u>Title page,</u>
Item [*], Notice, the following text should be deleted:
"The patent is subject to a terminal disclaimer."

Signed and Sealed this

Thirteenth Day of May, 2003

JAMES E. ROGAN
*Director of the United States Patent and Trademark Office*